United States Patent
Wright et al.

(10) Patent No.: US 12,076,420 B2
(45) Date of Patent: Sep. 3, 2024

(54) ADENO-ASSOCIATED VIRUS COMPOSITIONS FOR RESTORING PAH GENE FUNCTION AND METHODS OF USE THEREOF

(71) Applicant: Homology Medicines, Inc., Bedford, MA (US)

(72) Inventors: Jason Boke Wright, Bedford, MA (US); Danielle Lauren Sookiasian, Bedford, MA (US); Thia Baboval St. Martin, Bedford, MA (US); Omar Francone, Bedford, MA (US); Albert Barnes Seymour, Bedford, MA (US)

(73) Assignee: Homology Medicines, Inc., Bedford, MA (US)

( * ) Notice: Subject to any disclaimer, the term of this patent is extended or adjusted under 35 U.S.C. 154(b) by 142 days.

(21) Appl. No.: 17/303,343

(22) Filed: May 27, 2021

(65) Prior Publication Data
US 2021/0393804 A1 Dec. 23, 2021

Related U.S. Application Data

(60) Provisional application No. 63/117,252, filed on Nov. 23, 2020, provisional application No. 63/030,341, filed on May 27, 2020.

(51) Int. Cl.
| | | |
|---|---|---|
| *C12N 15/864* | (2006.01) | |
| *A61K 38/44* | (2006.01) | |
| *A61K 48/00* | (2006.01) | |
| *C12N 15/12* | (2006.01) | |
| *C12N 15/86* | (2006.01) | |
| *C12N 15/90* | (2006.01) | |

(52) U.S. Cl.
CPC .......... *A61K 48/0066* (2013.01); *A61K 38/44* (2013.01); *C12N 15/86* (2013.01); *C12N 2750/14143* (2013.01); *C12N 2750/14151* (2013.01); *C12N 2830/50* (2013.01); *C12Y 114/16001* (2013.01)

(58) Field of Classification Search
None
See application file for complete search history.

(56) References Cited

U.S. PATENT DOCUMENTS

| | | | |
|---|---|---|---|
| 5,252,479 A | 10/1993 | Srivastava | |
| 5,474,935 A | 12/1995 | Chatterjee et al. | |
| 5,589,377 A | 12/1996 | Lebkowski et al. | |
| 5,622,856 A | 4/1997 | Natsoulis | |
| 5,650,309 A | 7/1997 | Wong-Staal et al. | |
| 5,753,500 A | 5/1998 | Shenk et al. | |
| 5,780,447 A | 7/1998 | Nienhuis | |
| 5,895,759 A | 4/1999 | Strauss et al. | |
| 6,025,195 A | 2/2000 | Sandig et al. | |
| 6,153,436 A | 11/2000 | Hermonat et al. | |
| 6,156,303 A | 12/2000 | Russell et al. | |
| 6,180,613 B1 | 1/2001 | Kaplitt et al. | |
| 6,238,914 B1 | 5/2001 | Boyce | |
| 6,268,212 B1 | 7/2001 | Simonet | |
| 6,329,181 B1 | 12/2001 | Xiao et al. | |
| 6,338,962 B1 | 1/2002 | Boyce | |
| 6,387,670 B1 | 5/2002 | Leblois-Prehaud et al. | |
| 6,610,906 B1 | 8/2003 | Kurachi et al. | |
| 6,759,237 B1 | 7/2004 | Wilson et al. | |
| 6,919,209 B1 | 7/2005 | Chatterjee et al. | |
| 6,924,128 B2 | 8/2005 | Allen | |
| 6,936,243 B2 | 8/2005 | Snyder et al. | |
| 6,936,466 B2 | 8/2005 | Feldhaus | |
| 6,953,690 B1 | 10/2005 | Gao et al. | |
| 6,984,517 B1 | 1/2006 | Chiorini et al. | |
| 7,001,764 B2 | 2/2006 | Little et al. | |
| 7,022,519 B2 | 4/2006 | Gao et al. | |
| 7,056,502 B2 | 6/2006 | Hildinger et al. | |
| 7,091,029 B2 | 8/2006 | Hwang | |
| 7,094,604 B2 | 8/2006 | Snyder et al. | |
| 7,148,341 B2 | 12/2006 | Kleinschmidt et al. | |
| 7,157,571 B2 | 1/2007 | Wang et al. | |
| 7,172,893 B2 | 2/2007 | Rabinowitz et al. | |
| 7,179,903 B2 | 2/2007 | McArthur et al. | |
| 7,198,951 B2 | 4/2007 | Gao et al. | |
| 7,220,577 B2 | 5/2007 | Zolotukhin | |
| 7,235,393 B2 | 6/2007 | Gao et al. | |
| 7,259,151 B2 | 8/2007 | Arbetman et al. | |

(Continued)

FOREIGN PATENT DOCUMENTS

| | | |
|---|---|---|
| EP | 126544 A2 | 11/1984 |
| EP | 161788 A1 | 11/1985 |

(Continued)

OTHER PUBLICATIONS

Chen et al., Molecular characterization of precise in vivo targeted gene integration in human cells using AAVHSC15, PLoS One, 2020, pp. 1-24.*
"*Homo sapiens* phenylalanine hydroxylase (PAH) mRNA, complete cds," GenBank U49897.1. Accessed Oct. 28, 2022.
Adachi et al., "Drawing a high-resolution functional map of adeno-associated virus capsid by massively parallel sequencing," Nature Communications. 2014; 1-14.
Agarwal and Ansari, "Enhancement of Transcription by a Splicing-Competent Intron is Dependent on Promoter Directionality," PLoS Genet. 2016; 12(5):e1006047.
Azuma et al. "Robust expansion of human hepatocytes in Fah-/-/Rag2-/-/Il2rg-/-mice," Nat. Biotechnol. 2007; 25(8):903-10.
Beiberstein et al., "First exon length controls active chromatin signatures and transcription," Cell Rep. 2012;2(1):62-8.

(Continued)

*Primary Examiner* — Maria Marvich
(74) *Attorney, Agent, or Firm* — Dechert LLP; Andrew T. Wilkins; David M. Lee

(57) ABSTRACT

Provided herein are recombinant adeno-associated virus (rAAV) compositions that can restore phenylalanine hydroxylase (PAH) gene function in cells, and methods for using the same to treat diseases associated with reduction of PAH gene function (e.g., PKU). Also provided are nucleic acids, vectors, packaging systems, and methods for making the adeno-associated virus compositions.

18 Claims, 40 Drawing Sheets

Specification includes a Sequence Listing.

(56) References Cited

U.S. PATENT DOCUMENTS

| | | |
|---|---|---|
| 7,282,199 B2 | 10/2007 | Gao et al. |
| 7,351,813 B2 | 4/2008 | Miao et al. |
| 7,465,583 B2 | 12/2008 | Samulski et al. |
| 7,482,156 B2 | 1/2009 | Arroyo et al. |
| 7,588,772 B2 | 9/2009 | Kay et al. |
| 7,749,492 B2 | 7/2010 | Bartlett et al. |
| 7,790,154 B2 | 9/2010 | Samulski et al. |
| 7,906,111 B2 | 3/2011 | Wilson et al. |
| 8,030,065 B2 | 10/2011 | Gray |
| 8,067,156 B2 | 11/2011 | Kaplitt et al. |
| 8,163,543 B2 | 4/2012 | Urabe et al. |
| 8,168,425 B2 | 5/2012 | Gray |
| 8,241,622 B2 | 8/2012 | Englehardt et al. |
| 8,283,151 B2 | 10/2012 | Schmidt et al. |
| 8,298,818 B2 | 10/2012 | Boye et al. |
| 8,476,418 B2 | 7/2013 | Mueller et al. |
| 8,524,446 B2 | 9/2013 | Gao et al. |
| 8,628,966 B2 | 1/2014 | Chatterjee et al. |
| 8,632,764 B2 | 1/2014 | Xiao et al. |
| 8,716,461 B2 | 5/2014 | Delwart et al. |
| 8,846,387 B2 | 9/2014 | Russell et al. |
| 8,846,389 B2 | 9/2014 | Chiorini et al. |
| 8,926,958 B2 | 1/2015 | Shah et al. |
| 8,999,678 B2 | 4/2015 | Vandenberghe et al. |
| 8,999,948 B2 | 4/2015 | Tubert et al. |
| 9,114,161 B2 | 8/2015 | Barkats |
| 9,150,882 B2 | 10/2015 | Kay et al. |
| 9,169,299 B2 | 10/2015 | Lisowski et al. |
| 9,169,494 B2 | 10/2015 | Hewitt et al. |
| 9,193,956 B2 | 11/2015 | Schaffer et al. |
| 9,217,155 B2 | 12/2015 | Gao et al. |
| 9,222,105 B2 | 12/2015 | Cost et al. |
| 9,402,919 B2 | 8/2016 | Roeth et al. |
| 9,408,904 B2 | 8/2016 | Wright et al. |
| 9,409,953 B2 | 8/2016 | Asokan et al. |
| 9,441,244 B2 | 9/2016 | Schaffer et al. |
| 9,522,176 B2 | 12/2016 | DeRosa et al. |
| 9,525,116 B2 * | 12/2016 | Kamada .................. H01L 33/60 |
| 9,617,548 B2 | 4/2017 | Chuah et al. |
| 9,623,120 B2 | 4/2017 | Chatterjee et al. |
| 9,764,045 B2 | 9/2017 | Nathwani et al. |
| 9,783,824 B2 | 10/2017 | Kay et al. |
| 9,840,719 B2 | 12/2017 | High et al. |
| 9,890,396 B2 | 2/2018 | Chatterjee et al. |
| 9,926,574 B2 | 3/2018 | Barkats |
| 10,610,606 B2 | 4/2020 | Seymour et al. |
| 2003/0129203 A1 | 7/2003 | Vega et al. |
| 2003/0130221 A1 | 7/2003 | High et al. |
| 2003/0198620 A1 | 10/2003 | Ozawa et al. |
| 2004/0086485 A1 | 5/2004 | Aguilar-Cordova |
| 2004/0142416 A1 | 7/2004 | Laipis et al. |
| 2004/0235174 A1 | 11/2004 | Grimm et al. |
| 2005/0112765 A1 | 5/2005 | Li et al. |
| 2009/0191597 A1 | 7/2009 | Samulski et al. |
| 2009/0215879 A1 | 8/2009 | Diprimio et al. |
| 2010/0297084 A1 | 11/2010 | Bennett et al. |
| 2010/0316623 A1 | 12/2010 | Turner et al. |
| 2012/0046349 A1 | 2/2012 | Bell et al. |
| 2012/0093772 A1 | 4/2012 | Horsager et al. |
| 2012/0244127 A1 | 9/2012 | Lipschutz et al. |
| 2013/0023033 A1 | 1/2013 | Wilson et al. |
| 2013/0096182 A1 | 4/2013 | Chatterjee et al. |
| 2013/0189225 A1 | 7/2013 | Voit et al. |
| 2013/0280222 A1 | 10/2013 | Kay et al. |
| 2013/0287736 A1 | 10/2013 | Passini et al. |
| 2013/0310443 A1 | 11/2013 | Srivastava et al. |
| 2013/0323226 A1 | 12/2013 | Wilson et al. |
| 2014/0037585 A1 | 2/2014 | Wright et al. |
| 2014/0050701 A1 | 2/2014 | Zhong et al. |
| 2014/0107185 A1 | 4/2014 | Maclaren et al. |
| 2014/0271550 A1 | 9/2014 | Rabinowitz et al. |
| 2014/0271551 A1 | 9/2014 | Hirsch et al. |
| 2014/0336245 A1 | 11/2014 | Mingozzi et al. |
| 2014/0341883 A1 | 11/2014 | Weeks et al. |
| 2014/0359799 A1 | 12/2014 | Wang et al. |
| 2015/0004101 A1 | 1/2015 | Constable et al. |
| 2015/0023924 A1 | 1/2015 | High et al. |
| 2015/0024467 A1 | 1/2015 | Sheldon et al. |
| 2015/0065562 A1 | 3/2015 | Yazicioglu et al. |
| 2015/0079038 A1 | 3/2015 | Deverman et al. |
| 2015/0110762 A1 | 4/2015 | Holmes et al. |
| 2015/0111955 A1 | 4/2015 | High et al. |
| 2015/0184197 A1 | 7/2015 | Davidson et al. |
| 2015/0238550 A1 | 8/2015 | McCown et al. |
| 2015/0252384 A1 | 9/2015 | Kaspar et al. |
| 2015/0315610 A1 | 11/2015 | Nishie et al. |
| 2015/0352228 A1 | 12/2015 | Torbett et al. |
| 2015/0374803 A1 | 12/2015 | Wolfe |
| 2015/0376240 A1 | 12/2015 | Cronin et al. |
| 2015/0376650 A1 | 12/2015 | Auerbach et al. |
| 2016/0000887 A1 | 1/2016 | Wilson et al. |
| 2016/0017295 A1 | 1/2016 | Schaffer et al. |
| 2016/0032319 A1 | 2/2016 | Wright et al. |
| 2016/0123990 A1 | 5/2016 | High et al. |
| 2016/0175365 A1 | 6/2016 | Golden |
| 2016/0229904 A1 | 8/2016 | Xiao et al. |
| 2017/0087219 A1 | 3/2017 | Bunting et al. |
| 2017/0088856 A1 | 3/2017 | Barzel et al. |
| 2017/0119906 A1 | 5/2017 | Riley |
| 2017/0145439 A1 | 5/2017 | Gao et al. |
| 2017/0211094 A1 | 7/2017 | Chatterjee et al. |
| 2017/0211095 A1 | 7/2017 | Chatterjee et al. |
| 2017/0218395 A1 | 8/2017 | Byrne et al. |
| 2017/0326256 A1 | 11/2017 | Doering et al. |
| 2018/0298380 A1 | 10/2018 | Gao et al. |
| 2019/0256867 A1 | 8/2019 | Seymour et al. |
| 2020/0318081 A1 * | 10/2020 | Lahusen .................. C12N 7/00 |

FOREIGN PATENT DOCUMENTS

| | | |
|---|---|---|
| EP | 746624 A1 | 12/1996 |
| EP | 1497436 A1 | 1/2005 |
| WO | WO-1996008560 A1 | 3/1996 |
| WO | WO-1998009524 A1 | 3/1998 |
| WO | WO-1998021349 A1 | 5/1998 |
| WO | WO-1998027207 A1 | 6/1998 |
| WO | WO-1998028417 A1 | 7/1998 |
| WO | WO-1999003981 A1 | 1/1999 |
| WO | WO-1999018227 A1 | 4/1999 |
| WO | WO-1999055564 A1 | 11/1999 |
| WO | WO-1999064569 A1 | 12/1999 |
| WO | WO-2000049160 A1 | 8/2000 |
| WO | WO-2001036620 A2 | 5/2001 |
| WO | WO-2002066611 A2 | 8/2002 |
| WO | WO-2003052051 A2 | 6/2003 |
| WO | WO-2003087383 A1 | 10/2003 |
| WO | WO-2003093436 A2 | 11/2003 |
| WO | WO-2005111220 A2 | 11/2005 |
| WO | WO-2006096815 A2 | 9/2006 |
| WO | WO-2007019646 A1 | 2/2007 |
| WO | WO-2008021140 A2 | 2/2008 |
| WO | WO-2009000552 A2 | 12/2008 |
| WO | WO-2009130208 A1 | 10/2009 |
| WO | WO-2009134681 A2 | 11/2009 |
| WO | WO-2010124180 A1 | 10/2010 |
| WO | WO-2011038187 A1 | 3/2011 |
| WO | WO-2014064277 A1 | 5/2014 |
| WO | WO-2014089212 A1 | 6/2014 |
| WO | WO-2014193716 A2 | 12/2014 |
| WO | WO-2015061491 A1 | 4/2015 |
| WO | WO-2015143177 A1 | 9/2015 |
| WO | WO-2015164723 A1 | 10/2015 |
| WO | WO-2016049230 A1 | 3/2016 |
| WO | WO-2016097218 A1 | 6/2016 |
| WO | WO-2016097219 A1 | 6/2016 |
| WO | WO-2016100575 A1 | 6/2016 |
| WO | WO-2016146757 A1 | 9/2016 |
| WO | WO-2017015154 A1 | 1/2017 |
| WO | WO-2017100551 A1 | 6/2017 |
| WO | WO-2017106345 A1 | 6/2017 |
| WO | WO-2017136202 A1 | 8/2017 |
| WO | WO-2017149292 A1 | 9/2017 |
| WO | WO-2018035388 A1 | 2/2018 |
| WO | WO-2018046737 A1 | 3/2018 |

(56) References Cited

FOREIGN PATENT DOCUMENTS

| WO | WO-2018126112 A1 | 7/2018 |
|---|---|---|
| WO | WO-2018126116 A1 | 7/2018 |
| WO | WO-2018129586 A1 | 7/2018 |
| WO | WO-2018167621 A1 | 9/2018 |
| WO | WO-2018187231 A2 | 10/2018 |
| WO | WO-2018206168 A1 | 11/2018 |
| WO | WO-2018222925 A1 | 12/2018 |
| WO | WO-2019010091 A1 | 1/2019 |
| WO | WO-2019152841 A1 | 8/2019 |
| WO | WO-2019152843 A1 | 8/2019 |
| WO | WO-2019154939 A1 | 8/2019 |
| WO | WO-2019195854 A1 | 10/2019 |
| WO | WO-2019217513 A2 | 11/2019 |
| WO | WO-2019222132 A1 | 11/2019 |
| WO | WO-2020077250 A1 | 4/2020 |
| WO | WO-2020084162 A1 | 4/2020 |

OTHER PUBLICATIONS

Bonnet and Palancade, "Intron or No Intron: A Matter for Nuclear Pore Complexes," Nucleus. 2015;6(6):455-61.
Burset et al., "Analysis of Canonical and Non-Canonical Splice Sties in Mammalian Genomes" Nucleic Acids Research. 2000; 28(21):4364-75.
Burset et al., "SpliceDB: Database of Canonical and Non-canonical Mammalian Splice Sites," Nucleic Acids Research. 2001;29(1):255-59.
Clark et al., "GenBank," Nucleic Acids Res. 2016;44(Database issue):D67-72.
Dang, "Structure of the Hepatic Control Region of the Human Apolipoprotein E/C-I Gene Locus," J Biol Chem. 1995;270(38):22577-85.
De Sabbata et al., "Development of a novel AAV-based gene therapy in combination with tolerogenic nanoparticles for sustained treatment of ornithine transcarbamylase deficiency," Changing the Face of Modern Medicine: Stem Cell and Gene Therapy. Dec. 13, 2018;29(12):P343.
Di Mattia et al., "Structural Insight into the Unique Properties of Adeno-Associated Vims Serotype 9," J Vi. 2012; 86(12): 6947-6958.
Eperon et al., "Pathways for Selection of 5' Splice Sites by U1 snRNPs and SF2/ASF," The EMBO Journal. 1993; 12(9):3607-617.
Farre et al., "Identification of patterns in biological sequences at the ALGGEN server: PROMO and MALGEN," Nucleic Acids Res. 2003;31(13):3651-653.
Gao, "Human Branch Point Consensus Sequence is yUnAY," Nucleic Acids Research. 2008;36(7):2257-267.
Gatermann et al., "Introduction of Functional Artificial Introns into the Naturally Intronless ura4 Gene of Schizosaccharomyces pombe," Molecular and Cell Biology. 1989;9(4):1526-535.
Grisch-Chan et al., "Low-Dose Gene Therapy for Murine PKU Using Episomal Naked DNA Vectors Expressing PAH from its Endogenous Liver Promoter," Mol Ther Nucleic Acids. Jun. 16, 2017;7:339-349.
Hacein-Bey-Abina et al., "Insertional oncogenesis in 4 patients after retrovirus-mediated gene therapy of SCID-X1," J Clin Invest. 2008; 118(9):3132-42.
Houseley and Tollervey, "Apparent Non-Canonical Trans-Splicing is Generated by Reverse Transcriptase In Vivo," PLoS One. 2010;5(8):e12271 (7 pages).
Khan et al., "JASPAR 2018: update of the open-access database of transcription factor binding profiles and its web framework," Nucleic Acids Res. 2018; 46(D1):D260-D266.
Kramer et al., "In vitro and in vivo comparative study of chimeric liver-specific promoters," Mol Therapy. 2003; 7(3):375-85.
Lacy-Hulbert et al., "Interruption of Coding Sequences by Heterologous Introns can Enhance the Functional Expression of Recombinant Genes," Gene Therapy. 2001;8:649-53.

Lai et al., "Synthetic Intron Improves Transduction Efficiency of Trans-Splicing Adeno-Associated Viral Vectors," Hum Gene Ther. 2006; 17(10):1036-1042.
Landrum et al., "ClinVar: public archive of relationships among sequence variation and human phenotype," Nucleic Acids Res. 2014;42(Database issue):D980-5.
Laxa, "Intron-Mediated Enhancement: A Tool for Heterologous Gene Expression in Plants," Front. Plant Sci. 2017;7(1977): 13 pages.
Lee et al., "Adeno-Associated Virus (AAV) Vectors: Rational Design Strategies for Capsid Engineering," Curr Opin Biomed Eng. 2018; 7: 58-63.
Lizio et al., "Gateways to the FANTOM5 promoter level mammalian expression atlas," Genome Biol. 2015;16(22): 14 pages.
Lizio et al., "Update of the FANTOM web resource: high resolution transcriptome of diverse cell types in mammals," Nucleic Acids Res. 2017; 45(D1):D737-D743.
Lochrie et al., "Mutations on the External Surfaces of Adeno-Associated Virus Type 2 Capsids That Affect Transduction and Neutralization," J Vi. 2006; 80(2): 821-834.
Lu et al., "A 5' Noncoding Exon Containing Engineered Intron Enhances Transgene Expression from Recombinant AAV Vectors in vivo," Hum Gene Ther. 2017;28(1):125-34.
Lu et al., "A mini-intronic plasmid (MIP): a novel robust transgene expression vector in vivo and in vitro," Mol Ther. 2013;21(5):954-63.
MacDonald et al., "The Database of Genomic Variants: a curated collection of structural variation in the human genome," Nucleic Acids Res. 2014;42(Database issue):D986-92.
Mauro, "A critical analysis of codon optimization in human therapeutics," Trends Mol Med. 2014;20(11):604-13.
McDonald et al., "Pahphp-5: a mouse mutant deficient in phenylalanine hydroxylase," PNAS. 1990; 87:1965-67.
Messeguer et al., "PROMO: detection of known transcription regulatory elements using species-tailored searches," Bioinformatics. 2002;18(2):333-34.
Moabbi et al., "Role for Gene Looping in Intron-Mediated Enhancement of Transcription," PNAS. 2012;109(22):8505-510.
Neuberger and Williams, "The Intron Requirement for Immunoglobulin Gene Expression is Dependent Upon the Promoter," Nucleic Acids Research. 1988;16(14):6713-724.
Palmiter et al., "Heterologous Introns Can Enhance Expression of Transgenes in Mice," Proc. Nati. Acad. Sci. USA. 1991; 88(2):478-82.
Picanoco-Castro et al., "An enhancer/promoter combination strengthens the expression of blood-coagulation factor VIII in non-viral expression vectors," Genetics and Molecular Research. 2008;7(2):314-25.
Reed, "The Organization of 3' Splice-Site Sequences in Mammalian Introns," Genes & Development. 1989;3(12B):2113-123.
Regier et al., "Phenylalanine Hydroxylase Deficiency," GeneReviews. Jan. 10, 2000; Seattle (WA): University of Washington, Seattle; 1993-2019. Available from: <URL: https://www.ncbi.nlm.nih.gov/books/NBK1504>; Genbank supplement, pp. 1-3.
Savisaar and Hurst, "Exonic Splice Regulation Imposes Strong Selection at Synonymous Sites," Genome Research. 2018;28(10):1442-454.
Savy et al., "Impact of Inverted Terminal Repeat Integrity on rAAV8 Production Using the Baculovirus/Sf9 Cells System," Human Gene Therapy Methods. 2017;28(5):277-89.
Shapiro and Senapathy, "RNA Splice Junctions of Different Classes of Eukaryotes: Sequence Statistics and Functional Implications in Gene Expression," Nucleic Acids Research. 1987;15(17):7155-174.
Shaul, "How Introns Enhance Gene Expression," International Journal of Biochemistry and Cell Biology. 2017; 91(B):145-55.
Sherry et al., "dbSNP: the NCBI database of genetic variation," Nucleic Acids Res. 2001;29(1):308-11.
Sibley et al., "Lessons from non-canonical splicing," Nat Rev Gen. 2016; 17(7):407-21.
Thöny, "Long-term correction of murine phenylketonuria by viral gene transfer: liver versus muscle," J Inherit Metab Dis. Dec. 2010;33(6):677-80.

(56) References Cited

OTHER PUBLICATIONS

Wieringa et al., "A Minimal Intron Length but No Specific Internal Sequence is Required for Splicing the Large Rabbit B-Globin," Intron. Cell. 1984;37(3):915-25.

Xie et al., "Towards the atomic structure of the Adeno-Associated Virus 2 capsid," IDR. 2000; 2(3):136.

Yagi et al., "Complete Restoration of Phenylalanine Oxidation in Phenylketonuria Mouse by a Self-complementary Adeno-associated Virus Vector," J Gene Med. 2011; 13(2):114-22.

Zhuang et al., "UACUAAC is the preferred branch site for mammalian mRNA splicing," Proc. Natl. Acad. Sci. USA. 1988;86(8):2752-756.

\* cited by examiner

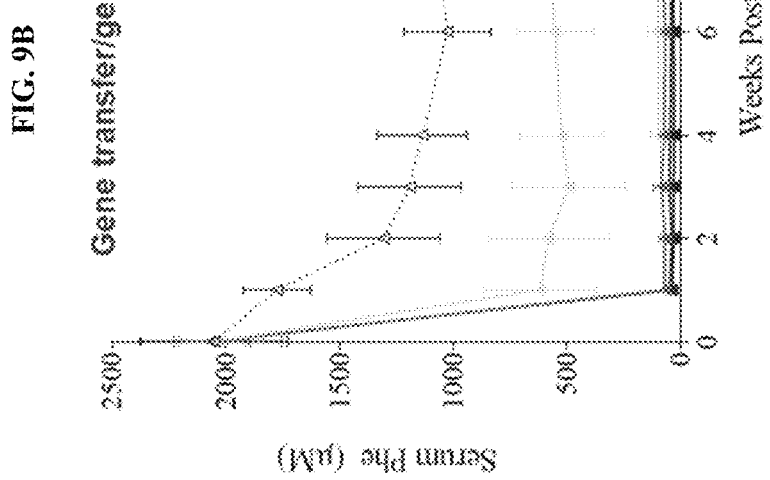
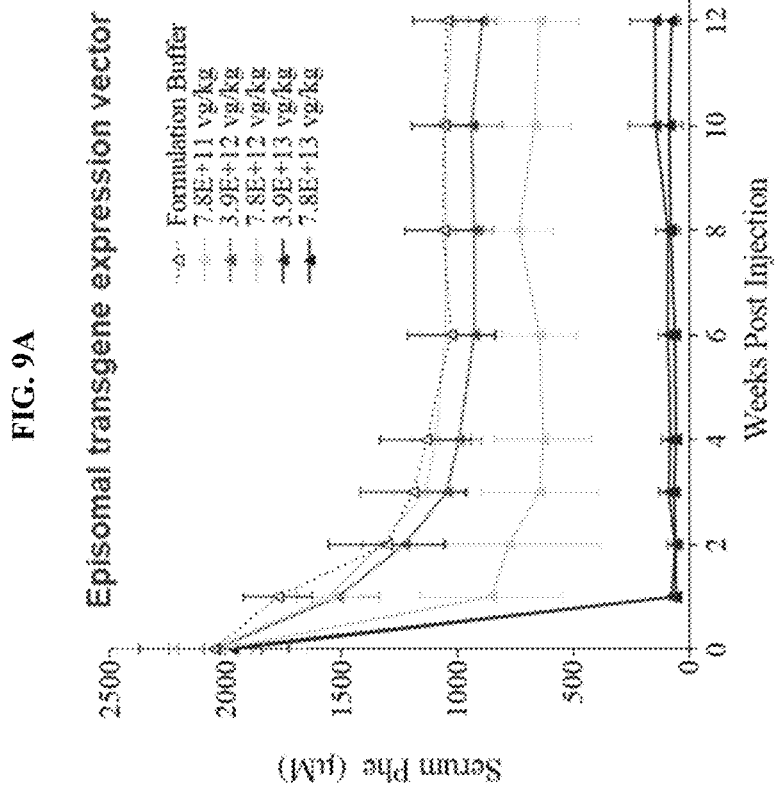

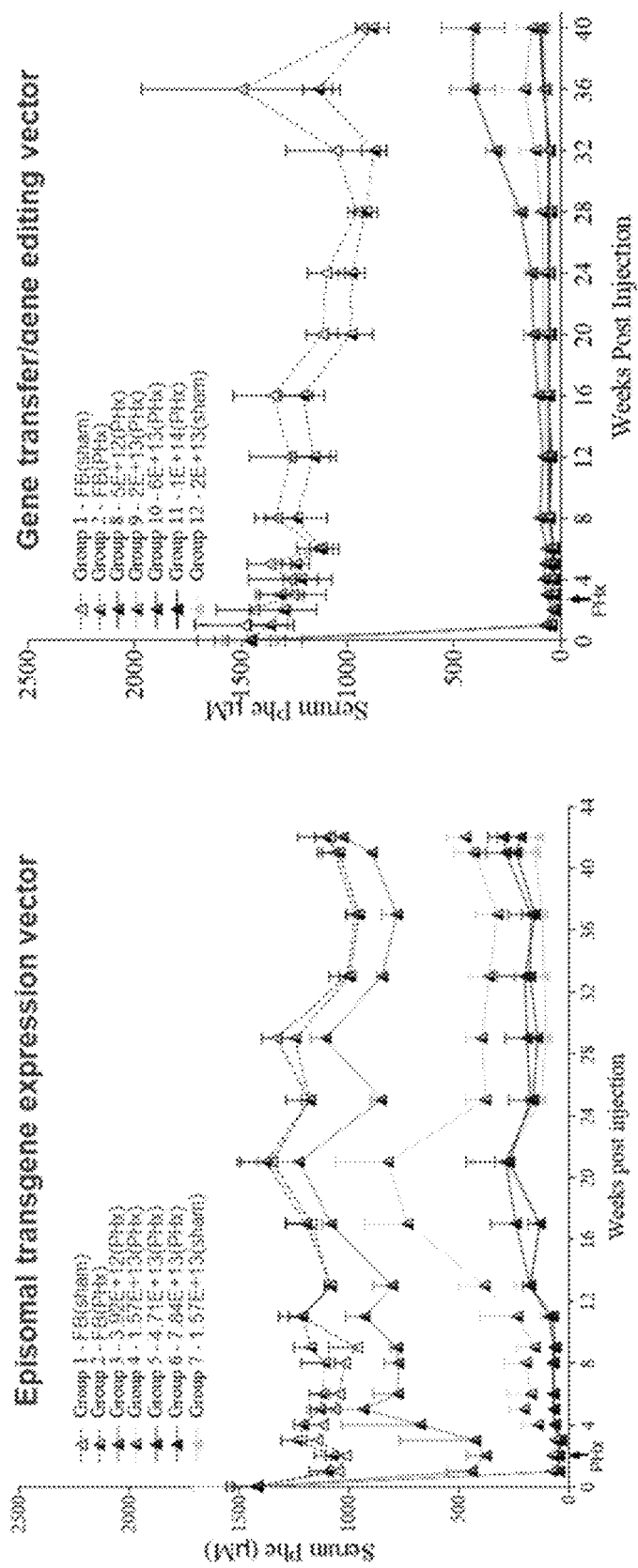

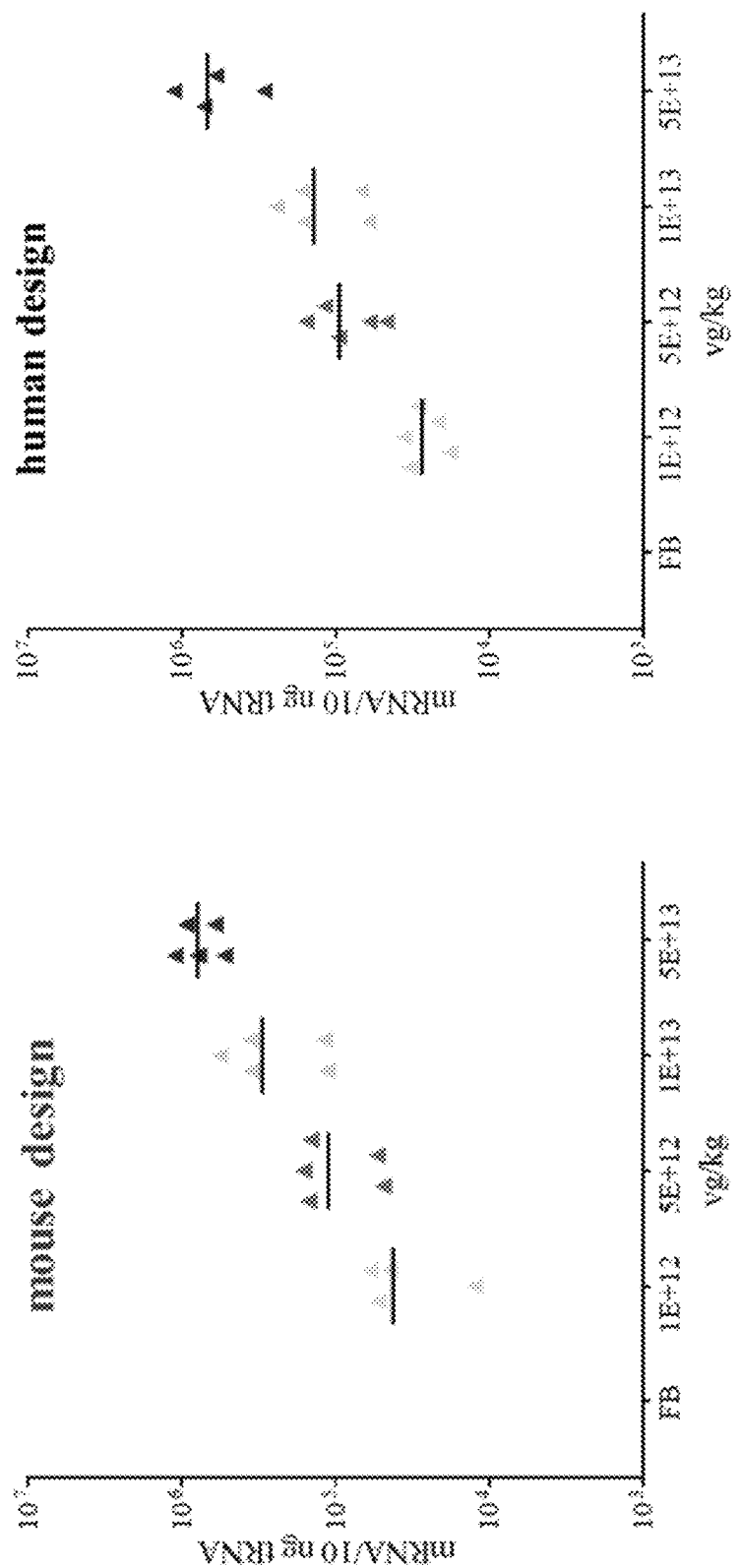

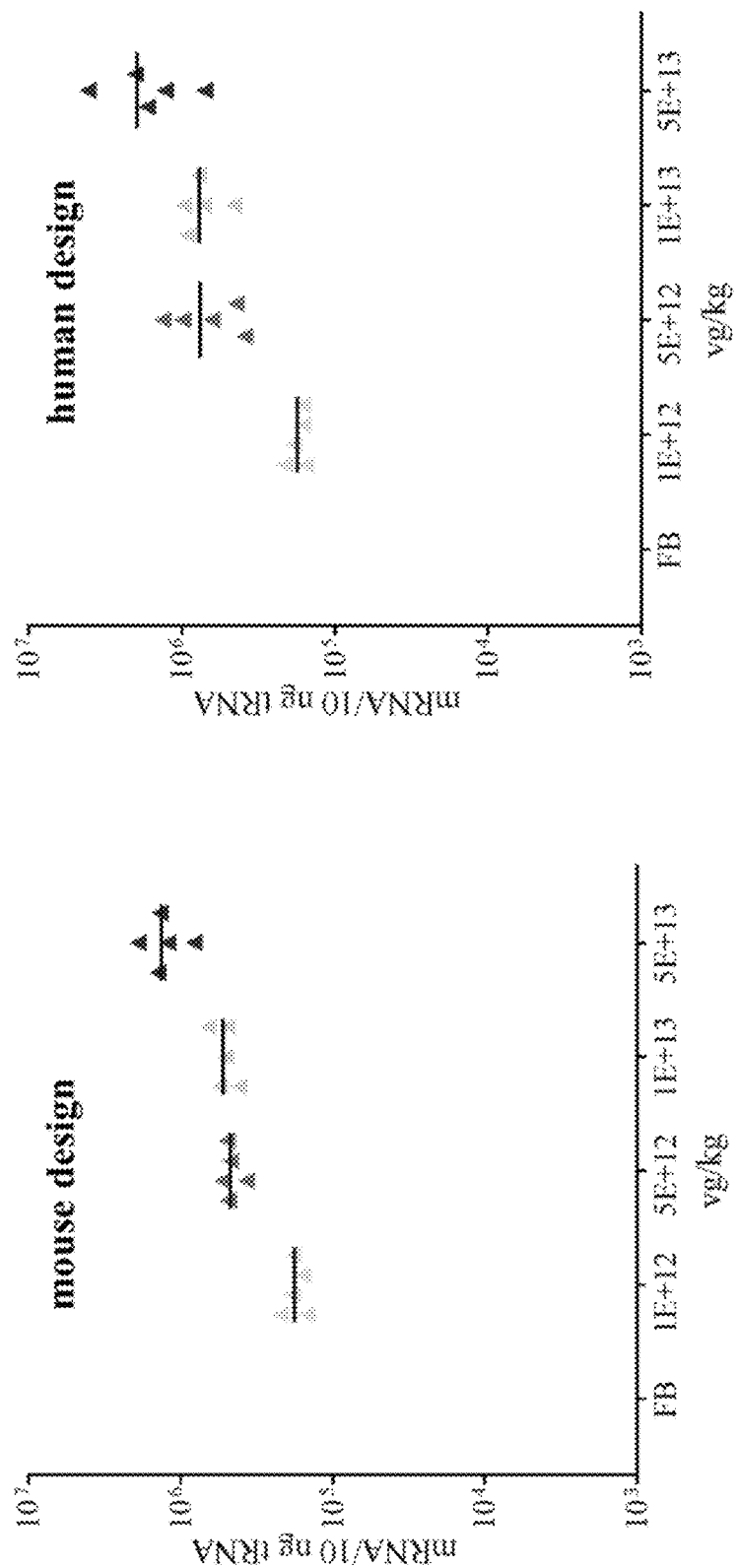

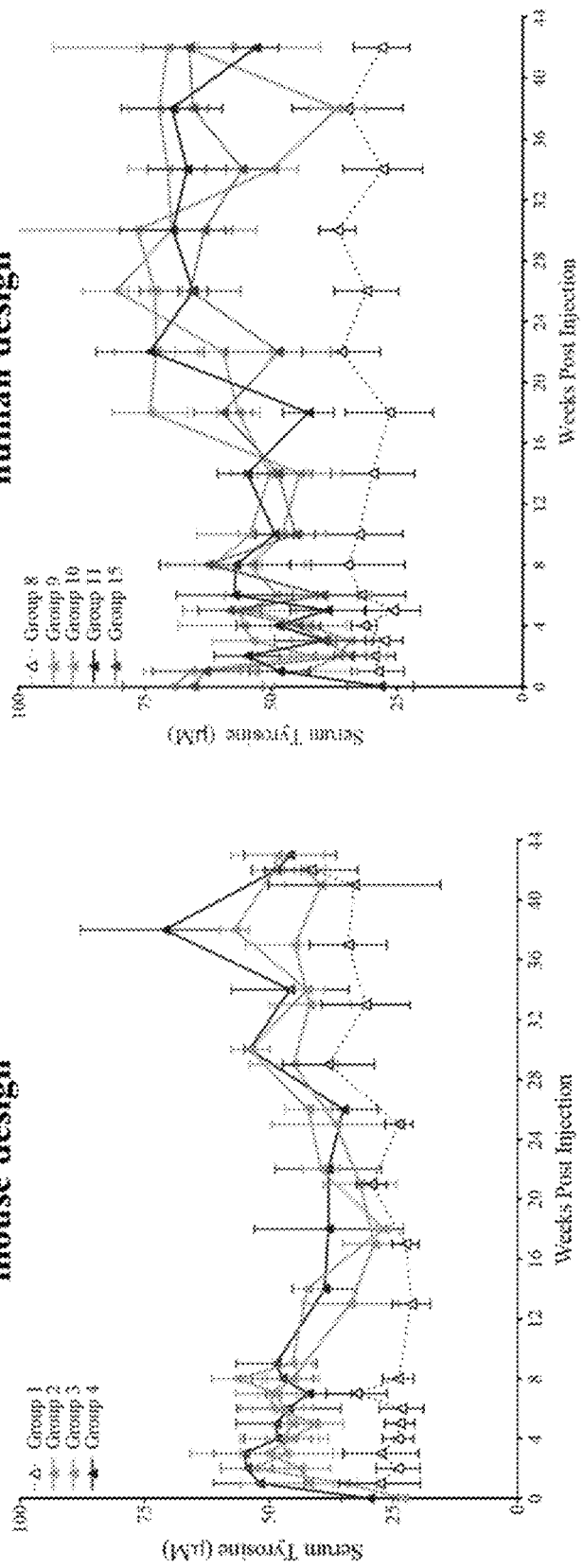
FIG. 11C mouse design
FIG. 11D human design

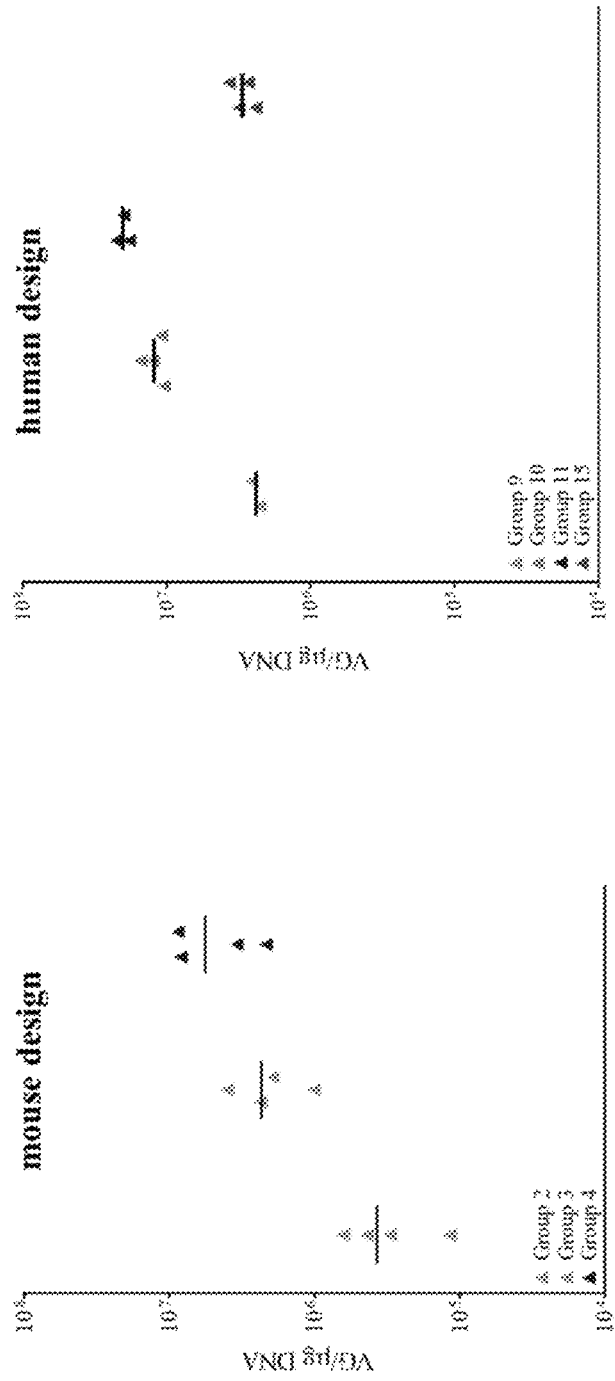
FIG. 11E mouse design
FIG. 11F human design

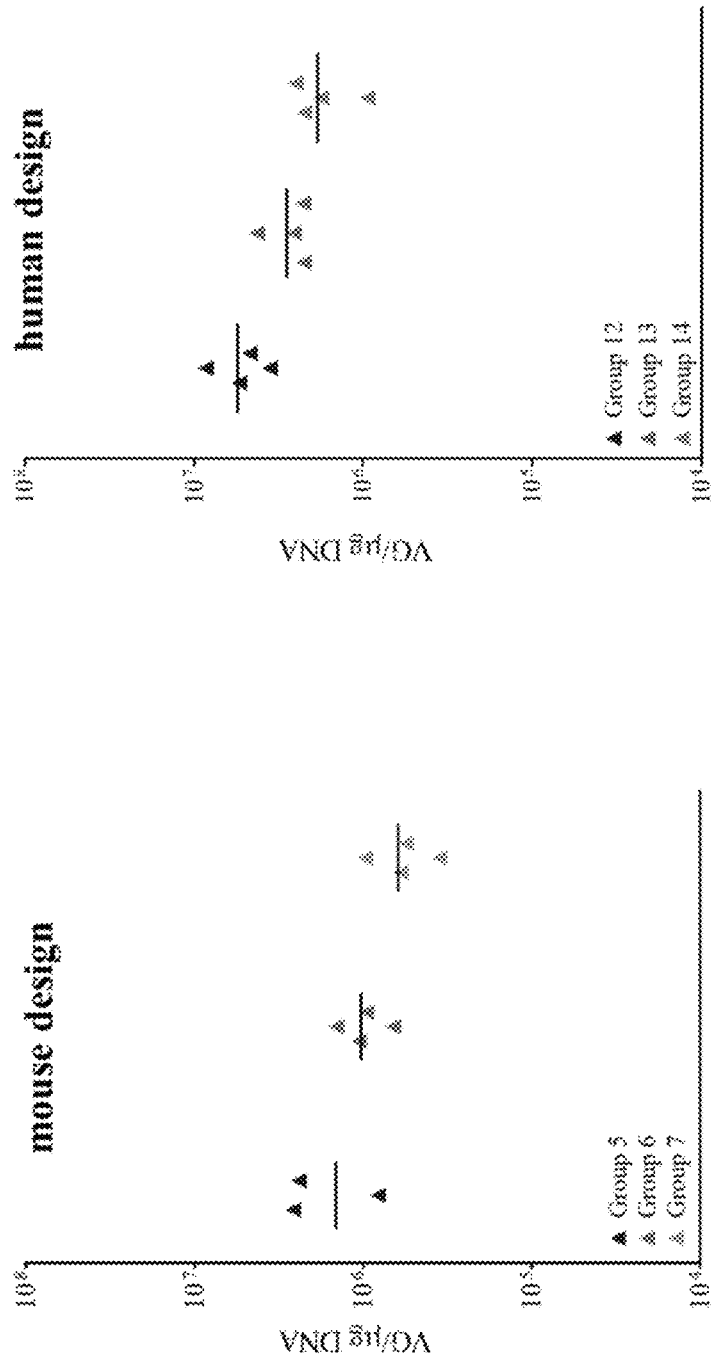

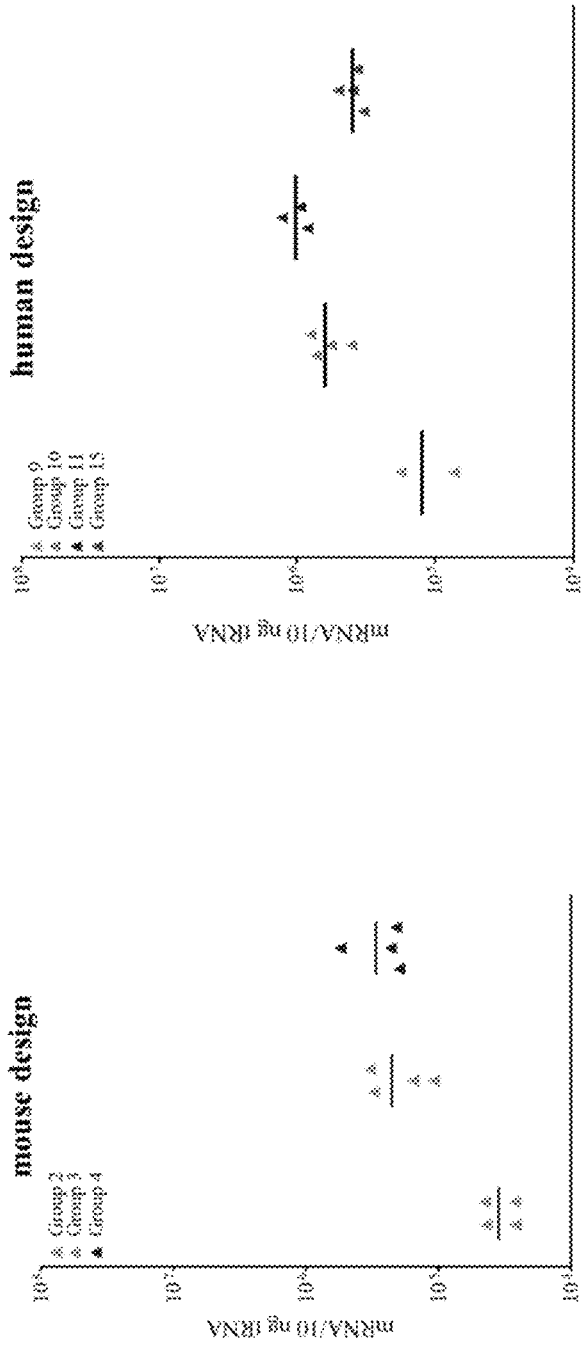

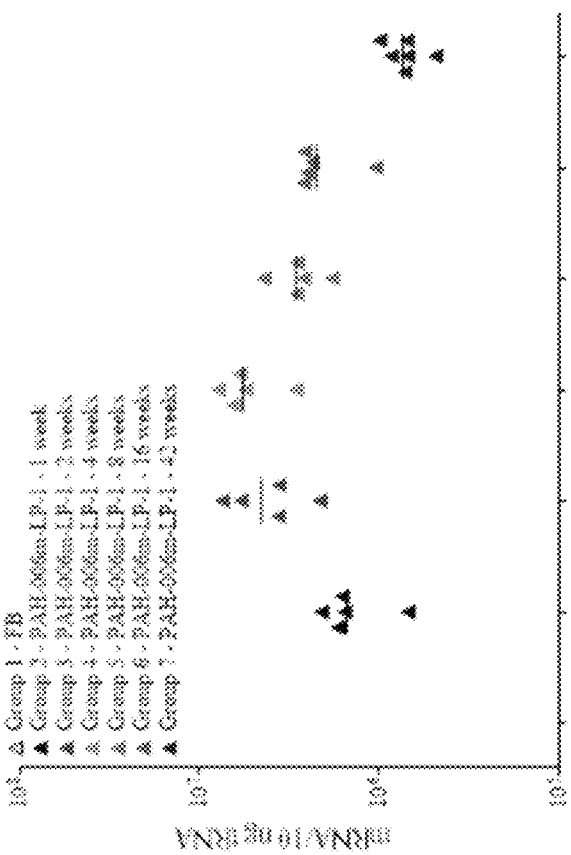
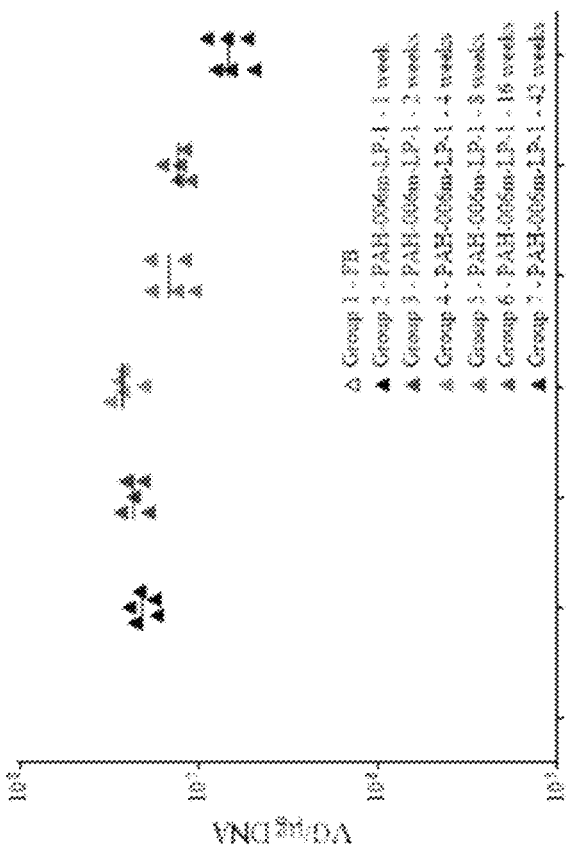
FIG. 12A
FIG. 12B

FIG. 12E

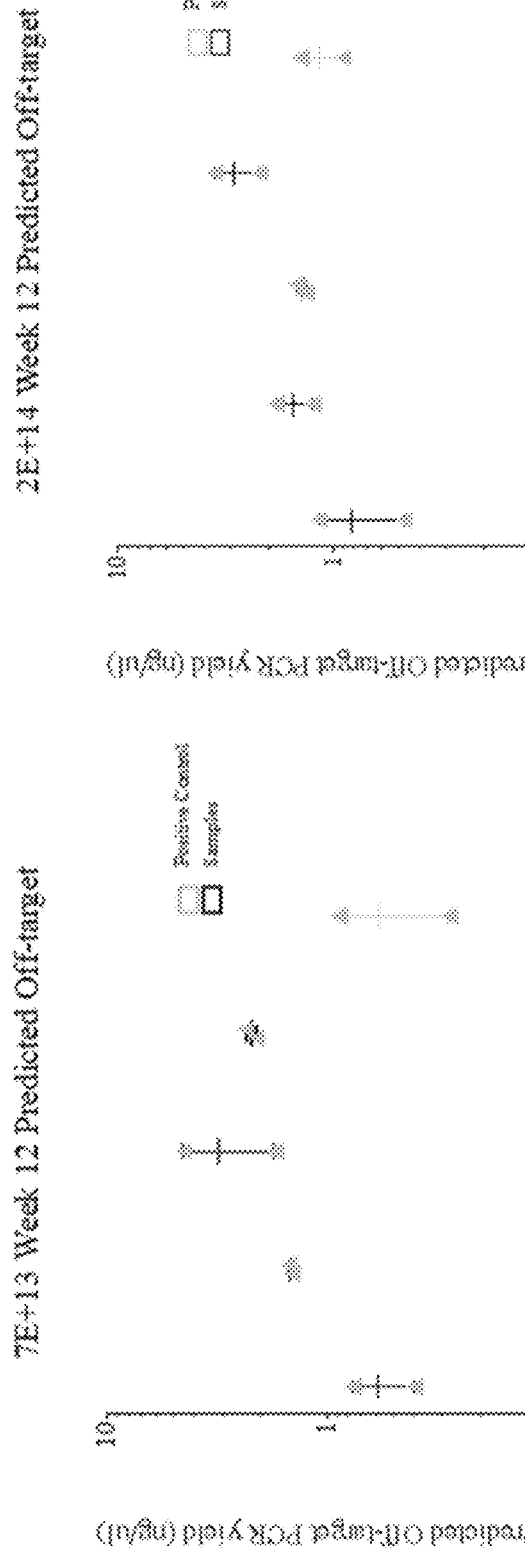

US 12,076,420 B2

SEQUENCE LISTING

<160> NUMBER OF SEQ ID NOS: 86

<210> SEQ ID NO 1
<211> LENGTH: 736
<212> TYPE: PRT
<213> ORGANISM: Artificial Sequence
<220> FEATURE:
<223> OTHER INFORMATION: adeno-associated virus 9

<400> SEQUENCE: 1

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
```

```
                355                 360                 365
Ala Asp Val Phe Met Ile Pro Gln Tyr Gly Tyr Leu Thr Leu Asn Asp
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Lys Thr Ile Asn Gly Ser Gly Gln Asn Gln Gln Thr Leu Lys Phe Ser
                450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
                500                 505                 510
Gly Arg Asn Ser Leu Met Asn Pro Gly Pro Ala Met Ala Ser His Lys
                515                 520                 525
Glu Gly Glu Asp Arg Phe Phe Pro Leu Ser Gly Ser Leu Ile Phe Gly
530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
                580                 585                 590
Thr Gly Trp Val Gln Asn Gln Gly Ile Leu Pro Gly Met Val Trp Gln
                595                 600                 605
Asp Arg Asp Val Tyr Leu Gln Gly Pro Ile Trp Ala Lys Ile Pro His
                610                 615                 620
Thr Asp Gly Asn Phe His Pro Ser Pro Leu Met Gly Gly Phe Gly Met
625                 630                 635                 640
Lys His Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
                660                 665                 670
Gln Tyr Ser Thr Gly Gln Val Ser Val Glu Ile Glu Trp Glu Leu Gln
                675                 680                 685
Lys Glu Asn Ser Lys Arg Trp Asn Pro Glu Ile Gln Tyr Thr Ser Asn
                690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 2
<211> LENGTH: 736
<212> TYPE: PRT
<213> ORGANISM: Artificial Sequence
<220> FEATURE:
<223> OTHER INFORMATION: AAV isolate
```

```
<400> SEQUENCE: 2

Met Thr Ala Asp Gly Tyr Leu Pro Asp Trp Leu Glu Asp Asn Leu Ser
1               5                  10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Gln Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415
```

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 3
<211> LENGTH: 736
<212> TYPE: PRT
<213> ORGANISM: Artificial Sequence
<220> FEATURE:
<223> OTHER INFORMATION: AAV isolate

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
                115                 120                 125

Leu Gly Leu Val Glu Glu Ala Ala Lys Thr Ala Pro Gly Lys Lys Arg
                130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
                195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
                290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
                370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
        500                 505                 510

Gly Arg Asn Ser Leu Met Asn Pro Gly Pro Ala Met Ala Ser His Lys
    515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Gly Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Gly Gly Val
705                 710                 715                 720

Tyr Ser Glu Pro Arg Pro Ile Gly Thr Arg Tyr Leu Thr Arg Asn Leu
                725                 730                 735

<210> SEQ ID NO 4
<211> LENGTH: 736
<212> TYPE: PRT
<213> ORGANISM: Artificial Sequence
<220> FEATURE:
<223> OTHER INFORMATION: AAV isolate

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Ile Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

```
Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
        340                 345                 350

Pro Tyr Val Leu Gly Ser Ala His Glu Gly Cys Leu Pro Pro Phe Pro
    355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
        420                 425                 430

Asp Arg Leu Met Asn Pro Leu Ile Asp Gln Tyr Leu Tyr Tyr Leu Ser
    435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
        500                 505                 510

Gly Arg Asn Ser Leu Met Asn Pro Gly Pro Ala Met Ala Ser His Lys
```

```
                    515                 520                 525
Glu Gly Glu Asp Arg Phe Phe Pro Leu Ser Gly Ser Leu Ile Phe Gly
    530                 535                 540
Lys Gln Gly Thr Gly Arg Asp Asn Val Asp Ala Asp Lys Val Met Ile
545                 550                 555                 560
Thr Asn Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
        595                 600                 605
Asp Arg Asp Val Tyr Leu Gln Gly Pro Ile Trp Ala Lys Ile Pro His
    610                 615                 620
Thr Tyr Gly Asn Phe His Pro Ser Pro Leu Met Gly Gly Phe Gly Met
625                 630                 635                 640
Lys His Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
    690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 5
<211> LENGTH: 736
<212> TYPE: PRT
<213> ORGANISM: Artificial Sequence
<220> FEATURE:
<223> OTHER INFORMATION: AAV isolate

<400> SEQUENCE: 5

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Glu Gln Ser Pro Gln Glu Pro Asp Ser Ser Ala Gly Ile Asp
```

```
            145                 150                 155                 160
        Lys Ser Gly Ala Gln Pro Ala Lys Lys Arg Leu Asn Phe Gly Gln Thr
                        165                 170                 175
        Gly Asp Thr Glu Ser Val Pro Asp Pro Gln Pro Ile Gly Glu Pro Pro
                        180                 185                 190
        Ala Ala Pro Ser Gly Val Gly Ser Leu Thr Met Ala Ser Gly Gly Gly
                        195                 200                 205
        Ala Pro Val Ala Asp Asn Asn Glu Gly Ala Asp Gly Val Gly Ser Ser
                        210                 215                 220
        Ser Gly Asn Trp His Cys Asp Ser Gln Trp Leu Gly Asp Arg Val Ile
        225                 230                 235                 240
        Thr Thr Ser Thr Arg Thr Trp Ala Leu Pro Thr Tyr Asn Asn His Leu
                        245                 250                 255
        Tyr Lys Gln Ile Ser Asn Ser Thr Ser Gly Gly Ser Ser Asn Asp Asn
                        260                 265                 270
        Ala Tyr Phe Gly Tyr Ser Thr Pro Trp Gly Tyr Phe Asp Phe Asn Arg
                        275                 280                 285
        Phe His Cys His Phe Ser Pro Arg Asp Trp Gln Arg Leu Ile Asn Asn
                290                 295                 300
        Asn Trp Gly Phe Arg Pro Lys Arg Leu Asn Phe Lys Leu Phe Asn Ile
        305                 310                 315                 320
        Gln Val Lys Glu Val Thr Asp Asn Asn Gly Val Lys Thr Ile Ala Asn
                        325                 330                 335
        Asn Leu Thr Ser Thr Val Gln Val Phe Thr Asp Ser Asp Tyr Gln Leu
                        340                 345                 350
        Pro Tyr Val Leu Gly Ser Ala His Glu Gly Cys Leu Pro Pro Phe Pro
                        355                 360                 365
        Ala Asp Val Phe Met Ile Pro Gln Tyr Gly Tyr Leu Thr Leu Asn Asp
                        370                 375                 380
        Gly Ser Gln Ala Val Gly Arg Ser Ser Phe Tyr Cys Leu Glu Tyr Phe
        385                 390                 395                 400
        Pro Ser Gln Met Leu Arg Thr Gly Asn Asn Phe Gln Phe Ser Tyr Glu
                        405                 410                 415
        Phe Glu Asn Val Pro Phe His Ser Ser Tyr Ala His Ser Gln Ser Leu
                        420                 425                 430
        Asp Arg Leu Met Asn Pro Leu Ile Asp Gln Tyr Leu Tyr Tyr Leu Ser
                        435                 440                 445
        Lys Thr Ile Asn Gly Ser Gly Gln Asn Gln Gln Thr Leu Lys Phe Ser
        450                 455                 460
        Val Ala Gly Pro Ser Asn Met Ala Val Gln Gly Arg Asn Tyr Ile Pro
        465                 470                 475                 480
        Gly Pro Ser Tyr Arg Gln Gln Arg Val Ser Thr Thr Val Thr Gln Asn
                        485                 490                 495
        Asn Asn Ser Glu Phe Ala Trp Pro Gly Ala Ser Ser Trp Ala Leu Asn
                        500                 505                 510
        Gly Arg Asn Ser Leu Met Asn Pro Gly Pro Ala Met Ala Ser His Lys
                        515                 520                 525
        Glu Gly Glu Asp Arg Phe Phe Pro Leu Ser Gly Ser Leu Ile Phe Gly
                        530                 535                 540
        Lys Gln Gly Thr Gly Arg Asp Asn Val Asp Ala Asp Lys Val Met Ile
        545                 550                 555                 560
        Thr Asn Glu Glu Glu Ile Lys Thr Thr Asn Pro Val Ala Thr Glu Ser
                        565                 570                 575
```

```
Tyr Gly Gln Val Ala Thr Asn His Gln Ser Ala Gln Ala Gln
            580                 585                 590
Thr Gly Trp Val Gln Asn Gly Ile Leu Pro Gly Met Val Trp Gln
            595                 600                 605
Asp Arg Asp Val Tyr Leu Gln Gly Pro Ile Trp Ala Lys Ile Pro His
610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                    645                 650                 655
Asp Pro Pro Thr Ala Phe Asn Lys Asp Lys Leu Asn Ser Phe Ile Thr
                660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735
```

<210> SEQ ID NO 6
<211> LENGTH: 736
<212> TYPE: PRT
<213> ORGANISM: Artificial Sequence
<220> FEATURE:
<223> OTHER INFORMATION: AAV isolate

<400> SEQUENCE: 6

```
Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Leu Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
```

```
Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Ser Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620
```

```
Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 7
<211> LENGTH: 736
<212> TYPE: PRT
<213> ORGANISM: Artificial Sequence
<220> FEATURE:
<223> OTHER INFORMATION: AAV isolate

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255
```

```
Tyr Lys Gln Ile Ser Asn Ser Thr Ser Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Arg Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
```

```
                675                 680                 685
Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 8
<211> LENGTH: 736
<212> TYPE: PRT
<213> ORGANISM: Artificial Sequence
<220> FEATURE:
<223> OTHER INFORMATION: AAV isolate

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Val Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
```

```
              305                 310                 315                 320
        Gln Val Lys Glu Val Thr Asp Asn Asn Gly Val Lys Thr Ile Ala Asn
                        325                 330                 335
        Asn Leu Thr Ser Thr Val Gln Val Phe Thr Asp Ser Asp Tyr Gln Leu
                        340                 345                 350
        Pro Tyr Val Leu Gly Ser Ala His Glu Gly Cys Leu Pro Phe Pro
                        355                 360             365
        Ala Asp Val Phe Met Ile Pro Gln Tyr Gly Tyr Leu Thr Leu Asn Asp
        370                 375                 380
        Gly Ser Gln Ala Val Gly Arg Ser Ser Phe Tyr Cys Leu Glu Tyr Phe
        385                 390                 395                 400
        Pro Ser Gln Met Leu Arg Thr Gly Asn Asn Phe Gln Phe Ser Tyr Glu
                        405                 410                 415
        Phe Glu Asn Val Pro Phe His Ser Ser Tyr Ala His Ser Gln Ser Leu
                        420                 425                 430
        Asp Arg Leu Met Asn Pro Leu Ile Asp Gln Tyr Leu Tyr Tyr Leu Ser
                        435                 440                 445
        Lys Thr Ile Asn Gly Ser Gly Gln Asn Gln Gln Thr Leu Lys Phe Ser
        450                 455                 460
        Val Ala Gly Pro Ser Asn Met Ala Val Gln Gly Arg Asn Tyr Ile Pro
        465                 470                 475                 480
        Gly Pro Ser Tyr Arg Gln Gln Arg Val Ser Thr Thr Val Thr Gln Asn
                        485                 490                 495
        Asn Asn Ser Glu Phe Ala Trp Pro Gly Ala Ser Ser Trp Ala Leu Asn
                        500                 505                 510
        Gly Arg Asn Ser Leu Met Asn Pro Gly Pro Ala Met Ala Ser His Lys
                        515                 520                 525
        Glu Gly Glu Asp Arg Phe Phe Pro Leu Ser Gly Ser Leu Ile Phe Gly
                        530                 535                 540
        Lys Gln Gly Thr Gly Arg Asp Asn Val Asp Ala Asp Lys Val Met Ile
        545                 550                 555                 560
        Thr Asn Glu Glu Glu Ile Lys Thr Thr Asn Pro Val Ala Thr Glu Ser
                        565                 570                 575
        Tyr Gly Gln Val Ala Thr Asn His Gln Ser Ala Gln Ala Gln Ala Gln
                        580                 585                 590
        Thr Gly Trp Val Gln Asn Gln Gly Ile Leu Pro Gly Met Val Trp Gln
                        595                 600                 605
        Asp Arg Asp Val Tyr Leu Gln Gly Pro Ile Trp Ala Lys Ile Pro His
        610                 615                 620
        Thr Asp Gly Asn Phe His Pro Ser Pro Leu Met Gly Gly Phe Gly Met
        625                 630                 635                 640
        Lys His Pro Pro Pro Gln Ile Leu Ile Lys Asn Thr Pro Val Pro Ala
                        645                 650                 655
        Asp Pro Pro Thr Ala Phe Asn Lys Asp Lys Leu Asn Ser Phe Ile Thr
                        660                 665                 670
        Gln Tyr Ser Thr Gly Gln Val Ser Val Glu Ile Glu Trp Glu Leu Gln
                        675                 680                 685
        Lys Glu Asn Ser Lys Arg Trp Asn Pro Glu Ile Gln Tyr Thr Ser Asn
                        690                 695                 700
        Tyr Tyr Lys Ser Asn Asn Val Glu Phe Ala Val Asn Thr Glu Gly Val
        705                 710                 715                 720
        Tyr Ser Glu Pro Arg Pro Ile Gly Thr Arg Tyr Leu Thr Arg Asn Leu
                        725                 730                 735
```

```
<210> SEQ ID NO 9
<211> LENGTH: 736
<212> TYPE: PRT
<213> ORGANISM: Artificial Sequence
<220> FEATURE:
<223> OTHER INFORMATION: AAV isolate

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Arg Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365
```

```
Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 10
<211> LENGTH: 736
<212> TYPE: PRT
<213> ORGANISM: Artificial Sequence
<220> FEATURE:
<223> OTHER INFORMATION: AAV isolate

<400> SEQUENCE: 10

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Cys Gly Gly
            195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415
```

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 11
<211> LENGTH: 736
<212> TYPE: PRT
<213> ORGANISM: Artificial Sequence
<220> FEATURE:
<223> OTHER INFORMATION: AAV isolate

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

```
Gly Tyr Lys Tyr Leu Gly Pro Gly Asn Gly Leu Asp Lys Gly Glu Pro
     50                  55                  60

Val Asn Ala Ala Asp Ala Ala Leu Glu His Asp Arg Ala Tyr Asp
 65              70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
```

```
            465                 470                 475                 480
        Gly Pro Ser Tyr Arg Gln Gln Arg Val Ser Thr Thr Val Thr Gln Asn
                        485                 490                 495

Asn Asn Ser Glu Phe Ala Trp Pro Gly Ala Ser Ser Trp Ala Leu Asn
                        500                 505                 510

Gly Arg Asn Ser Leu Met Asn Pro Gly Pro Ala Met Ala Ser His Lys
                        515                 520                 525

Glu Gly Glu Asp Arg Phe Phe Pro Leu Ser Gly Ser Leu Ile Phe Gly
                        530                 535                 540

Lys Gln Gly Thr Gly Arg Asp Asn Val Asp Ala Asp Lys Val Met Ile
        545                 550                 555                 560

Thr Asn Glu Glu Glu Ile Lys Thr Thr Asn Pro Val Ala Thr Glu Ser
                        565                 570                 575

Tyr Gly Gln Val Ala Thr Asn His Gln Ser Ala Gln Ala Gln Ala Gln
                        580                 585                 590

Thr Gly Trp Val Gln Asn Gln Gly Ile Leu Pro Gly Met Val Trp Gln
                        595                 600                 605

Asp Arg Asp Val Tyr Leu Gln Gly Pro Ile Trp Ala Lys Ile Pro His
                        610                 615                 620

Thr Asp Gly Asn Phe His Pro Ser Pro Leu Met Gly Gly Phe Gly Met
        625                 630                 635                 640

Lys His Pro Pro Gln Ile Leu Ile Lys Asn Thr Pro Val Pro Ala
                        645                 650                 655

Asp Pro Pro Thr Ala Phe Asn Lys Asp Lys Leu Asn Ser Phe Ile Thr
                        660                 665                 670

Gln Tyr Ser Thr Gly Gln Val Ser Val Glu Ile Glu Trp Glu Leu Gln
                        675                 680                 685

Lys Lys Asn Ser Lys Arg Trp Asn Pro Glu Ile Gln Tyr Thr Ser Asn
                        690                 695                 700

Tyr Tyr Lys Ser Asn Asn Val Glu Phe Ala Val Asn Thr Glu Gly Val
        705                 710                 715                 720

Tyr Ser Glu Pro Arg Pro Ile Gly Thr Arg Tyr Leu Thr Arg Asn Leu
                        725                 730                 735

<210> SEQ ID NO 12
<211> LENGTH: 736
<212> TYPE: PRT
<213> ORGANISM: Artificial Sequence
<220> FEATURE:
<223> OTHER INFORMATION: AAV isolate

<400> SEQUENCE: 12

Met Ala Ala Asp Gly Tyr Leu Pro Asp Trp Leu Glu Asp Asn Leu Ser
        1               5                   10                  15

Glu Gly Ile Arg Glu Trp Trp Ala Leu Lys Pro Gly Ala Pro Gln Pro
                        20                  25                  30

Lys Ala Asn Gln Gln His Gln Asp Asn Ala Arg Gly Leu Val Leu Pro
                        35                  40                  45

Gly Tyr Lys Tyr Leu Gly Pro Gly Asn Gly Leu Asp Lys Gly Glu Pro
                        50                  55                  60

Val Asn Ala Ala Asp Ala Ala Ala Leu Glu His Asp Lys Ala Tyr Asp
        65                  70                  75                  80

Gln Gln Leu Lys Ala Gly Asp Asn Pro Tyr Leu Lys Tyr Asn His Ala
                        85                  90                  95

Asp Ala Glu Phe Gln Glu Arg Leu Lys Glu Asp Thr Ser Phe Gly Gly
```

```
                        100                 105                 110
Asn Leu Gly Arg Ala Val Phe Gln Ala Lys Lys Arg Leu Leu Glu Pro
            115                 120                 125

Leu Gly Leu Val Glu Ala Ala Lys Thr Ala Pro Gly Lys Lys Arg
130                 135                 140

Pro Val Glu Gln Ser Pro Gln Glu Pro Asp Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
                275                 280                 285

Phe His Cys His Phe Ser Pro His Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Asn
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
                500                 505                 510

Gly Arg Asn Ser Leu Met Asn Pro Gly Pro Ala Met Ala Ser His Lys
            515                 520                 525
```

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Met Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 13
<211> LENGTH: 736
<212> TYPE: PRT
<213> ORGANISM: Artificial Sequence
<220> FEATURE:
<223> OTHER INFORMATION: AAV isolate

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

```
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
            195                 200                 205
Ala Pro Val Ala Asp Asn Asn Glu Gly Ala Asp Gly Val Gly Ser Ser
        210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
                260                 265                 270
Ala Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
        290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Pro Phe Pro
            355                 360                 365
Ala Asp Val Phe Met Ile Pro Gln Tyr Gly Tyr Leu Thr Leu Asn Asp
        370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
            435                 440                 445
Lys Thr Ile Asn Gly Ser Gly Gln Asn Gln Gln Thr Leu Lys Phe Ser
        450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Arg Ala Ser Ser Trp Ala Leu Asn
                500                 505                 510
Gly Arg Asn Ser Leu Met Asn Pro Gly Pro Ala Met Ala Ser His Lys
            515                 520                 525
Glu Gly Glu Asp Arg Phe Phe Pro Leu Ser Gly Ser Leu Ile Phe Gly
        530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
```

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
        660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 14
<211> LENGTH: 145
<212> TYPE: DNA
<213> ORGANISM: Artificial Sequence
<220> FEATURE:
<223> OTHER INFORMATION: Synthetic polynucleotide

<400> SEQUENCE: 14
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcct                                          145

<210> SEQ ID NO 15
<211> LENGTH: 736
<212> TYPE: PRT
<213> ORGANISM: Artificial Sequence
<220> FEATURE:
<223> OTHER INFORMATION: AAV isolate

<400> SEQUENCE: 15

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

```
Leu Gly Leu Val Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
                180                 185                 190
Ala Ala Pro Ser Gly Val Gly Ser Leu Thr Met Ala Ser Gly Gly Gly
                195                 200                 205
Ala Pro Val Ala Asp Asn Asn Glu Gly Ala Asp Gly Val Gly Ser Ser
210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
                260                 265                 270
Ala Tyr Phe Gly Tyr Ser Thr Pro Trp Gly Tyr Phe Asp Phe Asn Arg
                275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Pro Phe Pro
                355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Lys Thr Ile Asn Gly Ser Gly Gln Asn Gln Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Arg Ala Ser Ser Trp Ala Leu Asn
                500                 505                 510
Gly Arg Asn Ser Leu Met Asn Pro Gly Pro Ala Met Ala Ser His Lys
                515                 520                 525
Glu Gly Glu Asp Arg Phe Phe Pro Leu Ser Gly Ser Leu Ile Phe Gly
    530                 535                 540
```

-continued

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Arg Gln
            675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 16
<211> LENGTH: 736
<212> TYPE: PRT
<213> ORGANISM: Artificial Sequence
<220> FEATURE:
<223> OTHER INFORMATION: AAV isolate

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

```
Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Ala Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
```

-continued

```
                595                 600                 605
Asp Arg Asp Val Tyr Leu Gln Gly Pro Ile Trp Ala Lys Ile Pro His
610                 615                 620

Thr Asp Gly Asn Phe His Pro Ser Pro Leu Met Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 17
<211> LENGTH: 736
<212> TYPE: PRT
<213> ORGANISM: Artificial Sequence
<220> FEATURE:
<223> OTHER INFORMATION: AAV isolate

<400> SEQUENCE: 17

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
```

```
                    225                 230                 235                 240
            Thr Thr Ser Thr Arg Thr Trp Ala Leu Pro Thr Tyr Asn Asn His Leu
                            245                 250                 255
            Tyr Lys Gln Ile Ser Asn Ser Thr Ser Gly Ser Ser Asn Asp Asn
                            260                 265                 270
            Ala Tyr Phe Gly Tyr Ser Thr Pro Trp Gly Tyr Phe Asp Phe Asn Arg
                            275                 280                 285
            Phe His Cys His Phe Ser Pro Arg Asp Trp Gln Arg Leu Ile Asn Asn
                    290                 295                 300
            Asn Trp Gly Phe Arg Pro Lys Arg Leu Asn Phe Lys Leu Phe Asn Ile
            305                 310                 315                 320
            Gln Val Lys Glu Val Thr Asp Asn Asn Gly Val Lys Thr Ile Ala Asn
                            325                 330                 335
            Asn Leu Thr Ser Thr Val Gln Val Phe Thr Asp Ser Asp Tyr Gln Leu
                            340                 345                 350
            Pro Tyr Val Leu Gly Ser Ala His Glu Gly Cys Leu Pro Pro Phe Pro
                            355                 360                 365
            Ala Asp Val Phe Met Ile Pro Gln Tyr Gly Tyr Leu Thr Leu Asn Asp
                    370                 375                 380
            Gly Ser Gln Ala Val Gly Arg Ser Ser Phe Tyr Cys Leu Glu Tyr Phe
            385                 390                 395                 400
            Pro Ser Gln Met Leu Arg Thr Gly Asn Asn Phe Gln Phe Ser Tyr Glu
                            405                 410                 415
            Phe Glu Asn Val Pro Phe His Ser Ser Tyr Ala His Ser Gln Ser Leu
                            420                 425                 430
            Asp Arg Leu Met Asn Pro Leu Ile Asp Gln Tyr Leu Tyr Tyr Leu Ser
                    435                 440                 445
            Lys Thr Ile Asn Gly Ser Gly Gln Asn Gln Gln Thr Leu Lys Phe Ser
            450                 455                 460
            Val Ala Gly Pro Ser Asn Met Ala Val Gln Gly Arg Asn Tyr Ile Pro
            465                 470                 475                 480
            Gly Pro Ser Tyr Arg Gln Gln Arg Val Ser Thr Thr Val Thr Gln Asn
                            485                 490                 495
            Asn Asn Ser Glu Ile Ala Trp Pro Arg Ala Ser Ser Trp Ala Leu Asn
                            500                 505                 510
            Gly Arg Asn Ser Leu Met Asn Pro Gly Pro Ala Met Ala Ser His Lys
                    515                 520                 525
            Glu Gly Glu Asp Arg Phe Phe Pro Leu Ser Gly Ser Leu Ile Phe Gly
                    530                 535                 540
            Lys Gln Gly Thr Gly Arg Asp Asn Val Asp Ala Asp Lys Val Met Ile
            545                 550                 555                 560
            Thr Asn Glu Glu Glu Ile Lys Thr Thr Asn Pro Val Ala Thr Glu Ser
                            565                 570                 575
            Tyr Gly Gln Val Ala Thr Asn His Gln Ser Ala Gln Ala Gln Ala Gln
                            580                 585                 590
            Thr Gly Trp Val Gln Asn Gln Gly Ile Leu Pro Gly Met Val Trp Gln
                    595                 600                 605
            Asp Arg Asp Val Tyr Leu Gln Gly Pro Ile Trp Ala Lys Ile Pro His
                    610                 615                 620
            Thr Asp Gly Asn Phe His Pro Ser Pro Leu Met Gly Gly Phe Gly Met
            625                 630                 635                 640
            Lys His Pro Pro Pro Gln Ile Leu Ile Lys Asn Thr Pro Val Pro Ala
                            645                 650                 655
```

```
Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Cys Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 18
<211> LENGTH: 145
<212> TYPE: DNA
<213> ORGANISM: Artificial Sequence
<220> FEATURE:
<223> OTHER INFORMATION: Synthetic polynucleotide

<400> SEQUENCE: 18
aggaacccct agtgatggag ttggccactc cctctctgcg cgctcgctcg ctcactgagg    60
ccgggcgacc aaaggtcgcc cgacgcccgg gctttgcccg gcggcctca gtgagcgagc    120 gagcgcgcag agagggagtg gccaa                                         145

<210> SEQ ID NO 19
<211> LENGTH: 106
<212> TYPE: DNA
<213> ORGANISM: Artificial Sequence
<220> FEATURE:
<223> OTHER INFORMATION: Synthetic polynucleotide

<400> SEQUENCE: 19
ctgcgcgctc gctcgctcac tgaggccgcc cgggcaaagc ccgggcgtcg gcgaccttt    60 ggtcgcccgg cctcagtgag cgagcgagcg cgcagagagg gagtgg                  106

<210> SEQ ID NO 20
<211> LENGTH: 167
<212> TYPE: DNA
<213> ORGANISM: Artificial Sequence
<220> FEATURE:
<223> OTHER INFORMATION: Synthetic polynucleotide

<400> SEQUENCE: 20
ctctcccccc tgtcgcgttc gctcgctcgc tggctcgttt gggggggtgg cagctcaaag    60
agctgccaga cgacggccct ctggccgtcg ccccccaaa cgagccagcg agcgagcgaa    120
cgcgacaggg gggagagtgc cacactctca agcaaggggg ttttgta                  167

<210> SEQ ID NO 21
<211> LENGTH: 167
<212> TYPE: DNA
<213> ORGANISM: Artificial Sequence
<220> FEATURE:
<223> OTHER INFORMATION: Synthetic polynucleotide

<400> SEQUENCE: 21
tacaaaacct ccttgcttga gagtgtggca ctctcccccc tgtcgcgttc gctcgctcgc    60
tggctcgttt gggggggtgg cagctcaaag agctgccaga cgacggccct ctggccgtcg    120 ccccccaaa cgagccagcg agcgagcgaa cgcgacaggg gggagag                   167
```

<210> SEQ ID NO 22
<211> LENGTH: 621
<212> TYPE: PRT
<213> ORGANISM: Artificial Sequence
<220> FEATURE:
<223> OTHER INFORMATION: AAV2 Rep

<400> SEQUENCE: 22

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
```

```
                370               375               380
Lys Val Glu Ser Ala Lys Ala Ile Leu Gly Gly Ser Lys Val Arg
385               390               395               400

Val Asp Gln Lys Cys Lys Ser Ser Ala Gln Ile Asp Pro Thr Pro Val
                405               410               415

Ile Val Thr Ser Asn Thr Asn Met Cys Ala Val Ile Asp Gly Asn Ser
                420               425               430

Thr Thr Phe Glu His Gln Gln Pro Leu Gln Asp Arg Met Phe Lys Phe
            435               440               445

Glu Leu Thr Arg Arg Leu Asp His Asp Phe Gly Lys Val Thr Lys Gln
            450               455               460

Glu Val Lys Asp Phe Phe Arg Trp Ala Lys Asp His Val Val Glu Val
465               470               475               480

Glu His Glu Phe Tyr Val Lys Lys Gly Gly Ala Lys Lys Arg Pro Ala
                485               490               495

Pro Ser Asp Ala Asp Ile Ser Glu Pro Lys Arg Val Arg Glu Ser Val
                500               505               510

Ala Gln Pro Ser Thr Ser Asp Ala Glu Ala Ser Ile Asn Tyr Ala Asp
            515               520               525

Arg Tyr Gln Asn Lys Cys Ser Arg His Val Gly Met Asn Leu Met Leu
530               535               540

Phe Pro Cys Arg Gln Cys Glu Arg Met Asn Gln Asn Ser Asn Ile Cys
545               550               555               560

Phe Thr His Gly Gln Lys Asp Cys Leu Glu Cys Phe Pro Val Ser Glu
                565               570               575

Ser Gln Pro Val Ser Val Val Lys Lys Ala Tyr Gln Lys Leu Cys Tyr
                580               585               590

Ile His His Ile Met Gly Lys Val Pro Asp Ala Cys Thr Ala Cys Asp
            595               600               605

Leu Val Asn Val Asp Leu Asp Asp Cys Ile Phe Glu Gln
        610               615               620
```

<210> SEQ ID NO 23
<211> LENGTH: 960
<212> TYPE: DNA
<213> ORGANISM: Artificial Sequence
<220> FEATURE:
<223> OTHER INFORMATION: Synthetic polynucleotide

<400> SEQUENCE: 23

```
gcttcaggag cagttgtgcg aatagctgga gaacaccagg ctggatttaa acccagatcg      60
ctcttacatt tgctctttac ctgctgtgct cagcgttcac gtgccctcta gctgtagttt     120
tctgaagtca gcgcacagca aggcagtgtg cttagaggtt aacagaaggg aaaacaacaa     180
caacaaaaat ctaaatgaga atcctgactg tttcagctgg gggtaagggg gcggattat     240
tcatataatt gttataccag acggtcgcag gcttagtcca attgcagaga actcgcttcc     300
caggcttctg agagtcccgg aagtgcctaa acctgtctaa tcgacggggc ttgggtggcc     360
cgtcgctccc tggcttcttc cctttaccca gggcgggcag cgaagtggtg cctcctgcgt     420
cccccacacc ctccctcagc ccctccctc cggcccgtcc tgggcaggtg acctggagca     480
tccggcaggc tgccctggcc tcctgcgtca ggacaacgcc cacgagggc gttactgtgc     540
ggagatgcac cacgcaagag acacccttg taactctctt ctcctcccta gtgcgaggtt     600
aaaaccttca gccccacgtg ctgtttgcaa acctgcctgt acctgaggcc ctaaaaagcc     660
```

```
agagacctca ctcccgggga gccagcatgt ccactgcggt cctggaaaac ccaggcttgg      720
gcaggaaact ctctgacttt ggacaggtga gccacggcag cctgagctgc tcagttaggg      780
gaatttgggc ctccagagaa agagatctga agactgctgg tgcttcctgg tttcataagc      840
tcagtaagaa gtctgaattc gttggaagct gatgagaata tccaggaagt caacagacaa      900
atgtcctcaa caattgtttc taagtaggag aacatctgtc ctcggtggct ttcacaggaa      960
```

<210> SEQ ID NO 24
<211> LENGTH: 910
<212> TYPE: DNA
<213> ORGANISM: Artificial Sequence
<220> FEATURE:
<223> OTHER INFORMATION: Synthetic polynucleotide

<400> SEQUENCE: 24

```
ctgggatggg atgtggaatc cttctagatt tcttttgtaa tatttataaa gtgctctcag       60
caaggtatca aaatggcaaa attgtgagta actatcctcc tttcattttg ggaagaagat      120
gaggcatgaa gagaattcag acagaaactt actcagacca ggggaggcag aaactaagca      180
gagaggaaaa tgaccaagag ttagccctgg gcatggaatg tgaaagaacc ctaaacgtga      240
cttgaaaata atgcccaagg tatattccat tctccgggat ttgttggcat tttcttgagg      300
tgaagaattg cagaatacat tctttaatgt gacctacata tttacccatg ggaggaagtc      360
tgctcctgga ctcttgagat tcagtcataa agcccaggcc aggaaataa tgtaagtctg       420 caggcccctg tcatcagtag gattagggag aagagttctc agtagaaaac agggaggctg      480
gagagaaaag aatggttaat gttaacgtta atataactag aaagactgca gaacttagga      540
ctgattttta tttgaatcct taaaaaaaaa atttcttatg aaaatagtac atggctctta      600
ggagacagaa cttattgtac agaggaacag cgtgagagtc agagtgatcc cagaacaggt      660
cctggctcca tcctgcacat agttttggtg ctgctggcaa tacggtcccc acaactgtgg      720
gaaggggtta ggggcaggga tctcatcagg aaagcatagg ggtttaaagt tctttataga      780
gcacttagaa gattgagaat ccacaaatta tattaataac aaacaaagta gtgtcgtgtt      840
atatagtaaa tgtgaatttg cagacacatt tagggaaaag ttataattaa aaaaataggc      900
tgtatatata                                                             910
```

<210> SEQ ID NO 25
<211> LENGTH: 192
<212> TYPE: DNA
<213> ORGANISM: Artificial Sequence
<220> FEATURE:
<223> OTHER INFORMATION: Synthetic polynucleotide

<400> SEQUENCE: 25

```
ccctaaaatg ggcaaacatt gcaagcagca aacagcaaac acacagccct ccctgcctgc       60
tgaccttgga gctggggcag aggtcagaga cctctctggg cccatgccac ctccaacatc      120
cactcgaccc cttggaattt cggtggagag gagcagaggt tgtcctggcg tggtttaggt      180
agtgtgagag gg                                                          192
```

<210> SEQ ID NO 26
<211> LENGTH: 255
<212> TYPE: DNA
<213> ORGANISM: Artificial Sequence
<220> FEATURE:
<223> OTHER INFORMATION: Synthetic polynucleotide

<400> SEQUENCE: 26

```
aatgactcct tcggtaagt gcagtggaag ctgtacactg cccaggcaaa gcgtccgggc    60
agcgtaggcg ggcgactcag atcccagcca gtggacttag cccctgtttg ctcctccgat   120
aactggggtg accttggtta atattcacca gcagcctccc ccgttgcccc tctggatcca   180
ctgcttaaat acgacgagg acagggccct gtctcctcag cttcaggcac caccactgac   240
ctgggacagt gaatc                                                    255

<210> SEQ ID NO 27
<211> LENGTH: 448
<212> TYPE: DNA
<213> ORGANISM: Artificial Sequence
<220> FEATURE:
<223> OTHER INFORMATION: Synthetic polynucleotide

<400> SEQUENCE: 27
ccctaaaatg ggcaaacatt gcaagcagca acagcaaac acacagccct cctgcctgc     60 tgaccttgga gctggggcag aggtcagaga cctctctggg cccatgccac ctccaacatc   120
cactcgaccc cttggaattt cggtggagag gagcagaggt tgtcctggcg tggtttaggt   180
agtgtgagag gggaatgact cctttcggta agtgcagtgg aagctgtaca ctgcccaggc   240
aaagcgtccg ggcagcgtag gcgggcgact cagatcccag ccagtggact tagcccctgt   300
ttgctcctcc gataactggg gtgaccttgg ttaatattca ccagcagcct ccccgttgc    360 ccctctggat ccactgctta aatacggacg aggacagggc cctgtctcct cagcttcagg   420
caccaccact gacctgggac agtgaatc                                      448

<210> SEQ ID NO 28
<211> LENGTH: 1356
<212> TYPE: DNA
<213> ORGANISM: Artificial Sequence
<220> FEATURE:
<223> OTHER INFORMATION: Synthetic polynucleotide

<400> SEQUENCE: 28
atgtccaccg ctgtgctgga gaaccctggg ctggggagga aactgtcaga cttcgggcag    60
gagacttcat acattgagga taactgtaac cagaatggcg ccatctctct gatcttcagc   120
ctgaaggagg aagtgggcgc cctggcaaag gtgctgcgcc tgtttgagga gaacgacgtg   180
aatctgaccc acatcgagtc ccggccttct agactgaaga ggacgagta cgagttcttt   240 acccacctgg ataagcggtc cctgccagcc ctgacaaaca tcatcaagat cctgaggcac   300
gacatcggag caaccgtgca cgagctgtct cgggacaaga gaaggatac cgtgccctgg   360 ttccctcgga caatccagga gctggataga tttgccaacc agatcctgtc ttacggagca   420
gagctggacg cagatcaccc tggcttcaag gacccagtgt atcgggcccg gagaaagcag   480
tttgccgata tcgcctacaa ttataggcac ggacagccaa tccctcgcgt ggagtatatg   540
gaggaggaga agaagacctg ggcacagtg ttcaagaccc tgaagagcct gtacaagaca   600
cacgcctgct acgagtataa ccacatcttc ccctgctgg agaagtattg tggcttttcac   660 gaggacaata tccctcagct ggaggacgtg agccagttcc tgcagacctg cacaggcttt   720 aggctgagc cagtggcagg actgctgagc tcccgggact tcctgggagg actggccttc   780 agagtgttc actgcacccca gtacatcagg cacggctcca gccaatgta tacaccagag   840 cccgacatct gtcacgagct gctggcca gtgcccctgt ttagcgatag atccttcgcc   900
cagttttccc aggagatcgg actggcatct ctggagcac ctgacgagta catcgagaag   960
```

```
ctggccacca tctattggtt cacagtggag tttggcctgt gcaagcaggg cgatagcatc    1020
aaggcctacg gagcaggact gctgtctagc ttcggcgagc tgcagtattg tctgtccgag    1080
aagccaaagc tgctgcccct ggagctggag aagaccgcca tccagaacta caccgtgaca    1140
gagttccagc ccctgtacta tgtggccgag tcttttaacg atgccaagga gaaggtgaga    1200
aatttcgccg ccacaatccc taggcccttc agtgtgcgtt acgacccttg tacccagagg    1260
atcgaggtgc tggataatac acagcagctg aagatcctgg ctgactcaat caatagcgaa    1320
atcggaatcc tgtgctccgc cctgcagaaa atcaaa                              1356

<210> SEQ ID NO 29
<211> LENGTH: 93
<212> TYPE: DNA
<213> ORGANISM: Artificial Sequence
<220> FEATURE:
<223> OTHER INFORMATION: Synthetic polynucleotide

<400> SEQUENCE: 29
ctctaaggta aatataaaat ttttaagtgt ataatgtgtt aaactactga ttctaattgt      60
ttctctcttt tagattccaa cctttggaac tga                                  93

<210> SEQ ID NO 30
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 30
ctgacctctt ctcttcctcc cacagg                                          26

<210> SEQ ID NO 31
<211> LENGTH: 198
<212> TYPE: DNA
<213> ORGANISM: Artificial Sequence
<220> FEATURE:
<223> OTHER INFORMATION: Synthetic polynucleotide

<400> SEQUENCE: 31
gatccagaca tgataagata cattgatgag tttggacaaa ccacaactag aatgcagtga      60
aaaaaatgct ttatttgtga aatttgtgat gctattgctt tatttgtaac cattataagc     120
tgcaataaac aagttaacaa caacaattgc attcatttta tgtttcaggt tcaggggag      180 gtgtgggagg ttttttaa                                                   198

<210> SEQ ID NO 32
<211> LENGTH: 143
<212> TYPE: DNA
<213> ORGANISM: Artificial Sequence
<220> FEATURE:
<223> OTHER INFORMATION: Synthetic polynucleotide

<400> SEQUENCE: 32
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgcag agagggagtg gcc                                             143

<210> SEQ ID NO 33
<211> LENGTH: 452
<212> TYPE: PRT
<213> ORGANISM: Homo sapiens
```

```
<400> SEQUENCE: 33

Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
        35                  40                  45

Ala Lys Val Leu Arg Leu Phe Glu Glu Asn Asp Val Asn Leu Thr His
    50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
                100                 105                 110

Lys Lys Lys Asp Thr Val Pro Trp Phe Pro Arg Thr Ile Gln Glu Leu
            115                 120                 125

Asp Arg Phe Ala Asn Gln Ile Leu Ser Tyr Gly Ala Glu Leu Asp Ala
        130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
            260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
        355                 360                 365

Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
```

```
                    405                 410                 415
Tyr Thr Gln Arg Ile Glu Val Leu Asp Asn Thr Gln Gln Leu Lys Ile
                420                 425                 430

Leu Ala Asp Ser Ile Asn Ser Glu Ile Gly Ile Leu Cys Ser Ala Leu
        435                 440                 445

Gln Lys Ile Lys
    450

<210> SEQ ID NO 34
<211> LENGTH: 122
<212> TYPE: DNA
<213> ORGANISM: Artificial Sequence
<220> FEATURE:
<223> OTHER INFORMATION: Synthetic polynucleotide

<400> SEQUENCE: 34
aacttgttta ttgcagctta taatggttac aaataaagca atagcatcac aaatttcaca      60
aataaagcat ttttttcact gcattctagt tgtggtttgt ccaaactcat caatgtatct     120
ta                                                                    122

<210> SEQ ID NO 35
<211> LENGTH: 133
<212> TYPE: DNA
<213> ORGANISM: Artificial Sequence
<220> FEATURE:
<223> OTHER INFORMATION: Synthetic polynucleotide

<400> SEQUENCE: 35
tgctttattt gtgaaatttg tgatgctatt gctttatttg taaccattat aagctgcaat      60
aaacaagtta acaacaacaa ttgcattcat tttatgtttc aggttcaggg ggaggtgtgg     120 gaggttttt aaa                                                         133

<210> SEQ ID NO 36
<211> LENGTH: 1676
<212> TYPE: DNA
<213> ORGANISM: Artificial Sequence
<220> FEATURE:
<223> OTHER INFORMATION: Synthetic polynucleotide

<400> SEQUENCE: 36
ggcattgatt attgactagt tattaatagt aatcaattac ggggtcatta gttcatagcc      60
catatatgga gttccgcgtt acataactta cggtaaatgg cccgcctggc tgaccgccca     120 acgaccccg cccattgacg tcaataatga cgtatgttcc catagtaacg ccaatagga      180 ctttccattg acgtcaatgg gtggagtatt tacggtaaac tgcccacttg gcagtacatc     240
aagtgtatca tatgccaagt ccgccccta ttgacgtcaa tgacggtaaa tggcccgcct     300
ggcattatgc ccagtacatg acctacggg actttcctac ttggcagtac atctacgtat     360
tagtcatcgc tattaccatg gtcgaggtga gccccacgtt ctgcttcact ctccccatct     420 ccccccctc cccacccca attttgtatt tatttatttt ttaattattt tgtgcagcga     480
tgggggcggg ggggggggg gggcgcgcgc caggcgggc ggggcgggc gaggggcggg       540 gcggggcgag gcggagaggt gcggcggcag ccaatcagag cggcgcgctc cgaaagtttc     600 ctttatggc gaggcggcgg cggcggcggc cctataaaa gcgaagcgcg gcggggcgg       660 gagtcgctgc gcgctgcctt cgccccgtgc ccgctccgc cgccgcctcg cgccgcccgc     720
cccggctctg actgaccgcg ttactcccac aggtgagcgg gcgggacggc ccttctcctc     780
```

```
cgggctgtaa ttagcgcttg gtttaatgac ggcttgtttc ttttctgtgg ctgcgtgaaa    840
gccttgaggg gctccgggag ggccctttgt gcggggggag cggctcgggg ggtgcgtgcg    900
tgtgtgtgtg cgtggggagc gccgcgtgcg gctccgcgct gcccggcggc tgtgagcgct    960
gcgggcgcgg cgcggggctt tgtgcgctcc gcagtgtgcg cgaggggagc gcggccgggg   1020
gcggtgcccc gcggtgcggg gggggctgcg aggggaacaa aggctgcgtg cggggtgtgt   1080
gcgtgggggg gtgagcaggg ggtgtgggcg cgtcggtcgg gctgcaaccc ccctgcacc    1140 cccctccccg agttgctgag cacggcccgg cttcgggtgc ggggctccgt acggggcgtg   1200
gcgcggggct cgccgtgccg ggcgggggt ggcggcaggt gggggtgccg ggcggggcgg    1260
ggccgcctcg ggccggggag ggctcggggg aggggcgcgg cggcccccgg agcgccggcg   1320
gctgtcgagg cgcggcgagc cgcagccatt gccttttatg gtaatcgtgc gagagggcgc   1380
agggacttcc tttgtcccaa atctgtgcgg agccgaaatc tggaggcgc cgccgcaccc    1440 cctctagcgg gcgcggggcg aagcggtgcg gcgccggcag gaaggaaatg ggcggggagg   1500
gccttcgtgc gtcgccgcgc cgccgtcccc ttctccctct ccagcctcgg ggctgtccgc   1560 gggggggacgg ctgccttcgg gggggacggg gcagggcggg gttcggcttc tggcgtgtga  1620
ccggcggctc tagagcctct gctaaccatg ttcatgcctt cttcttttttc ctacag      1676
```

<210> SEQ ID NO 37
<211> LENGTH: 960
<212> TYPE: DNA
<213> ORGANISM: Artificial Sequence
<220> FEATURE:
<223> OTHER INFORMATION: Synthetic polynucleotide

<400> SEQUENCE: 37

```
gcttcaggag cagttgtgcg aatagctgga gaacaccagg ctggatttaa acccagatcg      60
ctcttacatt tgctctttac ctgctgtgct cagcgttcac gtgccctcta gctgtagttt    120
tctgaagtca gcgcacagca aggcagtgtg cttagaggtt aacagaaggg aaaacaacaa    180
caacaaaaat ctaaatgaga atcctgactg tttcagctgg gggtaagggg ggcggattat    240
tcatataatt gttataccag acggtcgcag gcttagtcca attgcagaga actcgcttcc    300
caggcttctg agagtcccgg aagtgcctaa acctgtctaa tcgacggggc ttgggtggcc    360
cgtcgctccc tggcttcttc cctttaccca gggcgggcag cgaagtgtg cctcctgcgt     420 cccccacacc ctccctcagc ccctcccctc cggcccgtcc tgggcaggtg acctggagca    480
tccggcaggc tgccctggcc tcctgcgtca ggacaacgcc cacgaggggc gttactgtgc    540
ggagatgcac cacgcaagag acacccttg taactctctt ctcctcccta gtgcgaggtt     600
aaaaccttca gccccacgtg ctgtttgcaa acctgcctgt acctgaggcc ctaaaaagcc    660
agagacctca ctcccgggga gccagcatgt ccactgcggt cctggaaaac ccaggcttgg    720
gcaggaaact ctctgacttt ggacaggtga gccacggcag cctgagctgc tcagttaggg    780
gaatttgggc ctccagagaa agagatccga agactgctgg tgcttcctgg tttcataagc    840
tcagtaagaa gtctgaattc gttggaagct gatgagaata ccaggaagt caacagacaa     900 atgtcctcaa caattgtttc taagtaggag aacatctgtc ctcggtggct ttcacaggaa    960
```

<210> SEQ ID NO 38
<211> LENGTH: 911
<212> TYPE: DNA
<213> ORGANISM: Artificial Sequence
<220> FEATURE:
<223> OTHER INFORMATION: Synthetic polynucleotide

<400> SEQUENCE: 38

```
ctgggatggg atgtggaatc cttctagatt tcttttgtaa tatttataaa gtgctctcag      60
caaggtatca aaatggcaaa attgtgagta actatcctcc tttcattttg ggaagaagat     120
gaggcatgaa gagaattcag acagaaactt actcagacca ggggaggcag aaactaagca     180
gagaggaaaa tgaccaagag ttagccctgg gcatggaatg tgaaagaacc ctaaacgtga     240
cttgaaaata atgcccaagg tatattccat tctccgggat tgttggcat tttcttgagg      300
tgaagaattg cagaatacat tctttaatgt gacctacata tttacccatg ggaggaagtc     360
tgctcctgga ctcttgagat tcagtcataa agcccaggcc agggaaataa tgtaagtctg     420
caggcccctg tcatcagtag gattagggag aagagttctc agtagaaaac agggaggctg     480
gagagaaaag aatggttaat gttaacgtta atataactag aaagactgca gaacttagga     540
ctgatttta tttgaatcct taaaaaaaaa aatttcttat gaaaatagta catggctctt       600
aggagacaga acttattgta cagaggaaca gcgtgagagt cagagtgatc ccagaacagg     660
tcctggctcc atcctgcaca tagttttggt gctgctggca atacggtccc cacaactgtg     720
ggaagggggtt aggggcaggg atctcatcag gaaagcatag gggtttaaag ttctttatag    780
agcacttaga agattgagaa tccacaaatt atattaataa caaacaaagt agtgtcgtgt     840
tatatagtaa atgtgaattt gcagacacat ttagggaaaa gttataatta aaaaaatagg    900
ctgtatatat a                                                          911
```

<210> SEQ ID NO 39
<211> LENGTH: 1168
<212> TYPE: DNA
<213> ORGANISM: Artificial Sequence
<220> FEATURE:
<223> OTHER INFORMATION: Synthetic polynucleotide

<400> SEQUENCE: 39

```
cgtgaggctc cggtgcccgt cagtgggcag agcgcacatc gcccacagtc cccgagaagt      60
tgggggggagg ggtcggcaat tgaaccggtg cctagagaag gtggcgcggg gtaaactggg    120
aaagtgatgt cgtgtactgg ctccgccttt ttcccgaggg tggggagaa ccgtatataa      180
gtgcagtagt cgccgtgaac gttcttttc gcaacgggtt tgccgccaga acacaggtaa     240
gtgccgtgtg tggttcccgc gggcctggcc tctttacggg ttatgccct tgcgtgcctt      300
gaattacttc cacctggctc cagtacgtga ttcttgatcc cgagctggag ccaggggcgg    360
gccttgcgct ttaggagccc cttcgcctcg tgcttgagtt gaggcctggc ctgggcgctg    420
gggccgccgc gtgcgaatct ggtggcacct tcgcgcctgt ctcgctgctt tcgataagtc    480
tctagccatt taaaattttt gatgacctgc tgcgacgctt tttttctggc aagatagtct    540
tgtaaatgcg ggccaggatc tgcacactgg tatttcggtt tttggggccg cgggcggcga    600
cggggcccgt gcgtcccagc gcacatgttc ggcgaggcgg ggcctgcgag gcggccacc    660
gagaatcgga cgggggtagt ctcaagctgg ccggcctgct ctggtgcctg gcctcgcgcc    720
gccgtgtatc gccccgccct gggcggcaag gctggcccgg tcggcaccag ttgcgtgagc    780
ggaaagatgg ccgcttcccg gccctgctcc aggggggctca aaatgaagga gcgcggcgctc   840
gggagagcgg gcgggtgagt cacccacaca aaggaaaggg gcctttccgt cctcagccgt    900
cgcttcatgt gactccacgg agtaccgggc gccgtccagg cacctcgatt agttctggag    960
cttttggagt acgtcgtctt taggttgggg ggagggggttt tatgcgatgg agtttcccca   1020
```

| | |
|---|---|
| cactgagtgg gtggagactg aagttaggcc agcttggcac ttgatgtaat tctccttgga | 1080 |
| atttgcccttt tttgagtttg gatcttggtt cattctcaag cctcagacag tggttcaaag | 1140 |
| tttttttctt ccatttcagg tgtcgtga | 1168 |

```
<210> SEQ ID NO 40
<211> LENGTH: 72
<212> TYPE: DNA
<213> ORGANISM: Artificial Sequence
<220> FEATURE:
<223> OTHER INFORMATION: Synthetic polynucleotide

<400> SEQUENCE: 40
```

| | |
|---|---|
| agatctggca gcggagaggg cagaggaagt cttctaacat gcggtgacgt ggaggagaat | 60 |
| cccggccta gg | 72 |

```
<210> SEQ ID NO 41
<211> LENGTH: 95
<212> TYPE: DNA
<213> ORGANISM: Artificial Sequence
<220> FEATURE:
<223> OTHER INFORMATION: Synthetic polynucleotide

<400> SEQUENCE: 41
```

| | |
|---|---|
| cctctgctaa ccatgttcat gccttcttct ttttcctaca gctcctgggc aacgtgctgg | 60 |
| ttattgtgct gtctcatcat tttggcaaag aattc | 95 |

```
<210> SEQ ID NO 42
<211> LENGTH: 1873
<212> TYPE: DNA
<213> ORGANISM: Artificial Sequence
<220> FEATURE:
<223> OTHER INFORMATION: Synthetic polynucleotide

<400> SEQUENCE: 42
```

| | |
|---|---|
| gatcttcaat attggccatt agccatatta ttcattggtt atatagcata atcaatatt | 60 |
| ggctattggc cattgcatac gttgtatcta tcataata tgtacattta tattggctca | 120 |
| tgtccaatat gaccgccatg ttggcattga ttattgacta gttattaata gtaatcaatt | 180 |
| acggggtcat tagttcatag cccatatatg gagttccgcg ttacataact acggtaaat | 240 |
| ggcccgcctg gctgaccgcc caacgacccc cgcccattga cgtcaataat gacgtatgtt | 300 |
| cccatagtaa cgccaatagg gactttccat tgacgtcaat gggtggagta tttacggtaa | 360 |
| actgcccact tggcagtaca tcaagtgtat catatgccaa gtccgcccc tattgacgtc | 420 |
| aatgacggta aatggcccgc ctggcattat gcccagtaca tgaccttacg gactttcct | 480 |
| acttggcagt acatctacgt attagtcatc gctattacca tggtcgaggt gagccccacg | 540 |
| ttctgcttca ctctccccat ctccccccc tccccacccc caattttgta tttatttatt | 600 |
| ttttaattat tttgtgcagc gatgggggcg gggggggggg ggggcgcgc gccaggcggg | 660 |
| gcgggcggg gcgaggggcg gggcggggcg aggcggagag gtgcggcggc agccaatcag | 720 |
| agcggcgcgc tccgaaagtt tccttttatg gcgaggcggc ggcggcggcg ccctataaa | 780 |
| aagcgaagcg cgcggcgggc gggagtcgct gcgacgctgc cttcgccccg tgccccgctc | 840 |
| cgccgccgcc tcgcgccgcc cgccccggct ctgactgacc gcgttactcc cacaggtgag | 900 |
| cgggcgggac ggcccttctc ctccgggctg taattagcgc ttggtttaat gacggcttgt | 960 |
| ttcttttctg tggctgcgtg aaagccttga ggggctccgg gagggccctt tgtgcggggg | 1020 |
| ggagcggctc gggggtgcg tgcgtgtgtg tgtgcgtggg gagcgccgcg tgcggcccgc | 1080 |

```
gctgcccggc ggctgtgagc gctgcgggcg cggcgcgggg ctttgtgcgc tccgcagtgt    1140
gcgcgagggg agcgcggccg ggggcggtgc cccgcggtgc ggggggggct gcaggggaa    1200 caaaggctgc gtgcggggtg tgtgcgtggg ggggtgagca ggggggtgtgg gcgcggcggt    1260 cgggctgtaa ccccccctg cacccccctc cccgagttgc tgagcacggc ccggcttcgg    1320
gtgcggggct ccgtacgggg cgtggcgcgg ggctcgccgt gccgggcggg gggtggcggc    1380 aggtggggggt gccgggcggg gcggggccgc ctcgggccgg ggagggctcg ggggaggggc    1440
gcggcggccc ccggagcgcc ggcggctgtc gaggcgcggc gagccgcagc cattgccttt    1500
tatggtaatc gtgcgagagg gcgcaggac ttcctttgtc ccaaatctgt gcggagccga    1560
aatctgggag gcgccgccgc accccctcta gcgggcgcgg ggcgaagcgg tgcggcgccg    1620
gcaggaagga aatgggcggg gagggccttc gtgcgtcgcc gcgccgccgt ccccttctcc    1680
ctctccagcc tcgggctgt ccgcgggggg acggctgcct tcgggggga cggggcaggg    1740 cggggttcgg cttctggcgt gtgaccggcg gctctagagc ctctgctaac catgttcatg    1800
ccttcttctt tttcctacag ctcctgggca acgtgctggt tattgtgctg tctcatcatt    1860
ttggcaaaga att                                                     1873

<210> SEQ ID NO 43
<211> LENGTH: 4046
<212> TYPE: DNA
<213> ORGANISM: Artificial Sequence
<220> FEATURE:
<223> OTHER INFORMATION: Synthetic polynucleotide

<400> SEQUENCE: 43
gcttcaggag cagttgtgcg aatagctgga gaacaccagg ctggatttaa acccagatcg      60
ctcttacatt tgctctttac ctgctgtgct cagcgttcac gtgccctcta gctgtagttt     120
tctgaagtca gcgcacagca aggcagtgtg cttagaggtt aacagaaggg aaaacaacaa     180
caacaaaaat ctaaatgaga atcctgactg tttcagctgg gggtaagggg ggcggattat     240
tcatataatt gttataccag acggtcgcag gcttagtcca attgcagaga actcgcttcc     300
caggcttctg agagtcccgg aagtgcctaa acctgtctaa tcgacggggc ttgggtggcc     360
cgtcgctccc tggcttcttc cctttaccca gggcgggcag cgaagtggtg cctcctgcgt     420
cccccacacc ctccctcagc ccctccctc cggcccgtcc tgggcaggtg acctggagca     480
tccggcaggc tgccctggcc tcctgcgtca ggacaacgcc cacgaggggc gttactgtgc     540
ggagatgcac cacgcaagag acaccctttg taactctctt ctcctcccta gtgcgaggtt     600
aaaaccttca gccccacgtg ctgtttgcaa acctgcctgt acctgaggcc ctaaaaagcc     660
agagacctca ctcccgggga gccagcatgt ccactgcggt cctggaaaac ccaggcttgg     720
gcaggaaact ctctgacttt ggacaggtga gccacggcag cctgagctgc tcagttaggg     780
gaatttgggc ctcagagaa agagatctga agactgctgg tgcttcctgg tttcataagc     840
tcagtaagaa gtctgaattc gttggaagct gatgagaata tccaggaagt caacagacaa     900
atgtcctcaa caattgtttc taagtaggag aacatctgtc ctcggtggct ttcacaggaa     960
ccctaaaatg gcaaacatt gcaagcagca acagcaaac acacagccct ccctgcctgc    1020
tgaccttgga gctggggcag aggtcagaga cctctctggg cccatgccac tccaacatc    1080 cactcgaccc cttggaattt cggtggagag gagcagaggt tgtcctggcg tggtttaggt    1140
agtgtgagag gggaatgact cctttcggta agtgcagtgg aagctgtaca ctgcccaggc    1200
```

```
aaagcgtccg ggcagcgtag gcgggcgact cagatcccag ccagtggact tagcccctgt    1260
ttgctcctcc gataactggg gtgacctTgg ttaatattca ccagcagcct cccccgttgc    1320
ccctctggat ccactgctta aatacggacg aggacagggc cctgtctcct cagcttcagg    1380
caccaccact gacctgggac agtgaatcct ctaaggtaaa tataaaattt ttaagtgtat    1440
aatgtgttaa actactgatt ctaattgttt ctctctttta gattccaacc tttggaactg    1500
accgccacca tgtccaccgc tgtgctggag aaccctgggc tggggaggaa actgtcagac    1560
ttcgggcagg agacttcata cattgaggat aactgtaacc agaatggcgc catctctctg    1620
atcttcagcc tgaaggagga agtgggcgcc ctggcaaagg tgctgcgcct gtttgaggag    1680
aacgacgtga atctgaccca catcgagtcc cggccttcta gactgaagaa ggacgagtac    1740
gagttcttta cccacctgga taagcggtcc ctgccagccc tgacaaacat catcaagatc    1800
ctgaggcacg acatcggagc aaccgtgcac gagctgtctc gggacaagaa gaaggatacc    1860
gtgccctggt tccctcggac aatccaggag ctggatagat tgccaaccca gatcctgtct    1920
tacggagcag agctggacgc agatcaccct ggcttcaagg acccagtgta tcgggcccgg    1980
agaaagcagt tgccgatat cgcctacaat tataggcacg acagccaat ccctcgcgtg     2040 gagtatatgg aggaggagaa gaagacctgg ggcacagtgt tcaagaccct gaagagcctg    2100
tacaagacac acgcctgcta cgagtataac cacatcttcc ccctgctgga gaagtattgt    2160
ggctttcacg aggacaatat ccctcagctg gaggacgtga ccagttcct gcagacctgc     2220 acaggcttta ggctgaggcc agtggcagga ctgctgagct cccgggactt cctgggagga    2280
ctggccttca gagtgtttca ctgcacccag tacatcaggc acggctccaa gccaatgtat    2340
acaccagagc ccgacatctg tcacgagctg ctgggccacg tgccctgtt tagcgataga    2400 tccttcgccc agttttccca ggagatcgga ctggcatctc tgggagcacc tgacgagtac    2460
atcgagaagc tggccaccat ctattggttc acagtggagt ttggcctgtg caagcagggc    2520
gatagcatca aggcctacgg agcaggactg ctgtctagct cggcgagct gcagtattgt    2580 ctgtccgaga agccaaagct gctgcccctg gagctggaga agaccgccat ccagaactac    2640
accgtgacag agttccagcc cctgtactat gtggccgagt cttttaacga tgccaaggag    2700
aaggtgagaa atttcgccgc cacaatccct aggcccttca gtgtgcgtta cgacccttat    2760
acccagagga tcgaggtgct ggataataca cagcagctga agatcctggc tgactcaatc    2820
aatagcgaaa tcggaatcct gtgctccgcc ctgcagaaaa tcaaatgaga attcaaggcc    2880
tctcgagcct ctagaactat agtgagtcgt attacgtaga tccagacatg ataagataca    2940
ttgatgagtt tggacaaacc acaactagaa tgcagtgaaa aaaatgcttt atttgtgaaa    3000
tttgtgatgc tattgcttta tttgtaacca ttataagctg caataaacaa gttaacaaca    3060
acaattgcat tcattttatg tttcaggttc aggggggaggt gtgggaggtt ttttaagctt    3120
tacgtacgat cgtcgactgg gatgggatgt ggaatccttc tagatttctt ttgtaatatt    3180
tataaagtgc tctcagcaag gtatcaaaat ggcaaaattg tgagtaacta tcctcctttc    3240
attttgggaa gaagatgagg catgaagaga attcagacag aaacttactc agaccagggg    3300
aggcagaaac taagcagaga ggaaaatgac caagagttag ccctgggcat ggaatgtgaa    3360
agaaccctaa acgtgacttg gaaataatgc ccaaggtata ttccattctc cgggatttgt    3420
tggcattttc ttgaggtgaa gaattgcaga atacattctt taatgtgacc tacatattta    3480
cccatgggag gaagtctgct cctggactct tgagattcag tcataaagcc caggccaggg    3540
aaataatgta agtctgcagg cccctgtcat cagtaggatt agggagaaga gttctcagta    3600
```

```
gaaaacaggg aggctggaga gaaaagaatg gttaatgtta acgttaatat aactagaaag    3660
actgcagaac ttaggactga tttttatttg aatccttaaa aaaaaaattt cttatgaaaa    3720
tagtacatgg ctcttaggag acagaactta ttgtacagag gaacagcgtg agagtcagag    3780
tgatcccaga acaggtcctg gctccatcct gcacatagtt ttggtgctgc tggcaatacg    3840
gtccccacaa ctgtgggaag gggttagggg cagggatctc atcaggaaag catagggggtt   3900 taaagttctt tatagagcac ttagaagatt gagaatccac aaattatatt aataacaaac    3960
aaagtagtgt cgtgttatat agtaaatgtg aatttgcaga cacatttagg gaaaagttat    4020
aattaaaaaa ataggctgta tatata                                        4046

<210> SEQ ID NO 44
<211> LENGTH: 913
<212> TYPE: DNA
<213> ORGANISM: Artificial Sequence
<220> FEATURE:
<223> OTHER INFORMATION: Synthetic polynucleotide

<400> SEQUENCE: 44
ggcatcctaa aaatattca gtggaaacgt aaaaacatta aagactgatt aaacatcgca      60
gcatgacaca gatttagcaa ctgagcataa ataatttgac tcggatactg ctccaaaatc    120
cgaagaggac caatttcttc caggaggaca actacctcgt cctctgcaga cccctctcct    180
cggcagctga aggagtgtgg ccaatctgcc tccacctccc cgcggacccc ctactctcag    240
gacctcctgc agcaccccaa actggaagtg gccgctgcag acccaaggac gaggggcacg    300
cgggagccgg cagccctagt ggagcggttg gagatgttga ggtgggaggg tcacccaggt    360
ggggtgaggc tggggtaggt agcggagtga acggcttccg aagctctggg ccgcccccag    420
gttggactaa gcaggcgctc tgtcttcgcc cccgcccagg gtgggcgtct cctgaggact    480
ccccgccaca cctgacccga gaccgcgcgc cagcctaga acgcttcccc gacccagcgt    540
agggccgccg cgactggcgg gcgagggtcg gcgggaggcc tggcgaaccc ggggggcggga    600 ccaggcgggc aaggcccggc tgccgcagcg ccgctctgcg cgaggcggct ccgccgcggc    660
ggagggatac ggcgcaccat atatatatcg cggggcgcag actcgcgctc cggcagtggt    720
gctgggagtg tcgtggacgc cgtgccgtta ctcgtagtca ggcggcggcg caggcggcgg    780
cggcggcata gcgcacagcg cgccttagca gcagcagcag cagcagcggc atcgaggta     840 cccccgccgt cgcagccccc gcgctggtgc agccaccctc gctccctctg ctcttcctcc    900
cttcgctcgc acc                                                       913

<210> SEQ ID NO 45
<211> LENGTH: 4452
<212> TYPE: DNA
<213> ORGANISM: Artificial Sequence
<220> FEATURE:
<223> OTHER INFORMATION: Synthetic polynucleotide

<400> SEQUENCE: 45
ttggccactc cctctctgcg cgctcgctcg ctcactgagg ccgggcgacc aaaggtcgcc     60
cgacgcccgg gctttgcccg gcggccctca gtgagcgagc gagcgcgcag agaggagtg    120 gccaactcca tcactagggg ttcctggagg ggtggagtcg tgacgtgaat tacgtcatag    180
ggttagggag gtcctgcata tgcggccgct tcaggagcag ttgtgcgaat agctggagaa    240
caccaggctg gatttaaacc cagatcgctc ttacatttgc tctttacctg ctgtgctcag    300
```

```
cgttcacgtg ccctctagct gtagttttct gaagtcagcg cacagcaagg cagtgtgctt    360
agaggttaac agaagggaaa acaacaacaa caaaaatcta aatgagaatc ctgactgttt    420
cagctggggg taagggggc ggattattca tataattgtt ataccagacg gtcgcaggct    480
tagtccaatt gcagagaact cgcttcccag gcttctgaga gtcccggaag tgcctaaacc    540
tgtctaatcg acggggcttg ggtggcccgt cgctccctgg cttcttccct ttacccaggg    600
cgggcagcga agtggtgcct cctgcgtccc ccacaccctc cctcagcccc tcccctccgg    660
cccgtcctgg gcaggtgacc tggagcatcc ggcaggctgc cctggcctcc tgcgtcagga    720
caacgcccac gaggggcgtt actgtgcgga gatgcaccac gcaagagaca ccctttgtaa    780
ctctcttctc ctcccctagtg cgaggttaaa accttcagcc ccacgtgctg tttgcaaacc    840
tgcctgtacc tgaggcccta aaagccaga gacctcactc ccggggagcc agcatgtcca    900
ctgcggtcct ggaaaaccca ggcttgggca ggaaactctc tgactttgga caggtgagcc    960
acggcagcct gagctgctca gttaggggaa tttgggcctc cagagaaaga gatctgaaga   1020
ctgctggtgc ttcctggttt cataagctca gtaagaagtc tgaattcgtt ggaagctgat   1080
gagaatatcc aggaagtcaa cagacaaatg tcctcaacaa ttgtttctaa gtaggagaac   1140
atctgtcctc ggtggctttc acaggaaccc taaaatgggc aaacattgca agcagcaaac   1200
agcaaacaca cagccctccc tgcctgctga ccttggagct ggggcagagg tcagagacct   1260
ctctgggccc atgccacctc caacatccac tcgaccccct tggaatttcgg tggagaggag   1320
cagaggttgt cctggcgtgg tttaggtagt gtgagagggg aatgactcct ttcggtaagt   1380
gcagtggaag ctgtacactg cccaggcaaa gcgtccgggc agcgtaggcg ggcgactcag   1440
atcccagcca gtggacttag cccctgtttg ctcctccgat aactggggtg accttggtta   1500
atattcacca gcagcctccc ccgttgcccc tctggatcca ctgcttaaat acggacgagg   1560
acagggccct gtctcctcag cttcaggcac caccactgac ctgggacagt gaatcctcta   1620
aggtaaatat aaaattttta agtgtataat gtgttaaact actgattcta attgtttctc   1680
tcttttagat tccaaccttt ggaactgacc gccaccatgt ccaccgctgt gctggagaac   1740
cctgggctgg ggaggaaact gtcagacttc gggcaggaga cttcatacat tgaggataac   1800
tgtaaccaga atggcgccat ctctctgatc ttcagcctga aggaggaagt gggcgccctg   1860
gcaaaggtgc tgcgcctgtt tgaggagaac gacgtgaatc tgacccacat cgagtcccgg   1920
ccttctagac tgaagaagga cgagtacgag ttctttaccc acctggataa gcggtccctg   1980
ccagccctga caaacatcat caagatcctg aggcacgaca tcggagcaac cgtgcacgag   2040
ctgtctcggg acaagaagaa ggataccgtg ccctggttcc ctcggacaat ccaggagctg   2100
gatagatttg ccaaccagat cctgtcttac ggagcagagc tggacgcaga tcaccctggc   2160
ttcaaggacc cagtgtatcg ggcccggaga aagcagtttg ccgatatcgc ctacaattat   2220
aggcacggac agccaatccc tcgcgtggag tatatggagg aggagaagaa gacctggggc   2280
acagtgttca gaccctgaa gagcctgtac aagacacacg cctgctacga gtataaccac   2340
atcttccccc tgctggagaa gtattgtggc tttcacgagg acaatatccc tcagctggag   2400
gacgtgagcc agttcctgca gacctgcaca ggctttaggc tgaggccagt ggcaggactg   2460
ctgagctccc gggacttcct gggaggactg gccttcagag tgtttcactg cacccagtac   2520
atcaggcacg gctccaagcc aatgtataca ccagagcccg acatctgtca cgagctgctg   2580
ggccacgtgc ccctgtttag cgatagatcc ttcgcccagt tttcccagga gatcggactg   2640
gcatctctgg gagcacctga cgagtacatc gagaagctgg ccaccatcta ttggttcaca   2700
```

```
gtggagtttg gcctgtgcaa gcagggcgat agcatcaagg cctacggagc aggactgctg   2760
tctagcttcg gcgagctgca gtattgtctg tccgagaagc caaagctgct gcccctggag   2820
ctggagaaga ccgccatcca gaactacacc gtgacagagt tccagcccct gtactatgtg   2880
gccgagtctt ttaacgatgc caaggagaag gtgagaaatt tcgccgccac aatccctagg   2940
cccttcagtg tgcgttacga cccttatacc cagaggatcg aggtgctgga taatacacag   3000
cagctgaaga tcctggctga ctcaatcaat agcgaaatcg aatcctgtg  ctccgccctg   3060 cagaaaatca aatgagaatt caaggcctct cgagcctcta gaactatagt gagtcgtatt   3120
acgtagatcc agacatgata agatacattg atgagtttgg acaaaccaca actagaatgc   3180
agtgaaaaaa atgctttatt tgtgaaattt gtgatgctat tgctttattt gtaaccatta   3240
taagctgcaa taaacaagtt aacaacaaca attgcattca ttttatgttt caggttcagg   3300
gggaggtgtg ggaggttttt taagctttac gtacgatcgt cgactgggat gggatgtgga   3360
atccttctag atttcttttg taatatttat aaagtgctct cagcaaggta tcaaaatggc   3420
aaaattgtga gtaactatcc tcctttcatt ttgggaagaa gatgaggcat gaagagaatt   3480
cagacagaaa cttactcaga ccaggggagg cagaaactaa gcagagga aaatgaccaa   3540 gagttagccc tgggcatgga atgtgaaaga accctaaacg tgacttggaa ataatgccca   3600
aggtatattc cattctccgg gatttgttgg cattttcttg aggtgaagaa ttgcagaata   3660
cattctttaa tgtgacctac atatttaccc atgggaggaa gtctgctcct ggactcttga   3720
gattcagtca taaagcccag gccagggaaa taatgtaagt ctgcaggccc ctgtcatcag   3780
taggattagg gagaagagtt ctcagtagaa acagggagg ctggagagaa aagaatggtt   3840
aatgttaacg ttaatataac tagaaagact gcagaactta ggactgattt ttatttgaat   3900
ccttaaaaaa aaaatttctt atgaaaatag tacatggctc ttaggagaca gaacttattg   3960
tacagaggaa cagcgtgaga gtcagagtga tcccagaaca ggtcctggct ccatcctgca   4020
catagttttg gtgctgctgg caatacggtc cccacaactg tgggaagggg ttaggggcag   4080
ggatctcatc aggaaagcat aggggttaa  agttctttat agagcactta gaagattgag   4140
aatccacaaa ttatattaat aacaaacaaa gtagtgtcgt gttatatagt aaatgtgaat   4200
ttgcagacac atttagggaa aagttataat taaaaaaata ggctgtatat atacctgcag   4260
gtctagatac gtagataagt agcatggcgg gttaatcatt aactcaagg  aacccctagt   4320 gatggagttg gccactccct ctctgcgcgc tcgctcgctc actgaggccg gcgaccaaa    4380 ggtcgcccga cgcccgggct tgcccgggc  ggcctcagtg agcgagcgag cgcgcagaga   4440
gggagtggcc aa                                                       4452
```

<210> SEQ ID NO 46
<211> LENGTH: 380
<212> TYPE: DNA
<213> ORGANISM: Artificial Sequence
<220> FEATURE:
<223> OTHER INFORMATION: Synthetic polynucleotide

<400> SEQUENCE: 46

```
ggcattgatt attgactagt tattaatagt aatcaattac ggggtcatta gttcatagcc     60
catatatgga gttccgcgtt acataactta cggtaaatgg cccgcctggc tgaccgccca    120 acgaccccg  cccattgacg tcaataatga cgtatgttcc catagtaacg ccaataggga    180
ctttccattg acgtcaatgg gtggagtatt tacggtaaac tgcccacttg gcagtacatc    240
```

```
aagtgtatca tatgccaagt ccgcccccta ttgacgtcaa tgacggtaaa tggcccgcct    300
ggcattatgc ccagtacatg accttacggg actttcctac ttggcagtac atctacgtat    360
tagtcatcgc tattaccatg                                                 380
```

<210> SEQ ID NO 47
<211> LENGTH: 1246
<212> TYPE: DNA
<213> ORGANISM: Artificial Sequence
<220> FEATURE:
<223> OTHER INFORMATION: Synthetic polynucleotide

<400> SEQUENCE: 47

```
tcgaggtgag ccccacgttc tgcttcactc tccccatctc ccccccctcc ccacccccaa     60
ttttgtattt atttattttt taattatttt gtgcagcgat gggggcgggg ggggggggg    120 ggcgcgcgcc aggcggggcg gggcggggcg agggcgggg cggggcgagg cggagaggtg    180
cggcggcagc caatcagagc ggcgcgctcc gaaagtttcc ttttatggcg aggcggcggc    240
ggcggcggcc ctataaaaag cgaagcgcgc ggcgggcggg agtcgctgcg cgctgccttc    300
gccccgtgcc ccgctccgcc gccgcctcgc gccgcccgcc ccggctctga ctgaccgcgt    360
tactcccaca ggtgagcggg cgggacggcc cttctcctcc gggctgtaat tagcgcttgg    420
tttaatgacg gcttgtttct tttctgtggc tgcgtgaaag ccttgagggg ctccgggagg    480
gccctttgtg cggggggagc ggctcggggg gtgcgtgcgt gtgtgtgtgc gtggggagcg    540
ccgcgtgcgg ctccgcgctg cccggcggct gtgagcgctg cgggcgcggc gcggggcttt    600
gtgcgctccg cagtgtgcgc gaggggagcg cggccggggg cggtgccccg cggtgcgggg    660
ggggctgcga ggggaacaaa ggctgcgtgc ggggtgtgtg cgtgggggg tgagcagggg    720 gtgtgggcgc gtcggtcggg ctgcaaccc ccctgcaccc ccctccccga gttgctgagc    780
acggcccggc ttcgggtgcg gggctccgta cggggcgtgg cgcggggctc gccgtgccgg    840 gcgggggtg gcggcaggtg gggtgccgg cggggcggg gccgcctcgg gccggggagg    900
gctcggggga ggggcgcggc ggccccgga gcgccggcgg ctgtcgaggc gcggcgagcc    960
gcagccattg cctttatgg taatcgtgcg agagggcgca gggacttcct ttgtcccaaa   1020
tctgtgcgga gccgaaatct ggggaggcgcc gccgcacccc ctctagcggg cgcggggcga   1080
agcggtgcgg cgccggcagg aaggaaatgg gcggggaggg ccttcgtgcg tcgccgcgcc   1140
gccgtcccct tctccctctc cagcctcggg gctgtccgcg gggggacggc tgccttcggg   1200
ggggacgggg cagggcgggg ttcggcttct ggcgtgtgac cggcgg              1246
```

<210> SEQ ID NO 48
<211> LENGTH: 1061
<212> TYPE: DNA
<213> ORGANISM: Artificial Sequence
<220> FEATURE:
<223> OTHER INFORMATION: Synthetic polynucleotide

<400> SEQUENCE: 48

```
tagggaggtc ctgcacgtta cataacttac ggtaaatggc ccgcctggct gaccgcccaa     60 cgaccccgc ccattgacgt caataatgac gtatgttccc atagtaacgc caatagggac    120
tttccattga cgtcaatggg tggagtattt acggtaaact gcccacttgg cagtacatca    180
agtgtatcat atgccaagta cgccccctat tgacgtcaat gacggtaaat ggcccgcctg    240
gcattatgcc cagtacatga ccttatggga ctttcctact tggcagtaca tctacgtatt    300
agtcatcgct attaccatgg tcgaggtgag ccccacgttc tgcttcactc tccccatctc    360
```

```
cccccectee ccacccccaa ttttgtattt atttattttt taattatttt gtgcagcgat      420 ggggcgggg ggggggggg gcgcgcgcca ggcggggcgg ggcggggcga ggggcggggc      480
ggggcgaggc ggagaggtgc ggcggcagcc aatcagagcg gcgcgctccg aaagtttcct      540
tttatggcga ggcggcggcg gcggcggccc tataaaagc gaagcgcgcg gcgggcggga      600
gtcgctgcgc gctgccttcg ccccgtgccc cgctccgccg ccgcctcgcg ccgcccgccc      660
cggctctgac tgaccgcgtt actaaaacag gtaagtccgg cctccgcgcc gggttttggc      720
gcctcccgcg ggcgccccce tcctcacggc gagcgctgcc acgtcagacg aagggcgcag      780
cgagcgtcct gatccttccg cccggacgct caggacagcg gcccgctgct cataagactc      840
ggccttagaa ccccagtatc agcagaagga cattttagga cgggacttgg gtgactctag      900
ggcactggtt ttctttccag agagcggaac aggcgaggaa aagtagtccc ttctcggcga      960
ttctgcggag ggatctccgt ggggcggtga acgccgatga tgcctctact aaccatgttc     1020
atgttttctt tttttttcta caggtcctgg gtgacgaaca g                        1061

<210> SEQ ID NO 49
<211> LENGTH: 953
<212> TYPE: DNA
<213> ORGANISM: Artificial Sequence
<220> FEATURE:
<223> OTHER INFORMATION: Synthetic polynucleotide

<400> SEQUENCE: 49
aattcggtac cctagttatt aatagtaatc aattacgggg tcattagttc atagcccata       60
tatggagttc cgcgttacat aacttacggt aaatggcccg cctggctgac cgcccaacga      120
cccccgccca ttgacgtcaa taatgacgta tgttcccata gtaacgccaa tagggacttt      180
ccattgacgt caatgggtgg actatttacg gtaaactgcc cacttggcag tacatcaagt      240
gtatcatatg ccaagtacgc cccctattga cgtcaatgac ggtaaatggc ccgcctggca      300
ttatgcccag tacatgacct tatgggactt tcctacttgg cagtacatct acgtattagt      360
catcgctatt accatggtcg aggtgagccc cacgttctgc ttcactctcc ccatctcccc      420
cccctcccca ccccaattt tgtatttatt tattttttaa ttattttgtg cagcgatggg      480
ggcggggggg ggggggggc gcgcgccagg cggggcgggg cggggcgagg ggcggggcgg      540
ggcgaggcgg agaggtgcgg cggcagccaa tcagagcggc gcgctccgaa agttccttt      600 tatggcgagg cggcggcggc ggcggcccta taaaagcga agcgcgcggc gggcgggagt      660
cgctgcgacg ctgccttcgc cccgtgcccc gctccgccgc cgcctcgcgc cgcccgcccc      720
ggctctgact gaccgcgtta ctcccacagg tgagcgggcg ggacggccct tctcctccgg      780
gctgtaatta gcgcttggtt taatgacggc ttgtttcttt tctgtggctg cgtgaaagcc      840 ttgagggct ccgggagcta gagcctctgc taaccatgtt catgccttct tctttttcct      900
acagctcctg gcaacgtgc tggttattgt gctgtctcat catttggca aag               953

<210> SEQ ID NO 50
<211> LENGTH: 541
<212> TYPE: DNA
<213> ORGANISM: Artificial Sequence
<220> FEATURE:
<223> OTHER INFORMATION: Synthetic polynucleotide

<400> SEQUENCE: 50
ccctaaaatg ggcaaacatt gcaagcagca aacagcaaac acacagccct ccctgcctgc       60
```

| | |
|---|---|
| tgaccttgga gctggggcag aggtcagaga cctctctggg cccatgccac ctccaacatc | 120 |
| cactcgaccc cttggaattt cggtggagag gagcagaggt tgtcctggcg tggtttaggt | 180 |
| agtgtgagag gggaatgact cctttcggta agtgcagtgg aagctgtaca ctgcccaggc | 240 |
| aaagcgtccg ggcagcgtag gcgggcgact cagatcccag ccagtggact tagcccctgt | 300 |
| ttgctcctcc gataactggg gtgaccttgg ttaatattca ccagcagcct ccccgttgc | 360 |
| ccctctggat ccactgctta aatacggacg aggacagggc cctgtctcct cagcttcagg | 420 |
| caccaccact gacctgggac agtgaatcct ctaaggtaaa tataaaattt ttaagtgtat | 480 |
| aatgtgttaa actactgatt ctaattgttt ctctctttta gattccaacc tttggaactg | 540 |
| a | 541 |

<210> SEQ ID NO 51
<211> LENGTH: 1908
<212> TYPE: DNA
<213> ORGANISM: Artificial Sequence
<220> FEATURE:
<223> OTHER INFORMATION: Synthetic polynucleotide

<400> SEQUENCE: 51

| | |
|---|---|
| ccctaaaatg gcaaacatt gcaagcagca aacagcaaac acacagccct ccctgcctgc | 60 |
| tgaccttgga gctggggcag aggtcagaga cctctctggg cccatgccac ctccaacatc | 120 |
| cactcgaccc cttggaattt cggtggagag gagcagaggt tgtcctggcg tggtttaggt | 180 |
| agtgtgagag gggaatgact cctttcggta agtgcagtgg aagctgtaca ctgcccaggc | 240 |
| aaagcgtccg ggcagcgtag gcgggcgact cagatcccag ccagtggact tagcccctgt | 300 |
| ttgctcctcc gataactggg gtgaccttgg ttaatattca ccagcagcct ccccgttgc | 360 |
| ccctctggat ccactgctta aatacggacg aggacagggc cctgtctcct cagcttcagg | 420 |
| caccaccact gacctgggac agtgaatcct ctaaggtaaa tataaaattt ttaagtgtat | 480 |
| aatgtgttaa actactgatt ctaattgttt ctctctttta gattccaacc tttggaactg | 540 |
| accgccacca tgtccaccgc tgtgctggag aaccctgggc tggggaggaa actgtcagac | 600 |
| ttcgggcagg agacttcata cattgaggat aactgtaacc agaatggcgc catctctctg | 660 |
| atcttcagcc tgaaggagga agtgggcgcc ctggcaaagg tgctgcgcct gtttgaggag | 720 |
| aacgacgtga atctgaccca catcgagtcc cggccttcta gactgaagaa ggacgagtac | 780 |
| gagttcttta cccacctgga taagcggtcc ctgccagccc tgacaaacat catcaagatc | 840 |
| ctgaggcacg acatcggagc aaccgtgcac gagctgtctc gggacaagaa gaaggatacc | 900 |
| gtgccctggt tccctcggac aatccaggag ctggatagat tgccaaccga tcctgtctct | 960 |
| tacgagcag agctggacgc agatcaccct ggcttcaagg acccagtgta tcgggcccgg | 1020 |
| agaaagcagt ttgccgatat cgcctacaat tataggcacg acagccaat ccctcgcgtg | 1080 |
| gagtatatgg aggaggagaa gaagacctgg ggcacagtgt tcaagaccct gaagagcctg | 1140 |
| tacaagacac acgcctgcta cgagtataac cacatcttcc cctgctgga aagtattgt | 1200 |
| ggctttcacg aggacaatat ccctcagctg gaggacgtga ccagttcct gcagacctgc | 1260 |
| acaggcttta gctgaggcc agtggcagga ctgctgagct cccggacctt cctgggagga | 1320 |
| ctggccttca gagtgtttca ctgcacccag tacatcaggc acggctccaa gccaatgtat | 1380 |
| acaccagagc ccgacatctg tcacgagctg ctgggccacg tgcccctgtt tagcgataga | 1440 |
| tccttcgccc agtttcccca ggagatcgga ctggcatctc tggagcacc tgacgagtac | 1500 |
| atcgagaagc tggccaccat ctattggttc acagtggagt ttggcctgtg caagcagggc | 1560 |

```
gatagcatca aggcctacgg agcaggactg ctgtctagct tcggcgagct gcagtattgt    1620
ctgtccgaga agccaaagct gctgcccctg gagctggaga agaccgccat ccagaactac    1680
accgtgacag agttccagcc cctgtactat gtggccgagt cttttaacga tgccaaggag    1740
aaggtgagaa atttcgccgc cacaatccct aggcccttca gtgtgcgtta cgacccttat    1800
acccagagga tcgaggtgct ggataataca cagcagctga agatcctggc tgactcaatc    1860
aatagcgaaa tcggaatcct gtgctccgcc ctgcagaaaa tcaaatga                 1908
```

<210> SEQ ID NO 52
<211> LENGTH: 2156
<212> TYPE: DNA
<213> ORGANISM: Artificial Sequence
<220> FEATURE:
<223> OTHER INFORMATION: Synthetic polynucleotide

<400> SEQUENCE: 52

```
ccctaaaatg gcaaacatt gcaagcagca aacagcaaac acacagccct ccctgcctgc     60
tgaccttgga gctggggcag aggtcagaga cctctctggg cccatgccac ctccaacatc   120
cactcgaccc cttggaattt cggtggagag agcagaggt tgtcctggcg tggtttaggt    180
agtgtgagag gggaatgact cctttcggta agtgcagtgg aagctgtaca ctgcccaggc   240
aaagcgtccg ggcagcgtag gcgggcgact cagatcccag ccagtggact tagcccctgt   300
ttgctcctcc gataactggg gtgaccttgg ttaatattca ccagcagcct ccccgttgc    360 ccctctggat ccactgctta aatacggacg aggacagggc cctgtctcct cagcttcagg   420
caccaccact gacctgggac agtgaatcct ctaaggtaaa tataaaattt ttaagtgtat   480
aatgtgttaa actactgatt ctaattgttt ctctctttta gattccaacc tttggaactg   540
accgccacca tgtccaccgc tgtgctggag acccctgggc tggggaggaa actgtcagac   600
ttcgggcagg agacttcata cattgaggat aactgtaacc agaatggcgc catctctctg   660
atcttcagcc tgaaggagga agtgggcgcc ctggcaaagg tgctgcgcct gtttgaggag   720
aacgacgtga atctgaccca catcgagtcc cggccttcta gactgaagaa ggacgagtac   780 gagttctttta cccacctgga taagcggtcc ctgccagccc tgacaaacat catcaagatc   840
ctgaggcacg acatcggagc aaccgtgcac gagctgtctc gggacaagaa gaaggatacc   900
gtgccctggt tccctcggac aatccaggag ctggatagat tgccaaccca gatcctgtct   960
tacggagcag agctggacgc agatcaccct ggcttcaagg acccagtgta tcgggcccgg  1020
agaaagcagt ttgccgatat cgcctacaat tataggcacg acagccaat ccctcgcgtg   1080 gagtatatgg aggaggagaa gaagacctgg ggcacagtgt tcaagaccct gaagagcctg  1140
tacaagacac acgcctgcta cgagtataac cacatcttcc ccctgctgga agtgtattgt   1200
ggctttcacg aggacaatat ccctcagctg gaggacgtga ccagttcct gcagacctgc   1260 acaggcttta gctgaggcc agtggcagga ctgctgagct cccggactt cctgggagga    1320 ctggccttca gagtgtttca ctgcacccag tacatcaggc acggctccaa gccaatgtat   1380
acaccagagc ccgacatctg tcacgagctg ctgggccacg tgcccctgtt tagcgataga  1440
tccttcgccc agttttccca ggagatcgga ctggcatctc tgggagcacc tgacgagtac   1500
atcgagaagc tggccaccat ctattggttc acagtggagt ttggcctgtg caagcagggc  1560
gatagcatca aggcctacgg agcaggactg ctgtctagct tcggcgagct gcagtattgt   1620
ctgtccgaga agccaaagct gctgcccctg gagctggaga agaccgccat ccagaactac  1680
```

```
accgtgacag agttccagcc cctgtactat gtggccgagt cttttaacga tgccaaggag    1740
aaggtgagaa atttcgccgc cacaatccct aggcccttca gtgtgcgtta cgacccttat    1800
acccagagga tcgaggtgct ggataataca cagcagctga agatcctggc tgactcaatc    1860
aatagcgaaa tcggaatcct gtgctccgcc ctgcagaaaa tcaaatgaga attcaaggcc    1920
tctcgagcct ctagaactat agtgagtcgt attacgtaga tccagacatg ataagataca    1980
ttgatgagtt tggacaaacc acaactagaa tgcagtgaaa aaaatgcttt atttgtgaaa    2040
tttgtgatgc tattgcttta tttgtaacca ttataagctg caataaacaa gttaacaaca    2100
acaattgcat tcattttatg tttcaggttc aggggggaggt gtgggaggtt ttttaa      2156

<210> SEQ ID NO 53
<211> LENGTH: 1356
<212> TYPE: DNA
<213> ORGANISM: Homo sapiens

<400> SEQUENCE: 53
atgtccactg cggtcctgga aacccaggc ttgggcagga aactctctga ctttggacag      60
gaaacaagct atattgaaga caactgcaat caaaatggtg ccatatcact gatcttctca     120
ctcaaagaag aagttggtgc attggccaaa gtattgcgct tatttgagga gaatgatgta     180
aacctgaccc acattgaatc tagaccttct cgtttaaaga agatgagta tgaattttc      240 acccatttgg ataaacgtag cctgcctgct ctgacaaaca tcatcaagat cttgaggcat     300
gacattggtg ccactgtcca tgagctttca cgagataaga agaaagacac agtgccctgg     360
ttcccaagaa ccattcaaga gctggacaga tttgccaatc agattctcag ctatggagcg     420
gaactggatg ctgaccaccc tggttttaaa gatcctgtgt accgtgcaag acggaagcag     480
tttgctgaca ttgcctacaa ctaccgccat gggcagccca tccctcgagt ggaatacatg     540
gaggaagaaa agaaaacatg gggcacagtg ttcaagactc tgaagtcctt gtataaaacc     600
catgcttgct atgagtacaa tcacattttt ccacttcttg aaaagtactg tggcttccat     660
gaagataaca ttccccagct ggaagacgtt tctcaattcc tgcagacttg cactggtttc     720
cgcctccgac tgtggctgg cctgcttccc tctcgggatt tcttgggtgg cctggccttc     780
cgagtcttcc actgcacaca gtacatcaga catggatcca agcccatgta taccccgaa      840 cctgacatct gccatgagct gttgggacat gtgcccttgt tttcagatcg cagctttgcc     900
cagttttccc aggaaattgg ccttgcctct ctgggtgcac ctgatgaata cattgaaaag     960
ctcgccacaa tttactggtt tactgtggag tttgggctct gcaaacaagg agactccata    1020
aaggcatatg gtgctgggct cctgtcatcc tttggtgaat acagtactg cttatcagag      1080 aagccaaagc ttctccccct ggagctggag aagacagcca tccaaaatta cactgtcacg    1140
gagttccagc ccctgtatta cgtggcagag agttttaatg atgccaagga gaaagtaagg    1200
aactttgctg ccacaatacc tcggcccttc tcagttcgct acgacccata cacccaaagg    1260
attgaggtct tggacaatac ccagcagctt aagattttgg ctgattccat taacagtgaa    1320
attggaatcc tttgcagtgc cctccagaaa ataaag                              1356

<210> SEQ ID NO 54
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 54
```

```
actcacgggg atttccaagt ctccacccca ttgacgtcaa tgggagtttg ttttggcacc    60
aaaatcaacg ggactttcca aaatgtcgta ataacccgc cccgttgacg caaatgggcg    120
gtaggcgtgt acggtgggag gtctatataa gcagagctcg tttagtgaac cgt          173
```

<210> SEQ ID NO 55
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 55

```
ccaaaatcaa cgggactttc caaaatgtcg taataacccc gccccgttga cgcaaatggg    60
cggtaggcgt gtacggtggg aggtctatat aagcagagct                         100
```

<210> SEQ ID NO 56
<211> LENGTH: 380
<212> TYPE: DNA
<213> ORGANISM: Artificial Sequence
<220> FEATURE:
<223> OTHER INFORMATION: Synthetic polynucleotide

<400> SEQUENCE: 56

```
ggcattgatt attgactagt tattaatagt aatcaattac ggggtcatta gttcatagcc    60
catatatgga gttccgcgtt acataactta cggtaaatgg cccgcctggc tgaccgccca    120 acgaccccg cccattgacg tcaataatga cgtatgttcc catagtaacg ccaatagga    180 ctttccattg acgtcaatgg gtggagtatt tacggtaaac tgcccacttg gcagtacatc    240
aagtgtatca tatgccaagt ccgcccccta ttgacgtcaa tgacggtaaa tggcccgcct    300
ggcattatgc ccagtacatg accttacggg actttcctac ttggcagtac atctacgtat    360
tagtcatcgc tattaccatg                                               380
```

<210> SEQ ID NO 57
<211> LENGTH: 1246
<212> TYPE: DNA
<213> ORGANISM: Artificial Sequence
<220> FEATURE:
<223> OTHER INFORMATION: Synthetic polynucleotide

<400> SEQUENCE: 57

```
tcgaggtgag ccccacgttc tgcttcactc tccccatctc ccccccctcc ccacccccaa    60
ttttgtattt atttatttt taattatttt gtgcagcgat ggggggcgggg ggggggggg    120 ggcgcgcgcc aggcggggcg gggcgggcg aggggcgggg cggggcgagg cggagaggtg    180
cggcggcagc caatcagagc ggcgcgctcc gaaagtttcc ttttatggcg aggcggcggc    240
ggcggcggcc ctataaaaag cgaagcgcgc ggcgggcggg agtcgctgcg cgctgccttc    300
gccccgtgcc ccgctccgcc gccgcctcgc gccgcccgcc ccggctctga ctgaccgcgt    360
tactcccaca ggtgagcggg cgggacggcc cttctcctcc gggctgtaat tagcgcttgg    420
tttaatgacg gcttgtttct tttctgtggc tgcgtgaaag ccttgagggg ctccgggagg    480
gccctttgtg cggggggagc ggctcggggg gtgcgtgcgt gtgtgtgtgc gtgggggagcg    540 ccgcgtgcgg ctccgcgctg cccggcggct gtgagcgctg cgggcgcggc gcgggcttt    600 gtgcgctccg cagtgtgcgc gaggggagcg cggccggggg cggtgccccg cggtgcgggg    660
ggggctgcga ggggaacaaa ggctgcgtgc ggggtgtgtg cgtgggggg tgagcagggg    720
```

```
gtgtgggcgc gtcggtcggg ctgcaaccc  ccctgcaccc ccctccccga gttgctgagc    780
acggcccggc ttcgggtgcg gggctccgta cggggcgtgg cgcggggctc gccgtgccgg    840 gcgggggggtg gcggcaggtg ggggtgccgg gcggggcggg gccgcctcgg gccggggagg   900
gctcggggga ggggcgcggc ggccccggga gcgccggcgg ctgtcgaggc gcggcgagcc    960
gcagccattg cctttatgg taatcgtgcg agagggcgca gggacttcct ttgtcccaaa    1020
tctgtgcgga gccgaaatct gggaggcgcc gccgcacccc ctctagcggg cgcggggcga   1080
agcggtgcgg cgccggcagg aaggaaatgg gcggggaggg ccttcgtgcg tcgccgcgcc   1140
gccgtcccct tctccctctc cagcctcggg gctgtccgcg gggggacggc tgccttcggg   1200
ggggacgggg cagggcgggg ttcggcttct ggcgtgtgac cggcgg                  1246

<210> SEQ ID NO 58
<211> LENGTH: 201
<212> TYPE: DNA
<213> ORGANISM: Artificial Sequence
<220> FEATURE:
<223> OTHER INFORMATION: Synthetic polynucleotide

<400> SEQUENCE: 58
gaattcgggc ggagttaggg cggagccaat cagcgtgcgc cgttccgaaa gttgcctttt     60
atggctgggc ggagaatggg cggtgaacgc cgatgattat ataaggacgc gccgggtgtg    120
gcacagctag ttccgtcgca gccgggattt gggtcgcggt tcttgtttgt ggatccctgt    180
gatcgtgatc atcacttgtg a                                              201

<210> SEQ ID NO 59
<211> LENGTH: 953
<212> TYPE: DNA
<213> ORGANISM: Artificial Sequence
<220> FEATURE:
<223> OTHER INFORMATION: Synthetic polynucleotide

<400> SEQUENCE: 59
aattcggtac cctagttatt aatagtaatc aattacgggg tcattagttc atagcccata     60
tatggagttc cgcgttacat aacttacggt aaatggcccg cctggctgac cgcccaacga    120
cccccgccca ttgacgtcaa taatgacgta tgttcccata gtaacgccaa tagggacttt    180
ccattgacgt caatgggtgg actatttacg gtaaactgcc cacttggcag tacatcaagt    240
gtatcatatg ccaagtacgc cccctattga cgtcaatgac ggtaaatggc ccgcctggca    300
ttatgcccag tacatgacct tatgggactt tcctacttgg cagtacatct acgtattagt    360
catcgctatt accatggtcg aggtgagccc cacgttctgc ttcactctcc ccatctcccc    420
cccctcccca cccccaattt tgtatttatt tattttttaa ttattttgtg cagcgatggg    480
ggcggggggg gggggggggc gcgcgccagg cggggcgggg cggggcgagg ggcggggcgg    540
ggcgaggcgg agaggtgcgg cggcagccaa tcagagcggc gcgctccgaa agtttccttt    600 tatgcgcgagg cggcggcggc ggcggcccta aaaaagcga agcgcgcggc gggcgggagt    660
cgctgcgacg ctgccttcgc cccgtgcccc gctccgccgc cgcctcgcgc cgcccgcccc    720
ggctctgact gaccgcgtta ctcccacagg tgagcgggcg gacgccct tctcctccgg     780 gctgtaatta gcgcttggtt taatgacggc ttgtttcttt tctgtggctg cgtgaaagcc    840 ttgagggggct ccgggagcta gagcctctgc taaccatgtt catgccttct tcttttcct    900 acagctcctg ggcaacgtgc tggttattgt gctgtctcat catttggca aag            953
```

<210> SEQ ID NO 60
<211> LENGTH: 1766
<212> TYPE: DNA
<213> ORGANISM: Artificial Sequence
<220> FEATURE:
<223> OTHER INFORMATION: Synthetic polynucleotide

<400> SEQUENCE: 60

```
gtaaatttta tggaatgtga atcataattc aattttttcaa catgcgttag gagggacatt     60
tcaaactctt ttttacccta gactttccta ccatcaccca gagtatccag ccaggagggg    120
aggggctaga gacaccagaa gtttagcagg gaggagggcg tagggattcg gggaatgaag    180
ggatgggatt cagactaggg ccaggaccca gggatggaga gaaagagatg agagtggttt    240
gggggcttgg tgacttagag aacagagctg caggctcaga ggcacacagg agtttctggg    300
ctcaccctgc cccttccaa cccctcagtt cccatcctcc agcagctgtt tgtgtgctgc    360
ctctgaagtc cacactgaac aaacttcagc ctactcatgt ccctaaaatg gcaaacatt    420
gcaagcagca aacagcaaac acacagccct ccctgcctgc tgaccttgga gctggggcag    480
aggtcagaga cctctctggg cccatgccac ctccaacatc cactcgaccc cttggaattt    540
cggtggagag gagcagaggt tgtcctggcg tggtttaggt agtgtgagag ggcttaagcg    600
tgaggctccg gtgcccgtca gtgggcagag cgcacatcgc ccacagtccc cgagaagttg    660
gggggagggg tcggcaattg aaccggtgcc tagagaaggt ggcgcggggt aaactgggaa    720
agtgatgtcg tgtactggct ccgccttttt cccgagggtg ggggagaacc gtatataagt    780
gcagtagtcg ccgtgaacgt tcttttttcgc aacgggtttg ccgccagaac acaggtaagt    840
gccgtgtgtg gttcccgcgg gcctggcctc tttacgggtt atggcccttg cgtgccttga    900
attacttcca cctggctcca gtacgtgatt cttgatcccg agctggagcc aggggcgggc    960
cttgcgcttt aggagcccct tcgcctcgtg cttgagttga ggcctggcct gggcgctggg   1020
gccgccgcgt gcgaatctgg tggcaccttc gcgcctgtct cgctgctttc gataagtctc   1080
tagccattta aaattttttga tgacctgctg cgacgctttt tttctggcaa gatagtcttg   1140
taaatgcggg ccaggatctg cacactggta tttcggtttt tggggccgcg gcggcgacg   1200
gggcccgtgc gtcccagcgc acatgttcgg cgaggcgggg cctgcgagcg cggccaccga   1260
gaatcggacg ggggtagtct caagctggcc ggcctgctct ggtgcctggc ctcgcgccgc   1320
cgtgtatcgc cccgccctgg gcggcaaggc tggcccggtc ggcaccagtt gcgtgagcgg   1380
aaagatggcc gcttcccggc cctgctccag ggggctcaaa atggaggacg cggcgctcgg   1440
gagagcgggc gggtgagtca cccacacaaa ggaaagggc ctttccgtcc tcagccgtcg   1500
cttcatgtga ctccacggag taccgggcgc cgtccaggca cctcgattag ttctggagct   1560
tttggagtac gtcgtctta ggttgggggg aggggtttta tgcgatggag ttcccccaca   1620
ctgagtgggt ggagactgaa gttaggccag cttggcactt gatgtaattc tccttggaat   1680
ttgcccttt tgagtttgga tcttggttca ttctcaagcc tcagacagtg gttcaaagtt   1740
tttttcttcc atttcaggtg tcgtga                                         1766
```

<210> SEQ ID NO 61
<211> LENGTH: 82
<212> TYPE: DNA
<213> ORGANISM: Artificial Sequence
<220> FEATURE:
<223> OTHER INFORMATION: Synthetic polynucleotide

<400> SEQUENCE: 61

```
gtaagggttt aagggatggt tggttggtgg ggtattaatg tttaattacc tggagcacct     60
gcctgaaatc acttttttc ag                                                82

<210> SEQ ID NO 62
<211> LENGTH: 95
<212> TYPE: DNA
<213> ORGANISM: Artificial Sequence
<220> FEATURE:
<223> OTHER INFORMATION: Synthetic polynucleotide

<400> SEQUENCE: 62
cctctgctaa ccatgttcat gccttcttct ttttcctaca gctcctgggc aacgtgctgg     60
ttattgtgct gtctcatcat tttggcaaag aattc                                95

<210> SEQ ID NO 63
<211> LENGTH: 1356
<212> TYPE: DNA
<213> ORGANISM: Artificial Sequence
<220> FEATURE:
<223> OTHER INFORMATION: Synthetic polynucleotide

<400> SEQUENCE: 63
atgtccaccg ctgtgctgga gaccctggg ctggggagga aactgtcaga cttcgggcag       60
gagacttcat acattgagga taactgtaac cagaatggcg ccatctctct gatcttcagc    120
ctgaaggagg aagtgggcgc cctggcaaag gtgctgcgcc tgtttgagga gaacgacgtg    180
aatctgaccc acatcgagtc ccggccttct agactgaaga aggacgagta cgagttcttt    240
acccacctgg ataagcggtc cctgccagcc ctgacaaaca tcatcaagat cctgaggcac    300
gacatcggag caaccgtgca cgagctgtct cgggacaaga agaaggatac cgtgccctgg    360
ttccctcgga caatccagga gctggataga tttgccaacc agatcctgtc ttacggagca    420
gagctggacg cagatcaccc tggcttcaag gacccagtgt atcgggcccg gagaaagcag    480
tttgccgata tcgcctacaa ttataggcac ggacagccaa tccctcgcgt ggagtatatg    540
gaggaggaga agaagacctg ggcacagtg ttcaagaccc tgaagagcct gtacaagaca     600
cacgcctgct acgagtataa ccacatcttc ccctgctgg agaagtattg tgctttcac      660 gaggacaata tccctcagct ggaggacgtg agccagttcc tgcagacctg cacaggcttt    720
aggctgaggc cagtggcagg actgctgagc tcccgggact tcctgggagg actgccttc     780 agagtgtttc actgcaccca gtacatcagg cacggctcca agccaatgta tacaccagag    840
cccgacatct gtcacgagct gctgggccac gtgcccctgt ttagcgatag atccttcgcc    900 cagtttttccc aggagatcgg actggcatct ctgggagcac ctgacgagta catcgagaag    960
ctggccacca tctattggtt cacagtggag tttggcctgt gcaagcaggg cgatagcatc   1020
aaggcctacg agcaggact gctgtctagc ttcggcgagc tgcagtattg tctgtccgag   1080
aagccaaagc tgctgcccct ggagctggag aagaccgcca tccagaacta caccgtgaca   1140
gagttccagc ccctgtacta tgtggccgag tcttttaacg atgccaagga gaaggtgaga   1200
aatttcgccg ccacaatccc taggcccttc agcgtgcggt acgacccta tacccagagg   1260 atcgaggtgc tggataatac acagcagctg aagatcctgg ctgactcaat caatagcgaa   1320
atcggaatcc tgtgctccgc cctgcagaaa atcaaa                             1356

<210> SEQ ID NO 64
<211> LENGTH: 1873
<212> TYPE: DNA
<213> ORGANISM: Artificial Sequence
```

```
<220> FEATURE:
<223> OTHER INFORMATION: Synthetic polynucleotide

<400> SEQUENCE: 64
gatcttcaat attggccatt agccatatta ttcattggtt atatagcata aatcaatatt      60
ggctattggc cattgcatac gttgtatcta tatcataata tgtacattta tattggctca     120
tgtccaatat gaccgccatg ttggcattga ttattgacta gttattaata gtaatcaatt     180
acggggtcat tagttcatag cccatatatg gagttccgcg ttacataact tacggtaaat     240
ggcccgcctg gctgaccgcc caacgacccc cgcccattga cgtcaataat gacgtatgtt     300
cccatagtaa cgccaatagg gactttccat tgacgtcaat gggtggagta tttacggtaa     360
actgcccact tggcagtaca tcaagtgtat catatgccaa gtccgccccc tattgacgtc     420
aatgacggta atggcccgc ctggcattat gcccagtaca tgaccttacg ggactttcct      480
acttggcagt acatctacgt attagtcatc gctattacca tggtcgaggt gagccccacg     540
ttctgcttca ctctccccat ctccccccc tccccacccc caattttgta tttatttatt      600
ttttaattat tttgtgcagc gatggggggcg ggggggggggg ggggcgcgc gccaggcggg    660
gcggggcggg gcgaggggcg gggcggggcg aggcggagag gtgcggcggc agccaatcag     720
agcggcgcgc tccgaaagtt ccttttatg gcgaggcggc ggcggcggcg ccctataaa      780
aagcgaagcg cgcggcgggc gggagtcgct gcgacgctgc cttcgccccg tgccccgctc     840
cgccgccgcc tcgcgccgcc cgccccggct ctgactgacc gcgttactcc cacaggtgag     900
cgggcgggac ggcccttctc ctccgggctg taattagcgc ttggtttaat gacggcttgt     960
ttcttttctg tggctgcgtg aaagccttga ggggctccgg gagggcccctt tgtgcgggggg  1020
ggagcggctc ggggggtgcg tgcgtgtgtg tgtgcgtggg gagcgccgcg tgcggcccgc    1080
gctgccggc ggctgtgagc gctgcgggcg cggcgcgggg ctttgtgcgc tccgcagtgt     1140
gcgcgagggg agcgcggccg ggggcggtgc cccgcggtgc gggggggggct gcgaggggaa   1200
caaaggctgc gtcggggtg tgtgcgtggg ggggtgagca ggggtgtgg gcgcggcggt      1260
cgggctgtaa cccccccctg caccccccctc cccgagttgc tgagcacggc ccggcttcgg   1320
gtgcggggct ccgtacgggg cgtggcgcgg ggctcgccgt gccgggcggg gggtggcggc    1380
aggtggggt gccgggcggg gcggggccgc ctcgggccgg ggagggctcg ggggaggggc     1440
gcggcggccc ccggagcgcc ggcggctgtc gaggcgcggc gagccgcagc cattgccttt    1500
tatggtaatc gtgcgagagg gcgcagggac ttcctttgtc ccaaatctgt gcggagccga    1560
aatctgggag gcgccgccgc accccctcta gcgggcgcgg ggcgaagcgg tgcggcgccg    1620
gcaggaagga aatgggcggg gagggccttc gtgcgtcgcc gcgccgccgt cccttctcc     1680
ctctccagcc tcggggctgt ccgcgggggg acggctgcct tcgggggga cggggcaggg    1740
cggggttcgg cttctggcgt gtgaccggcg gctctagagc ctctgctaac catgttcatg    1800
ccttcttctt tttcctacag ctcctgggca acgtgctggt tattgtgctg tctcatcatt    1860
ttggcaaaga att                                                       1873

<210> SEQ ID NO 65
<211> LENGTH: 1061
<212> TYPE: DNA
<213> ORGANISM: Artificial Sequence
<220> FEATURE:
<223> OTHER INFORMATION: Synthetic polynucleotide

<400> SEQUENCE: 65
```

| | |
|---|---|
| tagggaggtc ctgcacgtta cataacttac ggtaaatggc ccgcctggct gaccgcccaa | 60 |
| cgaccccgc ccattgacgt caataatgac gtatgttccc atagtaacgc caatagggac | 120 |
| tttccattga cgtcaatggg tggagtattt acggtaaact gcccacttgg cagtacatca | 180 |
| agtgtatcat atgccaagta cgccccctat tgacgtcaat gacggtaaat ggcccgcctg | 240 |
| gcattatgcc cagtacatga ccttatggga ctttcctact tggcagtaca tctacgtatt | 300 |
| agtcatcgct attaccatgg tcgaggtgag ccccacgttc tgcttcactc tccccatctc | 360 |
| cccccctcc ccaccccaa ttttgtattt atttattttt taattatttt gtgcagcgat | 420 |
| gggggcgggg ggggggggg gcgcgcgcca ggcggggcgg ggcggggcga ggggcggggc | 480 |
| ggggcgaggc ggagaggtgc ggcggcagcc aatcagagcg gcgcgctccg aaagtttcct | 540 |
| tttatggcga ggcggcggcg gcggcggccc tataaaaagc gaagcgcgcg gcgggcggga | 600 |
| gtcgctgcgc gctgccttcg ccccgtgccc cgctccgccg ccgcctcgcg ccgcccgccc | 660 |
| cggctctgac tgaccgcgtt actaaaacag gtaagtccgg cctccgcgcc gggttttggc | 720 |
| gcctcccgcg ggcgcccccc tcctcacggc gagcgctgcc acgtcagacg aagggcgcag | 780 |
| cgagcgtcct gatccttccg cccggacgct caggacagcg gcccgctgct cataagactc | 840 |
| ggccttagaa cccagtatc agcagaagga cattttagga cgggacttgg gtgactctag | 900 |
| ggcactggtt ttctttccag agagcggaac aggcgaggaa agtagtccc ttctcggcga | 960 |
| ttctgcggag ggatctccgt ggggcggtga acgccgatga tgcctctact aaccatgttc | 1020 |
| atgttttctt tttttttcta caggtcctgg gtgacgaaca g | 1061 |

<210> SEQ ID NO 66
<211> LENGTH: 170
<212> TYPE: DNA
<213> ORGANISM: Artificial Sequence
<220> FEATURE:
<223> OTHER INFORMATION: Synthetic polynucleotide

<400> SEQUENCE: 66

| | |
|---|---|
| cgatgctcta atctctctag acaaggttca tatttgtatg ggttacttat tctctctttg | 60 |
| ttgactaagt caataatcag aatcagcagg tttgcagtca gattggcagg gataagcagc | 120 |
| ctagctcagg agaagtgagt ataaaagccc caggctggga gcagccatca | 170 |

<210> SEQ ID NO 67
<211> LENGTH: 254
<212> TYPE: DNA
<213> ORGANISM: Artificial Sequence
<220> FEATURE:
<223> OTHER INFORMATION: Synthetic polynucleotide

<400> SEQUENCE: 67

| | |
|---|---|
| gggggaggct gctggtgaat attaaccaag gtcaccccag ttatcggagg agcaaacagg | 60 |
| ggctaagtcc acctcgagcc atggcgatgc tctaatctct ctagacaagg ttcatatttg | 120 |
| tatgggttac ttattctctc tttgttgact aagtcaataa tcagaatcag caggtttgca | 180 |
| gtcagattgg cagggataag cagcctagct caggagaagt gagtataaaa gccccaggct | 240 |
| gggagcagcc atca | 254 |

<210> SEQ ID NO 68
<211> LENGTH: 592
<212> TYPE: DNA
<213> ORGANISM: Artificial Sequence
<220> FEATURE:
<223> OTHER INFORMATION: Synthetic polynucleotide

<400> SEQUENCE: 68

```
gtaaatttta tggaatgtga atcataattc aattttttcaa catgcgttag gagggacatt    60
tcaaactctt ttttacccta gactttccta ccatcaccca gagtatccag ccaggagggg   120
aggggctaga gacaccagaa gtttagcagg gaggagggcg tagggattcg gggaatgaag   180
ggatgggatt cagactaggg ccaggaccca gggatggaga gaaagagatg agagtggttt   240
gggggcttgg tgacttagag aacagagctg caggctcaga ggcacacagg agtttctggg   300
ctcaccctgc cccccttccaa cccctcagtt cccatcctcc agcagctgtt tgtgtgctgc   360
ctctgaagtc cacactgaac aaacttcagc ctactcatgt ccctaaaatg gcaaacatt    420
gcaagcagca aacagcaaac acacagccct ccctgcctgc tgaccttgga gctggggcag   480
aggtcagaga cctctctggg cccatgccac ctccaacatc cactcgaccc cttgaatttt   540
cggtggagag gagcagaggt tgtcctggcg tggtttaggt agtgtgagag gg            592
```

<210> SEQ ID NO 69
<211> LENGTH: 205
<212> TYPE: DNA
<213> ORGANISM: Artificial Sequence
<220> FEATURE:
<223> OTHER INFORMATION: Synthetic polynucleotide

<400> SEQUENCE: 69

```
aatgactcct ttcggtaagt gcagtggaag ctgtacactg cccaggcaaa gcgtccgggc    60
agcgtaggcg ggcgactcag atcccagcca gtggacttag cccctgtttg ctcctccgat   120
aactggggtg accttggtta atattcacca gcagcctccc ccgttgcccc tctggatcca   180
ctgcttaaat acggacgagg acagg                                          205
```

<210> SEQ ID NO 70
<211> LENGTH: 423
<212> TYPE: DNA
<213> ORGANISM: Artificial Sequence
<220> FEATURE:
<223> OTHER INFORMATION: Synthetic polynucleotide

<400> SEQUENCE: 70

```
gctctaaccc actctgatct cccagggcgg cagtaagtct tcagcatcag gcattttggg    60
gtgactcagt aaatggtaga tcttgctacc agtggaacag ccactaagga ttctgcagtg   120
agagcagagg ccagctaag tggtactctc ccagagactg tctgactcac gccaccccct   180
ccaccttgga cacaggacgc tgtggtttct gagccaggta caatgactcc tttcggtaag   240
tgcagtggaa gctgtacact gcccaggcaa agcgtccggg cagcgtaggc gggcgactca   300
gatcccagcc agtggactta gccctgtttt gctcctccga taactggggt gaccttggtt   360
aatattcacc agcagcctcc cccgttgccc ctctggatcc actgcttaaa tacggacgag   420
gac                                                                  423
```

<210> SEQ ID NO 71
<211> LENGTH: 72
<212> TYPE: DNA
<213> ORGANISM: Artificial Sequence
<220> FEATURE:
<223> OTHER INFORMATION: Synthetic polynucleotide

<400> SEQUENCE: 71

```
gggggaggct gctggtgaat attaaccaag gtcaccccag ttatcggagg agcaaacagg    60
```

```
ggctaagtcc ac                                                            72
```

<210> SEQ ID NO 72
<211> LENGTH: 913
<212> TYPE: DNA
<213> ORGANISM: Artificial Sequence
<220> FEATURE:
<223> OTHER INFORMATION: Synthetic polynucleotide

<400> SEQUENCE: 72

```
tagggaggtc ctgcacagaa ggggaggagg gggcagcagc tgtctgacca ctgttggtct         60
tgcaacttgt gtccccaggt taattttttaa aaagcagtca aaagtccaag tggcccttgg       120
cagcatttac tctctctgtt tgctctggtt aataatctca ggagcacaaa cattcctgga       180
ggcaggagaa gaaatcaaca tcctggactt atcctctggg cctctcccca cccccaggat       240
tgtaactgaa atgcttcact ggtgctcctt ttgttttaag gcattggatc ttcatagcta       300
ctgatcgtgc ccaagcacac agtatctgca gcaaccactt aggcctccag gaatgtggtg       360
accattgacc ctaattcatt ccccttcatg gatcctatgt aaccatcctc caaaaagagc       420
tttcgcaaac tcaaataaac acaggaaagg aagaccttct tatctttgag agtatatgtt       480
tagccctata gctctaaccc actctgatct cccagggcgg cagtaagtct tcagcatcag       540
gcattttggg gtgactcagt aaatggtaga tcttgctacc agtggaacag ccactaagga       600
ttctgcagtg agagcagagg gccagctaag tggtactctc ccagagactg tctgactcac       660
gccacccccct ccaccttgga cacaggacgc tgtggtttct gagccaggta caatgactcc       720
tttcggtaag tgcagtggaa gctgtacact gcccaggcaa agcgtccggg cagcgtaggc       780
gggcgactca gatcccagcc agtggactta gccctgtttt gctcctccga taactggggt       840
gaccttggtt aatattcacc agcagcctcc cccgttgccc ctctggatcc actgcttaaa       900
tacggacgag gac                                                         913
```

<210> SEQ ID NO 73
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 73

```
gtagataagt agcatggcgg gttaatcatt aactaca                                 37
```

<210> SEQ ID NO 74
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 74

```
ggaggggtgg agtcgtgacg tgaattacgt catagggtta gggagg                       46
```

<210> SEQ ID NO 75
<211> LENGTH: 182
<212> TYPE: DNA
<213> ORGANISM: Artificial Sequence
<220> FEATURE:
<223> OTHER INFORMATION: Synthetic polynucleotide

<400> SEQUENCE: 75

```
gtagataagt agcatggcgg gttaatcatt aactacaagg aaccccctagt gatggagttg        60
```

```
gccactccct ctctgcgcgc tcgctcgctc actgaggccg ggcgaccaaa ggtcgcccga    120
cgcccgggct tgcccgggc ggcctcagtg agcgagcgag cgcgcagaga gggagtggcc    180
aa                                                                  182

<210> SEQ ID NO 76
<211> LENGTH: 191
<212> TYPE: DNA
<213> ORGANISM: Artificial Sequence
<220> FEATURE:
<223> OTHER INFORMATION: Synthetic polynucleotide

<400> SEQUENCE: 76
ttggccactc cctctctgcg cgctcgctcg ctcactgagg ccgggcgacc aaaggtcgcc     60
cgacgcccgg gctttgcccg gcggcctca gtgagcgagc gagcgcgcag agagggagtg    120
gccaactcca tcactagggg ttcctggagg ggtggagtcg tgacgtgaat tacgtcatag    180
ggttagggag g                                                        191

<210> SEQ ID NO 77
<211> LENGTH: 3230
<212> TYPE: DNA
<213> ORGANISM: Artificial Sequence
<220> FEATURE:
<223> OTHER INFORMATION: Synthetic polynucleotide

<400> SEQUENCE: 77
agcattagct tccatttatg cagtgtaaat ggtgagaaca gccccgactg aatacccaga     60
gcatcatctc gtctgtgtca ttcatgcaca taacatatct cagcgaggtg gcccttctgt    120
cctctttgca gagacccagc caccatacta gtacctagag aactggctgg atttcagccc    180
cgatacctcc gggcttttgc tcatgttcgc ctcatagggt catctgggtg gttgcctaag    240
gaaaagtatg tcatggagac taacttgctt ggcattgaat aaaaggtgag ttgagagtgg    300
agcgtgttta aattgcaatc ctgcctctat ttctgtgctt gcagggaaca gtcatcctta    360
attgctatcc tccatcatca tcatgattat ttctggtttt tctctggttg cggagaatcc    420
atactccagg tattccaatg tctcagcatt gccaggcctg tctgagcgtc aggatgtagg    480
tagtctgggc tctctgcctt ctattcttgt ccaggatact ctgccaaaag aatcatgttg    540
tggctgccac ccctcccaca aagcctcccg cttgggtcag tccaggactg gagttgggta    600
tggactgttc atgtctatcc actgctacgt cagggcaaca cccactgaga gtgaccttgt    660
agactgcagt gggagacacc cttcaaaacc tctcctctcc tgtcctgaga gccaggttaa    720
aaccatcagc cccgcatcct gagtgcaaac ttttcctaac cctgctgcta agctagacac    780
ctcacttact gagagccagc atgtccaccg ctgtgctgga gaaccctggg ctggggagga    840
aactgtcaga cttcgggcag gagacttcat acattgagga taactgtaac cagaatggcg    900
ccatctctct gatcttcagc ctgaaggagg aagtgggcgc cctggcaaag gtgctgcgcc    960
tgtttgagga gaacgacgtg aatctgaccc acatcgagtc ccggccttct agactgaaga   1020
aggacgagta cgagttcttt acccaccctg ataagcggtc cctgccagcc ctgacaaaca   1080
tcatcaagat cctgaggcac gacatcggag caaccgtgca cgagctgtct cgggacaaga   1140
agaaggatac cgtgccctgg ttccctcgga caatccagga gctggataga tttgccaacc   1200
agatcctgtc ttacggagca gagctggacg cagatcaccc tggcttcaag gacccagtgt   1260
atcgggcccg gagaaagcag tttgccgata tcgcctacaa ttataggcac ggacagccaa   1320
```

|                                                                              |      |
|------------------------------------------------------------------------------|------|
| tccctcgcgt ggagtatatg gaggaggaga agaagacctg ggcacagtg ttcaagaccc             | 1380 |
| tgaagagcct gtacaagaca cacgcctgct acgagtataa ccacatcttc cccctgctgg            | 1440 |
| agaagtattg tggctttcac gaggacaata tccctcagct ggaggacgtg agccagttcc            | 1500 |
| tgcagacctg cacaggcttt aggctgaggc cagtggcagg actgctgagc tcccgggact            | 1560 |
| tcctgggagg actggccttc agagtgtttc actgcaccca gtacatcagg cacggctcca            | 1620 |
| agccaatgta taccagagag cccgacatct gtcacgagct gctgggccac gtgcccctgt            | 1680 |
| ttagcgatag atccttcgcc cagttttccc aggagatcgg actggcatct ctgggagcac            | 1740 |
| ctgacgagta catcgagaag ctggccacca tctattggtt cacagtggag tttggcctgt            | 1800 |
| gcaagcaggg cgatagcatc aaggcctacg agcaggact gctgtctagc ttcggcgagc             | 1860 |
| tgcagtattg tctgtccgag aagccaaagc tgctgcccct ggagctggag aagaccgcca            | 1920 |
| tccagaacta caccgtgaca gagttccagc ccctgtacta tgtggccgag tcttttaacg            | 1980 |
| atgccaagga aaggtgagaa aatttcgccg ccacaatccc taggcccttc agcgtgcggt            | 2040 |
| acgacccta tacccagagg atcgaggtgc tggataatac acagcagctg aagatcctgg             | 2100 |
| ctgactcaat caatagcgaa atcggaatcc tgtgctccgc cctgcagaaa atcaaatgag            | 2160 |
| aattcaaggc ctctcgagcc tctagaacta tagtgagtcg tattacgtag atccagacat            | 2220 |
| gataagatac attgatgagt ttggacaaac cacaactaga atgcagtgaa aaaatgctt             | 2280 |
| tatttgtgaa atttgtgatg ctattgcttt atttgtaacc attataagct gcaataaaca            | 2340 |
| agttaacaac aacaattgca ttcattttat gtttcaggtt caggggggagg tgtgggaggt           | 2400 |
| tttttaagct ttacgtacga tcgtcgagca gctgttgtcc tggagaacgg agtcctgagc            | 2460 |
| agaaaactct cagactttgg gcaggtaagc ctgttgggct tccactgcta ggagagaatt            | 2520 |
| ggttccccac atgtgaaagc agtctgggaa atgctggtat ttccagtctc ctaaggctac            | 2580 |
| taagaaatat gactttattt agaggcgagg aaaatgccca ggaagtcaac tgatgagact            | 2640 |
| agtcttaaca agttgaggat acagaaagtt ggggatctga gctgctacca acatctgtgt            | 2700 |
| gtctttgggt ggctcattgg tatcctctgc ctattggctt tatcttctgt acactgaaag            | 2760 |
| gaaatggctg gtccttagtc acctggggtg ggagtcccta tctctccagg gatacttatt           | 2820 |
| caatcctttc ttctgggtat caaaatgaca agcttgtaag aaactgtcct ctttcggctt           | 2880 |
| tcaggaggtg atgtcgcatg aagagaattt ggggggggg acttactcag aaccaaggag             | 2940 |
| ggagaaatta aacagagagg gaaatgaaca ggagttagcc cggagcctga agcaccttgg            | 3000 |
| ggattatgct gggggtggag ggaatccatt gtcctcccta ggagggcttt gcagaacatg            | 3060 |
| ttctttctg tgatatttgt actttcccca gattgcaaat catggtttgt acactgagat             | 3120 |
| tcagtctctg gaggtaatat gccttttcta gcttttcctt ggacaggact aaggggttga            | 3180 |
| gggttgcctg gagtcagaga aattaactgt gttaaagaag gttgatatga                       | 3230 |

```
<210> SEQ ID NO 78
<211> LENGTH: 3637
<212> TYPE: DNA
<213> ORGANISM: Artificial Sequence
<220> FEATURE:
<223> OTHER INFORMATION: Synthetic polynucleotide

<400> SEQUENCE: 78
```

|                                                                              |     |
|------------------------------------------------------------------------------|-----|
| ttggccactc cctctctgcg cgctcgctcg ctcactgagg ccgggcgacc aaaggtcgcc            | 60  |
| cgacgcccgg gctttgcccg gcggcctca gtgagcgagc gagcgcgcag agagggagtg             | 120 |
| gccaactcca tcactagggg ttcctggagg ggtggagtcg tgacgtgaat tacgtcatag            | 180 |

```
ggttagggag gtcctgcata tgcggccgca gcattagctt ccatttatgc agtgtaaatg    240
gtgagaacag ccccgactga atcccagag catcatctcg tctgtgtcat tcatgcacat    300
aacatatctc agcgaggtgg cccttctgtc ctctttgcag agacccagcc accatactag    360
tacctagaga actggctgga tttcagcccc gatacctccg ggcttttgct catgttcgcc    420
tcatagggtc atctgggtgg ttgcctaagg aaaagtatgt catggagact aacttgcttg    480
gcattgaata aaaggtgagt tgagagtgga gcgtgtttaa attgcaatcc tgcctctatt    540
tctgtgcttg cagggaacag tcatccttaa ttgctatcct ccatcatcat catgattatt    600
tctggttttt ctctggttgc ggagaatcca tactccaggt attccaatgt ctcagcattg    660
ccaggcctgt ctgagcgtca ggatgtaggt agtctgggct ctctgccttc tattcttgtc    720
caggatactc tgccaaaaga atcatgttgt ggctgccacc cctcccacaa agcctcccgc    780
ttgggtcagt ccaggactgg agttgggtat ggactgttca tgtctatcca ctgctacgtc    840
agggcaacac ccactgagag tgaccttgta gactgcagtg ggagacaccc ttcaaaacct    900
ctcctctcct gtcctgagag ccaggttaaa accatcagcc ccgcatcctg agtgcaaact    960
tttcctaacc ctgctgctaa gctagacacc tcacttactg agagccagca tgtccaccgc   1020
tgtgctggag aaccctgggc tggggaggaa actgtcagac ttcgggcagg agacttcata   1080
cattgaggat aactgtaacc agaatggcgc catctctctg atcttcagcc tgaaggagga   1140
agtgggcgcc ctggcaaagg tgctgcgcct gtttgaggag aacgacgtga atctgaccca   1200
catcgagtcc cggccttcta gactgaagaa ggacgagtac gagttctttta cccacctgga   1260 taagcggtcc ctgccagccc tgacaaacat catcaagatc ctgaggcacg acatcggagc   1320
aaccgtgcac gagctgtctc gggacaagaa gaaggatacc gtgccctggt ccctcggac    1380 aatccaggag ctggatagat tgccaaacca gatcctgtct tacggagcag agctggacgc   1440
agatcaccct ggcttcaagg acccagtgta tcgggcccgg agaaagcagt ttgccgatat   1500
cgcctacaat tataggcacg acagccaat  ccctcgcgtg gagtatatgg aggaggagaa   1560
gaagacctgg ggcacagtgt tcaagaccct gaagagcctg tacaagacac acgcctgcta   1620
cgagtataac cacatcttcc ccctgctgga gaagtattgt ggctttcacg aggacaatat   1680
ccctcagctg gaggacgtga gccagttcct gcagacctgc acaggcttta ggctgaggcc   1740
agtggcagga ctgctgagct cccgggactt cctgggagga ctggccttca gagtgtttca   1800
ctgcacccag tacatcaggc acggctccaa gccaatgtat acaccagagc ccgacatctg   1860
tcacgagctg ctgggccacg tgcccctgtt tagcgataga tccttcgccc agttttccca   1920
ggagatcgga ctggcatctc tgggagcacc tgacgagtac atcgagaagc tggccaccat   1980
ctattggttc acagtggagt ttggcctgtg caagcagggc gatagcatca aggcctacgg   2040
agcaggactg ctgtctagct tcggcgagct gcagtattgt ctgtccgaga gccaaagct    2100 gctgcccctg gagctggaga agaccgccat ccagaactac accgtgacag agttccagcc   2160
cctgtactat gtggccgagt cttttaacga tgccaaggag aaggtgagaa atttcgccgc   2220
cacaatccct aggccctttca gcgtgcggta cgacccttat accccagagga tcgaggtgct   2280 ggataataca cagcagctga agatcctggc tgactcaatc aatagcgaaa tcggaatcct   2340
gtgctccgcc ctgcagaaaa tcaaatgaga attcaaggcc tctcgagcct ctagaactat   2400
agtgagtcgt attacgtaga tccagacatg ataagataca ttgatgagtt tggacaaacc   2460
acaactagaa tgcagtgaaa aaaatgcttt atttgtgaaa tttgtgatgc tattgcttta   2520
```

```
tttgtaacca ttataagctg caataaacaa gttaacaaca acaattgcat tcattttatg      2580
tttcaggttc aggggaggt gtgggaggtt ttttaagctt tacgtacgat cgtcgagcag        2640
ctgttgtcct ggagaacgga gtcctgagca gaaaactctc agactttggg caggtaagcc      2700
tgttgggctt ccactgctag gagagaattg gttccccaca tgtgaaagca gtctgggaaa      2760
tgctggtatt tccagtctcc taaggctact aagaaatatg actttattta gaggcgagga      2820
aaatgcccag gaagtcaact gatgagacta gtcttaacaa gttgaggata cagaaagttg      2880
gggatctgag ctgctaccaa catctgtgtg tctttgggtg gctcattggt atcctctgcc      2940
tattggcttt atcttctgta cactgaaagg aaatggctgg tccttagtca cctggggtgg      3000
gagtccctat ctctccaggg atacttattc aatcctttct tctgggtatc aaaatgacaa      3060
gcttgtaaga aactgtcctc tttcggcttt caggaggtga tgtcgcatga agagaatttg      3120 gggggggga cttactcaga accaaggagg agaaattaa acagagaggg aaatgaacag        3180
gagttagccc ggagcctgaa gcaccttggg gattatgctg ggggtggagg gaatccattg      3240
tcctccctag ggagggcttg cagaacatgt tcttttctgt gatatttgta ctttccccag      3300
attgcaaatc atggtttgta cactgagatt cagtctctgg aggtaatatg ccttttctag      3360
cttttccttg gacaggacta aggggttgag ggttgcctgg agtcagagaa atttgtgtta     3420
aagaaggttg atatgaaacc tgcaggtcta gatacgtaga taagtagcat ggcgggttaa      3480
tcattaacta caaggaaccc ctagtgatgg agttggccac tccctctctg cgcgctcgct      3540
cgctcactga ggccgggcga ccaaaggtcg cccgacgccc gggctttgcc cgggcggcct      3600
cagtgagcga gcgagcgcgc agagagggag tggccaa                               3637

<210> SEQ ID NO 79
<211> LENGTH: 3776
<212> TYPE: DNA
<213> ORGANISM: Artificial Sequence
<220> FEATURE:
<223> OTHER INFORMATION: Synthetic polynucleotide

<400> SEQUENCE: 79
agcattagct tccatttatg cagtgtaaat ggtgagaaca gccccgactg aatacccaga        60
gcatcatctc gtctgtgtca ttcatgcaca taacatatct cagcgaggtg gcccttctgt       120
cctctttgca gagacccagc caccatacta gtacctagag aactggctgg atttcagccc       180
cgatacctcc gggcttttgc tcatgttcgc ctcataggt catctgggtg gttgcctaag       240
gaaaagtatg tcatggagac taacttgctt ggcattgaat aaaaggtgag ttgagagtgg       300
agcgtgttta aattgcaatc ctgcctctat ttctgtgctt gcagggaaca gtcatcctta       360
attgctatcc tccatcatca tcatgattat ttctggtttt tctctggttg cggagaatcc       420
atactccagg tattccaatg tctcagcatt gccaggcctg tctgagcgtc aggatgtagg       480
tagtctgggc tctctgcctt ctattcttgt ccaggatact ctgccaaaag aatcatgttg       540
tggctgccac ccctcccaca aagcctcccg cttgggtcag tccaggactg agttgggta       600 tggactgttc atgtctatcc actgctacgt cagggcaaca cccactgaga gtgaccttgt       660
agactgcagt gggagacacc cttcaaaacc tctcctctcc tgtcctgaga gccaggttaa      720
aaccatcagc cccgcatcct gagtgcaaac ttttcctaac cctgctgcta agctagacac      780
cccacttact gagagccagc ccctaaaatg ggcaaacatt gcaagcagca aacagcaaac      840
acacagccct ccctgcctgc tgaccttgga gctggggcag aggtcagaga cctctctggg      900
cccatgccac ctccaacatc cactcgaccc cttggaattt cggtggagag gagcagaggt      960
```

```
tgtcctggcg tggtttaggt agtgtgagag gggaatgact cctttcggta agtgcagtgg    1020
aagctgtaca ctgcccaggc aaagcgtccg ggcagcgtag gcgggcgact cagatcccag    1080
ccagtggact tagcccctgt ttgctcctcc gataactggg gtgaccttgg ttaatattca    1140
ccagcagcct cccccgttgc ccctctggat ccactgctta aatacggacg aggacagggc    1200
cctgtctcct cagcttcagg caccaccact gacctgggac agtgaatcct ctaaggtaaa    1260
tataaaattt ttaagtgtat aatgtgttaa actactgatt ctaattgttt ctctctttta    1320
gattccaacc tttggaactg accgccacca tgtccaccgc tgtgctggag aaccctgggc    1380
tggggaggaa actgtcagac ttcgggcagg agacttcata cattgaggat aactgtaacc    1440
agaatggcgc catctctctg atcttcagcc tgaaggagga agtgggcgcc ctggcaaagg    1500
tgctgcgcct gtttgaggag aacgacgtga atctgaccca catcgagtcc ggccttcta     1560 gactgaagaa ggacgagtac gagttcttta cccacctgga taagcggtcc ctgccagccc    1620
tgacaaacat catcaagatc ctgaggcacg acatcggagc aaccgtgcac gagctgtctc    1680
gggacaagaa gaaggatacc gtgccctggt ccctcggac aatccaggag ctggatagat     1740
ttgccaacca gatcctgtct tacggagcag agctggacgc agatcaccct ggcttcaagg    1800
acccagtgta tcgggcccgg agaaagcagt tgccgatat cgcctacaat tataggcacg     1860
gacagccaat ccctcgcgtg gagtatatgg aggaggagaa gaagacctgg ggcacagtgt    1920
tcaagaccct gaagagcctg tacaagacac acgcctgcta cgagtataac cacatcttcc    1980
ccctgctgga gaagtattgt ggctttcacg aggacaatat ccctcagctg gaggacgtga    2040
gccagttcct gcagacctgc acaggcttta ggctgaggcc agtggcagga ctgctgagct    2100
cccgggactt cctgggagga ctggccttca gagtgtttca ctgcacccag tacatcaggc    2160
acggctccaa gccaatgtat acaccagagc ccgacatctg tcacgagctg ctgggccacg    2220 tgccctgtt tagcgataga tccttcgccc agttttccca ggagatcgga ctggcatctc     2280
tgggagcacc tgacgagtac atcgagaagc tggccaccat ctattggttc acagtggagt    2340
ttggcctgtg caagcagggc gatagcatca aggcctacgg agcaggactg ctgtctagct    2400
tcggcgagct gcagtattgt ctgtccgaga gccaaagct gctgccctg gagctggaga     2460 agaccgccat ccagaactac accgtgacag agttccagcc cctgtactat gtggccgagt    2520
cttttaacga tgccaaggag aaggtgagaa atttcgccgc cacaatccct aggcccttca    2580
gtgtgcgtta cgacccttat acccagagga tcgaggtgct ggataataca cagcagctga    2640
agatcctggc tgactcaatc aatagcgaaa tcggaatcct gtgctccgcc ctgcagaaaa    2700
tcaaatgaga attcaaggcc tctcgagcct ctagaactat agtgagtcgt attacgtaga    2760
tccagacatg ataagataca ttgatgagtt tggacaaacc acaactagaa tgcagtgaaa    2820
aaaatgcttt atttgtgaaa tttgtgatgc tattgcttta tttgtaacca ttataagctg    2880
caataaacaa gttaacaaca acaattgcat tcattttatg tttcaggttc agggggaggt    2940
gtgggaggtt ttttaagctt tacgtacgat cgtcgagcag ctgttgtcct ggagaacgga    3000
gtcctgagca gaaaactctc agactttggg caggtaagcc tgttgggctt ccactgctag    3060
gagagaattg gttccccaca tgtgaaagca gtctgggaaa tgctggtatt ccagtctcc    3120 taaggctact aagaaatatg actttattta gaggcgagga aaatgcccag gaagtcaact    3180
gatgagacta gtcttaacaa gttgaggata cagaaagttg gggatctgag ctgctaccaa    3240
catctgtgtg tctttgggtg gctcattggt atcctctgcc tattggcttt atcttctgta    3300
```

| cactgaaagg aaatggctgg tccttagtca cctggggtgg gagtccctat ctctccaggg | 3360 |
| atacttattc aatcctttct tctgggtatc aaaatgacaa gcttgtaaga aactgtcctc | 3420 |
| tttcggcttt caggaggtga tgtcgcatga agagaatttg ggggggggga cttactcaga | 3480 |
| accaaggagg gagaaattaa acagagaggg aaatgaacag gagttagccc ggagcctgaa | 3540 |
| gcaccttggg gattatgctg ggggtggagg gaatccattg tcctccctag ggagggcttg | 3600 |
| cagaacatgt tcttttctgt gatatttgta ctttccccag attgcaaatc atggtttgta | 3660 |
| cactgagatt cagtctctgg aggtaatatg cctttcctag cttttccttg gacaggacta | 3720 |
| aggggttgag ggttgcctgg agtcagagaa atttgtgtta aagaaggttg atatga | 3776 |

<210> SEQ ID NO 80
<211> LENGTH: 4186
<212> TYPE: DNA
<213> ORGANISM: Artificial Sequence
<220> FEATURE:
<223> OTHER INFORMATION: Synthetic polynucleotide

<400> SEQUENCE: 80

| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctggagg ggtggagtcg tgacgtgaat tacgtcatag | 180 |
| ggttagggag gtcctgcata tgcggccgca gcattagctt ccatttatgc agtgtaaatg | 240 |
| gtgagaacag ccccgactga atacccagag catcatctcg tctgtgtcat tcatgcacat | 300 |
| aacatatctc agcgaggtgg ccctctgtc ctctttgcag agacccagcc accatactag | 360 |
| tacctagaga actggctgga tttcagcccc gatacctccg ggcttttgct catgttcgcc | 420 |
| tcataggtc atctgggtgg ttgcctaagg aaaagtatgt catggagact aacttgcttg | 480 |
| gcattgaata aaaggtgagt tgagagtgga gcgtgtttaa attgcaatcc tgcctctatt | 540 |
| tctgtgcttg cagggaacag tcatccttaa ttgctatcct ccatcatcat catgattatt | 600 |
| tctggttttt ctctggttgc ggagaatcca tactccaggt attccaatgt ctcagcattg | 660 |
| ccaggcctgt ctgagcgtca ggatgtaggt agtctgggct ctctgccttc tattcttgtc | 720 |
| caggatactc tgccaaaaga atcatgttgt ggctgccacc cctcccacaa agcctcccgc | 780 |
| ttgggtcagt ccaggactgg agttgggtat ggactgttca tgtctatcca ctgctacgtc | 840 |
| agggcaacac ccactgagag tgaccttgta gactgcagtg ggagacaccc ttcaaaacct | 900 |
| ctcctctcct gtcctgagag ccaggttaaa accatcagcc ccgcatcctg agtgcaaact | 960 |
| tttcctaacc ctgctgctaa gctagacacc ccacttactg agagccagcc cctaaaatgg | 1020 |
| gcaaacattg caagcagcaa acagcaaaca cacagccctc cctgcctgct gaccttggag | 1080 |
| ctggggcaga ggtcagagac ctctctgggc ccatgccacc tccaacatcc actcgaccc | 1140 |
| ttggaatttc ggtggagagg agcagaggtt gtcctggcgt ggtttaggta gtgtgagagg | 1200 |
| ggaatgactc ctttcggtaa gtgcagtgga agctgtacac tgcccaggca aagcgtccgg | 1260 |
| gcagcgtagg cgggcgactc agatcccagc cagtggactt agcccctgtt tgctcctccg | 1320 |
| ataactgggg tgaccttggt taatattcac cagcagcctc cccgttgcc cctctggatc | 1380 |
| cactgcttaa atacggacga ggacagggcc ctgtctcctc agcttcaggc accaccactg | 1440 |
| acctgggaca gtgaatcctc taaggtaaat ataaaatttt taagtgtata atgtgttaaa | 1500 |
| ctactgattc taattgtttc tctcttttag attccaacct ttggaactga ccgccaccat | 1560 |
| gtccaccgct gtgctggaga accctgggct ggggaggaaa ctgtcagact tcgggcagga | 1620 |

```
gacttcatac attgaggata actgtaacca gaatggcgcc atctctctga tcttcagcct  1680
gaaggaggaa gtgggcgccc tggcaaaggt gctgcgcctg tttgaggaga acgacgtgaa  1740
tctgacccac atcgagtccc ggccttctag actgaagaag gacgagtacg agttctttac  1800
ccacctggat aagcggtccc tgccagccct gacaaacatc atcaagatcc tgaggcacga  1860
catcggagca accgtgcacg agctgtctcg ggacaagaag aaggataccg tgccctggtt  1920
ccctcggaca atccaggagc tggatagatt tgccaaccag atcctgtctt acggagcaga  1980
gctggacgca gatcaccctg gcttcaagga cccagtgtat cgggcccgga gaaagcagtt  2040
tgccgatatc gcctacaatt ataggcacgg acagccaatc cctcgcgtgg agtatatgga  2100
ggaggagaag aagacctggg gcacagtgtt caagaccctg aagagcctgt acaagacaca  2160
cgcctgctac gagtataacc acatcttccc cctgctggag aagtattgtg ctttcacga  2220 ggacaatatc cctcagctgg aggacgtgag ccagttcctg cagacctgca caggctttag  2280
gctgaggcca gtggcaggac tgctgagctc ccgggacttc ctgggaggac tggccttcag  2340
agtgtttcac tgcacccagt acatcaggca cggctccaag ccaatgtata caccagagcc  2400
cgacatctgt cacgagctgc tgggccacgt gcccctgttt agcgatagat ccttcgccca  2460
gttttcccag gagatcggac tggcatctct gggagcacct gacgagtaca tcgagaagct  2520
ggccaccatc tattggttca cagtggagtt tggcctgtgc aagcagggcg atagcatcaa  2580
ggcctacgga gcaggactgc tgtctagctt cggcgagctg cagtattgtc tgtccgagaa  2640
gccaaagctg ctgcccctgg agctggaaaa gaccgccatc cagaactaca ccgtgacaga  2700
gttccagccc ctgtactatg tggccgagtc ttttaacgat gccaaggaga aggtgagaaa  2760
tttcgccgcc acaatcccta ggcccttcag tgtgcgttac gacccttata cccagaggat  2820
cgaggtgctg ataatacac agcagctgaa gatcctggct gactcaatca atagcgaaat  2880
cggaatcctg tgctccgccc tgcagaaaat caaatgagaa ttcaaggcct ctcgagcctc  2940
tagaactata gtgagtcgta ttacgtagat ccagacatga taagatacat tgatgagttt  3000
ggacaaacca caactagaat gcagtgaaaa aaatgcttta tttgtgaaat ttgtgatgct  3060
attgctttat ttgtaaccat tataagctgc aataaacaag ttaacaacaa caattgcatt  3120
cattttatgt ttcaggttca gggggaggtg tgggaggttt tttaagcttt acgtacgatc  3180
gtcgagcagc tgttgtcctg gagaacggag tcctgagcag aaaactctca gactttgggc  3240
aggtaagcct gttgggcttc cactgctagg agagaattgg ttccccacat gtgaaagcag  3300
tctgggaaat gctggtattt ccagtctcct aaggctacta gaaatatga ctttatttag  3360 aggcgaggaa aatgcccagg aagtcaactg atgagactag tcttaacaag ttgaggatac  3420
agaaagttgg ggatctgagc tgctaccaac atctgtgtgt ctttgggtgg ctcattggta  3480
tcctctgcct attggcttta tcttctgtac actgaaagga aatggctggt ccttagtcac  3540
ctggggtggg agtccctatc tctccaggga tacttattca atccttcctt ctgggtatca  3600 aaaatgacaag cttgtaagaa actgtcctct ttcggctttc aggaggtgat gtcgcatgaa  3660
gagaatttgg gggggggggac ttactcagaa ccaaggaggg agaaattaaa cagagaggga  3720
aatgaacagg agttagcccg gagcctgaag caccttgggg attatgctgg gggtggaggg  3780
aatccattgt cctccctagg gagggcttgc agaacatgtt ctttctgtg atatttgtac  3840 tttcccccaga ttgcaaatca tggtttgtac actgagattc agtctctgga ggtaatatgc  3900 ctttctagc ttttccttgg acaggactaa ggggttgagg gttgcctgga gtcagagaaa  3960
```

```
tttgtgttaa agaaggttga tatgaaacct gcaggtctag atacgtagat aagtagcatg    4020
gcgggttaat cattaactac aaggaacccc tagtgatgga gttggccact ccctctctgc    4080
gcgctcgctc gctcactgag gccgggcgac caaaggtcgc ccgacgcccg ggctttgccc    4140
gggcggcctc agtgagcgag cgagcgcgca gagagggagt ggccaa                   4186

<210> SEQ ID NO 81
<211> LENGTH: 3713
<212> TYPE: DNA
<213> ORGANISM: Artificial Sequence
<220> FEATURE:
<223> OTHER INFORMATION: Synthetic polynucleotide

<400> SEQUENCE: 81
gcttcaggag cagttgtgcg aatagctgga gaacaccagg ctggatttaa acccagatcg      60
ctcttacatt tgctctttac ctgctgtgct cagcgttcac gtgccctcta gctgtagttt     120
tctgaagtca gcgcacagca aggcagtgtg cttagaggtt aacagaaggg aaaacaacaa     180
caacaaaaat ctaaatgaga atcctgactg tttcagctgg gggtaagggg ggcggattat     240
tcatataatt gttataccag acggtcgcag gcttagtcca attgcagaga actcgcttcc     300
caggcttctg agagtcccgg aagtgcctaa acctgtctaa tcgacggggc ttgggtggcc     360
cgtcgctccc tggcttcttc cctttaccca gggcgggcag cgaagtggtg cctcctgcgt     420
cccccacacc ctccctcagc ccctccctc cggcccgtcc tgggcaggtg acctggagca     480
tccggcaggc tgccctggcc tctgcgtca ggacaacgcc cacgaggggc gttactgtgc     540
ggagatgcac cacgcaagag acaccctttg taactctctt ctcctcccta gtgcgaggtt     600
aaaaccttca gccccacgtg ctgtttgcaa acctgcctgt acctgaggcc ctaaaaagcc     660
agagacctca ctcccgggga gccagcatgt ccactgcgt cctggaaaac ccaggcttgg     720
gcaggaaact ctctgacttt ggacaggtga gccacggcag cctgagctgc tcagttaggg     780
gaatttgggc ctccagagaa agagatctga agactgctgg tgcttcctgg tttcataagc     840
tcagtaagaa gtctgaattc gttggaagct gatgagaata tccaggaagt caacagacaa     900
atgtcctcaa caattgtttc taagtaggag aacatctgtc ctcggtggct ttcacaggaa     960
aagcttctga cctcttctct tcctcccaca gggcggtacc agatctggca gcggagaggg    1020
cagaggaagt cttctaacat gcggtgacgt ggaggagaat cccggcccta ggggtacctc    1080
caccgctgtg ctggagaacc ctgggctggg gaggaaactg tcagacttcg ggcaggagac    1140
ttcatacatt gaggataact gtaaccagaa tggcgccatc tctctgatct tcagcctgaa    1200
ggaggaagtg ggcgccctgg caaaggtgct gcgcctgttt gaggagaacg acgtgaatct    1260
gacccacatc gagtcccggc cttctagact gaagaaggac gagtacgagt tctttaccca    1320
cctggataag cggtccctgc cagccctgac aaacatcatc aagatcctga ggcacgacat    1380
cggagcaacc gtgcacgagc tgtctcggga caagaagaag gataccgtgc cctggttccc    1440
tcggacaatc caggagctgg atagatttgc caaccagatc ctgtcttacg agcagagctc    1500
ggacgcagat caccctggct tcaaggaccc agtgtatcgg gccggagaaa agcagtttgc    1560
cgatatcgcc tacaattata ggcacggaca gccaatccct cgcgtggagt atatggagga    1620
ggagaagaag acctggggca cagtgttcaa gaccctgaag agcctgtaca agacacacgc    1680
ctgctacgag tataaccaca tcttccccct gctggagaag tattgtggct ttcacgagga    1740
caatatccct cagctggagg acgtgagcca gttcctgcag acctgcacag gctttaggct    1800
gaggccagtg gcaggactgc tgagctcccg ggacttcctg ggaggactgg ccttcagagt    1860
```

```
gtttcactgc acccagtaca tcaggcacgg ctccaagcca atgtatacac cagagcccga   1920
catctgtcac gagctgctgg gccacgtgcc cctgtttagc gatagatcct tcgcccagtt   1980
ttcccaggag atcggactgg catctctggg agcacctgac gagtacatcg agaagctggc   2040
caccatctat tggttcacag tggagtttgg cctgtgcaag cagggcgata gcatcaaggc   2100
ctacggagca ggactgctgt ctagcttcgg cgagctgcag tattgtctgt ccgagaagcc   2160
aaagctgctg cccctggagc tggagaagac cgccatccag aactcaccg tgacagagtt   2220 ccagcccctg tactatgtgg ccgagtcttt taacgatgcc aaggagaagg tgagaaattt   2280
cgccgccaca atccctaggc ccttcagcgt gcggtacgac ccttataccc agaggatcga   2340
ggtgctggat aatacacagc agctgaagat cctggctgac tcaatcaata gcgaaatcgg   2400
aatcctgtgc tccgccctgc agaaaatcaa aggtaagcct atccctaacc ctctcctcgg   2460
tctcgattct acgtgatctt gtggaaagga cgaaacaccg gggaattcaa ggcctctcga   2520
gcctctagaa tccccgagac gtttcgtctc gggatcacta tagtgagtcg tattacgtac   2580
acagtgcagg ggaaagaata gtagagatcc agacatgata agatacattg atgagtttgg   2640
acaaaccaca actagaatgc agtgaaaaaa atgctttatt tgtgaaattt gtgatgctat   2700
tgctttattt gtaaccatta taagctgcaa taaacaagtt aacaacaaca attgcattca   2760
ttttatgttt caggttcagg gggaggtgtg ggaggttttt taactgggat gggatgtgga   2820
atccttctag atttctttg taatatttat aaagtgctct cagcaaggta tcaaaatggc   2880
aaaattgtga gtaactatcc tcctttcatt ttgggaagaa gatgaggcat gaagagaatt   2940
cagacagaaa cttactcaga ccaggggagg cagaaactaa gcagagagga aaatgaccaa   3000
gagttagccc tgggcatgga atgtgaaaga accctaaacg tgacttggaa ataatgccca   3060
aggtatattc cattctccgg gatttgttgg catttcttg aggtgaagaa ttgcagaata   3120
cattctttaa tgtgacctac atatttaccc atgggaggaa gtctgctcct ggactcttga   3180
gattcagtca taaagcccag gccagggaaa taatgtaagt ctgcaggccc ctgtcatcag   3240
taggattagg gagaagagtt ctcagtagaa acaggagg ctggagagaa agaatggtt   3300 aatgttaacg ttaatataac tagaaagact gcagaactta ggactgatt ttatttgaat   3360 ccttaaaaaa aaaatttctt atgaaaatag tacatggctc ttaggagaca gaacttattg   3420
tacagaggaa cagcgtgaga gtcagagtga tcccagaaca ggtcctggct ccatcctgca   3480
catagttttg gtgctgctgg caatacggtc cccacaactg tgggaagggg ttaggggcag   3540
ggatctcatc aggaaagcat aggggtttaa agttctttat agagcactta gaagattgag   3600
aatccacaaa ttatattaat aacaaacaaa gtagtgtcgt gttatatagt aaatgtgaat   3660
ttgcagacac atttagggaa aagttataat taaaaaaata ggctgtatat ata          3713
```

<210> SEQ ID NO 82
<211> LENGTH: 4139
<212> TYPE: DNA
<213> ORGANISM: Artificial Sequence
<220> FEATURE:
<223> OTHER INFORMATION: Synthetic polynucleotide

<400> SEQUENCE: 82

```
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcctggagg ggtggagtcg tgacgtgaat tacgtcatag   180
```

-continued

```
ggttagggag gtcctgcata tgcggccgct tcaggagcag ttgtgcgaat agctggagaa    240
caccaggctg gatttaaacc cagatcgctc ttacatttgc tctttacctg ctgtgctcag    300
cgttcacgtg ccctctagct gtagttttct gaagtcagcg cacagcaagg cagtgtgctt    360
agaggttaac agaagggaaa acaacaacaa caaaaatcta aatgagaatc ctgactgttt    420
cagctggggg taagggggggc ggattattca tataattgtt ataccagacg gtcgcaggct    480
tagtccaatt gcagagaact cgcttcccag gcttctgaga gtcccggaag tgcctaaacc    540
tgtctaatcg acgggcttg ggtggcccgt cgctccctgg cttcttccct ttacccaggg     600
cgggcagcga agtggtgcct cctgcgtccc ccacaccctc cctcagcccc tcccctccgg    660
cccgtcctgg gcaggtgacc tggagcatcc ggcaggctgc cctggcctcc tgcgtcagga    720
caacgcccac gagggcgtt actgtgcgga gatgcaccac gcaagagaca ccctttgtaa     780
ctctcttctc ctccctagtg cgaggttaaa accttcagcc ccacgtgctg tttgcaaacc    840
tgcctgtacc tgaggcccta aaagccaga gacctcactc ccggggagcc agcatgtcca     900
ctgcggtcct ggaaaaccca ggcttgggca ggaaactctc tgactttgga caggtgagcc    960
acggcagcct gagctgctca gttagggaa tttgggcctc cagagaaaga gatctgaaga    1020
ctgctggtgc ttcctggttt cataagctca gtaagaagtc tgaattcgtt ggaagctgat   1080
gagaatatcc aggaagtcaa cagacaaatg tcctcaacaa ttgtttctaa gtaggagaac   1140
atctgtcctc ggtggctttc acaggaaaag cttctgacct cttctcttcc tcccacaggg   1200
cggtaccaga tctggcagcg gagagggcag aggaagtctt ctaacatgcg gtgacgtgga   1260
ggagaatccc ggccctaggg gtacctccac cgctgtgctg gagaaccctg ggctggggag   1320
gaaactgtca gacttcgggc aggagacttc atacattgag gataactgta accagaatgg   1380
cgccatctct ctgatcttca gcctgaagga ggaagtgggc gccctggcaa aggtgctgcg   1440
cctgtttgag gagaacgacg tgaatctgac ccacatcgag tcccggcctt ctagactgaa   1500
gaaggacgag tacgagttct ttacccacct ggataagcgg tccctgccag ccctgacaaa   1560
catcatcaag atcctgaggc acgacatcgg agcaaccgtg cacgagctgt ctcgggacaa   1620
gaagaaggat accgtgccct ggttccctcg gacaatccag gagctggata gatttgccaa   1680
ccagatcctg tcttacggag cagagctgga cgcagatcac cctggcttca aggacccagt   1740
gtatcgggcc cggagaaagc agtttgccga tatcgcctac aattataggc acggacagcc   1800
aatccctcgc gtggagtata tggaggagga gaagaagacc tggggcacag tgttcaagac   1860
cctgaagagc ctgtacaaga cacacgcctg ctacgagtat aaccacatct tccccctgct   1920
ggagaagtat tgtggctttc acgaggacaa tatccctcag ctggaggacg tgagccagtt   1980
cctgcagacc tgcacaggct ttaggctgag gccagtggca ggactgctga gctcccggga   2040
cttcctggga ggactggcct tcagagtgtt tcactgcacc cagtacatca ggcacggctc   2100
caagccaatg tataccaccag agcccgacat ctgtcgagag ctgctgggcc acgtgcccct   2160
gtttagcgat agatccttcg cccagttttc ccaggagatc ggactggcat ctctgggagc   2220
acctgacgag tacatcgaga agctggccac catctattgg ttcacagtgg agtttggcct   2280
gtgcaagcag ggcgatagca tcaaggccta cggagcagga ctgctgtcta gcttcggcga   2340
gctgcagtat tgtctgtccg agaagccaaa gctgctgccc ctggagctgg agaagaccgc   2400
catccagaac tacaccgtga cagagttcca gccctgtac tatgtggccg agtcttttaa    2460
cgatgccaag gagaaggtga gaaatttcgc cgccacaatc cctaggccct tcagcgtgcg   2520 gtacgacccct tatacccaga ggatcgaggt gctggataat acacagcagc tgaagatcct   2580
```

```
ggctgactca atcaatagcg aaatcggaat cctgtgctcc gccctgcaga aaatcaaagg    2640
taagcctatc cctaaccctc tcctcggtct cgattctacg tgatcttgtg gaaaggacga    2700
aacaccgggg aattcaaggc ctctcgagcc tctagaatcc ccgagacgtt tcgtctcggg    2760
atcactatag tgagtcgtat tacgtacaca gtgcagggga agaatagta gagatccaga     2820 catgataaga tacattgatg agtttggaca aaccacaact agaatgcagt gaaaaaaatg    2880
ctttatttgt gaaatttgtg atgctattgc tttatttgta accattataa gctgcaataa    2940
acaagttaac aacaacaatt gcattcattt tatgtttcag gttcaggggg aggtgtggga    3000
ggttttttaa ctgggatggg atgtggaatc cttctagatt tcttttgtaa tatttataaa    3060
gtgctctcag caaggtatca aaatggcaaa attgtgagta actatcctcc tttcattttg    3120
ggaagaagat gaggcatgaa gagaattcag acagaaactt actcagacca ggggaggcag    3180
aaactaagca gagaggaaaa tgaccaagag ttagccctgg gcatggaatg tgaaagaacc    3240
ctaaacgtga cttggaaata atgcccaagg tatattccat tctccgggat tgttggcat    3300 tttcttgagg tgaagaattg cagaatacat tctttaatgt gacctacata tttacccatg    3360
ggaggaagtc tgctcctgga ctcttgagat tcagtcataa agcccaggcc agggaaataa    3420
tgtaagtctg caggcccctg tcatcagtag gattagggag aagagttctc agtagaaaac    3480
agggaggctg gagagaaaag aatggttaat gttaacgtta atataactag aaagactgca    3540
gaacttagga ctgatttta tttgaatcct taaaaaaaa atttcttatg aaaatagtac     3600
atggctctta ggagacagaa cttattgtac agaggaacag cgtgagagtc agagtgatcc    3660
cagaacaggt cctggctcca tcctgcacat agttttggtg ctgctggcaa tacggtcccc    3720
acaactgtgg gaaggggtta ggggcaggga tctcatcagg aaagcatagg ggtttaaagt    3780
tctttataga gcacttagaa gattgagaat ccacaaatta tattaataac aaacaaagta    3840
gtgtcgtgtt atatagtaaa tgtgaatttg cagacacatt tagggaaaag ttataattaa    3900
aaaaataggc tgtatatata ctagatacgt agataagtag cctgcaggtc tagatacgta    3960
gataagtagc atggcgggtt aatcattaac tacaaggaac ccctagtgat ggagttggcc    4020
actccctctc tgcgcgctcg ctcgctcact gaggccgggc gaccaaaggt cgcccgacgc    4080
ccgggctttg cccgggcggc ctcagtgagc gagcgagcgc gcagagaggg agtggccaa     4139
```

<210> SEQ ID NO 83
<211> LENGTH: 1353
<212> TYPE: DNA
<213> ORGANISM: Artificial Sequence
<220> FEATURE:
<223> OTHER INFORMATION: Synthetic polynucleotide

<400> SEQUENCE: 83

```
tccaccgctg tgctggagaa ccctgggctg gggaggaaac tgtcagactt cgggcaggag     60
acttcataca ttgaggataa ctgtaaccag aatggcgcca tctctctgat cttcagcctg    120
aaggaggaag tgggcgccct ggcaaaggtg ctgcgcctgt tgaggagaa cgacgtgaat     180 ctgacccaca tcgagtcccg gccttctaga ctgaagaagg acgagtacga gttctttacc    240
cacctggata agcggtccct gccagccctg acaaacatca tcaagatcct gaggcacgac    300
atcggagcaa ccgtgcacga gctgtctcgg gacaagaaga aggataccgt gccctggttc    360
cctcggacaa tccaggagct ggatagattt gccaaccaga tcctgtctta cggagcagag    420
ctggacgcag atcaccctgg cttcaaggac ccagtgtatc gggcccggag aaagcagttt    480
```

```
gccgatatcg cctacaatta taggcacgga cagccaatcc ctcgcgtgga gtatatggag      540
gaggagaaga agacctgggg cacagtgttc aagaccctga agagcctgta caagacacac      600
gcctgctacg agtataacca catcttcccc ctgctggaga agtattgtgg ctttcacgag      660
gacaatatcc ctcagctgga ggacgtgagc cagttcctgc agacctgcac aggctttagg      720
ctgaggccag tggcaggact gctgagctcc cgggacttcc tgggaggact ggccttcaga      780
gtgtttcact gcacccagta catcaggcac ggctccaagc caatgtatac accagagccc      840
gacatctgtc acgagctgct gggccacgtg cccctgttta gcgatagatc cttcgcccag      900
ttttcccagg agatcggact ggcatctctg gagcacctg acgagtacat cgagaagctg       960
gccaccatct attggttcac agtggagttt ggcctgtgca agcagggcga tagcatcaag     1020
gcctacggag caggactgct gtctagcttc ggcgagctgc agtattgtct gtccgagaag     1080
ccaaagctgc tgcccctgga gctggagaag accgccatcc agaactacac cgtgacagag     1140
ttccagcccc tgtactatgt ggccgagtct tttaacgatg ccaaggagaa ggtgagaaat     1200
ttcgccgcca caatccctag gcccttcagc gtgcggtacg acccttatac ccagaggatc     1260
gaggtgctgg ataatacaca gcagctgaag atcctggctg actcaatcaa tagcgaaatc     1320
ggaatcctgt gctccgccct gcagaaaatc aaa                                  1353
```

<210> SEQ ID NO 84  
<211> LENGTH: 800  
<212> TYPE: DNA  
<213> ORGANISM: Artificial Sequence  
<220> FEATURE:  
<223> OTHER INFORMATION: Synthetic polynucleotide

<400> SEQUENCE: 84

```
agcattagct tccatttatg cagtgtaaat ggtgagaaca gccccgactg aatacccaga       60
gcatcatctc gtctgtgtca ttcatgcaca taacatatct cagcgaggtg gcccttctgt      120
cctctttgca gagacccagc caccatacta gtacctagag aactggctgg atttcagccc      180
cgatacctcc gggcttttgc tcatgttcgc tcatagggt catctgggtg gttgcctaag       240
gaaaagtatg tcatggagac taacttgctt ggcattgaat aaaaggtgag ttgagagtgg      300
agcgtgttta aattgcaatc ctgcctctat ttctgtgctt gcagggaaca gtcatcctta     360
attgctatcc tccatcatca tcatgattat ttctggtttt tctctggttg cggagaatcc     420
atactccagg tattccaatg tctcagcatt gccaggcctg tctgagcgtc aggatgtagg      480
tagtctgggc tctctgcctt ctattcttgt ccaggatact ctgccaaaag aatcatgttg     540
tggctgccac ccctcccaca aagcctcccg cttgggtcag tccaggactg gagttgggta     600
tggactgttc atgtctatcc actgctacgt cagggcaaca cccactgaga gtgaccttgt     660
agactgcagt gggagacacc cttcaaaacc tctcctctcc tgtcctgaga gccaggttaa     720
aaccatcagc cccgcatcct gagtgcaaac ttttcctaac cctgctgcta agctagacac     780
ctcacttact gagagccagc                                                  800
```

<210> SEQ ID NO 85  
<211> LENGTH: 800  
<212> TYPE: DNA  
<213> ORGANISM: Artificial Sequence  
<220> FEATURE:  
<223> OTHER INFORMATION: Synthetic polynucleotide

<400> SEQUENCE: 85

```
agcattagct tccatttatg cagtgtaaat ggtgagaaca gccccgactg aatacccaga       60
```

```
gcatcatctc gtctgtgtca ttcatgcaca taacatatct cagcgaggtg gcccttctgt    120
cctctttgca gagacccagc caccatacta gtacctagag aactggctgg atttcagccc    180
cgatacctcc gggcttttgc tcatgttcgc tcatagggt catctgggtg gttgcctaag     240
gaaaagtatg tcatggagac taacttgctt ggcattgaat aaaaggtgag ttgagagtgg    300
agcgtgttta aattgcaatc ctgcctctat ttctgtgctt gcagggaaca gtcatcctta    360
attgctatcc tccatcatca tcatgattat ttctggtttt tctctggttg cggagaatcc    420
atactccagg tattccaatg tctcagcatt gccaggcctg tctgagcgtc aggatgtagg    480
tagtctgggc tctctgcctt ctattcttgt ccaggatact ctgccaaaag aatcatgttg    540
tggctgccac ccctcccaca aagcctcccg cttgggtcag tccaggactg gagttgggta    600
tggactgttc atgtctatcc actgctacgt cagggcaaca cccactgaga gtgaccttgt    660
agactgcagt gggagacacc cttcaaaacc tctcctctcc tgtcctgaga gccaggttaa    720
aaccatcagc cccgcatcct gagtgcaaac ttttcctaac cctgctgcta agctagacac    780
cccacttact gagagccagc                                                800

<210> SEQ ID NO 86
<211> LENGTH: 800
<212> TYPE: DNA
<213> ORGANISM: Artificial Sequence
<220> FEATURE:
<223> OTHER INFORMATION: Synthetic polynucleotide

<400> SEQUENCE: 86
gcagctgttg tcctggagaa cggagtcctg agcagaaaac tctcagactt tgggcaggta     60
agcctgttgg gcttccactg ctaggagaga attggttccc cacatgtgaa agcagtctgg    120
gaaatgctgg tatttccagt ctcctaaggc tactaagaaa tatgactta tttagaggcg     180 aggaaaatgc ccaggaagtc aactgatgag actagtctta acaagttgag gatacagaaa    240
gttggggatc tgagctgcta ccaacatctg tgtgtctttg ggtggctcat tggtatcctc    300
tgcctattgg ctttatcttc tgtacactga aaggaaatgg ctggtcctta gtcacctggg    360
gtgggagtcc ctatctctcc agggatactt attcaatcct ttcttctggg tatcaaaatg    420
acaagcttgt aagaaactgt cctctttcgg ctttcaggag gtgatgtcgc atgaagagaa    480 tttgggggg gggacttact cagaaccaag gagggagaaa ttaaacagag agggaaatga    540
acaggagtta gcccggagcc tgaagcacct tggggattat gctgggggtg gagggaatcc    600
attgtcctcc ctagggaggg cttgcagaac atgttctttt ctgtgatatt tgtactttcc    660
ccagattgca aatcatggtt tgtacactga gattcagtct ctggaggtaa tatgcctttt    720
ctagcttttc cttggacagg actaagggggt tgagggttgc ctggagtcag agaaatttgt    780
gttaaagaag gttgatatga                                                800
```

ADENO-ASSOCIATED VIRUS COMPOSITIONS FOR RESTORING PAH GENE FUNCTION AND METHODS OF USE THEREOF

RELATED APPLICATIONS

This application claims priority to U.S. Provisional Patent Application Serial Nos. 63/030,341, filed May 27, 2020, and 63/117,252, filed Nov. 23, 2020, the entire disclosures of which are hereby incorporated herein by reference.

SEQUENCE LISTING

This application contains a sequence listing which has been submitted electronically in ASCII format and is hereby incorporated by reference in its entirety (said ASCII copy, created on May 24, 2021, is named "404217-HMW-040US-183160_SL.txt" and is 213,352 bytes in size).

BACKGROUND

Phenylketonuria (PKU) is an autosomal recessive genetic disorder where the majority of cases are caused by mutations in the phenylalanine hydroxylase (PAH) gene. The PAH gene encodes a hepatic enzyme that catalyzes the hydroxylation of L-phenylalanine (Phe) to L-tyrosine (Tyr) upon multimerization. Reduction or loss of PAH activity leads to phenylalanine accumulation and its conversion into phenylpyruvate (also known as phenylketone). This abnormality in phenylalanine metabolism impairs neuronal maturation and the synthesis of myelin, resulting in mental retardation, seizures, and other serious medical problems.

Currently, there is no cure for PKU. The standard of care is diet management by minimizing foods that contain high amounts of phenylalanine. Dietary management from birth with a low phenylalanine formula largely prevents the development of the neurological consequences of the disorder. However, even on a low-protein diet, children still suffer from growth retardation, and adults often have osteoporosis and vitamin deficiencies. Moreover, adherence to life-long dietary treatment is difficult, particularly beyond school age.

New treatment strategies have recently emerged, including large neutral amino acid (LNAA) supplementation, cofactor tetrahydrobiopterin therapy, enzyme replacement therapy, and genetically modified probiotic therapy. However, these strategies suffer from shortcomings. The LNAA supplementation is suitable only for adults not adhering to a low Phe diet. The cofactor tetrahydrobiopterin can only be used in some mild forms of PKU. Enzyme replacement by administration of a substitute for PAH, e.g., phenylalanine ammonia-lyase (PAL), can lead to immune responses that reduce the efficacy and/or cause side effects. As to genetically modified probiotic therapy, the pathogenicity of PAL-expressing E. coli has been a concern.

Gene therapy provides a unique opportunity to cure PKU. Retroviral vectors, including lentiviral vectors, are capable of integrating nucleic acids into host cell genomes. However, these vectors may raise safety concerns due to their non-targeted insertion into the genome. For example, there is a risk of the vector disrupting a tumor suppressor gene or activating an oncogene, thereby causing a malignancy. Indeed, in a clinical trial for treating X-linked severe combined immunodeficiency (SCID) by transducing CD34[+] bone marrow precursors with a gammaretroviral vector, four out of ten patients developed leukemia (Hacein-Bey-Abina et al. *J Clin Invest.* (2008) 118(9):3132-42).

It has also been speculated that nuclease-based gene editing technologies, such as meganucleases, zinc finger nucleases (ZFNs), transcription activator-like effector nucleases (TALENs), and clustered, regularly interspaced, short palindromic repeat (CRISPR) technology, may be used to correct defects in the PAH gene in PKU patients. However, each of these technologies raises safety concerns due to the potential for off-target mutation of sites in the human genome similar in sequence to the intended target site.

Accordingly, there is a need in the art for improved gene therapy compositions and methods that can efficiently and safely restore PAH gene function in PKU patients.

SUMMARY

Provided herein are recombinant adeno-associated virus (rAAV) compositions that can restore PAH gene function in cells, and methods for using the same to treat diseases associated with reduction of PAH gene function (e.g., PKU). Also provided are nucleic acids, vectors, packaging systems, and methods for making the adeno-associated virus compositions. The rAAV compositions provided herein are particularly advantageous in that they can efficiently edit the genome of cells (e.g., liver cells) in a subject to express PAH under the control of a liver-specific promoter, and thereby offer a potential cure for PKU patients.

Accordingly, in one aspect, the instant disclosure provides a recombinant adeno-associated virus (rAAV) comprising: (a) an AAV capsid comprising an AAV capsid protein; and (b) an rAAV genome comprising: (i) an editing element for editing a target locus in a PAH gene, comprising at least a portion of a PAH coding sequence operably linked to a transcriptional regulatory element; (ii) a 5' homology arm nucleotide sequence position 5' of the editing element, having homology to a first genomic region 5' to the target locus; and (iii) a 3' homology arm nucleotide sequence positioned 3' of the editing element, having homology to a second genomic region 3' to the target locus.

In certain embodiments, the editing element comprises a PAH coding sequence. In certain embodiments, the PAH coding sequence encodes an amino acid sequence set forth in SEQ ID NO: 33. In certain embodiments, the PAH coding sequence comprises the nucleotide sequence set forth in SEQ ID NO: 53. In certain embodiments, the PAH coding sequence is silently altered. In certain embodiments, the PAH coding sequence comprises a nucleotide sequence that is at least 85%, 86%, 87%, 88%, 89%, 90%, 91%, 92%, 93%, 94%, 95%, 96%, 97%, 98%, or 99% identical to the nucleotide sequence set forth in SEQ ID NO: 28, 63, or 83. In certain embodiments, the PAH coding sequence comprises the nucleotide sequence set forth in SEQ ID NO: 28. In certain embodiments, the PAH coding sequence comprises the nucleotide sequence set forth in SEQ ID NO: 63. In certain embodiments, the PAH coding sequence comprises the nucleotide sequence set forth in SEQ ID NO: 83.

In certain embodiments, the transcriptional regulatory element is capable of mediating transcription in a hepatocyte, a renal cell, or a cell in the brain, pituitary gland, adrenal gland, pancreas, urinary bladder, gallbladder, colon, small intestine, or breast. In certain embodiments, the transcriptional regulatory element is endogenous to the PAH gene. In certain embodiments, the transcriptional regulatory element is exogenous to the PAH gene. In certain embodiments, the transcriptional regulatory element is liver specific, optionally wherein the transcriptional regulatory element comprises one or more elements selected from the group consisting of a human albumin promoter, a human transthyretin (TTR) promoter, a human ApoE/C-I hepatic control region (HCR) 1 or 2, a human ApoH promoter, a human SERPINA1 (hAAT) promoter, and a hepatic specific regulatory module thereof. In certain embodiments, the transcriptional regulatory element comprises a nucleotide sequence at least 90% identical to a sequence selected from the group consisting of SEQ ID NO: 25, 26, 27, or 69. In certain embodiments, the transcriptional regulatory element comprises a nucleotide sequence at least 90% identical to the nucleotide sequence set forth in SEQ ID NO: 27. In certain embodiments, the transcriptional regulatory element comprises the nucleotide sequence set forth in SEQ ID NO: 27. In certain embodiments, the transcriptional regulatory element consists of the nucleotide sequence set forth in SEQ ID NO: 27.

In certain embodiments, the editing element further comprises an intron element positioned 5' to the PAH coding sequence and 3' to the transcriptional regulatory element. In certain embodiments, the intron element is an exogenous intron element, optionally wherein the exogenous intron element is an SV40 intron element. In certain embodiments, the SV40 intron element comprises a nucleotide sequence at least 90% identical to the nucleotide sequence set forth in SEQ ID NO: 29. In certain embodiments, the SV40 intron element comprises the nucleotide sequence set forth in SEQ ID NO: 29. In certain embodiments, the SV40 intron element consists of the nucleotide sequence set forth in SEQ ID NO: 29.

In certain embodiments, the editing element further comprises a polyadenylation sequence 3' to the PAH coding sequence. In certain embodiments, the polyadenylation sequence is an exogenous polyadenylation sequence, optionally wherein the exogenous polyadenylation sequence is an SV40 polyadenylation sequence. In certain embodiments, the SV40 polyadenylation sequence comprises a nucleotide sequence at least 90% identical to the nucleotide sequence set forth in SEQ ID NO: 31. In certain embodiments, the SV40 polyadenylation sequence comprises the nucleotide sequence set forth in SEQ ID NO: 31. In certain embodiments, the SV40 polyadenylation sequence consists of the nucleotide sequence set forth in SEQ ID NO: 31.

In certain embodiments, the nucleotide 5' to the target locus is in an intron of a PAH gene. In certain embodiments, the nucleotide 5' to the target locus is in intron 1 of a PAH gene. In certain embodiments, the nucleotide 3' to the target locus is in an intron of a PAH gene. In certain embodiments, the nucleotide 3' to the target locus is in intron 1 of a PAH gene.

In certain embodiments, the PAH gene is a human PAH gene. In certain embodiments, the human PAH gene is wild-type. In certain embodiments, the human PAH gene is a variant PAH gene.

In certain embodiments, the editing element comprises a nucleotide sequence selected from the group consisting of SEQ ID NO: 25, 26, 27, 28, 29, 31, 50, 51, 52, 69, or 70.

In certain embodiments, the 5' homology arm nucleotide sequence is at least 90%, 91%, 92%, 93%, 94%, 95%, 96%, 97%, 98%, 99%, or 100% identical to the first genomic region. In certain embodiments, the 3' homology arm nucleotide sequence is at least 90%, 91%, 92%, 93%, 94%, 95%, 96%, 97%, 98%, 99%, or 100% identical to the second genomic region. In certain embodiments, the first genomic region is located in a first editing window, and the second genomic region is located in a second editing window. In certain embodiments, the first editing window consists of the region of the human genome corresponding to the nucleotide sequence set forth in SEQ ID NO: 37. In certain embodiments, the second editing window consists of the region of the human genome corresponding to the nucleotide sequence set forth in SEQ ID NO: 38. In certain embodiments, the first genomic region consists of the region of the human genome corresponding to the nucleotide sequence set forth in SEQ ID NO: 37. In certain embodiments, the second genomic region consists of the region of the human genome corresponding to the nucleotide sequence set forth in SEQ ID NO: 38. In certain embodiments, each of the 5' and 3' homology arm nucleotide sequences independently has a length of about 100 to about 2000 nucleotides. In certain embodiments, the 5' homology arm comprises a nucleotide sequence that is at least 90%, 91%, 92%, 93%, 94%, 95%, 96%, 97%, 98%, 99%, or 100% identical to the nucleotide sequence set forth in SEQ ID NO: 23. In certain embodiments, the 5' homology arm comprises the nucleotide sequence set forth in SEQ ID NO: 23. In certain embodiments, the nucleotide sequence of the 5' homology arm consists of the nucleotide sequence set forth in SEQ ID NO: 23. In certain embodiments, the 3' homology arm comprises a nucleotide sequence that is at least 90%, 91%, 92%, 93%, 94%, 95%, 96%, 97%, 98%, 99%, or 100% identical to the nucleotide sequence set forth in SEQ ID NO: 24. In certain embodiments, the 3' homology arm comprises the nucleotide sequence set forth in SEQ ID NO: 24. In certain embodiments, the nucleotide sequence of the 3' homology arm consists of the nucleotide sequence set forth in SEQ ID NO: 24.

In certain embodiments, the rAAV genome comprises a nucleotide sequence that is at least 85%, 86%, 87%, 88%, 89%, 90%, 91%, 92%, 93%, 94%, 95%, 96%, 97%, 98%, 99%, or 100% identical to the nucleotide sequence set forth in SEQ ID NO: 43. In certain embodiments, the rAAV genome comprises the nucleotide sequence set forth in SEQ ID NO: 43.

In certain embodiments, the rAAV genome further comprises a 5' inverted terminal repeat (5' ITR) nucleotide sequence 5' of the 5' homology arm nucleotide sequence, and a 3' inverted terminal repeat (3' ITR) nucleotide sequence 3' of the 3' homology arm nucleotide sequence. In certain embodiments, the 5' ITR nucleotide sequence is at least 85%, 86%, 87%, 88%, 89%, 90%, 91%, 92%, 93%, 94%, 95%, 96%, 97%, 98%, 99%, or 100% identical to the nucleotide sequence set forth in SEQ ID NO: 14, and the 3' ITR nucleotide sequence is at least 85%, 86%, 87%, 88%, 89%, 90%, 91%, 92%, 93%, 94%, 95%, 96%, 97%, 98%, 99% or 100% identical to the nucleotide sequence set forth in SEQ ID NO: 18.

In certain embodiments, the rAAV genome comprises the nucleotide sequence set forth in SEQ ID NO: 73 and/or 74. In certain embodiments, the rAAV genome comprises the nucleotide sequence set forth in SEQ ID NO: 75 and/or 76.

In certain embodiments, the rAAV genome comprises a nucleotide sequence that is at least 85%, 86%, 87%, 88%, 89%, 90%, 91%, 92%, 93%, 94%, 95%, 96%, 97%, 98%, 99%, or 100% identical to the nucleotide sequence set forth in SEQ ID NO: 45. In certain embodiments, the rAAV genome comprises the nucleotide sequence set forth in SEQ ID NO: 45. In certain embodiments, the nucleotide sequence of the rAAV genome consists of the nucleotide sequence set forth in SEQ ID NO: 45.

In certain embodiments, the AAV capsid protein comprises an amino acid sequence that is at least 95% identical to the amino acid sequence of amino acids 203-736 of SEQ ID NO: 1, 2, 3, 4, 5, 6, 7, 8, 9, 10, 11, 12, 13, 15, 16, or 17.

In certain embodiments, the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G. In certain embodiments:

(a) the amino acid in the capsid protein corresponding to amino acid 626 of SEQ ID NO: 16 is G, and the amino acid in the capsid protein corresponding to amino acid 718 of SEQ ID NO: 16 is G;
(b) the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M;
(c) the amino acid in the capsid protein corresponding to amino acid 505 of SEQ ID NO: 16 is R, and the amino acid in the capsid protein corresponding to amino acid 687 of SEQ ID NO: 16 is R;
(d) the amino acid in the capsid protein corresponding to amino acid 346 of SEQ ID NO: 16 is A, and the amino acid in the capsid protein corresponding to amino acid 505 of SEQ ID NO: 16 is R; or
(e) the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C.

In certain embodiments, the capsid protein comprises the amino acid sequence of amino acids 203-736 of SEQ ID NO: 1, 2, 3, 4, 5, 6, 7, 8, 9, 10, 11, 12, 13, 15, 16, or 17.

In certain embodiments, the AAV capsid protein comprises an amino acid sequence that is at least 95% identical to the amino acid sequence of amino acids 138-736 of SEQ ID NO: 1, 2, 3, 4, 5, 6, 7, 8, 9, 10, 11, 12, 13, 15, 16, or 17. In certain embodiments, the amino acid in the capsid protein corresponding to amino acid 151 of SEQ ID NO: 16 is R; the amino acid in the capsid protein corresponding to amino acid 160 of SEQ ID NO: 16 is D; the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G. In certain embodiments, (a) the amino acid in the capsid protein corresponding to amino acid 626 of SEQ ID NO: 16 is G, and the amino acid in the capsid protein corresponding to amino acid 718 of SEQ ID NO: 16 is G;
(b) the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M;
(c) the amino acid in the capsid protein corresponding to amino acid 505 of SEQ ID NO: 16 is R, and the amino acid in the capsid protein corresponding to amino acid 687 of SEQ ID NO: 16 is R;
(d) the amino acid in the capsid protein corresponding to amino acid 346 of SEQ ID NO: 16 is A, and the amino acid in the capsid protein corresponding to amino acid 505 of SEQ ID NO: 16 is R; or
(e) the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C.

In certain embodiments, the capsid protein comprises the amino acid sequence of amino acids 138-736 of SEQ ID NO: 2, 3, 4, 5, 6, 7, 9, 10, 11, 12, 13, 15, 16, or 17.

In certain embodiments, the AAV capsid protein comprises an amino acid sequence that is at least 95% identical to the amino acid sequence of amino acids 1-736 of SEQ ID NO: 1, 2, 3, 4, 5, 6, 7, 8, 9, 10, 11, 12, 13, 15, 16, or 17. In certain embodiments, the amino acid in the capsid protein corresponding to amino acid 2 of SEQ ID NO: 16 is T; the amino acid in the capsid protein corresponding to amino acid 65 of SEQ ID NO: 16 is I; the amino acid in the capsid protein corresponding to amino acid 68 of SEQ ID NO: 16 is V; the amino acid in the capsid protein corresponding to amino acid 77 of SEQ ID NO: 16 is R; the amino acid in the capsid protein corresponding to amino acid 119 of SEQ ID NO: 16 is L; the amino acid in the capsid protein corresponding to amino acid 151 of SEQ ID NO: 16 is R; the amino acid in the capsid protein corresponding to amino acid 160 of SEQ ID NO: 16 is D; the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G. In certain embodiments:

(a) the amino acid in the capsid protein corresponding to amino acid 2 of SEQ ID NO: 16 is T, and the amino acid in the capsid protein corresponding to amino acid 312 of SEQ ID NO: 16 is Q;
(b) the amino acid in the capsid protein corresponding to amino acid 65 of SEQ ID NO: 16 is I, and the amino acid in the capsid protein corresponding to amino acid 626 of SEQ ID NO: 16 is Y;
(c) the amino acid in the capsid protein corresponding to amino acid 77 of SEQ ID NO: 16 is R, and the amino acid in the capsid protein corresponding to amino acid 690 of SEQ ID NO: 16 is K;
(d) the amino acid in the capsid protein corresponding to amino acid 119 of SEQ ID NO: 16 is L, and the amino acid in the capsid protein corresponding to amino acid 468 of SEQ ID NO: 16 is S;
(e) the amino acid in the capsid protein corresponding to amino acid 626 of SEQ ID NO: 16 is G, and the amino acid in the capsid protein corresponding to amino acid 718 of SEQ ID NO: 16 is G;
(f) the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M;
(g) the amino acid in the capsid protein corresponding to amino acid 505 of SEQ ID NO: 16 is R, and the amino acid in the capsid protein corresponding to amino acid 687 of SEQ ID NO: 16 is R;
(h) the amino acid in the capsid protein corresponding to amino acid 346 of SEQ ID NO: 16 is A, and the amino acid in the capsid protein corresponding to amino acid 505 of SEQ ID NO: 16 is R; or
(i) the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C.

In certain embodiments, the capsid protein comprises the amino acid sequence of amino acids 1-736 of SEQ ID NO: 1, 2, 3, 4, 5, 6, 7, 8, 9, 10, 11, 12, 13, 15, 16, or 17.

In certain embodiments, the integration efficiency of the editing element into the target locus is at least 1% when the AAV is administered to a mouse implanted with human hepatocytes in the absence of an exogenous nuclease under standard AAV administration conditions. In certain embodiments, the allelic frequency of integration of the editing element into the target locus is at least 0.5% when the AAV is administered to a mouse implanted with human hepatocytes in the absence of an exogenous nuclease under standard AAV administration conditions.

In another aspect, the instant disclosure provides a pharmaceutical composition comprising an rAAV disclosed herein.

In another aspect, the instant disclosure provides a polynucleotide comprising the nucleic acid sequence set forth in SEQ ID NO: 43, 45, 51, or 52.

In another aspect, the instant disclosure provides a method for treating a subject having phenylketonuria (PKU), the method comprising administering to the subject an effective amount of an rAAV, or pharmaceutical composition disclosed herein. In certain embodiments, the rAAV or pharmaceutical composition is administered intravenously. In certain embodiments, the PKU is associated with a PAH gene mutation. In certain embodiments, the subject is a human subject.

In another aspect, the instant disclosure provides a packaging system for preparation of an rAAV, wherein the packaging system comprises: (a) a first nucleotide sequence encoding one or more AAV Rep proteins; (b) a second nucleotide sequence encoding a capsid protein disclosed herein; and (c) a third nucleotide sequence comprising an rAAV genome sequence of an rAAV disclosed herein. In certain embodiments, the packaging system comprises a first vector comprising the first nucleotide sequence and the second nucleotide sequence, and a second vector comprising the third nucleotide sequence. In certain embodiments, the packaging system further comprises a fourth nucleotide sequence comprising one or more helper virus genes. In certain embodiments, the fourth nucleotide sequence is comprised within a third vector. In certain embodiments, the fourth nucleotide sequence comprises one or more genes from a virus selected from the group consisting of adenovirus, herpes virus, vaccinia virus, and cytomegalovirus (CMV). In certain embodiments, the first vector, second vector, and/or the third vector is a plasmid.

In another aspect, the instant disclosure provides a method for recombinant preparation of an rAAV, the method comprising introducing a packaging system disclosed herein into a cell under conditions whereby the rAAV is produced.

An rAAV, pharmaceutical composition, or polynucleotide disclosed herein, for use as a medicament. An rAAV, pharmaceutical composition, or polynucleotide disclosed herein, for use in the treatment of PKU. An rAAV, pharmaceutical composition, or polynucleotide disclosed herein, for use in a method of treating a subject having PKU, the method comprising administering to the subject an effective amount of the rAAV, the pharmaceutical composition, or the polynucleotide.

BRIEF DESCRIPTION OF THE DRAWINGS

FIG. 8A shows the full data set, while FIG. 8B shows the data over a certain range in time with a reduced y-axis scale in order to show differences between the dose levels. FIG. 8C shows the on-target integration of PAH-006m-LP-1 in PAH$^{enu2}$ mice, as measured by next generation sequencing.

FIGS. 9A-9L are plots showing the efficacy of the gene transfer/gene editing vector PAH-006m-LP-1 and an episomal transgene expression vector. FIGS. 9A and 9B are plots showing the effect of the episomal transgene expression vector and PAH-006m-LP-1, respectively, packaged in AAVHSC15 capsid, on the serum Phe levels of PAH$^{enu2}$ mice, up to 12 weeks post-dosing at the indicated doses. FIGS. 9C and 9D are plots showing the effect of the episomal transgene expression vector and PAH-006m-LP-1, respectively, packaged in AAVHSC15 capsid, on the serum Tyr levels of PAH$^{enu2}$ mice, up to 12 weeks post-dosing at the indicated doses. FIGS. 9E and 9F are plots showing the effect of the episomal transgene expression vector and PAH-006m-LP-1, respectively, packaged in AAVHSC15 capsid, on the level of vector genomes detected per ug of genomic DNA in PAH$^{enu2}$ mice, at the indicated doses. FIGS. 9G and 9H are plots showing the effect of the episomal transgene expression vector and PAH-006m-LP-1, respectively, packaged in AAVHSC15 capsid, on the level of mRNA expression per 10 ng of total RNA detected in PAH$^{enu2}$ mice, at the indicated doses. FIG. 9I is a plot showing the level of on-target integration presented by the number of viral genomes per allele detected by ddPCR across various doses as indicated, at 12 weeks post-dosing of vector packaged in AAVHSC15 as indicated. FIG. 9J is a plot showing the frequency of on-target insertion detected across various doses as indicated, at 12 weeks post-dosing of vector packaged in AAVHSC15 as indicated. FIGS. 9K and 9L are plots showing time courses out to 42 weeks (FIG. 9K) or 40 weeks (FIG. 9L) post-dosing of PAH$^{enu2}$ mice with vector and dosage as indicated, of the results of the effect of a partial hepatectomy (PHx) on serum Phe levels. PHx or sham surgery was performed at around 2 weeks post-dosing.

FIGS. 11A-11K are plots showing the effect the age of PAHenu2 mice has on the response to a single dose of the mouse-specific gene transfer/gene editing AAV vector (PAH-006m-LP-1; "mouse design"), or the human-specific gene transfer/gene editing AAV vector (hPAH-hI1C-032-LP1-SD3; "human design"). Serum Phe and Tyr levels (FIGS. 11A-11D) and vector genome and mRNA levels (FIGS. 11E-11K) were examined overtime for the various dosing groups set forth in Table 2.

FIGS. 12A-12C are plots showing the kinetics and durability of integration over time, of PAH$^{enu2}$ mice administered a mouse-specific gene transfer/gene editing AAV vector (PAH-006m-LP-1) packaged in AAVHSC15 capsid at a dose of 1E14 vg/kg. FIGS. 12A and 12B are plots showing the effect of PAH-006m-LP-1 packaged in AAVHSC15 capsid on the level of vector genomes detected per ug of genomic DNA, and the level of mRNA expression detected per 10 ng of total RNA in PAH$^{enu2}$ mice, respectively, over time. FIG. 12C is a plot showing the frequency of on-target insertion detected at various time points post-dosing of PAH-006m-LP-1 packaged in AAVHSC15 capsid. FIGS. 12D and 12E are graphs showing the effect on serum Phe (FIG. 12D) and Tyr (FIG. 12E) in PAH$^{enu2}$ mice administered PAH-006m-LP-1 packaged in AAVHSC15 capsid at a dose of 1E14 vg/kg, up to 42 weeks post-injection.

FIGS. 14A-14D are plots showing the amount of integration at predicted off-target integration sites detected in genomic DNA isolated from HuLiv mice administered the human-specific gene transfer/gene editing vector, hPAH-hI1C-032-LP1-SD3, packaged in AAVHSC15 capsid.

DETAILED DESCRIPTION

Figure 1:
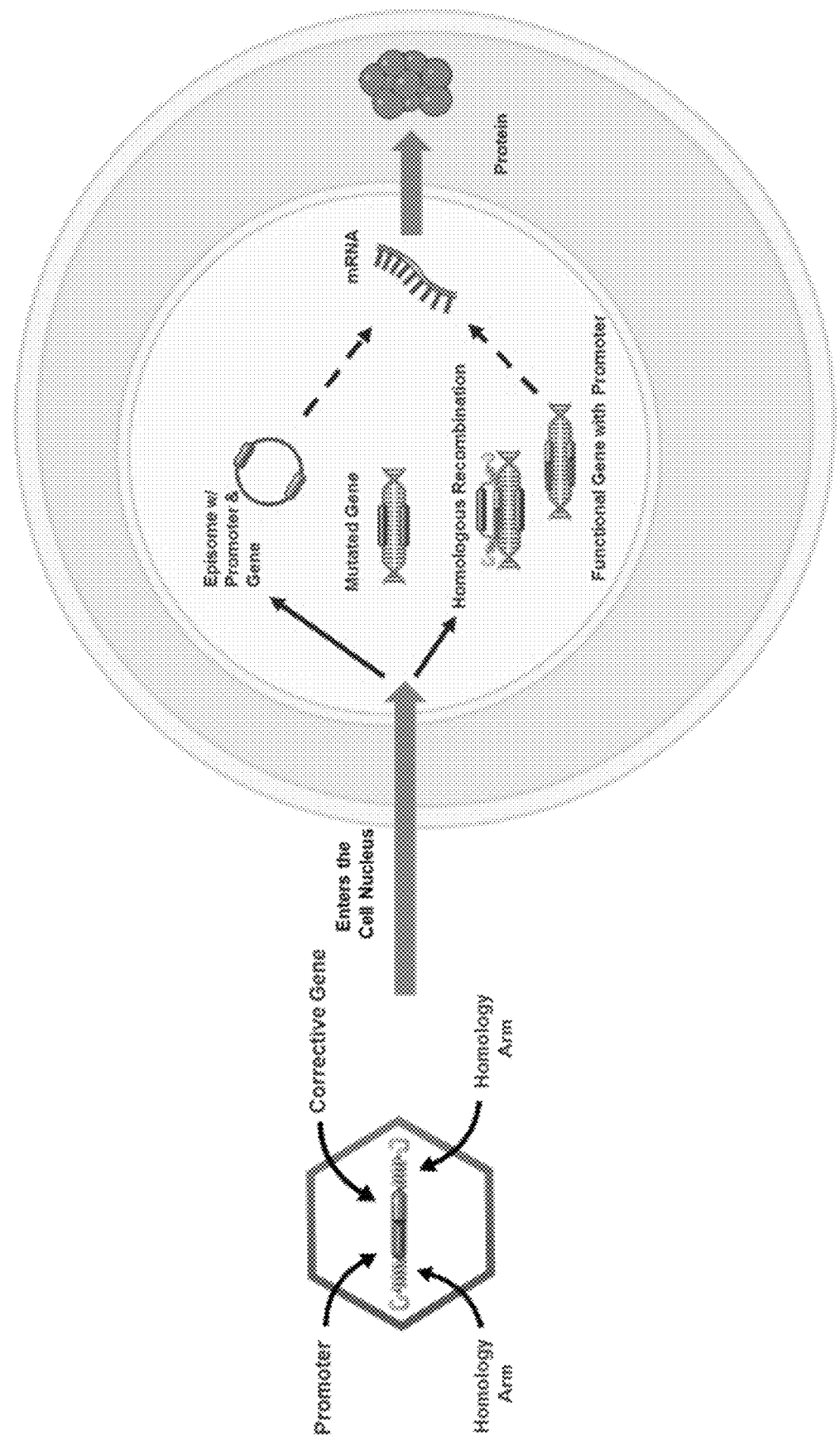
FIG. 1 is a schematic showing the gene transfer and gene editing mechanism of an rAAV as disclosed herein.

Provided herein are recombinant adeno-associated virus (rAAV) compositions that can restore PAH gene function in cells, and methods for using the same to treat diseases associated with reduction of PAH gene function (e.g., PKU). Also provided are nucleic acids, vectors, packaging systems, and methods for making the adeno-associated virus compositions.

I. DEFINITIONS

As used herein, the terms "recombinant adeno-associated virus" or "rAAV" refers to an AAV comprising a genome lacking functional rep and cap genes.

As used herein, the term "PAH gene" refers to the phenylalanine hydroxylase (PAH) gene, including but not limited to the coding regions, exons, introns, 5' UTR, 3' UTR, and transcriptional regulatory regions of the PAH gene. The human PAH gene is identified by Entrez Gene ID 5053. An exemplary nucleotide sequence of a PAH mRNA is provided as SEQ ID NO: 53. An exemplary amino acid sequence of a PAH polypeptide is provided as SEQ ID NO: 33. In certain embodiments, the PAH gene is a variant PAH gene. Variant PAH genes are known to those of skill in the art and may comprise one or more nucleotide differences as compared to the reference human genome. In certain embodiments, a variant PAH gene is a common variant observed in the general populace. For example, variant rs1522296 comprises a single nucleotide difference from the reference human genome at the genomic location in the human genome build Hg38 at chr12: 103310787. This variant is seen in >30% of the global population and has no known association to either changes in PAH expression or disease risk.

As used herein, the term "rAAV genome" refers to a recombinant AAV genome that is capable of integrating an editing element (e.g., one or more nucleotides or an internucleotide bond) via homologous recombination into a target locus to correct a genetic defect in a PAH gene. In certain embodiments, the target locus is in the human PAH gene. The skilled artisan will appreciate that the portion of an rAAV genome comprising the 5' homology arm, editing element, and 3' homology arm can be in the sense or antisense orientation relative to the target locus (e.g., the human PAH gene).

As used herein, the term "editing element" refers to the portion of an rAAV genome that when integrated at a target locus modifies the target locus. An editing element can mediate insertion, deletion, or substitution of one or more nucleotides at the target locus.

As used herein, the term "target locus" refers to a region of a chromosome or an internucleotide bond (e.g., a region or an internucleotide bond of the human PAH gene) that is modified by an editing element.

As used herein, the term "homology arm" refers to a portion of an rAAV genome positioned 5' or 3' of an editing element that is substantially identical to the genome flanking a target locus. In certain embodiments, the target locus is in a human PAH gene, and the homology arm comprises a sequence substantially identical to the genome flanking the target locus.

As used herein, the term "AAV capsid protein" refers to an AAV VP1, VP2, or VP3 capsid protein. As used herein, the term "Clade F capsid protein" refers to an AAV VP1, VP2, or VP3 capsid protein that comprises an amino acid sequence having at least 90% identity with the VP1, VP2, or VP3 amino acid sequences set forth, respectively, in amino acids 1-736, 138-736, and 203-736 of SEQ ID NO: 1 herein.

As used herein, the "percentage identity" between two nucleotide sequences or between two amino acid sequences is calculated by multiplying the number of matches between the pair of aligned sequences by 100, and dividing by the length of the aligned region, including internal gaps. Identity scoring only counts perfect matches and does not consider the degree of similarity of amino acids to one another. Note that only internal gaps are included in the length, not gaps at the sequence ends.

As used herein, the term "a disease or disorder associated with a PAH gene mutation" refers to any disease or disorder caused by, exacerbated by, or genetically linked with variation of a PAH gene. In certain embodiments, the disease or disorder associated with a PAH gene mutation is phenylketonuria (PKU).

As used herein, the term "silently altered" refers to alteration of a coding sequence or a stuffer-inserted coding sequence of a gene (e.g., by nucleotide substitution) without changing the amino acid sequence of the polypeptide encoded by the coding sequence or stuffer-inserted coding sequence. Codon alteration can be conducted by any method known in the art (e.g., as described in Mauro & Chappell (2014) Trends Mol Med. 20(11):604-13, which is incorporated by reference herein in its entirety). Such silent alteration is advantageous in that it reduces the likelihood of integration of the rAAV genome into loci of other genes or pseudogenes paralogous to the target gene. Such silent alteration also reduces the homology between the editing element and the target gene, thereby reducing undesired integration mediated by the editing element rather than by a homology arm.

As used herein, the term "coding sequence" refers to the portion of a complementary DNA (cDNA) that encodes a polypeptide, starting at the start codon and ending at the stop codon. A gene may have one or more coding sequences due to alternative splicing and/or alternative translation initiation. A coding sequence may either be wild-type or silently altered. An exemplary wild-type PAH coding sequence is set forth in SEQ ID NO: 53.

As used herein, the term "polyadenylation sequence" refers to a DNA sequence that when transcribed into RNA constitutes a polyadenylation signal sequence. The polyadenylation sequence can be native (e.g., from the PAH gene) or exogenous. The exogenous polyadenylation sequence can be a mammalian or a viral polyadenylation sequence (e.g., an SV40 polyadenylation sequence).

As used herein, the term "intron element" refers to a cis-acting nucleotide sequence, for example, a DNA sequence, that regulates (e.g., controls, increases, or reduces) expression of a transgene. In certain embodiments, an intron element is a modified intron, e.g., a synthetic intron sequence. In certain embodiments, an intron element is an exogenous intron element and is derived from an intron exogenous to the transgene it may regulate. In certain embodiments, an intron element comprises a modified splice acceptor and/or splice donor resulting in more robust splicing activity. While not wishing to be bound by theory, it is hypothesized that introns can increase transgene expression, for example, by reducing transcriptional silencing and enhancing mRNA export from the nucleus to the cytoplasm. A skilled worker will appreciate that synthetic intron sequences can be designed to mediate RNA splicing by introducing any consensus splicing motifs known in the art (e.g., in Sibley et al. (2016) *Nature Reviews Genetics*, 17, 407-21, which is incorporated by reference herein in its entirety). Exemplary intron sequences are provided in Lu et al. (2013) *Molecular Therapy* 21(5): 954-63, and Lu et al. (2017) *Hum. Gene Ther.* 28(1): 125-34, which are incorporated by reference herein in their entirety.

As used herein, the term "transcriptional regulatory element" or "TRE" refers to a cis-acting nucleotide sequence, for example, a DNA sequence, that regulates (e.g., controls, increases, or reduces) transcription of an operably linked nucleotide sequence by an RNA polymerase to form an RNA molecule. A TRE relies on one or more trans-acting molecules, such as transcription factors, to regulate transcription. Thus, one TRE may regulate transcription in different ways when it is in contact with different trans-acting molecules, for example, when it is in different types of cells. A TRE may comprise one or more promoter elements and/or enhancer elements. A skilled artisan would appreciate that the promoter and enhancer elements in a gene may be close in location, and the term "promoter" may refer to a sequence comprising a promoter element and an enhancer element. Thus, the term "promoter" does not exclude an enhancer element in the sequence. The promoter and enhancer elements do not need to be derived from the same gene or species, and the sequence of each promoter or enhancer element may be either identical or substantially identical to the corresponding endogenous sequence in the genome.

As used herein, the term "operably linked" is used to describe the connection between a TRE and a coding sequence to be transcribed. Typically, gene expression is placed under the control of a TRE comprising one or more promoter and/or enhancer elements. The coding sequence is "operably linked" to the TRE if the transcription of the coding sequence is controlled or influenced by the TRE. The promoter and enhancer elements of the TRE may be in any orientation and/or distance from the coding sequence, as long as the desired transcriptional activity is obtained. In certain embodiments, the TRE is upstream from the coding sequence.

In the instant disclosure, nucleotide positions in a PAH gene are specified relative to the first nucleotide of the start codon. The first nucleotide of a start codon is position 1; the nucleotides 5' to the first nucleotide of the start codon have negative numbers; the nucleotides 3' to the first nucleotide of the start codon have positive numbers. As used herein, nucleotide 1 of the human PAH gene is nucleotide 5,473 of the NCBI Reference Sequence: NG_008690.1, and nucleotide −1 of the human PAH gene is nucleotide 5,472 of the NCBI Reference Sequence: NG_008690.1.

In the instant disclosure, exons and introns in a PAH gene are specified relative to the exon encompassing the first nucleotide of the start codon, which is nucleotide 5473 of the NCBI Reference Sequence: NG_008690.1. The exon encompassing the first nucleotide of the start codon is exon 1. Exons 3' to exon 1 are from 5' to 3': exon 2, exon 3, etc. Introns 3' to exon 1 are from 5' to 3': intron 1, intron 2, etc. Accordingly, the PAH gene comprises from 5' to 3': exon 1, intron 1, exon 2, intron 2, exon 3, etc. As used herein, exon 1 of the human PAH gene is nucleotides 5001-5532 of the NCBI Reference Sequence: NG_008690.1, and intron 1 of the human PAH gene is nucleotides 5533-9704 of the NCBI Reference Sequence: NG_008690.1.

As used herein, the term "integration" refers to introduction of an editing element into a target locus (e.g., of a PAH gene) by homologous recombination between an rAAV genome and the target locus. Integration of an editing element can result in substitution, insertion and/or deletion of one or more nucleotides in a target locus (e.g., of a PAH gene).

As used herein, the term "integration efficiency of the editing element into the target locus" refers to the percentage of cells in a transduced population in which integration of the editing element into the target locus has occurred.

As used herein, the term "allelic frequency of integration of the editing element into the target locus" refers to the percentage of alleles in a population of transduced cells in which integration of the editing element into the target locus has occurred.

As used herein, the term "standard AAV administration conditions" refers to transduction of human hepatocytes implanted into a mouse following hepatocyte ablation, wherein the AAV is administered intravenously at a dose of $1 \times 10^{13}$ vector genomes per kilogram of body weight.

As used herein, the term "effective amount" in the context of the administration of an AAV to a subject refers to the amount of the AAV that achieves a desired prophylactic or therapeutic effect.

As used herein, the term "about" or "approximately" when referring to a measurable value, such as the expression level of an IDS protein, encompasses variations of ±20% or ±10%, ±5%, ±1%, or ±0.1% of a given value or range, as are appropriate to perform the methods disclosed herein.

II. ADENO-ASSOCIATED VIRUS COMPOSITIONS

In one aspect, provided herein are novel rAAV compositions useful for restoring PAH expression in cells with reduced or otherwise defective PAH gene function. Such rAAV compositions are highly efficient at editing the genome of cells (e.g., liver cells) in a subject to express PAH under the control of a liver-specific promoter, and do not require cleavage of the genome at the target locus by the action of an exogenous nuclease (e.g., a meganuclease, a zinc finger nuclease, a transcriptional activator-like nuclease (TALEN), or an RNA-guided nuclease such as a Cas9) to facilitate such editing. Accordingly, in certain embodiments, the rAAV compositions disclosed herein do not comprise or require an exogenous nuclease or a nucleotide sequence that encodes an exogenous nuclease.

In certain embodiments, the rAAV disclosed herein comprises: (a) an AAV capsid comprising an AAV capsid protein (e.g., an AAV Clade F capsid protein); and (b) an rAAV genome comprising: (i) an editing element for editing a target locus in a PAH gene, comprising at least a portion of a PAH coding sequence operably linked to a transcriptional regulatory element; (ii) a 5' homology arm nucleotide sequence position 5' of the editing element, having homology to a first genomic region 5' to the target locus; and (iii) a 3' homology arm nucleotide sequence positioned 3' of the editing element, having homology to a second genomic region 3' to the target locus. In certain embodiments, the rAAV disclosed herein has the potential to express a PAH transgene both via episomal expression and through insertion of the editing element into the genome at the target locus in the PAH gene (see, FIG. 1). In certain embodiments, the rAAV disclosed herein allows for the expression of PAH to be maintained throughout the period of hepatic growth, during which episomal expression may be lost. Accordingly, the rAAV compositions are particularly useful for treating juvenile PKU.

A capsid protein from any capsid known in the art can be used in the rAAV compositions disclosed herein, including, without limitation, a capsid protein from an AAV1, AAV2, AAV3, AAV4, AAV5, AAV6, AAV7, AAV8, or AAV9 serotype. For example, in certain embodiments, the capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 203-736 of SEQ ID NO: 1, 2, 3, 4, 5, 6, 7, 8, 9, 10, 11, 12, 13, 15, 16, or 17. In certain embodiments, the capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 203-736 of SEQ ID NO: 1, 2, 3, 4, 5, 6, 7, 8, 9, 10, 11, 12, 13, 15, 16, or 17, wherein: the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G. In certain embodiments, the amino acid in the capsid protein corresponding to amino acid 626 of SEQ ID NO: 16 is G, and the amino acid in the capsid protein corresponding to amino acid 718 of SEQ ID NO: 16 is G. In certain embodiments, the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M. In certain embodiments, the amino acid in the capsid protein corresponding to amino acid 505 of SEQ ID NO: 16 is R, and the amino acid in the capsid protein corresponding to amino acid 687 of SEQ ID NO: 16 is R. In certain embodiments, the amino acid in the capsid protein corresponding to amino acid 346 of SEQ ID NO: 16 is A, and the amino acid in the capsid protein corresponding to amino acid 505 of SEQ ID NO: 16 is R. In certain embodiments, the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C. In certain embodiments, the capsid protein comprises the amino acid sequence of amino acids 203-736 of SEQ ID NO: 1, 2, 3, 4, 5, 6, 7, 8, 9, 10, 11, 12, 13, 15, 16, or 17.

For example, in certain embodiments, the capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 138-736 of SEQ ID NO: 1, 2, 3, 4, 5, 6, 7, 8, 9, 10, 11, 12, 13, 15, 16, or 17. In certain embodiments, the capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 138-736 of SEQ ID NO: 1, 2, 3, 4, 5, 6, 7, 8, 9, 10, 11, 12, 13, 15, 16, or 17, wherein: the amino acid in the capsid protein corresponding to amino acid 151 of SEQ ID NO: 16 is R; the amino acid in the capsid protein corresponding to amino acid 160 of SEQ ID NO: 16 is D; the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G. In certain embodiments, the amino acid in the capsid protein corresponding to amino acid 626 of SEQ ID NO: 16 is G, and the amino acid in the capsid protein corresponding to amino acid 718 of SEQ ID NO: 16 is G. In certain embodiments, the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M. In certain embodiments, the amino acid in the capsid protein corresponding to amino acid 505 of SEQ ID NO: 16 is R, and the amino acid in the capsid protein corresponding to amino acid 687 of SEQ ID NO: 16 is R. In certain embodiments, the amino acid in the capsid protein corresponding to amino acid 346 of SEQ ID NO: 16 is A, and the amino acid in the capsid protein corresponding to amino acid 505 of SEQ ID NO: 16 is R. In certain embodiments, the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C. In certain embodiments, the capsid protein comprises the amino acid sequence of amino acids 138-736 of SEQ ID NO: 1, 2, 3, 4, 5, 6, 7, 8, 9, 10, 11, 12, 13, 15, 16, or 17.

For example, in certain embodiments, the capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 1-736 of SEQ ID NO: 1, 2, 3, 4, 5, 6, 7, 8, 9, 10, 11, 12, 13, 15, 16, or 17. In certain embodiments, the capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 1-736 of SEQ ID NO: 1, 2, 3, 4, 5, 6, 7, 8, 9, 10, 11, 12, 13, 15, 16, or 17, wherein: the amino acid in the capsid protein corresponding to amino acid 2 of SEQ ID NO: 16 is T; the amino acid in the capsid protein corresponding to amino acid 65 of SEQ ID NO: 16 is I; the amino acid in the capsid protein corresponding to amino acid 68 of SEQ ID NO: 16 is V; the amino acid in the capsid protein corresponding to amino acid 77 of SEQ ID NO: 16 is R; the amino acid in the capsid protein corresponding to amino acid 119 of SEQ ID NO: 16 is L; the amino acid in the capsid protein corresponding to amino acid 151 of SEQ ID NO: 16 is R; the amino acid in the capsid protein corresponding to amino acid 160 of SEQ ID NO: 16 is D; the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G. In certain embodiments, the amino acid in the capsid protein corresponding to amino acid 2 of SEQ ID NO: 16 is T, and the amino acid in the capsid protein corresponding to amino acid 312 of SEQ ID NO: 16 is Q. In certain embodiments, the amino acid in the capsid protein corresponding to amino acid 65 of SEQ ID NO: 16 is I, and the amino acid in the capsid protein corresponding to amino acid 626 of SEQ ID NO: 16 is Y. In certain embodiments, the amino acid in the capsid protein corresponding to amino acid 77 of SEQ ID NO: 16 is R, and the amino acid in the capsid protein corresponding to amino acid 690 of SEQ ID NO: 16 is K. In certain embodiments, the amino acid in the capsid protein corresponding to amino acid 119 of SEQ ID NO: 16 is L, and the amino acid in the capsid protein corresponding to amino acid 468 of SEQ ID NO: 16 is S. In certain embodiments, the amino acid in the capsid protein corresponding to amino acid 626 of SEQ ID NO: 16 is G, and the amino acid in the capsid protein corresponding to amino acid 718 of SEQ ID NO: 16 is G. In certain embodiments, the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M. In certain embodiments, the amino acid in the capsid protein corresponding to amino acid 505 of SEQ ID NO: 16 is R, and the amino acid in the capsid protein corresponding to amino acid 687 of SEQ ID NO: 16 is R. In certain embodiments, the amino acid in the capsid protein corresponding to amino acid 346 of SEQ ID NO: 16 is A, and the amino acid in the capsid protein corresponding to amino acid 505 of SEQ ID NO: 16 is R. In certain embodiments, the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C. In certain embodiments, the capsid protein comprises the amino acid sequence of amino acids 1-736 of SEQ ID NO: 1, 2, 3, 4, 5, 6, 7, 8, 9, 10, 11, 12, 13, 15, 16, or 17.

In certain embodiments, the AAV capsid comprises two or more of: (a) a capsid protein comprising the amino acid sequence of amino acids 203-736 of SEQ ID NO: 1, 2, 3, 4, 6, 7, 10, 11, 12, 13, 15, 16, or 17; (b) a capsid protein comprising the amino acid sequence of amino acids 138-736 of SEQ ID NO: 1, 2, 3, 4, 5, 6, 7, 9, 10, 11, 12, 13, 15, 16, or 17; and (c) a capsid protein comprising the amino acid sequence of amino acids 1-736 of SEQ ID NO: 1, 2, 3, 4, 5, 6, 7, 8, 9, 10, 11, 12, 13, 15, 16, or 17. In certain embodiments, the AAV capsid comprises: (a) a capsid protein having an amino acid sequence consisting of amino acids 203-736 of SEQ ID NO: 1, 2, 3, 4, 6, 7, 10, 11, 12, 13, 15, 16, or 17; (b) a capsid protein having an amino acid sequence consisting of amino acids 138-736 of SEQ ID NO: 1, 2, 3, 4, 5, 6, 7, 9, 10, 11, 12, 13, 15, 16, or 17; and (c) a capsid protein having an amino acid sequence consisting of amino acids 1-736 of SEQ ID NO: 1, 2, 3, 4, 5, 6, 7, 8, 9, 10, 11, 12, 13, 15, 16, or 17.

In certain embodiments, the AAV capsid comprises one or more of: (a) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 203-736 of SEQ ID NO: 8; (b) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 138-736 of SEQ ID NO: 8; and (c) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 1-736 of SEQ ID NO: 8. In certain embodiments, the AAV capsid comprises one or more of: (a) a capsid protein comprising the amino acid sequence of amino acids 203-736 of SEQ ID NO: 8; (b) a capsid protein comprising the amino acid sequence of amino acids 138-736 of SEQ ID NO: 8; and (c) a capsid protein comprising the amino acid sequence of amino acids 1-736 of SEQ ID NO: 8. In certain embodiments, the AAV capsid comprises two or more of: (a) a capsid protein comprising the amino acid sequence of amino acids 203-736 of SEQ ID NO: 8; (b) a capsid protein comprising the amino acid sequence of amino acids 138-736 of SEQ ID NO: 8; and (c) a capsid protein comprising the amino acid sequence of amino acids 1-736 of SEQ ID NO: 8. In certain embodiments, the AAV capsid comprises: (a) a capsid protein having an amino acid sequence consisting of amino acids 203-736 of SEQ ID NO: 8; (b) a capsid protein having an amino acid sequence consisting of amino acids 138-736 of SEQ ID NO: 8; and (c) a capsid protein having an amino acid sequence consisting of amino acids 1-736 of SEQ ID NO: 8.

In certain embodiments, the AAV capsid comprises one or more of: (a) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 203-736 of SEQ ID NO: 11; (b) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 138-736 of SEQ ID NO: 11; and (c) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 1-736 of SEQ ID NO: 11. In certain embodiments, the AAV capsid comprises one or more of: (a) a capsid protein comprising the amino acid sequence of amino acids 203-736 of SEQ ID NO: 11; (b) a capsid protein comprising the amino acid sequence of amino acids 138-736 of SEQ ID NO: 11; and (c) a capsid protein comprising the amino acid sequence of amino acids 1-736 of SEQ ID NO: 11. In certain embodiments, the AAV capsid comprises two or more of: (a) a capsid protein comprising the amino acid sequence of amino acids 203-736 of SEQ ID NO: 11; (b) a capsid protein comprising the amino acid sequence of amino acids 138-736 of SEQ ID NO: 11; and (c) a capsid protein comprising the amino acid sequence of amino acids 1-736 of SEQ ID NO: 11. In certain embodiments, the AAV capsid comprises: (a)

a capsid protein having an amino acid sequence consisting of amino acids 203-736 of SEQ ID NO: 11; (b) a capsid protein having an amino acid sequence consisting of amino acids 138-736 of SEQ ID NO: 11; and (c) a capsid protein having an amino acid sequence consisting of amino acids 1-736 of SEQ ID NO: 11.

In certain embodiments, the AAV capsid comprises one or more of: (a) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 203-736 of SEQ ID NO: 13; (b) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 138-736 of SEQ ID NO: 13; and (c) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 1-736 of SEQ ID NO: 13. In certain embodiments, the AAV capsid comprises one or more of: (a) a capsid protein comprising the amino acid sequence of amino acids 203-736 of SEQ ID NO: 13; (b) a capsid protein comprising the amino acid sequence of amino acids 138-736 of SEQ ID NO: 13; and (c) a capsid protein comprising the amino acid sequence of amino acids 1-736 of SEQ ID NO: 13. In certain embodiments, the AAV capsid comprises two or more of: (a) a capsid protein comprising the amino acid sequence of amino acids 203-736 of SEQ ID NO: 13; (b) a capsid protein comprising the amino acid sequence of amino acids 138-736 of SEQ ID NO: 13; and (c) a capsid protein comprising the amino acid sequence of amino acids 1-736 of SEQ ID NO: 13. In certain embodiments, the AAV capsid comprises: (a) a capsid protein having an amino acid sequence consisting of amino acids 203-736 of SEQ ID NO: 13; (b) a capsid protein having an amino acid sequence consisting of amino acids 138-736 of SEQ ID NO: 13; and (c) a capsid protein having an amino acid sequence consisting of amino acids 1-736 of SEQ ID NO: 13.

In certain embodiments, the AAV capsid comprises one or more of: (a) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 16; (b) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 16; and (c) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 16. In certain embodiments, the AAV capsid comprises one or more of: (a) a capsid protein comprising the amino acid sequence of amino acids 203-736 of SEQ ID NO: 16; (b) a capsid protein comprising the amino acid sequence of amino acids 138-736 of SEQ ID NO: 16; and (c) a capsid protein comprising the amino acid sequence of amino acids 1-736 of SEQ ID NO: 16. In certain embodiments, the AAV capsid comprises two or more of: (a) a capsid protein comprising the amino acid sequence of amino acids 203-736 of SEQ ID NO: 16; (b) a capsid protein comprising the amino acid sequence of amino acids 138-736 of SEQ ID NO: 16; and (c) a capsid protein comprising the amino acid sequence of amino acids 1-736 of SEQ ID NO: 16. In certain embodiments, the AAV capsid comprises: (a) a capsid protein having an amino acid sequence consisting of amino acids 203-736 of SEQ ID NO: 16; (b) a capsid protein having an amino acid sequence consisting of amino acids 138-736 of SEQ ID NO: 16; and (c) a capsid protein having an amino acid sequence consisting of amino acids 1-736 of SEQ ID NO: 16.

rAAV genomes useful in the AAV compositions disclosed herein generally comprise: (i) an editing element for editing a target locus in a PAH gene, comprising at least a portion of a PAH coding sequence operably linked to a transcriptional regulatory element; (ii) a 5' homology arm nucleotide sequence position 5' of the editing element, having homology to a first genomic region 5' to the target locus; and (iii) a 3' homology arm nucleotide sequence positioned 3' of the editing element, having homology to a second genomic region 3' to the target locus. In certain embodiments, the rAAV genome comprises a 5' inverted terminal repeat (5' ITR) nucleotide sequence 5' of the 5' homology arm nucleotide sequence, and a 3' inverted terminal repeat (3' ITR) nucleotide sequence 3' of the 3' homology arm nucleotide sequence.

Editing elements used in the rAAV genomes disclosed herein can mediate insertion, deletion, or substitution of one or more nucleotides at the target locus.

In certain embodiments, when correctly integrated by homologous recombination at the target locus, the editing element inserts a nucleotide sequence comprising at least a portion of a PAH coding sequence into a PAH gene. In certain embodiments, the editing element comprises a PAH coding sequence (e.g., a complete PAH coding sequence).

In certain embodiments, the PAH coding sequence encodes a wild-type PAH polypeptide (e.g., having the amino acid sequence set forth in SEQ ID NO: 33). In certain embodiments, the PAH coding sequence is wild-type (e.g., comprising the nucleotide sequence set forth in SEQ ID NO: 53). In certain embodiments, the PAH coding sequence is silently altered to be less than 100% (e.g., less than 95%, 90%, 85%, 80%, 75%, 70%, 65%, 60%, 55%, or 50%) identical to the corresponding exons of the wild-type PAH gene. In certain embodiments, the PAH coding sequence comprises or consists of a nucleotide sequence that is at least 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the nucleotide sequence set forth in SEQ ID NO: 28, 63, or 83. In certain embodiments, the PAH coding sequence comprises the nucleotide sequence set forth in SEQ ID NO: 28. In certain embodiments, the PAH coding sequence consists of the nucleotide sequence set forth in SEQ ID NO: 28. In certain embodiments, the PAH coding sequence comprises the nucleotide sequence set forth in SEQ ID NO: 63. In certain embodiments, the PAH coding sequence consists of the nucleotide sequence set forth in SEQ ID NO: 63. In certain embodiments, the PAH coding sequence comprises the nucleotide sequence set forth in SEQ ID NO: 83. In certain embodiments, the PAH coding sequence consists of the nucleotide sequence set forth in SEQ ID NO: 83.

In certain embodiments, rAAV genomes useful in the AAV compositions disclosed herein comprise a transcriptional regulatory element (TRE) operably linked to at least a portion of a PAH coding sequence. In certain embodiments, rAAV genomes useful in the AAV compositions disclosed herein comprise from 5' to 3': a TRE, and the at least a portion of a PAH coding sequence.

The rAAV genome can be used to express PAH in any mammalian cells (e.g., human cells). Thus, the TRE can be active in any mammalian cells (e.g., human cells). In certain embodiments, the TRE is active in a broad range of human cells. Such TREs may comprise constitutive promoter and/or enhancer elements including cytomegalovirus (CMV) promoter/enhancer (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 54, 55, or 56), SV40 promoter, chicken ACTB promoter (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 47 or 57), JeT promoter (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 58), smCBA promoter (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 59), human elongation factor 1 alpha (EF1α) promoter (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 39), minute virus of mouse (MVM) intron which comprises transcription factor binding sites (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 61), human phosphoglycerate kinase (PGK1) promoter, human ubiquitin C (Ubc) promoter, human beta actin promoter, human neuron-specific enolase (ENO2) promoter, human beta-glucuronidase (GUSB) promoter, a rabbit beta-globin element (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 41 or 62), human calmodulin 1 (CALM1) promoter (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 44), and/or human Methyl-CpG Binding Protein 2 (MeCP2) promoter. Any of these TREs can be combined in any order to drive efficient transcription. For example, an rAAV genome may comprise a CMV enhancer, a CBA promoter, and the splice acceptor from exon 3 of the rabbit beta-globin gene, collectively called a CAG promoter (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 42 or 64). For example, an rAAV genome may comprise a hybrid of CMV enhancer and CBA promoter followed by a splice donor and splice acceptor, collectively called a CASI promoter region (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 48 or 65).

Alternatively, the TRE may be a tissue-specific TRE, i.e., it is active in specific tissue(s) and/or organ(s). A tissue-specific TRE comprises one or more tissue-specific promoter and/or enhancer elements, and optionally one or more constitutive promoter and/or enhancer elements. A skilled artisan would appreciate that tissue-specific promoter and/or enhancer elements can be isolated from genes specifically expressed in the tissue by methods well known in the art.

In certain embodiments, the TRE is liver-specific (e.g., hepatocyte-specific). Exemplary liver-specific TREs may comprise one or more elements selected from the group consisting of human albumin promoter, human transthyretin (TTR) promoter (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 66), human APOE/C-I hepatic control region (HCR) 1 or 2 (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 25 or 68), human APOH promoter, and human SERPINA1 (hAAT) promoter (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 26, 69 or 70) or a hepatic specific regulatory module thereof (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 71). In certain embodiments, an hAAT promoter region comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 72. More liver-specific promoter elements are disclosed in WO 2009/130208 and Kramer et al. *Molecular Therapy* (2003) 7, 375-385, which are incorporated by reference herein in their entirety.

In certain embodiments, the TRE is kidney-specific (e.g., renal epithelial cell-specific). Exemplary kidney-specific TREs may comprise one or more elements selected from the group consisting of human nephrin promoter, human parathyroid hormone receptor promoter, human uromodulin promoter, and human SLC12A1 promoter. In certain embodiments, the TRE is brain-specific (e.g., neuron-specific, glial cell-specific, astrocyte-specific, oligodendrocyte-specific, microglia-specific and/or central nervous system-specific). Exemplary brain-specific TREs may comprise one or more elements selected from the group consisting of human glial fibrillary acidic protein (GFAP) promoter and human synapsin 1 (SYN1) promoter. More brain-specific promoter elements are disclosed in WO 2016/100575A1, which is incorporated by reference herein in its entirety.

In certain embodiments, the rAAV genome comprises two or more TREs, optionally comprising at least one of the TREs disclosed above. A skilled person in the art would appreciate that any of these TREs can be combined in any order, and combinations of a constitutive TRE and a tissue-specific TRE can drive efficient and tissue-specific transcription. For example, in certain embodiments, the rAAV genome comprises a human HCR1 (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 25 or 68) and a human EF-1α promoter (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 39), optionally wherein the human HCR1 is 5' to the human EF-1α promoter. In certain embodiments, the rAAV genome comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the sequence nucleotide set forth in SEQ ID NO: 60.

Similarly, combinations of two or more tissue-specific TREs can drive efficient and tissue-specific transcription. For example, in certain embodiments, the rAAV genome comprises a human HCR1 (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 25) and a hAAT promoter (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 26), optionally wherein the human HCR1 is 5' to the hAAT promoter. In certain embodiments, the rAAV genome comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence set forth in SEQ ID NO: 27. In certain embodiments, the rAAV genome comprises a human HCR1 (e.g., comprising the nucleotide sequence set forth in SEQ ID NO: 25) and a hAAT promoter (e.g., comprising the nucleotide sequence set forth in SEQ ID NO: 26), optionally wherein the human HCR1 is 5' to the hAAT promoter. In certain embodiments, the rAAV genome comprises the nucleotide sequence set forth in SEQ ID NO: 27.

In certain embodiments, the rAAV genome comprises a hepatic specific regulatory module of hAAT promoter (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 71) and a human TTR promoter (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 66), optionally wherein the hepatic specific regulatory module is 5' to the human TTR promoter. In certain embodiments, the rAAV genome comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleotide sequence set forth in SEQ ID NO: 67. In certain embodiments, the rAAV genome comprises a hepatic specific regulatory module of hAAT promoter (e.g., comprising the nucleotide sequence set forth in SEQ ID NO: 71) and a human TTR promoter (e.g., comprising the nucleotide sequence set forth in SEQ ID NO: 66), optionally wherein the hepatic specific regulatory module is 5' to the human TTR promoter. In certain embodiments, the rAAV genome comprises the nucleotide sequence set forth in SEQ ID NO: 67.

In certain embodiments, the rAAV genome further comprises an intron element 5' to the at least a portion of a PAH coding sequence. Such intron elements can increase transgene expression, for example, by reducing transcriptional silencing and enhancing mRNA export from the nucleus to the cytoplasm. In certain embodiments, the rAAV genome comprises from 5' to 3': a TRE, an intron element, and the at least a portion of a PAH coding sequence.

The intron element can comprise at least a portion of a native intron sequence of the PAH gene, or the intron element can be an exogenous intron element (e.g., comprising at least an intron sequence from a different species or a different gene from the same species, and/or a synthetic intron sequence). In certain embodiments, the intron element is an exogenous intron element comprising at least a portion of an intron sequence from a different species. In certain embodiments, the intron element is an exogenous intron element comprising at least a portion of an intron sequence from a different gene from the same species. In certain embodiments, the intron element is an exogenous intron element comprising a synthetic intron sequence. In certain embodiments, the intron element is an exogenous intron element comprising a combination of at least an intron sequence from a different species or a different gene from the same species, and/or a synthetic intron sequence.

A skilled worker will appreciate that intron elements can be designed to mediate RNA splicing by introducing any consensus splicing motifs known in the art (e.g., in Sibley et al. (2016) *Nature Reviews Genetics*, 17, 407-21, which is incorporated by reference herein in its entirety). Exemplary intron sequences are provided in Lu et al. (2013) *Molecular Therapy* 21(5): 954-63, and Lu et al. (2017) *Hum. Gene Ther.* 28(1): 125-34, which are incorporated by reference herein in their entirety.

In certain embodiments, the rAAV genome comprises an exogenous intron element. In certain embodiments, the rAAV comprises an SV40 intron element (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 29) or a minute virus of mouse (MVM) intron (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 61). In certain embodiments, the rAAV genome comprises an SV40 intron element (e.g., comprising the nucleotide sequence set forth in SEQ ID NO: 29) or a minute virus of mouse (MVM) intron element (e.g., comprising the nucleotide sequence set forth in SEQ ID NO: 61).

In certain embodiments, the rAAV genome disclosed herein further comprises a transcription terminator (e.g., a polyadenylation sequence). In certain embodiments, the transcription terminator is 3' to the at least a portion of a PAH coding sequence. The transcription terminator may be any sequence that effectively terminates transcription, and a skilled artisan would appreciate that such sequences can be isolated from any genes that are expressed in the cell in which transcription of the at least a portion of a PAH coding sequence is desired. In certain embodiments, the transcription terminator comprises a polyadenylation sequence. In certain embodiments, the polyadenylation sequence is identical or substantially identical to the endogenous polyadenylation sequence of the human PAH gene. In certain embodiments, the polyadenylation sequence is an exogenous polyadenylation sequence. In certain embodiments, the polyadenylation sequence is an SV40 polyadenylation sequence (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 31, 34, or 35, or a nucleotide sequence complementary thereto). In certain embodiments, the polyadenylation sequence comprises the nucleotide sequence set forth in SEQ ID NO: 31. In certain embodiments, the polyadenylation sequence consists of the nucleotide sequence set forth in SEQ ID NO: 31.

In certain embodiments, the rAAV genome comprises from 5' to 3': a TRE, an intron element, at least a portion of a PAH coding sequence, and a polyadenylation sequence. In certain embodiments, the TRE has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any one of SEQ ID NOs: 25-27, 30, 36, 39, 40-42, 44, 46-49, 54-60, or 62-72; the intron element has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 29 or 61; the at least a portion of a PAH coding sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 28; and/or the polyadenylation sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any one of SEQ ID NOs: 31, 34, or 35. In certain embodiments, the TRE comprises a nucleotide sequence selected from the group consisting of SEQ ID NOs: 25-27, 30, 36, 39, 40-42, 44, 46-49, 54-60, and 62-72; the intron element comprises a nucleotide sequence selected from the group consisting of SEQ ID NOs: 29 and 61; the at least a portion of a PAH coding sequence comprises the nucleotide sequence set forth in SEQ ID NO: 28; and/or the polyadenylation sequence comprises a nucleotide sequence selected from the group consisting of SEQ ID NOs: 31, 34, and 35.

In certain embodiments, the TRE comprises or consists of the nucleotide sequence set forth in SEQ ID NO: 25, 26, or 27; the intron element comprises or consists of the nucleotide sequence set forth in SEQ ID NO: 29; the at least a portion of a PAH coding sequence comprises or consists of the nucleotide sequence set forth in SEQ ID NO: 28; and/or the polyadenylation sequence comprises or consists of the nucleotide sequence set forth in SEQ ID NO: 31. In certain embodiments, the TRE comprises from 5' to 3' the nucleotide sequence set forth in SEQ ID NO: 25, and the nucleotide sequence set forth in SEQ ID NO: 26 (e.g., the TRE comprises the nucleotide sequence set forth in SEQ ID NO: 27); the intron element comprises the nucleotide sequence set forth in SEQ ID NO: 29; the at least a portion of a PAH coding sequence comprises the nucleotide sequence set forth in SEQ ID NO: 28; and/or the polyadenylation sequence comprises the nucleotide sequence set forth in SEQ ID NO: 31.

Homology arms used in the rAAV genomes disclosed herein can be directed to any region of the PAH gene or a gene nearby on the genome. The precise identity and positioning of the homology arms are determined by the identity of the editing element and/or the target locus.

Homology arms employed in the rAAV genomes disclosed herein are substantially identical to the genome flanking a target locus (e.g., a target locus in a PAH gene). In certain embodiments, the 5' homology arm has at least about 90% (e.g., at least about 91%, 92%, 93%, 94%, 95%, 96%, 97%, 98%, 99%, or 99.5%) nucleotide sequence identity to a first genomic region 5' to the target locus. In certain embodiments, the 5' homology arm has 100% nucleotide sequence identity to the first genomic region. In certain embodiments, the 3' homology arm has at least about 90% (e.g., at least about 91%, 92%, 93%, 94%, 95%, 96%, 97%, 98%, 99%, or 99.5%) nucleotide sequence identity to a second genomic region 3' to the target locus. In certain embodiments, the 3' homology arm has 100% nucleotide sequence identity to the second genomic region. In certain embodiments, the 5' and 3' homology arms are each at least about 90% (e.g., at least about 91%, 92%, 93%, 94%, 95%, 96%, 97%, 98%, 99%, or 99.5%) identical to the first and second genomic regions flanking the target locus (e.g., a target locus in the PAH gene), respectively. In certain embodiments, the 5' and 3' homology arms are each 100% identical to the first and second genomic regions flanking the target locus (e.g., a target locus in the PAH gene), respectively. In certain embodiments, differences in nucleotide sequences of the 5' homology arm and/or the 3' homology arm and the corresponding regions the genome flanking a target locus comprise, consist essentially of, or consist of non-coding differences in nucleotide sequences.

The skilled worker will appreciate that homology arms do not need to be 100% identical to the genomic sequence flanking the target locus to be able to mediate integration of an editing element into that target locus by homologous recombination. For example, the homology arms can comprise one or more genetic variations in the human population, and/or one or more modifications (e.g., nucleotide substitutions, insertions, or deletions) designed to improve expression level or specificity. Human genetic variations include both inherited variations and de novo variations that are private to the target genome, and encompass simple nucleotide polymorphisms, insertions, deletions, rearrangements, inversions, duplications, micro-repeats, and combinations thereof. Such variations are known in the art, and can be found, for example, in the databases of dnSNP (see Sherry et al. *Nucleic Acids Res.* 2001; 29(1):308-11), the Database of Genomic Variants (see *Nucleic Acids Res.* 2014; 42 (Database issue): D986-92), ClinVar (see *Nucleic Acids Res.* 2014; 42 (Database issue): D980-D985), Genbank (see *Nucleic Acids Res.* 2016; 44 (Database issue): D67-D72), ENCODE (genome.ucsc.edu/encode/terms.html), JASPAR (see *Nucleic Acids Res.* 2018; 46(D1): D260-D266), and PROMO (see Messeguer et al. *Bioinformatics* 2002; 18(2): 333-334; Farré et al. *Nucleic Acids Res.* 2003; 31(13):3651-3653), each of which is incorporated herein by reference. The skilled worker will further appreciate that in situations where a homology arm is not 100% identical to the genomic sequence flanking the target locus, homologous recombination between the homology arm and the genome may alter the genomic sequence flanking the target locus such that it becomes identical to the sequence of the homology arm used.

In certain embodiments, the first genomic region 5' to the target locus is located in a first editing window, wherein the first editing window consists of the region of the human genome corresponding to the nucleotide sequence set forth in SEQ ID NO: 37. In certain embodiments, the second genomic region 3' to the target locus is located in a second editing window, wherein the second editing window consists of the region of the human genome corresponding to the nucleotide sequence set forth in SEQ ID NO: 38. In certain embodiments, the first genomic region 5' to the target locus is located in a first editing window, wherein the first editing window consists of the region of the human genome corresponding to the nucleotide sequence set forth in SEQ ID NO: 37; and the second genomic region 3' to the target locus is located in a second editing window, wherein the second editing window consists of the region of the human genome corresponding to the nucleotide sequence set forth in SEQ ID NO: 38.

In certain embodiments, the first and second editing windows are different. In certain embodiments, the first editing window is located 5' to the second editing window. In certain embodiments, the first genomic region consists of a sequence shorter than the sequence of the first editing window in which the first genomic region is located. In certain embodiments, the first genomic region consists of the sequence of the first editing window in which the first genomic region is located. In certain embodiments, the second genomic region consists of a sequence shorter than the sequence of the second editing window in which the second genomic region is located. In certain embodiments, the second genomic region consists of the sequence of the second editing window in which the second genomic region is located.

In certain embodiments, the first and second editing windows are the same. In certain embodiments, the target locus is an internucleotide bond or a nucleotide sequence in the editing window, wherein the first genomic region consists of a first portion of the editing window 5' to the target locus, and the second genomic region consists of a second portion of the editing window 3' to the target locus. In certain embodiments, the first portion of the editing window consists of the sequence from the 5' end of the editing window to the nucleotide adjacently 5' to the target locus. In certain embodiments, the second portion of the editing window consists of the sequence from the nucleotide adjacently 3' to the target locus to the 3' end of the editing window. In certain embodiments, the first portion of the editing window consists of the sequence from the 5' end of the editing window to the nucleotide adjacently 5' to the target locus, and the second portion of the editing window consists of the sequence from the nucleotide adjacently 3' to the target locus to the 3' end of the editing window. In certain embodiments, the editing window consists of the region of the human genome corresponding to the nucleotide sequence set forth in SEQ ID NO: 37 or 38. In certain embodiments, the first and second portions of the editing windows have substantially equal lengths (e.g., the ratio of the length of the shorter portion to the length of the longer portion is greater than 0.5, 0.55, 0.6, 0.65, 0.7, 0.75, 0.8, 0.85, 0.9, 0.95, 0.96, 0.97, 0.98, or 0.99).

In certain embodiments, the 5' homology arm has a length of about 50 to about 4000 nucleotides (e.g., about 100 to about 3000, about 200 to about 2000, about 500 to about 1000 nucleotides). In certain embodiments, the 5' homology arm has a length of about 800 nucleotides. In certain embodiments, the 5' homology arm has a length of about 100 nucleotides. In certain embodiments, the 3' homology arm has a length of about 50 to about 4000 nucleotides (e.g., about 100 to about 3000, about 200 to about 2000, about 500 to about 1000 nucleotides). In certain embodiments, the 3' homology arm has a length of about 800 nucleotides. In certain embodiments, the 3' homology arm has a length of about 100 nucleotides. In certain embodiments, each of the 5' and 3' homology arms independently has a length of about 50 to about 4000 nucleotides (e.g., about 100 to about 3000, about 200 to about 2000, about 500 to about 1000 nucleotides). In certain embodiments, each of the 5' and 3' homology arms independently has a length of about 800 nucleotides.

In certain embodiments, the 5' and 3' homology arms have substantially equal nucleotide lengths. In certain embodiments, the 5' and 3' homology arms have asymmetrical nucleotide lengths. In certain embodiments, the asymmetry in nucleotide length is defined by a difference between the 5' and 3' homology arms of up to 90% in the length, such as up to an 80%, 70%, 60%, 50%, 40%, 30%, 20%, or 10% difference in the length.

In certain embodiments, the 5' homology arm has at least about 90% (e.g., at least about 91%, 92%, 93%, 94%, 95%, 96%, 97%, 98%, 99%, or 99.5%) nucleotide sequence identity to the nucleotide sequence set forth in SEQ ID NO: 37. In certain embodiments, the 5' homology arm further comprises one or more genetic variations in the human population. In certain embodiments, the 5' homology arm comprises the nucleotide sequence set forth in SEQ ID NO: 23. In certain embodiments, the 5' homology arm consists of the nucleotide sequence set forth in SEQ ID NO: 23.

In certain embodiments, the 3' homology arm has at least about 90% (e.g., at least about 91%, 92%, 93%, 94%, 95%, 96%, 97%, 98%, 99%, or 99.5%) nucleotide sequence identity to the nucleotide sequence set forth in SEQ ID NO: 38. In certain embodiments, the 3' homology arm further comprises one or more genetic variations in the human population. In certain embodiments, the 3' homology arm comprises the nucleotide sequence set forth in SEQ ID NO: 24. In certain embodiments, the 3' homology arm consists of the nucleotide sequence set forth in SEQ ID NO: 24.

In certain embodiments, the 5' homology arm and the 3' homology arm each has at least about 90% (e.g., at least about 91%, 92%, 93%, 94%, 95%, 96%, 97%, 98%, 99%, or 99.5%) nucleotide sequence identity to the nucleotide sequences set forth in SEQ ID NOs: 37 and 38, respectively. In certain embodiments, the 5' homology arm and the 3' homology arm each has at least about 90% (e.g., at least about 91%, 92%, 93%, 94%, 95%, 96%, 97%, 98%, 99%, or 99.5%) nucleotide sequence identity to the nucleotide sequences set forth in SEQ ID NOs: 23 and 24, respectively. In certain embodiments, the 5' homology arm and the 3' homology arm comprise the nucleotide sequences set forth in SEQ ID NOs: 37 and 38, 23 and 24, 37 and 24, or 23 and 38, respectively. In certain embodiments, the 5' homology arm and the 3' homology arm consist of the nucleotide sequences set forth in SEQ ID NOs: 37 and 38, 23 and 24, 37 and 24, or 23 and 38, respectively.

In certain embodiments, the rAAV genome comprises a nucleotide sequence at least 80% (e.g., at least 80%, 81%, 82%, 83%, 84%, 85%, 86%, 87%. 88%, 89%, 90%. 91% 92%, 93%, 94%, 95%, 96%, 97%, 98%, 99%, or 99.5%) identical to SEQ ID NO: 43. In certain embodiments, the rAAV genome comprises the nucleotide sequence set forth in SEQ ID NO: 43. In certain embodiments, the rAAV genome consists of the nucleotide sequence set forth in SEQ ID NO: 43.

In certain embodiments, the rAAV genomes disclosed herein further comprise a 5' inverted terminal repeat (5' ITR) nucleotide sequence 5' of the TRE, and a 3' inverted terminal repeat (3' ITR) nucleotide sequence 3' of the PAH coding sequence. ITR sequences from any AAV serotype or variant thereof can be used in the rAAV genomes disclosed herein. The 5' and 3' ITR can be from an AAV of the same serotype or from AAVs of different serotypes. Exemplary ITRs for use in the rAAV genomes disclosed herein are set forth in SEQ ID NOs: 14, 18, 19, 20, 21, and 32, herein.

In certain embodiments, the 5' ITR or 3' ITR is from AAV2. In certain embodiments, both the 5' ITR and the 3' ITR are from AAV2. In certain embodiments, the 5' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 14, or the 3' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 18. In certain embodiments, the 5' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 14, and the 3' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 18. In certain embodiments, the rAAV genome comprises a nucleotide sequence set forth in SEQ ID NO: 43, a 5' ITR nucleotide sequence having the sequence of SEQ ID NO: 14, and a 3' ITR nucleotide sequence having the sequence of SEQ ID NO: 18.

In certain embodiments, the 5' ITR or 3' ITR are from AAV5. In certain embodiments, both the 5' ITR and 3' ITR are from AAV5. In certain embodiments, the 5' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 20, or the 3' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 21. In certain embodiments, the 5' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 20, and the 3' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 21. In certain embodiments, the rAAV genome comprises a nucleotide sequence set forth in any one of SEQ ID NO: 43, a 5' ITR nucleotide sequence having the sequence of SEQ ID NO: 20, and a 3' ITR nucleotide sequence having the sequence of SEQ ID NO: 21.

In certain embodiments, the 5' ITR nucleotide sequence and the 3' ITR nucleotide sequence are substantially complementary to each other (e.g., are complementary to each other except for mismatch at 1, 2, 3, 4, or 5 nucleotide positions in the 5' or 3' ITR).

In certain embodiments, the 5' ITR or the 3' ITR is modified to reduce or abolish resolution by Rep protein ("non-resolvable ITR"). In certain embodiments, the non-resolvable ITR comprises an insertion, deletion, or substitution in the nucleotide sequence of the terminal resolution site. Such modification allows formation of a self-complementary, double-stranded DNA genome of the AAV after the rAAV genome is replicated in an infected cell. Exemplary non-resolvable ITR sequences are known in the art (see e.g., those provided in U.S. Pat. Nos. 7,790,154 and 9,783,824, which are incorporated by reference herein in their entirety). In certain embodiments, the 5' ITR comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 19. In certain embodiments, the 5' ITR consists of a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 19. In certain embodiments, the 5' ITR consists of the nucleotide sequence set forth in SEQ ID NO: 19. In certain embodiments, the 3' ITR comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 32. In certain embodiments, the 5' ITR consists of a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 32. In certain embodiments, the 3' ITR consists of the nucleotide sequence set forth in SEQ ID NO: 32. In certain embodiments, the 5' ITR consists of the nucleotide sequence set forth in SEQ ID NO: 19, and the 3' ITR consists of the nucleotide sequence set forth in SEQ ID NO: 32. In certain embodiments, the 5' ITR consists of the nucleotide sequence set forth in SEQ ID NO: 19, and the 3' ITR consists of the nucleotide sequence set forth in SEQ ID NO: 32.

In certain embodiments, the 5' ITR is flanked by an additional nucleotide sequence derived from a wild-type AAV2 genomic sequence. In certain embodiments, the 5' ITR is flanked by an additional 46 bp sequence derived from a wild-type AAV2 sequence that is adjacent to a wild-type AAV2 ITR in an AAV2 genome. In certain embodiments, the additional 46 bp sequence is 3' to the 5' ITR in the rAAV genome. In certain embodiments, the 46 bp sequence consists of the nucleotide sequence set forth in SEQ ID NO: 74.

In certain embodiments, the 3' ITR is flanked by an additional nucleotide sequence derived from a wild-type AAV2 genomic sequence. In certain embodiments, the 3' ITR is flanked by an additional 37 bp sequence derived from a wild-type AAV2 sequence that is adjacent to a wild-type AAV2 ITR in an AAV2 genome. See, e.g., Savy et al. *Human Gene Therapy Methods* (2017) 28(5): 277-289 (which is hereby incorporated by reference herein in its entirety). In certain embodiments, the additional 37 bp sequence is 5' to the 3' ITR in the rAAV genome. In certain embodiments, the 37 bp sequence consists of the nucleotide sequence set forth in SEQ ID NO: 73.

In certain embodiments, the 5' homology arm has at least about 80%, 81%, 82%, 83%, 84%, 85%, 86%, 87%, 88%, 89%, 90%, 91%, 92%, 93%, 94%, 95%, 96%, 97%, 98%, 99%, or 100% nucleotide sequence identity to the nucleotide sequence set forth in SEQ ID NO: 37. In certain embodiments, the 5' homology arm further comprises one or more genetic variations in the human population. In certain embodiments, the 5' homology arm comprises the nucleotide sequence set forth in SEQ ID NO: 23. In certain embodiments, the 5' homology arm consists of the nucleotide sequence set forth in SEQ ID NO: 23.

In certain embodiments, the 3' homology arm has at least about 80%, 81%, 82%, 83%, 84%, 85%, 86%, 87%, 88%, 89%, 90%, 91%, 92%, 93%, 94%, 95%, 96%, 97%, 98%, 99%, or 100% nucleotide sequence identity to the nucleotide sequence set forth in SEQ ID NO: 38. In certain embodiments, the 3' homology arm further comprises one or more genetic variations in the human population. In certain embodiments, the 3' homology arm comprises the nucleotide sequence set forth in SEQ ID NO: 24. In certain embodiments, the 3' homology arm consists of the nucleotide sequence set forth in SEQ ID NO: 24.

In certain embodiments, the rAAV genome comprises from 5' to 3': a 5' homology arm, a 5' ITR, a TRE, an intron element, at least a portion of a PAH coding sequence, a polyadenylation sequence, a 3' ITR, and/or a 3' homology arm. In certain embodiments, the 5' homology arm has at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 37 or 23; the 5' ITR has at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 14, 19, or 20; the TRE has at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 25, 26, 27, 30, 36, 39, 40, 41, 42, 44, 46, 47, 48, 49, 54, 55, 56, 57, 58, 59, 60, 62, 64, 65, 66, 67, 68, 69, 70, 72, or 72; the intron element has at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 29 or 61; the at least a portion of a PAH coding sequence has at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 28;

the polyadenylation sequence has at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 31, 34, or 35; the 3' ITR has at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 18, 21, or 32; and/or the 3' homology arm has at least about 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 38 or 24.

In certain embodiments, the 5' homology arm comprises a nucleotide sequence selected from the group consisting of SEQ ID NOs: 37 and 23; the 5' ITR comprises a nucleotide sequence selected from the group consisting of SEQ ID NOs: 14, 19, or 20; the TRE comprises a nucleotide sequence selected from the group consisting of SEQ ID NOs: 25-27, 30, 36, 39, 40-42, 44, 46-49, 54-60, and 62-72; the intron comprises a nucleotide sequence selected from the group consisting of SEQ ID NOs: 29 and 61; the at least a portion of a PAH coding sequence comprises the nucleotide sequence set forth in SEQ ID NO: 28; the polyadenylation sequence comprises a nucleotide sequence selected from the group consisting of SEQ ID NOs: 31, 34, and 35; the 3 ITR comprises a nucleotide sequence selected from the group consisting of SEQ ID NOs: 18, 21, and 32; and/or the 3' homology arm comprises a nucleotide sequence selected from the group consisting of SEQ ID NOs: 38 and 24.

In certain embodiments, the 5' homology arm comprises or consists of the nucleotide sequence set forth in SEQ ID NO: 23; the 5' ITR comprises or consists of the nucleotide sequence set forth in SEQ ID NO: 14; the TRE comprises or consists of the nucleotide sequence set forth in SEQ ID NO: 25, 26, or 27; the intron element comprises or consists of the nucleotide sequence set forth in SEQ ID NO: 29; the at least a portion of a PAH coding sequence comprises or consists of the nucleotide sequence set forth in SEQ ID NO: 28; the polyadenylation sequence comprises or consists of the nucleotide sequence set forth in SEQ ID NO: 31; the 3' ITR comprises or consists of the nucleotide sequence set forth in SEQ ID NO: 18; and/or the 5' homology arm comprises or consists of the nucleotide sequence set forth in SEQ ID NO: 24.

In certain embodiments, the rAAV genome comprises from 5' to 3': the 5' homology arm comprising the nucleotide sequence set forth in SEQ ID NO: 23; the 5' ITR comprising the nucleotide sequence set forth in SEQ ID NO: 14; the TRE comprising from 5' to 3' the nucleotide sequence set forth in SEQ ID NO: 25, and the nucleotide sequence set forth in SEQ ID NO: 26 (e.g., the TRE comprises the nucleotide sequence set forth in SEQ ID NO: 27); the intron element comprising the nucleotide sequence set forth in SEQ ID NO: 29; the at least a portion of a PAH coding sequence comprising the nucleotide sequence set forth in SEQ ID NO: 28; the polyadenylation sequence comprising the nucleotide sequence set forth in SEQ ID NO: 31; the 3' ITR comprising of the nucleotide sequence set forth in SEQ ID NO: 18; and the 5' homology arm comprising the nucleotide sequence set forth in SEQ ID NO: 24.

In certain embodiments, the rAAV genome comprises a nucleotide sequence at least 80% (e.g., at least 80%, 81%, 82%, 83%, 84%, 85%, 86%, 87%. 88%, 89%, 90%. 91% 92%, 93%, 94%, 95%, 96%, 97%, 98%, or 99%) identical to SEQ ID NO: 45. In certain embodiments, the rAAV genome comprises the nucleotide sequence set forth in SEQ ID NO: 45. In certain embodiments, the rAAV genome consists of the nucleotide sequence set forth in SEQ ID NO: 45.

In another aspect, provided herein is a polynucleotide comprising a nucleic acid sequence that is at least 80% (e.g., at least 80%, 81%, 82%, 83%, 84%, 85%, 86%, 87%. 88%, 89%, 90%. 91% 92%, 93%, 94%, 95%, 96%, 97%, 98%, or 99%) identical to the nucleic acid sequence set forth in SEQ ID NO: 28, 43, 45, 51, or 52. In certain embodiments, the polynucleotide comprises or consists of the nucleic acid sequence set forth in SEQ ID NO: 43, 45, 51, or 52.

In another aspect, the instant disclosure provides pharmaceutical compositions comprising an AAV as disclosed herein together with a pharmaceutically acceptable excipient, adjuvant, diluent, vehicle or carrier, or a combination thereof. A "pharmaceutically acceptable carrier" includes any material which, when combined with an active ingredient of a composition, allows the ingredient to retain biological activity and without causing disruptive physiological reactions, such as an unintended immune reaction. Pharmaceutically acceptable carriers include water, phosphate buffered saline, emulsions such as oil/water emulsion, and wetting agents. Compositions comprising such carriers are formulated by well-known conventional methods such as those set forth in *Remington's Pharmaceutical Sciences*, current Ed., Mack Publishing Co., Easton Pa. 18042, USA; A. Gennaro (2000) *"Remington: The Science and Practice of Pharmacy,"* 20th edition, Lippincott, Williams, & Wilkins; *Pharmaceutical Dosage Forms and Drug Delivery Systems* (1999) H. C. Ansel et al, 7th ed., Lippincott, Williams, & Wilkins; and *Handbook of Pharmaceutical Excipients* (2000) A. H. Kibbe et al, 3rd ed. Amer. *Pharmaceutical Assoc.*

In another aspect, the instant disclosure provides a polynucleotide comprising a coding sequence encoding a human PAH protein or a fragment thereof, wherein the coding sequence has been silently altered to have less than 100% (e.g., less than 99%, 98%, 97%, 96%, 95%, 90%, 85%, 80%, 75%, 70%, 65%, 60%, 55%, or 50%) identical to a wild-type human PAH gene. In certain embodiments, the polynucleotide comprises the nucleotide sequence set forth in SEQ ID NO: 28. The polynucleotide can comprise DNA, RNA, modified DNA, modified RNA, or a combination thereof. In certain embodiments, the polynucleotide is an expression vector.

The AAV compositions disclosed herein are particularly advantageous in that they are capable of editing a PAH gene in a cell with high efficiency both in vivo and in vitro. In certain embodiments, the integration efficiency of the editing element into the target locus is at least 1% (e.g., at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is administered to a mouse implanted with human hepatocytes in the absence of an exogenous nuclease under standard AAV administration conditions. In certain embodiments, the allelic frequency of integration of the editing element into the target locus is at least 0.5% (e.g., at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is administered to a mouse implanted with human hepatocytes in the absence of an exogenous nuclease under standard AAV administration conditions.

Any methods of determining the efficiency of editing of the PAH gene can be employed. In certain embodiments, individual cells are separated from the population of transduced cells and subject to single-cell PCR using PCR primers that can identify the presence of an editing element correctly integrated into the target locus of the PAH gene. Such method can further comprise single-cell PCR of the same cells using PCR primers that selectively amplify an unmodified target locus. In this way, the genotype of the cells can be determined. For example, if the single cell PCR showed that a cell has both an edited target locus and an unmodified target locus, then the cell would be considered heterozygous for the edited PAH gene.

Additionally or alternatively, in certain embodiments, linear amplification mediated PCR (LAM-PCR), quantitative PCR (qPCR) or digital droplet PCR (ddPCR) can be performed on DNA extracted from the population of transduced cells using primers and probes that only detect edited PAH alleles. Such methods can further comprise an additional qPCR or ddPCR (either in the same reaction or a separate reaction) to determine the number of total genomes in the sample and the number of unedited PAH alleles. These numbers can be used to determine the allelic frequency of integration of the editing element into the target locus.

Additionally or alternatively, in certain embodiments, the PAH locus can be amplified from DNA extracted from the population of transduced cells either by PCR using primers that bind to regions of the PAH gene flanking the target locus, or by LAM-PCR using a primer that binds a region within the rAAV genome (e.g., a region comprising an exogenous sequence non-native to the locus). The resultant PCR amplicons can be individually sequenced using single molecule next generation sequencing (NGS) techniques to determine the relative number of edited and unedited PAH alleles present in the population of transduced cells. These numbers can be used to determine the allelic frequency of integration of the editing element into the target locus.

In another aspect, the instant disclosure provides pharmaceutical compositions comprising an AAV as disclosed herein together with a pharmaceutically acceptable excipient, adjuvant, diluent, vehicle or carrier, or a combination thereof. A "pharmaceutically acceptable carrier" includes any material which, when combined with an active ingredient of a composition, allows the ingredient to retain biological activity and without causing disruptive physiological reactions, such as an unintended immune reaction. Pharmaceutically acceptable carriers include water, phosphate buffered saline, emulsions such as oil/water emulsion, and wetting agents. Compositions comprising such carriers are formulated by well-known conventional methods such as those set forth in *Remington's Pharmaceutical Sciences*, current Ed., Mack Publishing Co., Easton Pa. 18042, USA; A. Gennaro (2000) "*Remington: The Science and Practice of Pharmacy,*" 20th edition, Lippincott, Williams, & Wilkins; *Pharmaceutical Dosage Forms and Drug Delivery Systems* (1999) H. C. Ansel et al, 7th ed., Lippincott, Williams, & Wilkins; and *Handbook of Pharmaceutical Excipients* (2000) A. H. Kibbe et al, 3rd ed. Amer. Pharmaceutical Assoc.

III. METHODS OF USE

In another aspect, the instant disclosure provides methods for restoring PAH gene function in a cell. The methods generally comprise transducing the cell with an rAAV as disclosed herein. Such methods are highly efficient at editing the PAH gene function in a cell, and do not require cleavage of the genome at the target locus by the action of an exogenous nuclease (e.g., a meganuclease, a zinc finger nuclease, a transcriptional activator-like nuclease (TALEN), or an RNA-guided nuclease such as a Cas9) to facilitate such correction. Accordingly, in certain embodiments, the methods disclosed herein involve transducing the cell with an rAAV as disclosed herein without co-transducing or co-administering an exogenous nuclease or a nucleotide sequence that encodes an exogenous nuclease.

The methods disclosed herein can be applied to any cell harboring a mutation in the PAH gene. The skilled worker will appreciate that cells that actively express PAH are of particular interest. Accordingly, in certain embodiments, the method is applied to cells in the liver, kidney, brain, pituitary gland, adrenal gland, pancreas, urinary bladder, gallbladder, colon, small intestine, or breast. In certain embodiments, the method is applied to hepatocytes and/or renal cells.

The methods disclosed herein can be performed in vitro for research purposes or can be performed ex vivo or in vivo for therapeutic purposes.

In certain embodiments, the cell to be transduced is in a mammalian subject and the AAV is administered to the subject in an amount effective to transduce the cell in the subject. Accordingly, in certain embodiments, the instant disclosure provides a method for treating a subject having a disease or disorder associated with a PAH gene mutation, the method generally comprising administering to the subject an effective amount of an rAAV as disclosed herein. The subject can be a human subject or a rodent subject (e.g., a mouse) containing human liver cells. Suitable mouse subjects include without limitation, mice into which human liver cells (e.g., human hepatocytes) have been engrafted. Any disease or disorder associated with a PAH gene mutation can be treated using the methods disclosed herein. Suitable diseases or disorders include, without limitation, phenylketonuria. In certain embodiments, the cell is transduced without co-transducing or co-administering an exogenous nuclease or a nucleotide sequence that encodes an exogenous nuclease.

The methods disclosed herein are particularly advantageous in that they are capable of editing a PAH gene in a cell with high efficiency both in vivo and in vitro. In certain embodiments, the integration efficiency of the editing element into the target locus is at least 1% (e.g., at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is administered to a mouse implanted with human hepatocytes in the absence of an exogenous nuclease under standard AAV administration conditions. In certain embodiments, the allelic frequency of integration of the editing element into the target locus is at least 0.5% (e.g., at least 1%, 2%, 3%, 4%, 5%, 6%, 7%, 8%, 9%, 10%, 15%, 20%, 25%, 30%, 3%, 40%, 45%, 50%, 55%, 60%, 65%, 70%, 75%, 80%, 85%, 90%, or 95%) when the AAV is administered to a mouse implanted with human hepatocytes in the absence of an exogenous nuclease under standard AAV administration conditions.

The methods disclosed herein can be performed in vitro for research purposes or can be performed ex vivo or in vivo for therapeutic purposes.

In certain embodiments, the cell to be transduced is in a mammalian subject and the AAV is administered to the subject in an amount effective to transduce the cell in the subject. Accordingly, in certain embodiments, the instant disclosure provides a method for treating a subject having a disease or disorder associated with a PAH gene mutation, the method generally comprising administering to the subject an effective amount of an rAAV as disclosed herein. The subject can be a human subject, a non-human primate subject (e.g., a cynomolgus), or a rodent subject (e.g., a mouse) with a PAH gene mutation. Any disease or disorder associated with a PAH gene mutation can be treated using the methods disclosed herein. Suitable diseases or disorders include, without limitation, phenylketonuria (PKU).

In certain embodiments, the foregoing methods employ an rAAV comprising: (a) an AAV capsid protein comprising the amino acid sequence of amino acids 203-736 of SEQ ID NO: 16, and an rAAV genome comprising 5' to 3' following genetic elements: a 5' homology arm (e.g., the 5' homology arm comprising the nucleotide sequence set forth in SEQ ID NO: 23), a 5' ITR (e.g., the 5' ITR comprising the nucleotide sequence set forth in SEQ ID NO: 14), a transcriptional regulatory element (e.g., a TRE comprising the nucleotide sequence set forth in SEQ ID NO: 27), an intron element (e.g., the intron element comprising the nucleotide sequence set forth in SEQ ID NO: 29), at least a portion of a PAH coding sequence (e.g., the PAH coding sequence comprising the nucleotide sequence set forth in SEQ ID NO: 28), a polyadenylation sequence (e.g., the SV40 polyadenylation sequence of SEQ ID NO: 31), a 3' ITR (e.g., the 3' ITR comprising the nucleotide sequence set forth in SEQ ID NO: 18), and a 3' homology arm (e.g., the 3' homology arm comprising the nucleotide sequence set forth in SEQ ID NO: 24); (b) an AAV capsid protein comprising the amino acid sequence of amino acids 138-736 of SEQ ID NO: 16, and an rAAV genome comprising 5' to 3' following genetic elements: a 5' homology arm (e.g., the 5' homology arm comprising the nucleotide sequence set forth in SEQ ID NO: 23), a 5' ITR (e.g., the 5' ITR comprising the nucleotide sequence set forth in SEQ ID NO: 14), a transcriptional regulatory element (e.g., a TRE comprising the nucleotide sequence set forth in SEQ ID NO: 27), an intron element (e.g., the intron element comprising the nucleotide sequence set forth in SEQ ID NO: 29), at least a portion of a PAH coding sequence (e.g., the PAH coding sequence comprising the nucleotide sequence set forth in SEQ ID NO: 28), a polyadenylation sequence (e.g., the SV40 polyadenylation sequence of SEQ ID NO: 31), a 3' ITR (e.g., the 3' ITR comprising the nucleotide sequence set forth in SEQ ID NO: 18), and a 3' homology arm (e.g., the 3' homology arm comprising the nucleotide sequence set forth in SEQ ID NO: 24); and/or (c) an AAV capsid protein comprising the amino acid sequence of SEQ ID NO: 16, and an rAAV genome comprising 5' to 3' following genetic elements: a 5' homology arm (e.g., the 5' homology arm comprising the nucleotide sequence set forth in SEQ ID NO: 23), a 5' ITR (e.g., the 5' ITR comprising the nucleotide sequence set forth in SEQ ID NO: 14), a transcriptional regulatory element (e.g., a TRE comprising the nucleotide sequence set forth in SEQ ID NO: 27), an intron element (e.g., the intron element comprising the nucleotide sequence set forth in SEQ ID NO: 29), at least a portion of a PAH coding sequence (e.g., the PAH coding sequence comprising the nucleotide sequence set forth in SEQ ID NO: 28), a polyadenylation sequence (e.g., the SV40 polyadenylation sequence of SEQ ID NO: 31), a 3' ITR (e.g., the 3' ITR comprising the nucleotide sequence set forth in SEQ ID NO: 18), and a 3' homology arm (e.g., the 3' homology arm comprising the nucleotide sequence set forth in SEQ ID NO: 24).

In certain embodiments, transduction of a cell with an AAV composition disclosed herein can be performed as provided herein or by any method of transduction known to one of ordinary skill in the art. In certain embodiments, the cell may be contacted with the AAV at a multiplicity of infection (MOI) of 50,000; 100,000; 150,000; 200,000; 250,000; 300,000; 350,000; 400,000; 450,000; or 500,000, or at any MOI that provides for optimal transduction of the cell.

An AAV composition disclosed herein can be administered to a subject by any appropriate route including, without limitation, intravenous, intraperitoneal, subcutaneous, intramuscular, intranasal, topical or intradermal routes. In certain embodiments, the composition is formulated for administration via intravenous injection or subcutaneous injection.

IV. AAV PACKAGING SYSTEMS

In another aspect, the instant disclosure provides packaging systems for recombinant preparation of a recombinant adeno-associated virus (rAAV) disclosed herein. Such packaging systems generally comprise: first nucleotide encoding one or more AAV Rep proteins; a second nucleotide encoding a capsid protein of any of the AAVs as disclosed herein; and a third nucleotide sequence comprising any of the rAAV genomes as disclosed herein, wherein the packaging system is operative in a cell for enclosing the rAAV genome in the capsid to form the AAV.

In certain embodiments, the packaging system comprises a first vector comprising the first nucleotide sequence encoding the one or more AAV Rep proteins and the second nucleotide sequence encoding the AAV capsid protein, and a second vector comprising the third nucleotide sequence comprising the rAAV genome. As used in the context of a packaging system as described herein, a "vector" refers to a nucleic acid molecule that is a vehicle for introducing nucleic acids into a cell (e.g., a plasmid, a virus, a cosmid, an artificial chromosome, etc.).

Any AAV Rep protein can be employed in the packaging systems disclosed herein. In certain embodiments of the packaging system, the Rep nucleotide sequence encodes an AAV2 Rep protein. Suitable AAV2 Rep proteins include, without limitation, Rep 78/68 or Rep 68/52. In certain embodiments of the packaging system, the nucleotide sequence encoding the AAV2 Rep protein comprises a nucleotide sequence that encodes a protein having a minimum percent sequence identity to the AAV2 Rep amino acid sequence of SEQ ID NO: 22, wherein the minimum percent sequence identity is at least 70% (e.g., at least 75%, at least 80%, at least 85%, at least 90%, at least 95%, at least 98%, at least 99%, or 100%) across the length of the amino acid sequence of the AAV2 Rep protein. In certain embodiments of the packaging system, the AAV2 Rep protein has the amino acid sequence set forth in SEQ ID NO: 22.

In certain embodiments of the packaging system, the packaging system further comprises a fourth nucleotide sequence comprising one or more helper virus genes. In certain embodiments of the packaging system, the packaging system further comprises a third vector, e.g., a helper virus vector, comprising the fourth nucleotide sequence comprising the one or more helper virus genes. The third vector may be an independent third vector, integral with the first vector, or integral with the second vector.

In certain embodiments of the packaging system, the helper virus is selected from the group consisting of adenovirus, herpes virus (including herpes simplex virus (HSV)), poxvirus (such as vaccinia virus), cytomegalovirus (CMV), and baculovirus. In certain embodiments of the packaging system, where the helper virus is adenovirus, the adenovirus genome comprises one or more adenovirus RNA genes selected from the group consisting of E1, E2, E4 and VA. In certain embodiments of the packaging system, where the helper virus is HSV, the HSV genome comprises one or more of HSV genes selected from the group consisting of UL5/8/52, ICP0, ICP4, ICP22 and UL30/UL42.

In certain embodiments of the packaging system, the first, second, and/or third vector are contained within one or more plasmids. In certain embodiments, the first vector and the third vector are contained within a first plasmid. In certain embodiments the second vector and the third vector are contained within a second plasmid.

In certain embodiments of the packaging system, the first, second, and/or third vector are contained within one or more recombinant helper viruses. In certain embodiments, the first vector and the third vector are contained within a recombinant helper virus. In certain embodiments, the second vector and the third vector are contained within a recombinant helper virus.

In a further aspect, the disclosure provides a method for recombinant preparation of an AAV as described herein, wherein the method comprises transfecting or transducing a cell with a packaging system as described herein under conditions operative for enclosing the rAAV genome in the capsid to form the rAAV as described herein. Exemplary methods for recombinant preparation of an rAAV include transient transfection (e.g., with one or more transfection plasmids containing a first, and a second, and optionally a third vector as described herein), viral infection (e.g., with one or more recombinant helper viruses, such as a adenovirus, poxvirus (such as vaccinia virus), herpes virus (including HSV, cytomegalovirus, or baculovirus), containing a first, and a second, and optionally a third vector as described herein), and stable producer cell line transfection or infection (e.g., with a stable producer cell, such as a mammalian or insect cell, containing a Rep nucleotide sequence encoding one or more AAV Rep proteins and/or a Cap nucleotide sequence encoding one or more AAV capsid proteins as described herein, and with an rAAV genome as described herein being delivered in the form of a plasmid or a recombinant helper virus).

Accordingly, the instant disclosure provides a packaging system for preparation of a recombinant AAV (rAAV), wherein the packaging system comprises a first nucleotide sequence encoding one or more AAV Rep proteins; a second nucleotide sequence encoding a capsid protein of any one of the AAVs described herein; a third nucleotide sequence comprising an rAAV genome sequence of any one of the AAVs described herein; and optionally a fourth nucleotide sequence comprising one or more helper virus genes.

V. EXAMPLES

These examples are offered by way of illustration, and not by way of limitation.

Example 1: hPAH Correction Vector Designs

Mouse-Specific PAH Gene Editing Vector PAH-006m

Figure 2A:
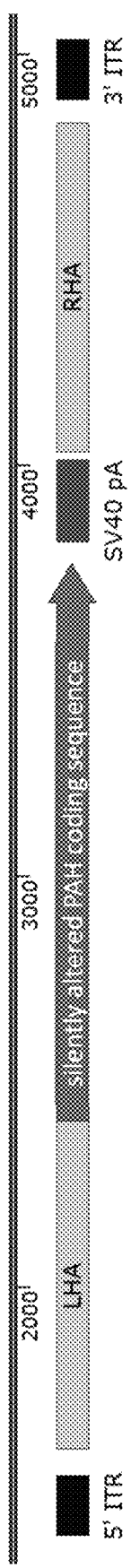
FIGS. 2A-2D are schematics showing the plasmid maps of PAH-006m (FIG. 2A), PAH-006m-LP-1 (FIG. 2B), PAH-032h (FIG. 2C), and hPAH-hI1C-032-LP1-SD3 (FIG. 2D).

The mouse-specific gene editing AAV vector, PAH-006m, is shown in FIG. 2A. This vector was designed to integrate a human PAH coding sequence into the mouse PAH gene locus using left and right homology arms that are specific to the mouse sequence. PAH-006m comprises, from 5' to 3', the following genetic elements: a 5' ITR element; a 5' homology arm; a silently altered human PAH coding sequence; an SV40 polyadenylation sequence; a 3' homology arm; and a 3' ITR element. The sequences of these elements are set forth in Table 1. PAH-006m does not comprise a heterologous promoter.

Mouse-Specific PAH Gene Transfer Gene Editing Vector PAH-006m-LP-1

Figure 2B:
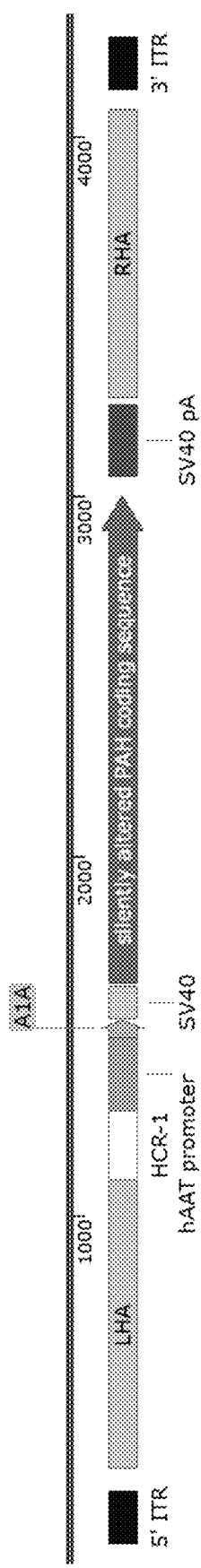

The mouse-specific gene transfer/gene editing AAV vector, PAH-006m-LP-1, is shown in FIG. 2B. This vector was designed to integrate a human PAH coding sequence into the mouse PAH gene locus using mouse left and right homology arms, and also to allow expression of human PAH under the control of a heterologous liver-specific promoter in a cell in the absence of genomic integration. PAH-006m-LP-1 comprises, from 5' to 3', the following genetic elements: a 5' ITR element; a 5' homology arm; a transcriptional regulatory element comprising a human apolipoprotein hepatic control region (HCR) element, a human alpha-1-antitrypsin (hAAT) promoter element, and a hAAT exon 1; an SV40 element; a silently altered human PAH coding sequence; an SV40 polyadenylation sequence; a 3' homology arm; and a 3' ITR element. The sequences of these elements are set forth in Table 1.

Human-Specific PAH Gene Editing Vector PAH-032h

Figure 2C:
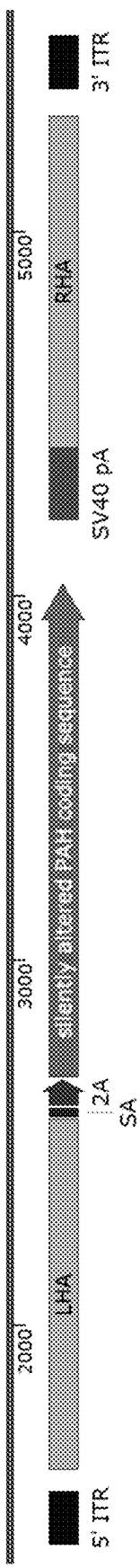

The human-specific gene editing AAV vector, PAH-032h, is shown in FIG. 2C. This vector was designed to integrate a human PAH coding sequence into the human PAH gene locus using left and right homology arms that are specific to the human sequence. PAH-032h comprises, from 5' to 3', the following genetic elements: a 5' ITR element; a 5' homology arm; a splice acceptor; a 2A element; a silently altered human PAH coding sequence; an SV40 polyadenylation sequence; a 3' homology arm; and a 3' ITR element. The sequences of these elements are set forth in Table 1. PAH-032h does not comprise a heterologous promoter.

Human-Specific PAH Gene Transfer Gene Editing Vector hPAH-hI1C-032-LP1-SD3

Figure 2D:
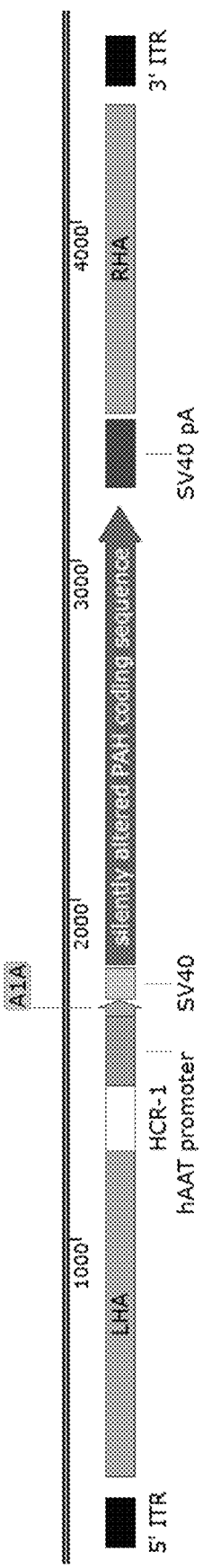

The human-specific gene transfer/gene editing AAV vector, hPAH-hI1C-032-LP1-SD3, is shown in FIG. 2D. This vector was designed to integrate a human PAH coding sequence into the human PAH gene locus using human left and right homology arms, and also to allow expression of human PAH under the control of a heterologous liver-specific promoter in a cell in the absence of genomic integration. hPAH-hI1C-032-LP1-SD3 comprises, from 5' to 3', the following genetic elements: a 5' ITR element; a 5' homology arm; a transcriptional regulatory element comprising a human apolipoprotein hepatic control region (HCR) element, a human alpha-1-antitrypsin (hAAT) promoter element, and a hAAT exon 1; an SV40 element; a silently altered human PAH coding sequence; an SV40 polyadenylation sequence; a 3' homology arm; and a 3' ITR element. The sequences of these elements are set forth in Table 1.

TABLE 1

Selected genetic elements in PAH correction vectors PAH-006m, PAH-006m-LP-1, PAH-032h, and hPAH-hI1C-032-LP1-5D3

| Genetic Element | PAH-006m | PAH-006m-LP-1 | PAH-032h | hPAH-hI1C-032-LP1-5D3 |
|---|---|---|---|---|
| | | SEQ ID NO: | | |
| 5' ITR element | 14 | 14 | 14 | 14 |
| 5' homology arm | 84 | 85 | 23 | 23 |
| Splice acceptor | — | — | 30 | — |
| 2A element | — | — | 40 | — |
| transcriptional regulatory element | — | 27 | — | 27 |
| SV40 intron element | — | 29 | — | 29 |
| silently altered human PAH coding sequence | 83 | 28 | 83 | 28 |
| SV40 polyadenylation sequence | 31 | 31 | 31 | 31 |
| 3' homology arm | 86 | 86 | 24 | 24 |
| 3' ITR element | 18 | 18 | 18 | 18 |

TABLE 1-continued

Selected genetic elements in PAH correction vectors PAH-006m,
PAH-006m-LP-1, PAH-032h, and hPAH-hI1C-032-LP1-5D3

| Genetic Element | PAH-006m | PAH-006m-LP-1 | PAH-032h | hPAH-hI1C-032-LP1-5D3 |
|---|---|---|---|---|
| | | SEQ ID NO: | | |
| AAV genome from 5' homology arm to 3' homology arm | 77 | 79 | 81 | 43 |
| AAV genome from 5' ITR to 3' ITR | 78 | 80 | 82 | 45 |

"—" signifies an absence of this element

Example 2: Analysis of hPAH Correction Vectors in Mouse Models

Materials and Methods

PAH$^{enu2}$ Mouse Model:

The PAH$^{enu2}$ mouse model was used to establish dose response for PAH correction vectors packaged in AAVHSC15 capsid through measurement of vector genomes, percent target gene insertion, hPAH mRNA expression, and Phe/Tyr concentration.

The PAH$^{enu2}$ mouse line was produced by germline ethylnitrosourea mutagenesis followed by a Phe clearance screen to isolate a mutant mouse line deficient in PAH activity (see McDonald J D, et al. *PNAS* 1990; 87:1965-1967, which is hereby incorporated by reference in its entirety). It has a homozygous missense mutation (F263S in exon 7) in the region encoding the PAH active site, resulting in abolished activity of PAH. Mutations within exon 7 are common in humans with PAH deficiency, although PAH deficiency in humans is typically expressed in a compound heterozygous background. PAH$^{enu2}$ mice exhibit present with blood Phe levels consistently above 1200 μmol/L.

FRG® Mouse Human Liver Xenograft Model:

Fah$^{-/-}$/Rag2$^{-/-}$/Il2rg$^{-/-}$ (FRG) mice (Azuma et al. (2007) *Nat. Biotechnol.* 25(8): 903-910) containing human liver tissue were used to measure in vivo transduction of vector genomes, human DNA target gene insertion, and mRNA expression of hPAH in human liver tissue, following administration of correction vectors packaged in AAVHSC15 capsid across a range of doses.

The FRG® human liver xenograft model is an immunocompromised mouse strain harboring triple gene knockouts of Fah$^{-/-}$, IL2rg$^{-/-}$ and Rag2$^{-/-}$. Because of the IL2rg$^{-/-}$ and Rag2$^{-/-}$ knockouts these mice lack B-cell, T-cell and NK-cells resulting in acceptance of engraftment with human cells. The Fah$^{-/-}$ genotype renders these mice dependent on the liver protective drug, 2-(2-nitro-4-trifluoromethylbenzoyl)-1,3-cyclohexanedione (NTBC), such that its withdrawal leads to loss of hepatocytes and animal death within 4-8 weeks.

To generate humanized livers in FRG mice, human primary hepatocytes were implanted concurrent with NTBC withdrawal. Since the human hepatocytes have an intact FAH gene, only murine hepatocytes are affected, resulting in the gradual repopulation of the mouse liver compartment with human hepatocytes. The human repopulated livers show >90% human hepatocytes and restored hepatic function (Azuma et al. (2007) *Nat. Biotechnol.* 25(8): 903-910).

On-Target Insertion—ddPCR Linkage Assay:

To determine the level of target insertion per allele at the PAH gene locus, an assay that uses droplet digital PCR (ddPCR) was employed. In this assay, target insertion was determined by measuring genetic linkage between the hPAH transgene and the genomic target. Linkage is a measurement of how often two sequences are on the same strand of DNA. Determining the amount of linked to unlinked vector and genome sequences can be used to measure insertion efficiency, which is reported as percent insertion per allele.

To measure target insertion via linkage, two primer and probe sets were used, one targeting the silently altered hPAH payload and a second targeting the Pah genomic sequence beyond the homology arms. Each probe consisted of a fluorophore in either the FAM or HEX channel such that when DNA is analyzed in partitioned droplets, each droplet can be scored by its emission signature as producing one of three possible signals: FAM-positive (silently altered hPAH payload alone); HEX-positive (genomic alone); and HEX+FAM positive (contains silently altered hPAH payload and genomic sequence). Target insertion was measured by determining the proportion of droplets containing both the payload and the genomic sequence in excess of expectation due to probability, divided by the total number of Pah alleles tested.

As the relative concentration of vector to genome can vary across doses and models, it is important to ensure each measurement is within the linear range of detection for both the vector and the target genomic sequence. Therefore, prior to measuring target insertion, the relative abundance of vector and target genome was measured across a range of sample input concentrations from 1 ng, 5 ng, 10 ng, 100 ng. The ratio of vector to genome was used to determine the sample input concentration in which both the vector and genomes fall within the limits of detection by ddPCR which are between 0.25-5000 molecules per μl.

On-Target Insertion—Next Generation Sequencing (NGS) Assay:

This approach was used to calculate target insertion using assays spanning both left and right integration sites of the human PAH editing construct. Each of the two amplicons share their respective outward primer located on the genomic DNA flanking each homology arm, while the inward primers were unique for unedited alleles or for the edited alleles respectively. Each number of wild-type (WT) and edited sequences were tallied by counting the number of sequences covering the junction between the homology arm and either the inserted gene or the unedited wild-type sequence. Having separate assays covering both the left and right side of the insertion site provides redundant quantitation of insertion. By using this NGS approach, the percentage of target insertions can be detected per total number of alleles, and in addition, sequences of the entire insertion site can be collected, enabling the detection of de novo mutations (e.g., incorrect insertion and deletion events and ITR integration).

Differences of uninserted and inserted amplification efficiency were accounted for using an 11-step standard for both left and right integration sites. Each control panel consists of purified uninserted amplicon and edited amplicon at the following ratios: 0% edited, 1%, 2%, 5%, 10% 50%, 60%, 90%, 95%, 98%, 99% and 100% edited control sequence. Target insertion efficiency calculations were as follows: the sequencing reads specific to uninserted and inserted genomic loci are tallied and target insertion was calculated by (insertion read counts/total read counts*100%) and fitted to the standard curve. As editing quantitation per sample was measured by two independent assays, each spanning opposite homology arms into the native genome, the consistency between each measurement was determined.

On-Target Accuracy—Next Generation Sequencing (NGS) Assay:

To determine if target gene insertion is accompanied by de novo mutation at the integration sites, PCR amplicons spanning genomic sequences beyond both left and right of the homologous arms and into the target insertion site were sequenced. A total of four amplicons were sequenced per sample. Insertion specific amplicons spanning each homology arm (hPAH dependent PCR) or WT/uninserted alleles spanning each homology arm (no hPAH insertion) were assessed.

To identify the detection limit of the assay, an amplicon-based control panel was built by mixing two right homologous arm amplicons, varied by one base (a T to G variation), at 0%, 0.1%, 0.5%, 1%, 2%, 5%, 10%, 50, and 100%. The amplicon control panel went through the same processing steps. Based on the quantitative variant calling from the standard curve, false-positive variants were observed at a frequency of 0.1-0.25% at non-random positions. Sequencing coverage for almost all positions was above 10,000. A variant was considered to be a true positive with the following criteria: (1) at >0.5% variant frequency and pass filters; (2) appear in both technical sequencing duplicates; and (3) not observed in WT alleles given comparable sequence depth and quality.

Results

A study was performed in $PAH^{enu2}$ mice using the mouse-specific correction vector, PAH-006m, which contains homology arms targeting the mouse PAH locus. PAH-006m does not contain a liver specific promoter, and as such, expression is driven by the endogenous promoter elements. Three male mice per group were administered either 1E+14 vg/kg PAH-006m packaged in AAVHSC15 capsid, or formulation buffer, and blood Phe level was measured weekly for 12 weeks. At the 12-week timepoint, mice were sacrificed to measure target insertion at the PAH locus, and mRNA expression levels.

Figure 3:
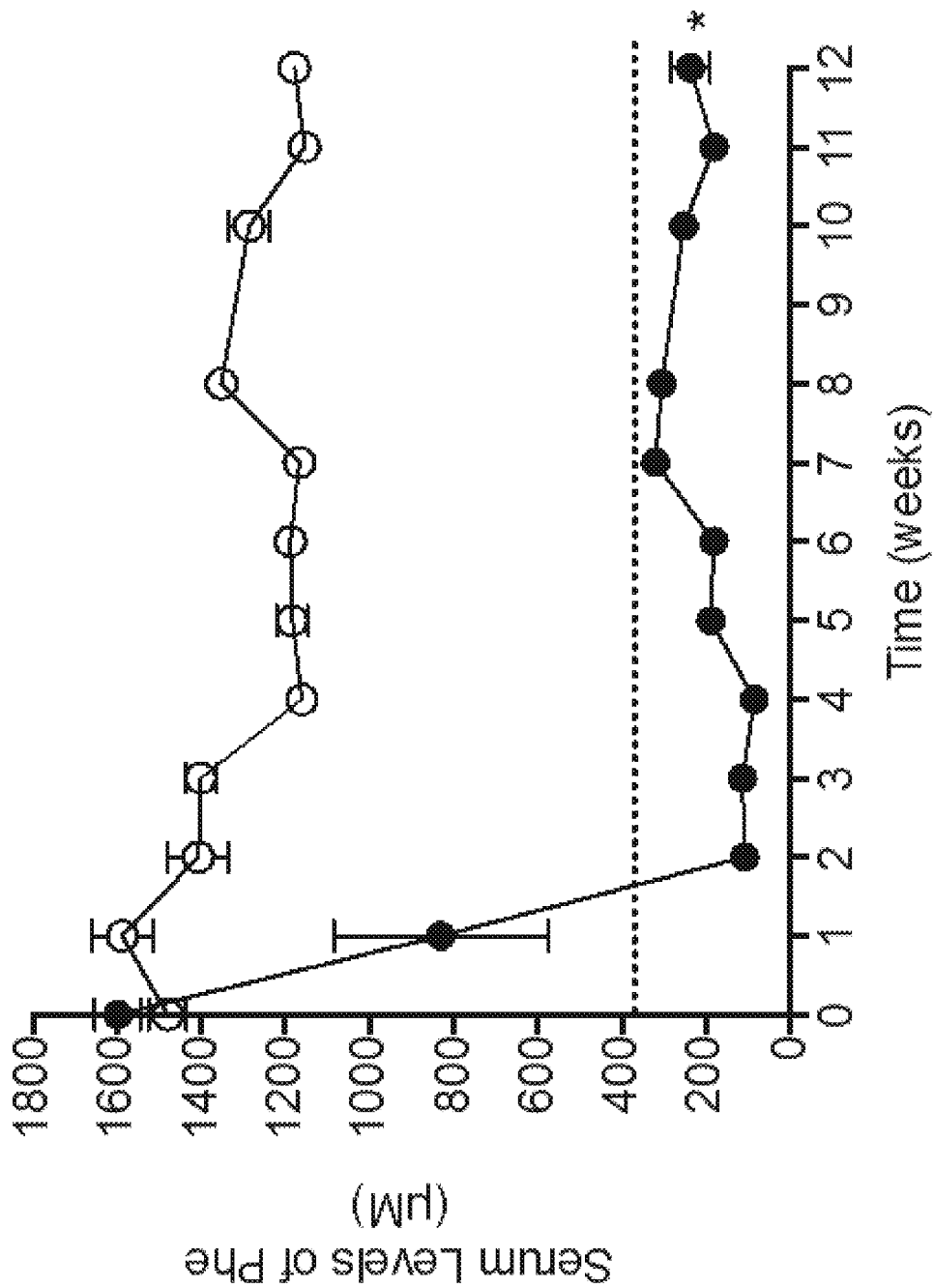
FIG. 3 is a plot showing the effect of PAH-006m on blood Phe levels in PAH$^{enu2}$ mice.

Blood Phe levels were reduced to normal levels by 2 weeks post-administration of PAH-006m packaged in AAVHSC15 capsid, as shown in FIG. 3. Reduction of blood Phe was maintained at levels of <360 µM for the duration of the 12-week study.

Figure 4:
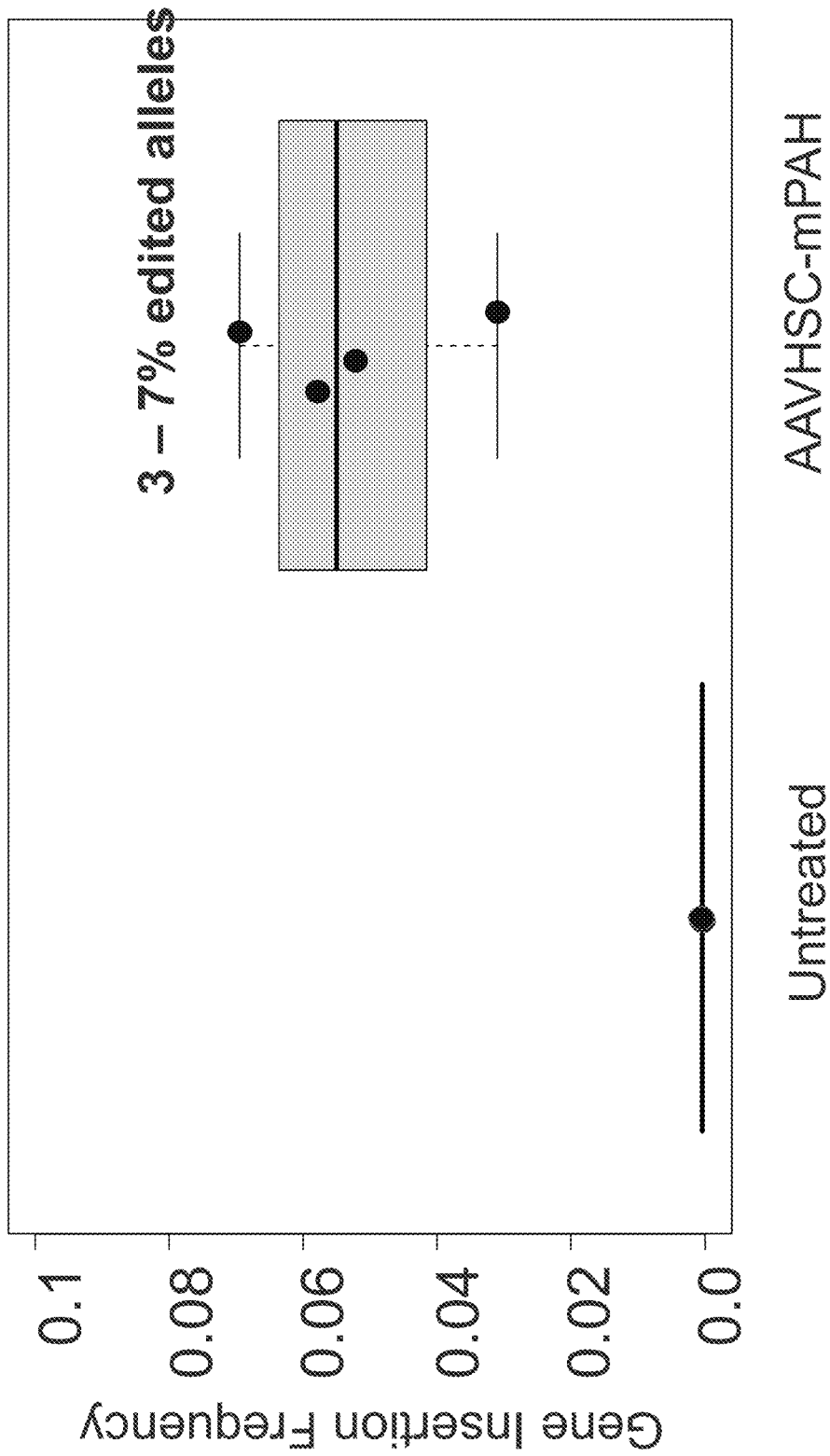
FIG. 4 is a plot showing on-target insertion at the mouse PAH locus following administration of PAH-006m.
Figure 5:
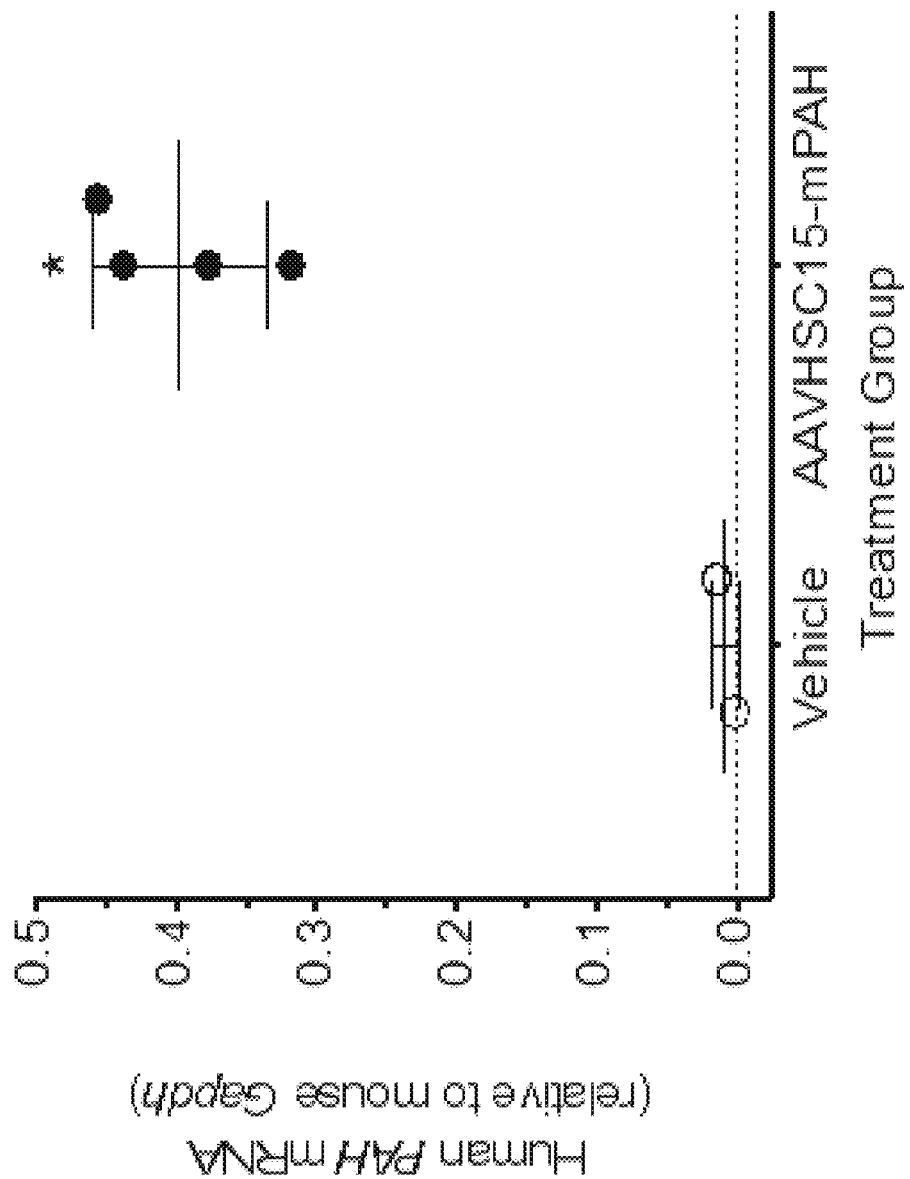
FIG. 5 is a plot showing the effect of PAH-006m on mRNA expression relative to mouse GAPDH.

The level of on-target insertion at the PAH locus was measured using the ddPCR linkage assay as described in the Materials and Methods above. A range of 3-7% target insertion per allele was detected in the liver at the 12-week timepoint, as shown in FIG. 4. The level of silently altered hPAH mRNA was also measured (relative to mouse GAPDH) and is shown in FIG. 5. The expression of silently altered hPAH mRNA was detected (PAH/GAPDH mRNA ratio was 0.38±0.06). Of note, the level of on-target insertion per allele was found to be directly correlated to the level of mRNA expression (R-squared 0.82; P<0.02).

To determine if similar levels of on-target insertion and mRNA expression could be achieved in human liver, experiments were conducted in the FRG® mouse containing a human liver xenograft. Mice were treated with a single IV dose of 1E+14 vg/kg PAH-032h packaged in AAVHSC15 capsid. PAH-032h does not contain the liver specific promoter, and as such, expression is driven by the endogenous human promoter elements, similar to construct PAH-006m.

Expression of hPAH mRNA derived from silently altered hPAH was evaluated in liver cells from the FRG® mouse. Expression was measured by RT-ddPCR and expressed as a ratio to GAPDH to allow for comparison across human and mouse hepatocytes. In the human hepatocytes isolated from the FRG® mouse model, 6-weeks after administration of PAH-032h packaged in AAVHSC15 capsid, hPAH mRNA derived from silently altered hPAH was expressed (hPAH/GAPDH mRNA ratio=0.57±0.11). Levels of silently altered hPAH mRNA in mouse hepatocytes were significantly lower (PAH/GAPDH mRNA ratio=0.13±0.08, p<0.003 vs human) and could be entirely accounted for by the presence of contaminating human hepatocytes in the preparations used (approximately 15-20% human). The proportion of mouse cells in human samples and human cells in mouse samples was calculated by measuring the relative abundance of human and mouse GAPDH gene in each sample.

Figure 6:
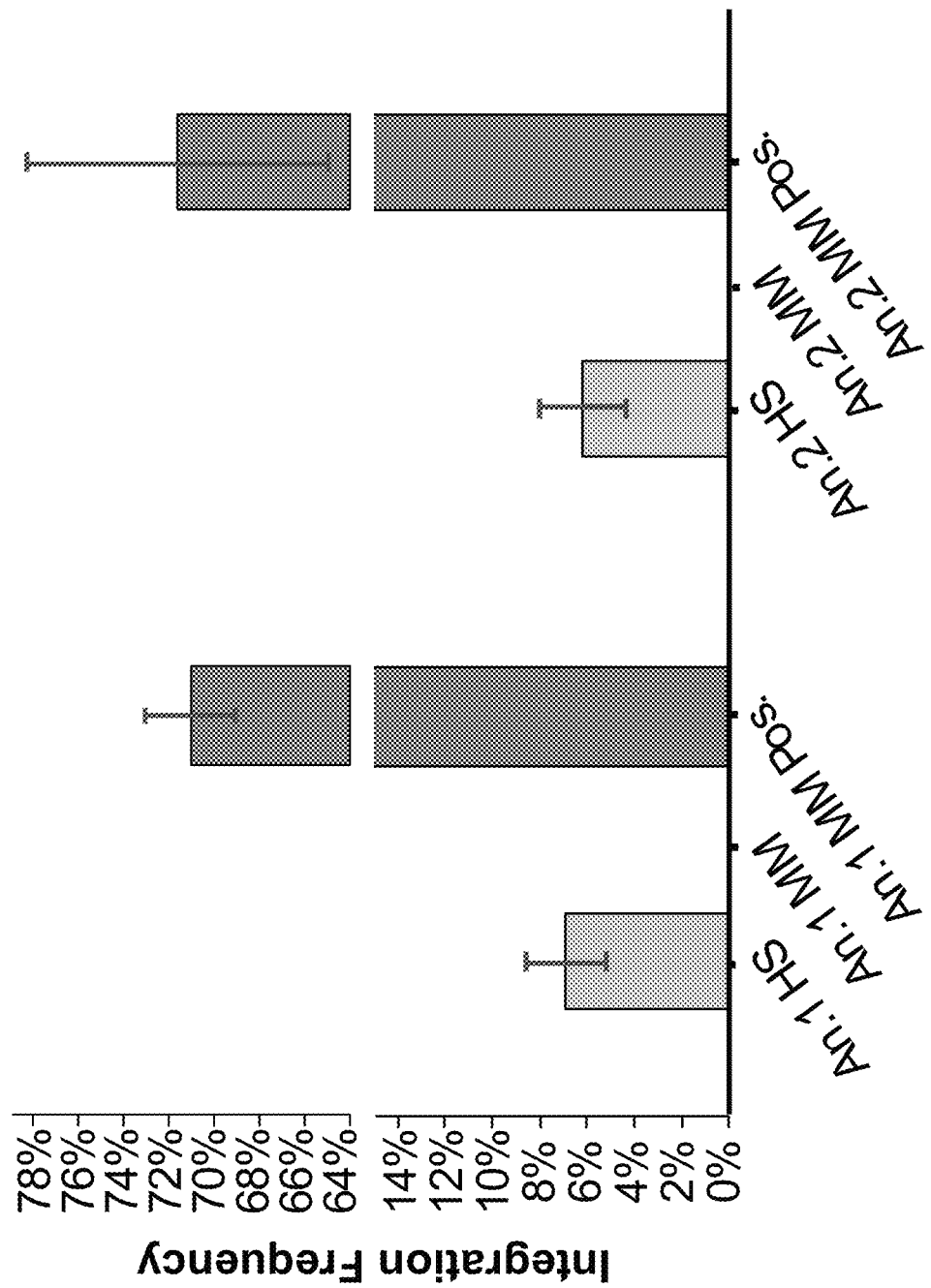
FIG. 6 is a plot showing on-target insertion in FRG® mice following administration of PAH-032h as measured by species specific ddPCR editing assays.

Confirmation of human-specific target insertion into the human PAH locus was done in a separate study in FRG® mice where levels of on-target insertion (~6% using the linkage ddPCR method; FIG. 6) and levels of hPAH mRNA derived from silently altered hPAH (hPAH/GAPDH mRNA ratio=0.45±0.26) were achieved in human cells with treatment of PAH-032h packaged in AAVHSC15 capsid. Target gene insertion efficiency was characterized using the NGS assay in which quantitation of integration is based on two separate measurements that cover both the left and right homology arms, respectively, with coverage extending into the genomic targeted integration sites and past the end of each homology arm, as described in the Materials and Methods above. Untreated wild-type genomic DNA was used to detect the false-positive rate for this experiment. Integration of hPAH into the PAH locus was confirmed with orthogonal assays (linkage ddPCR and NGS) reporting integration efficiencies of 6%. These results are shown in FIG. 7.

Figure 7:
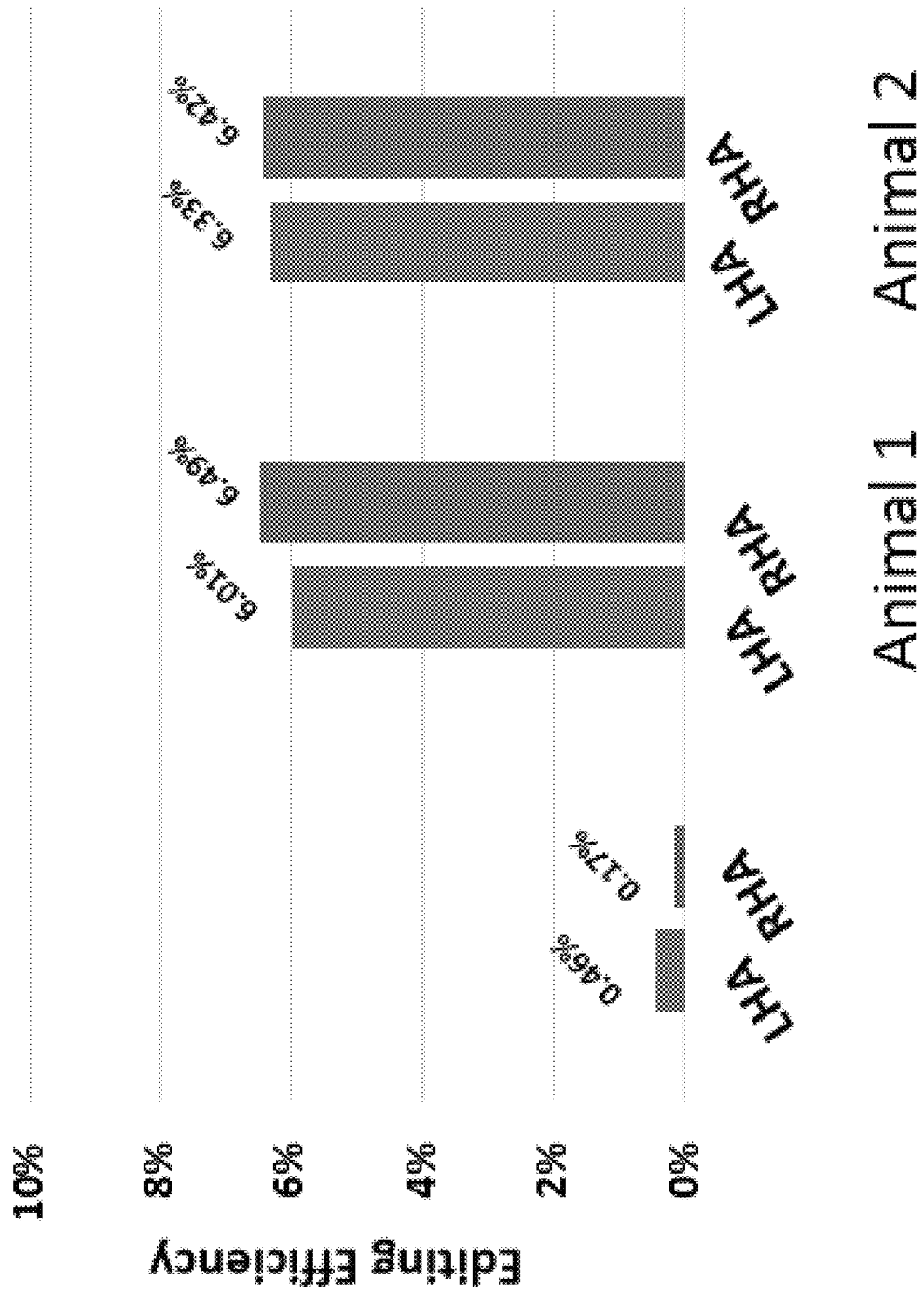
FIG. 7 is a plot showing editing of human hepatocytes in FRG mice as measured by quantitative next generation sequencing assays.

FIG. 6 and FIG. 7 show targeted insertion frequency in hepatocytes isolated from treated FRG mice. FIG. 6 shows insertion of the human-targeting PAH-032h correction vector packaged in AAVHSC15 capsid into mouse and human PAH loci, as measured by the species specific ddPCR editing assays described herein. As a positive control linkage between a mouse-specific PAH locus probe and a probe for the homologous insertion site was used. In FIG. 6, An.1 HS refers to Animal 1 *Homo sapiens* Cells, An.1 MM refers to Animal 1 *Mus musculus* cells, An.1 MM Pos. refers to Animal 1 *Mus musculus* positive control, An.2 HS refers to Animal 2 *Homo sapiens* Cells, An.2 MM refers to Animal 2 *Mus musculus* cells, and An.2 MM Pos. refers to Animal 2 *Mus musculus* positive control. FIG. 7 shows the editing of human hepatocytes as measured by quantitative NGS assays spanning both left and right homology arms. Editing efficiency was measured by read counts of edits specific to wild-type specific sequences. Untreated human DNA mixed with PAH-032h vector served as a negative control.

From these studies, it can be concluded that: (1) blood Phe concentration is reduced to a therapeutically relevant threshold (≤360 µM) following administration of the mouse construct PAH-006m packaged in AAVHSC15 capsid into $PAH^{enu2}$ mice; (2) similar levels of mRNA expression were observed across species between the mouse-specific construct PAH-006m in $PAH^{enu2}$ mice and the human specific construct PAH-032h in the human liver tissue of FRG® mice, both packaged in AAVHSC15 capsid; (3) no significant target insertion was observed in mouse hepatocytes (using mouse-specific assays) following administration of the human specific construct PAH-032h packaged in AAVHSC15 capsid into FRG® mice, demonstrating the sequence/species specificity of the human homology arms; and (4) similar levels of on-target integration per allele were achieved across species between the mouse-specific construct PAH-006m in the PAH$^{enu2}$ mouse (4-7%) and the human specific construct PAH-032h in the FRG mouse (~6%).

Example 3: In Vivo Efficacy of PAH-006m-LP-1 in PAH$^{enu2}$ Mice

The ability of the PAH-006m-LP-1 vector to reduce blood Phe levels in mice was assessed and correlated with hPAH mRNA expression and target insertion at the mouse PAH locus. Specifically, four PAH$^{enu2}$ mice received single intravenous administration of the murine specific PAH-006m-LP-1 vector packaged in AAVHSC15 capsid covering a ~2-log dose range, with dose levels of 5E+12, 1E+13, 1E+14, and 2E+14 vg/kg ("GE 5E12," "GE 1E13," "GE 1E14," and "GE 2E14," respectively). In addition, a control arm containing an AAV gene transfer construct expressing hPAH but with no homology arms was administered at a dose of 1E+13 vg/kg ("GT (+) control 1E13"). Four PAH$^{enu2}$ mice were also administered formulation buffer as a negative control ("FB"). Blood Phe concentration was measured over the course of the experiment.

Figure 8A:
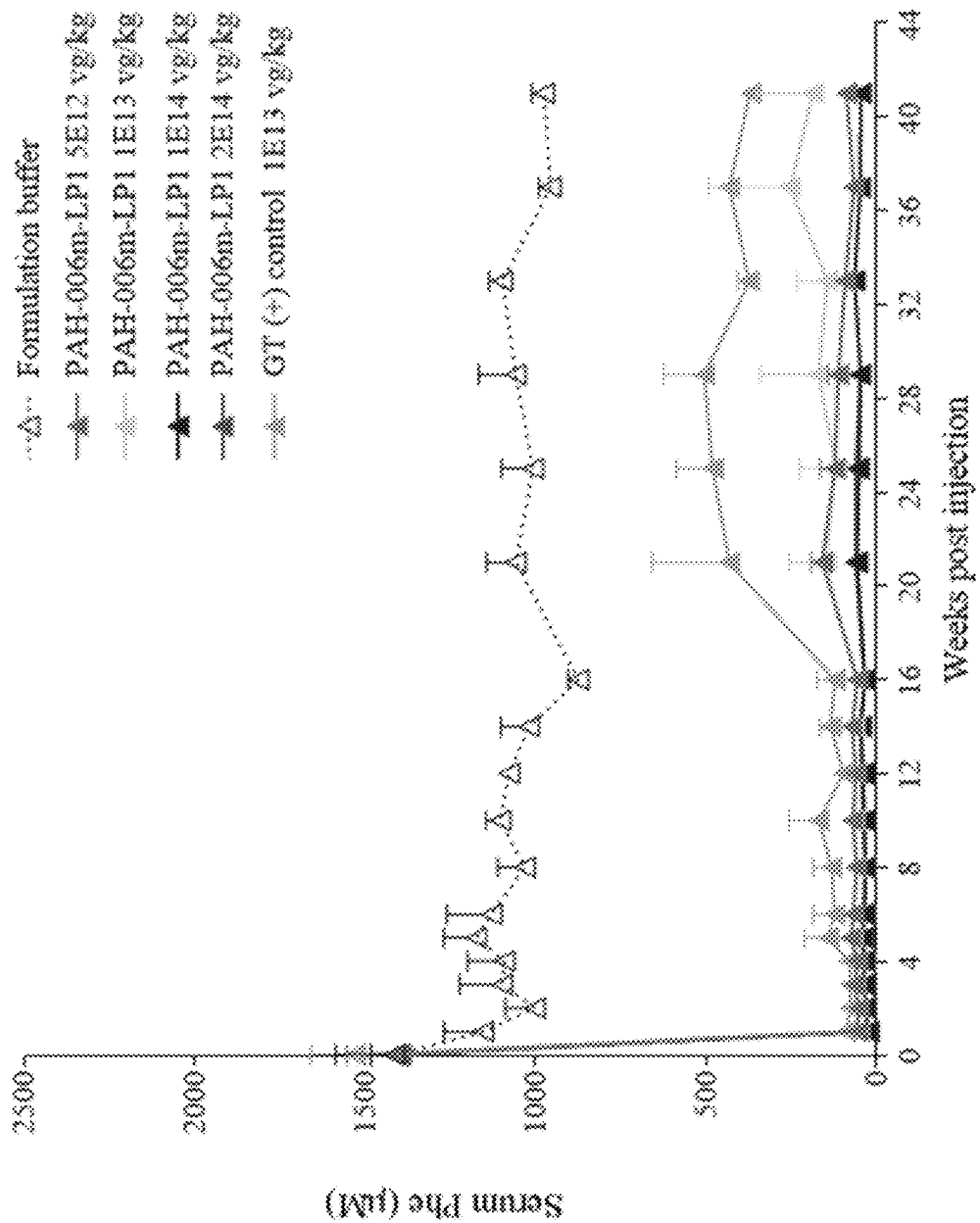
FIGS. 8A-8C are plots showing the effect of PAH-006m-LP-1 on blood Phe concentration in PAH$^{enu2}$ mice over time.
Figure 8B:
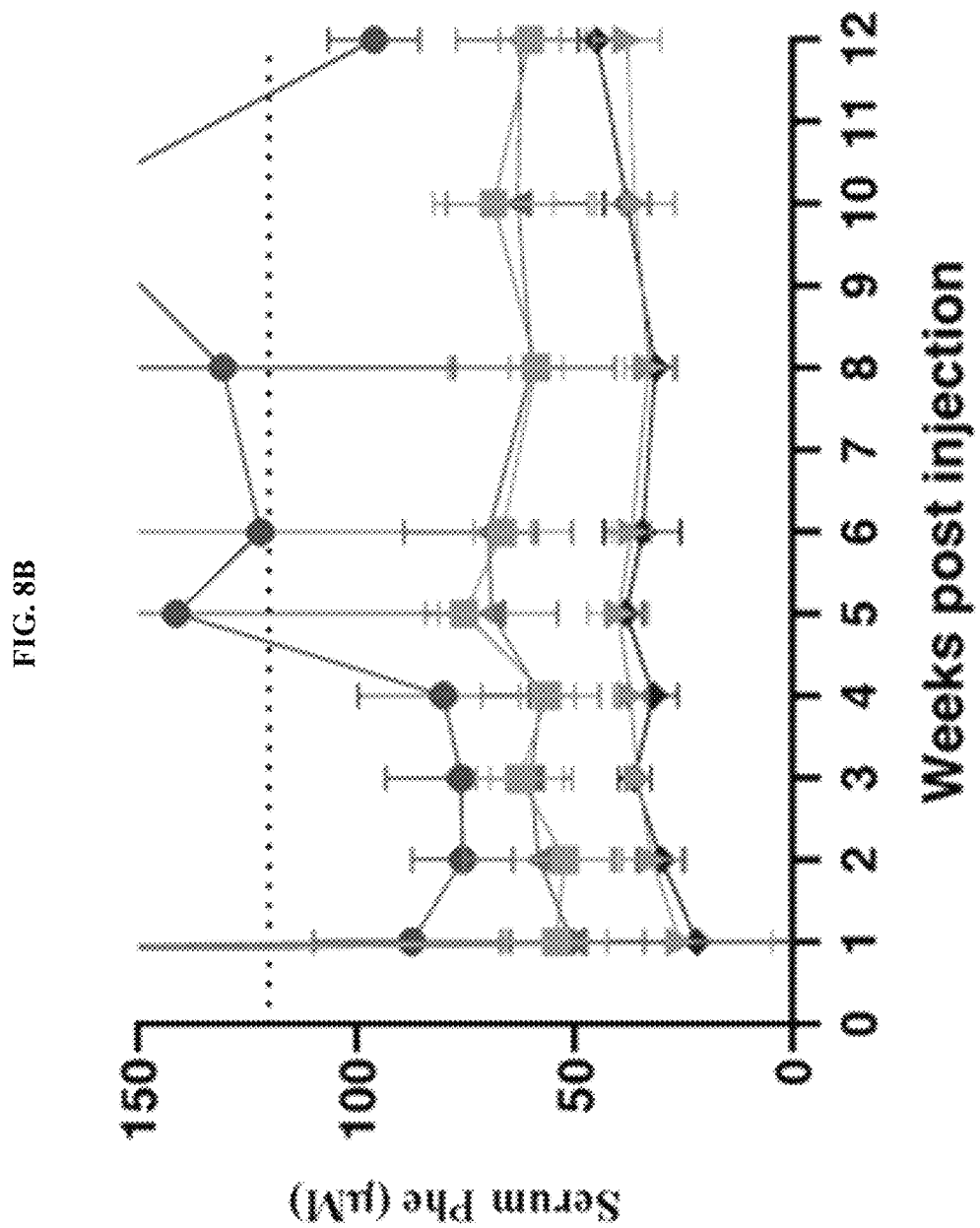

A subset of animals dosed at 1E+14 vg/kg were sacrificed at the 2-week timepoint to measure the level of target gene insertion in the liver. A level of 5±2% target gene insertion per allele was detected. The blood Phe concentrations in the mice through week 41 are shown in FIG. 8A. FIG. 8A shows the full data set, while FIG. 8B shows the data out to 12 weeks with a reduced y-axis scale to allow differences between the dose levels to be seen more clearly. Blood Phe concentration was reduced to normal levels by one week following administration of all dose levels, with the 1E+14 and 2E+14 doses resulting in the lowest levels.

Figure 8C:
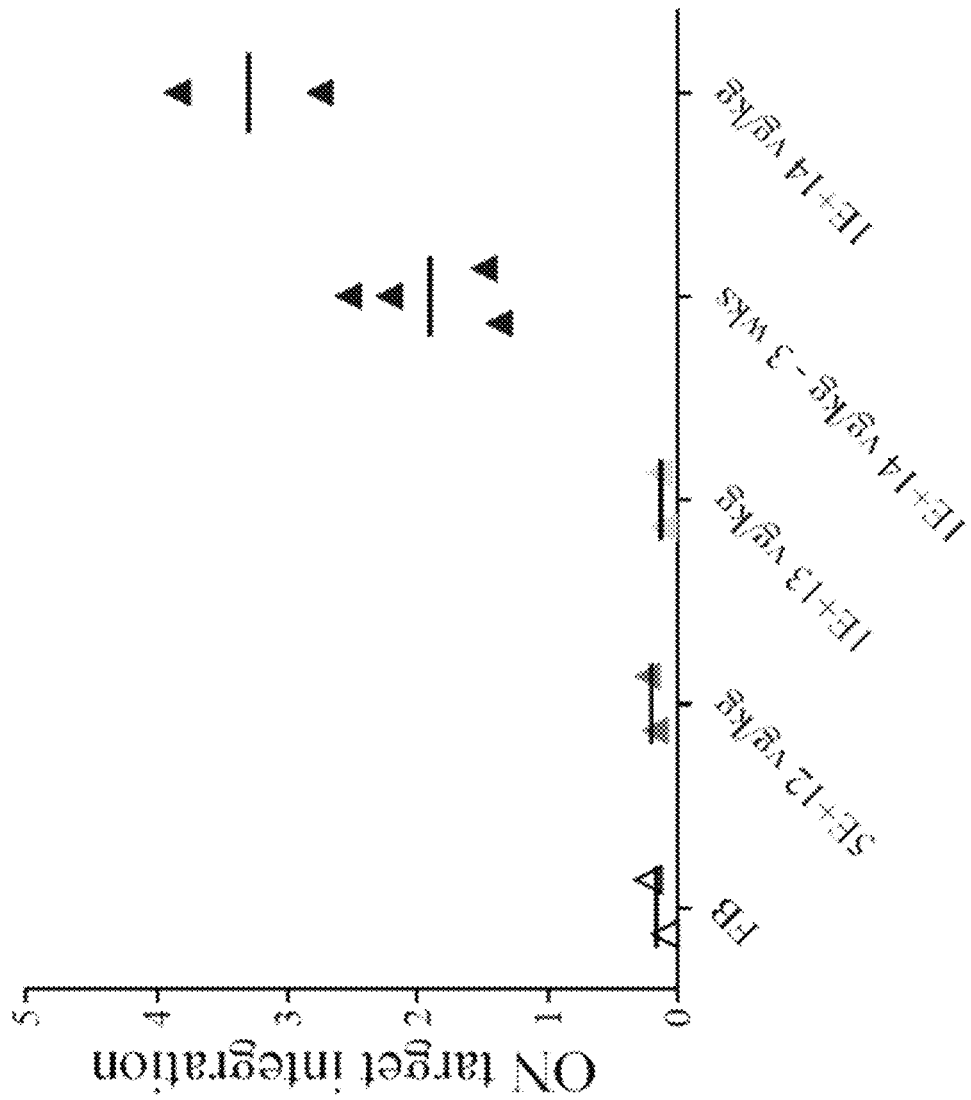

On-target analysis was performed on animals dosed at 5E12 vg/kg ("5E+12"), 1E13 vg/kg ("1E+13"), and 1E14 vg/kg ("1E+14"), as indicated (FIG. 8C). On-target integration was measured by next generation sequencing as described in Example 2. Integration rates were calculated based on the number of sequences with the integration divided by total number of sequences (with or without the integration event). In FIG. 8C, all data was collected at 43 weeks post-dosing, except "1E+14 vg/kg—3 wks" where the data was collected at 3 weeks post-dosing. As shown, on-target integration was detected in animals dosed with 1E14 vg/kg PAH-006m-LP-1 vector packaged in AAVHSC15 capsid at both 3 and 43 weeks post-dosing.

Example 4: In Vitro Editing Specificity of PAH-032h in Non-Human Primate and Human Hepatocytes Cynomolgus monkeys exhibit 94.2% sequence identity at the PAH locus to the human homology arm sequences of PAH-032h. To determine the specificity of PAH-032h for the human PAH locus, the ability of PAH-032h to edit the PAH locus in a mixture of primary cynomolgus monkey and primary human hepatocytes was assessed. A total of 5E+5 hepatocytes from a single cynomolgus monkey and a single human donor were treated with 1.5E+5 vg/cell of PAH-032h vector packaged in an AAVHSC15 capsid. Editing of the PAH locus was assessed by PCR using primers specific for the human edited allele and primers specific for the non-human primate edited allele. These PCR primers were designed to show either presence or absence of integration and were not quantitative. Accordingly, measurements of PCR efficiency were determined in positive control DNA across a standard curve of dilutions. This PCR assay had a lower limit of detection of 15 copies of edited allele (2.618E-5 amol).

Targeted integration of the payload into the PAH locus of human hepatocytes was observed. In contrast, no integration of the payload into the homologous cynomolgus monkey loci was detected. These results indicate that the human homology arms were specific for the human PAH locus in these assays.

Example 5: Comparison Between Gene Transfer/Gene Editing Vector and Episomal Transgene Expression Vector To investigate the dose response of integrated transgene expression and episomal transgene expression, a head-to-head comparison was performed using the mouse-specific gene transfer/gene editing AAV vector, PAH-006m-LP-1, and an episomal transgene expression AAV vector (containing the same transcriptional regulatory element as PAH-006m-LP-1, but lacking homology arms), packaged in AAVHSC15 capsid. The only difference between the payloads of the two vectors was the presence of two silent nucleotide changes in the PAH coding sequence of PAH-006m-LP-1. Five male, 4-week-old PAH$^{enu2}$ mice were intravenously administered 1E12 vg/kg ("1E+12"), 5E12 vg/kg ("5E+12"), 1E13 vg/kg ("1E+13"), 5E13 vg/kg ("5E+13"), or 1E14 vg/kg ("1E+14") doses of either the mouse-specific gene transfer/gene editing vector or the episomal transgene expression vector, in each case packaged in AAVHSC15, or a formulation buffer control (FB). For the episomal transgene expression vector packaged in AAVHSC15, after an official titering procedure, the titer of the lot used was accordingly adjusted to 7.8E11 vg/kg ("7.8E+11"), 3.9E12 vg/kg ("3.9E+12 vg/kg"), 7.8E12 vg/kg ("7.8E+12"), 3.9E13 vg/kg ("3.9E+13"), and 7.8E13 vg/kg ("7.8E+13"). It was found that targeted integration in mice dosed with PAH-006m-LP-1 was detectible and stable. A dose response between phenotype correction and levels of integration was also found.

Figure 9D:
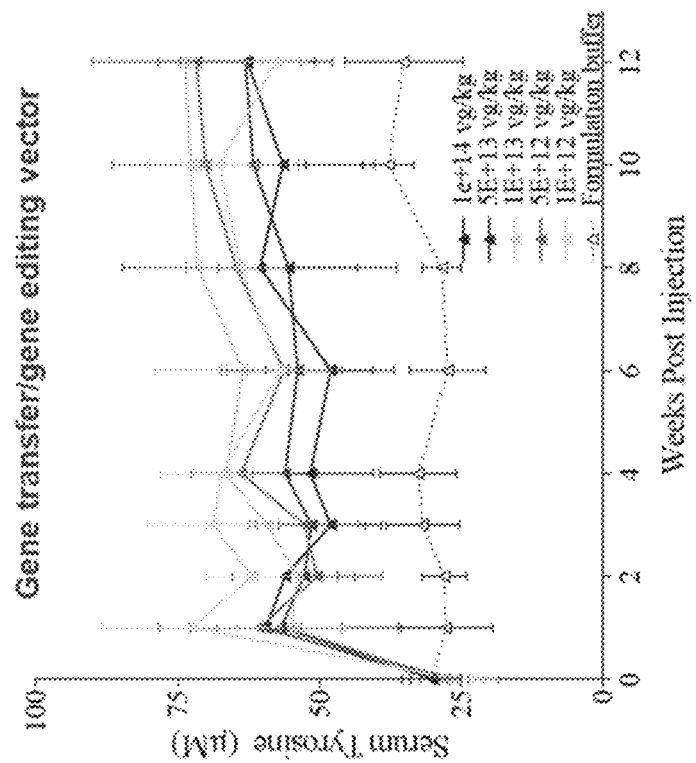
Figure 9C:
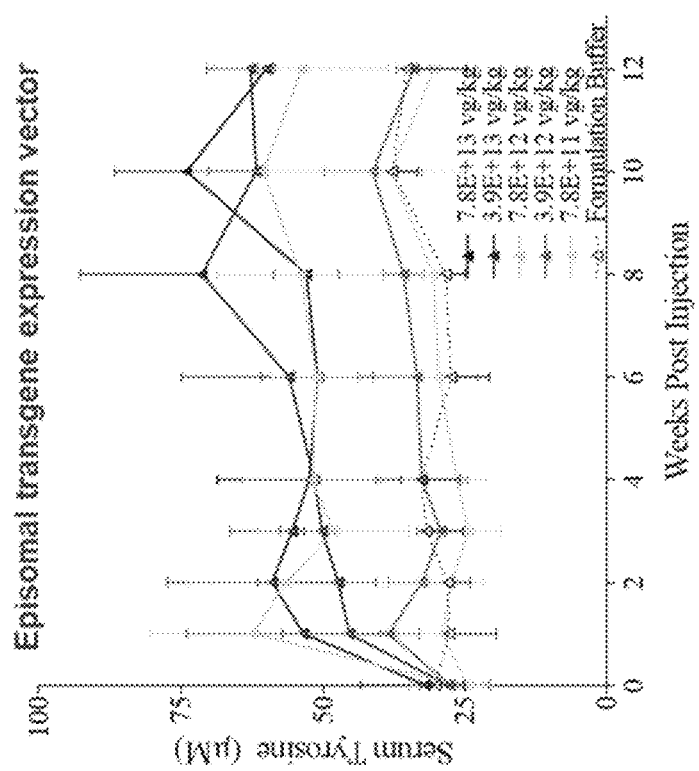

FIGS. 9A and 9B show 12-week time courses of the serum Phe levels in the mice that were dosed as described above. As shown, a reduction in serum Phe was observed in mice that received the episomal transgene expression vector packaged in AAVHSC15 capsid (FIG. 9A), or the gene transfer/gene editing vector packaged in AAVHSC15 capsid (FIG. 9B). Corresponding increases in blood Tyr concentration, a downstream metabolite of Phe, were also observed in mice that received the episomal transgene expression vector packaged in AAVHSC15 capsid (FIG. 9C), or the gene transfer/gene editing vector packaged in AAVHSC15 capsid (FIG. 9D).

Figure 9E:
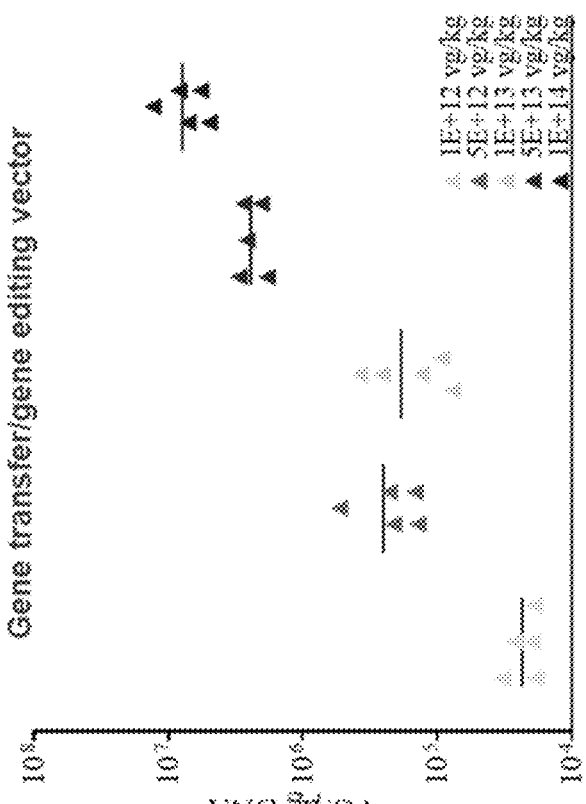
Figure 9F:
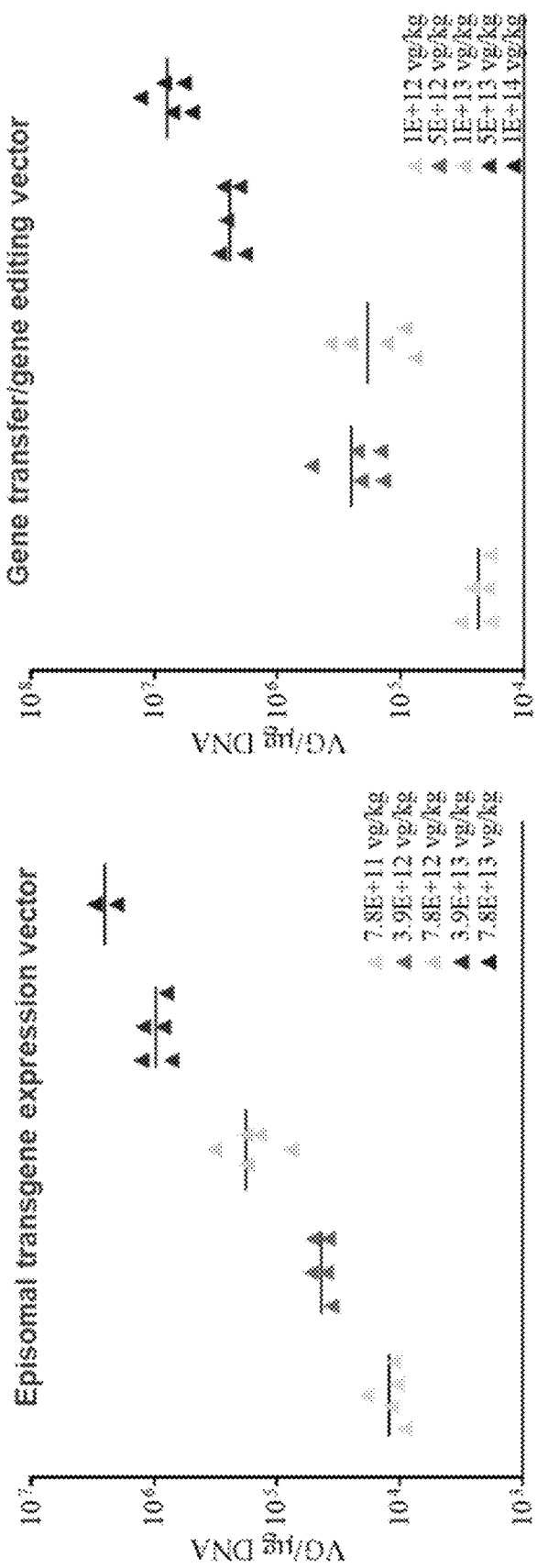

FIGS. 9E and 9F show the vector genome levels in PAH$^{enu2}$ mice dosed with the episomal transgene expression vector (FIG. 9E) or PAH-006m-LP1 (FIG. 9F), in each case packaged in AAVHSC15 capsid, at the indicated doses. Vector genomes per ug of DNA were measured using quantitative PCR using a coding sequence specific primer and probes relative to input genomic DNA target. A dose response in both vector genome copy number and mRNA was observed for both PAH-006m-LP-1 and the episomal transgene expression vector. The vector copy number for PAH-006m-LP-1 (FIG. 9F) was higher across all doses compared to the episomal transgene expression vector (FIG. 9E). Differences in VG/ug between the transgene and the integration vector are observed and may reflect differences in stability between self-complementary and single-stranded vectors.

Figure 9H:
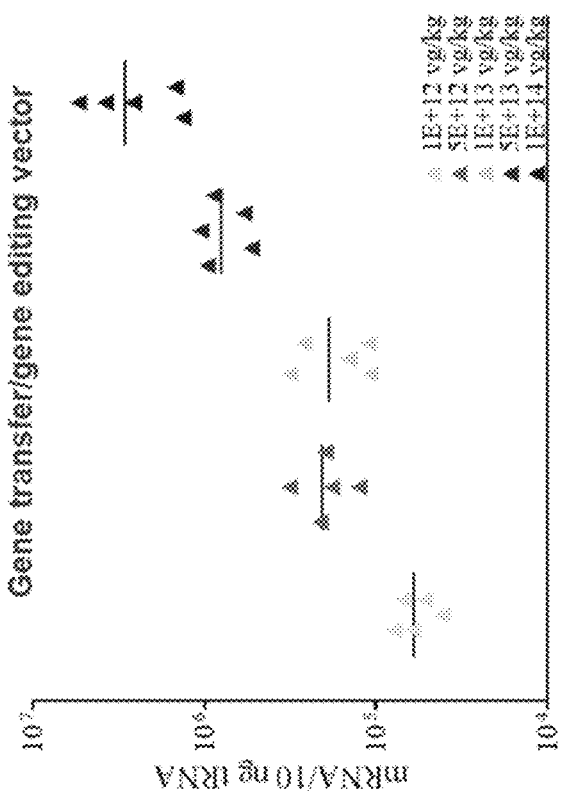
Figure 9G:
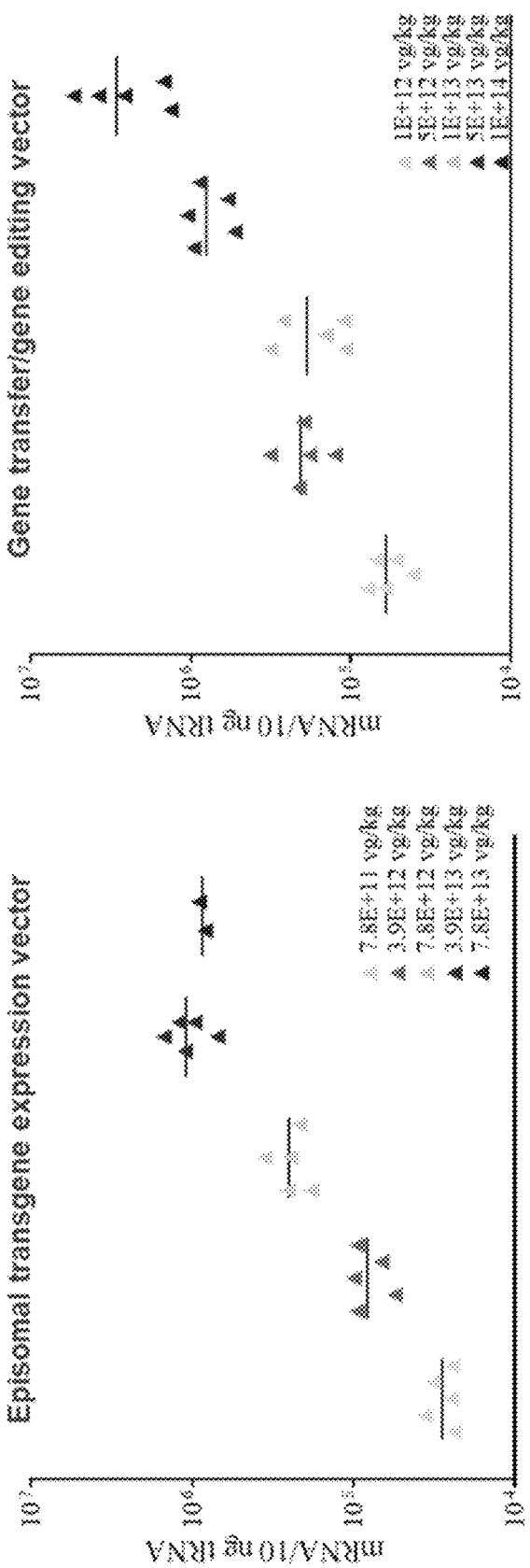

FIGS. 9G and 9H show the PAH transgene mRNA expression levels in PAH$^{enu2}$ mice dosed with the episomal transgene expression vector (FIG. 9G) or PAH-006m-LP1 (FIG. 9H), in each case packaged in AAVHSC15 capsid, at the indicated doses. mRNA levels were measured by quantitative RT-PCR using coding sequence specific primers and probes relative to total RNA. As shown, mRNA expression was found to be dose-responsive, and expression level was found to be slightly higher in mice that received PAH-006m-LP-1 packaged in AAVHSC15 capsid as compared to mice that received the episomal transgene expression vector packaged in AAVHSC15 capsid.

To assess the quantity and fidelity of target locus integration in PAH$^{enu2}$ mice, two methods were performed to detect integration events: ddPCR and next generation sequencing.

Figure 9I:
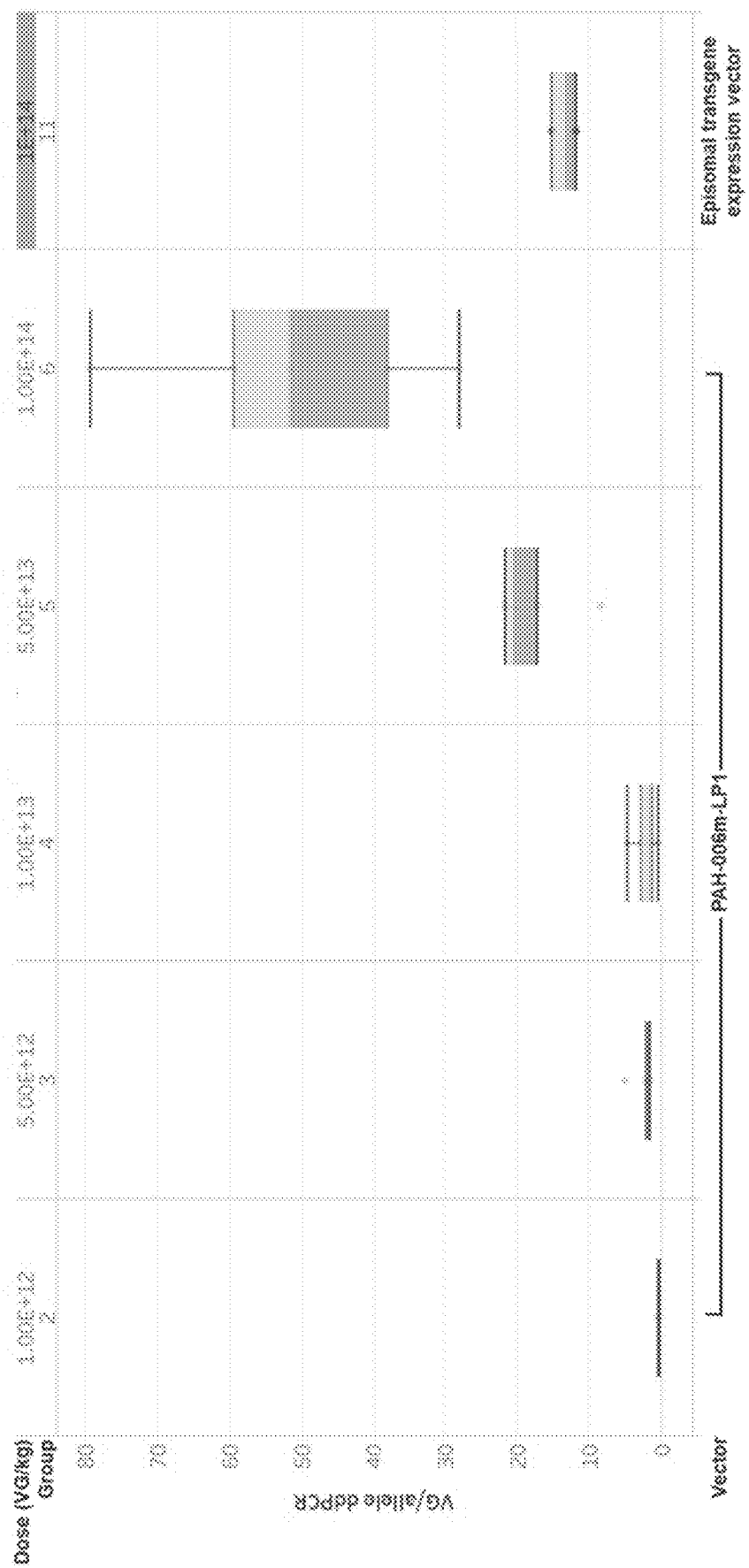

The level of on-target integration at the PAH locus was measured using the ddPCR linkage assay as described in Example 2. FIG. 9I shows the amount of on-target integration (measured in viral genomes per PAH allele detected by ddPCR) at 12 weeks post-dosing for the various doses of PAH-006m-LP1 and episomal transgene expression vector control indicated. As shown, a dose response of targeted integration detected by ddPCR was observed in mice that received PAH-006m-LP1 packaged in AAVHSC15 capsid (FIG. 9I; Groups 2, 3, 4, 5, and 6). In comparison, no targeted integration was detected by ddPCR in mice that received the episomal transgene expression vector packaged in AAVHSC15 capsid (FIG. 9I; Group 11).

Figure 9J:
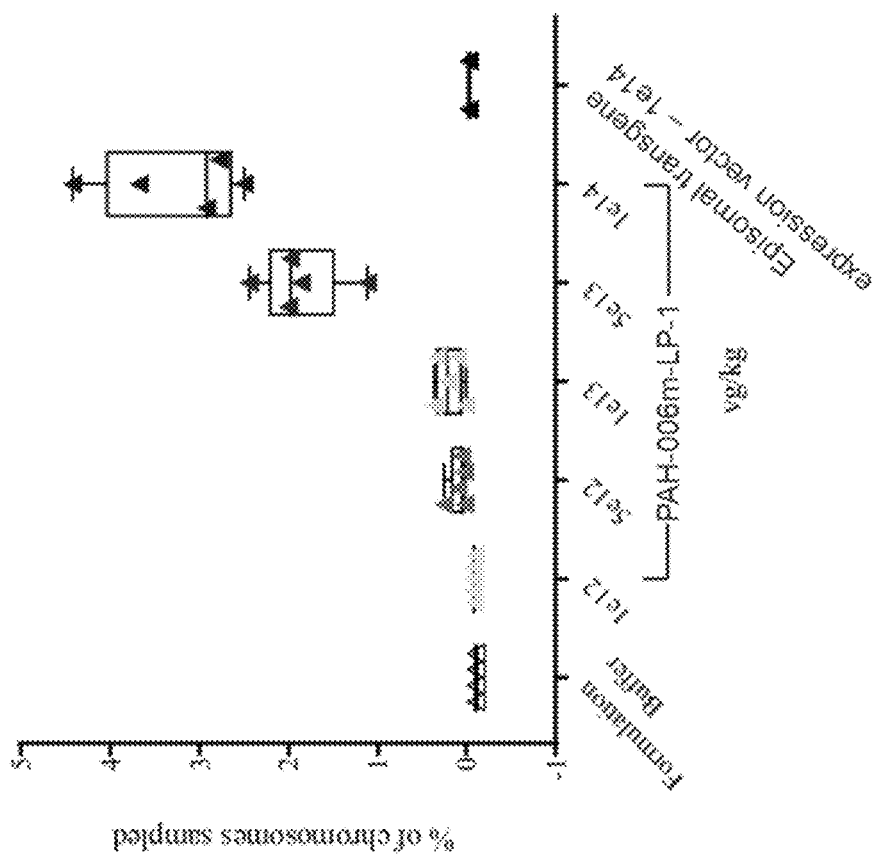

FIG. 9J shows the frequency of on-target vector insertion detected (using the NGS approach described in Example 2) 12 weeks post-dosing with the indicated doses of PAH-006m-LP1 packaged in AAVHSC15. As shown, a dose response of targeted integration detected by NGS was observed in mice that received PAH-006m-LP1 packaged in AAVHSC15 capsid. In comparison, no targeted integration was detected by NGS in mice that received the episomal transgene expression vector packaged in AAVHSC15 capsid. Integration level was found to be dose-responsive and higher than 2% at doses greater than 5E13 vg/kg.

To evaluate the effect of integrated transgene expression and episomal transgene expression in proliferating cell populations, 10-week-old PAH$^{enu2}$ mice were intravenously administered 5E12 vg/kg, 2E13 vg/kg, 6E13 vg/kg, or 1E15 vg/kg doses of either the mouse-specific gene transfer/gene editing vector or the episomal transgene expression vector, in each case packaged in AAVHSC15, or a formulation buffer control (FB). For the episomal transgene expression vector packaged in AAVHSC15, after an official titering procedure, the titer of the lot used was accordingly adjusted to 3.92E12 vg/kg ("3.92E+12"), 1.57E13 vg/kg ("1.57E+13 vg/kg"), 4.71E13 vg/kg ("4.71E+13"), and 7.84E13 vg/kg ("7.84E+13"). About 2 weeks post-dosing, the mice underwent either a 70% partial hepatectomy (PHx) to induce rapid hepatocyte cycling, or a sham surgery (sham). FIGS. 9K and 9L show a time course out to 42 weeks (FIG. 9K) or 40 weeks (FIG. 9L) of the serum Phe levels in these mice. As shown, in mice treated with the episomal transgene expression vector (FIG. 9K), serum Phe levels were reduced at weeks 1 and 2. Following hepatectomy at the 2-week timepoint, the Phe levels at the 5E12 vg/kg and 2E13 vg/kg dose levels increased during the period of accelerated liver regeneration. The sham surgery animals treated with 2E13 vg/kg episomal transgene expression vector did not show a loss of this response, indicating that the increase in serum Phe levels in the episomal transgene expression vector treated hepatectomized mice may be due to vector dilution under conditions of accelerated liver growth that occurred following hepatectomy. Mice treated with the gene transfer/gene editing vector (FIG. 9L) showed a stable reduction in Phe levels throughout the period of accelerated liver growth in the partially hepatectomized mice. This result may be indicative of the benefit of integration at the target mouse Pah locus.

Example 6: Comparison Between Mouse-Specific Vector and Human-Specific Vector

To investigate dose range differences between the mouse-specific gene transfer/gene editing AAV vector (PAH-006m-LP-1; "mouse design"), and the human-specific gene transfer/gene editing AAV vector (hPAH-hI1C-032-LP1-SD3; "human design") was used in a head-to-head study. Four to five male, 4-week-old (FIGS. 10A-10H) or 10-week-old (FIGS. 10I-10P) PAH$^{enu2}$ mice were intravenously administered 1E12 vg/kg, 5E12 vg/kg, 1E13 vg/kg, or 5E13 vg/kg of either the mouse design vector (FIGS. 10A, 10C, 10E, 10G, 10I, 10K, 10M, and 10O) or the human design vector (FIGS. 10B, 10D, 10F, 10H, 10J, 10L, 10N, and 10P), in each case packaged in AAVHSC15, or a formulation buffer control (FB).

Figure 10B:
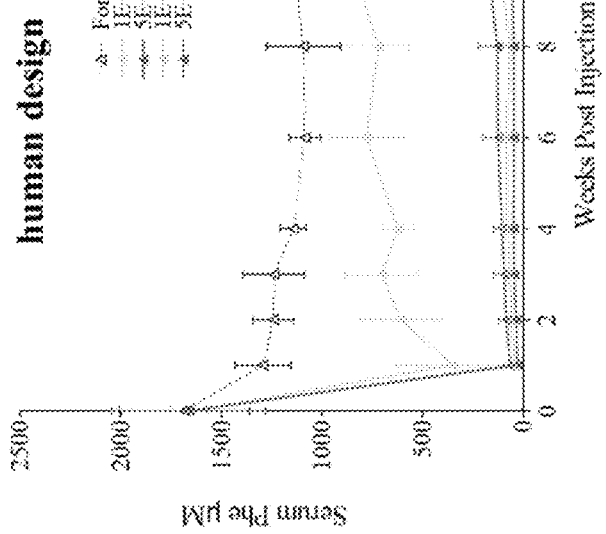
FIGS. 10A-10P are plots showing dose range differences between the mouse-specific gene transfer/gene editing AAV vector (PAH-006m-LP-1; "mouse design"), and the human-specific gene transfer/gene editing AAV vector (hPAH-hI1C-032-LP1-SD3; "human design") in 4-week (FIGS. 10A-10H) or 10-week-old (FIGS. 10I-10P) PAH$^{enu2}$ mice administered the vector packaged in AAVHSC15 capsid as indicated, at the dosage as indicated.
Figure 10A:
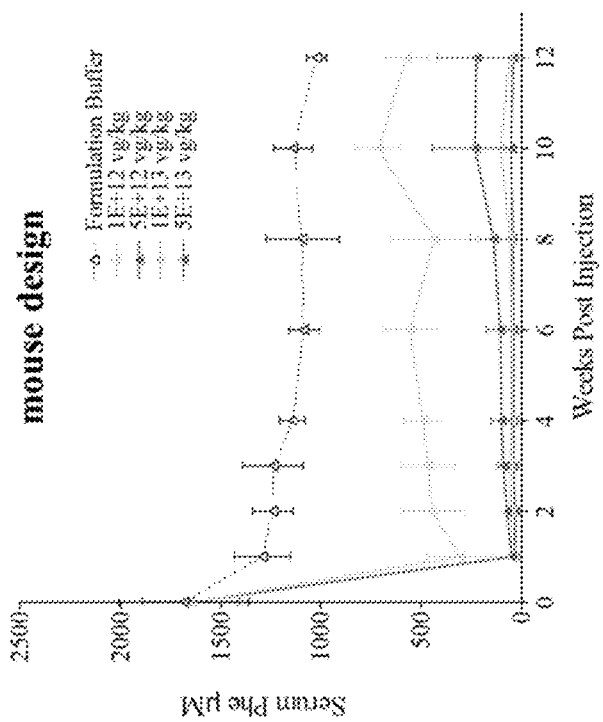
Figure 10D:
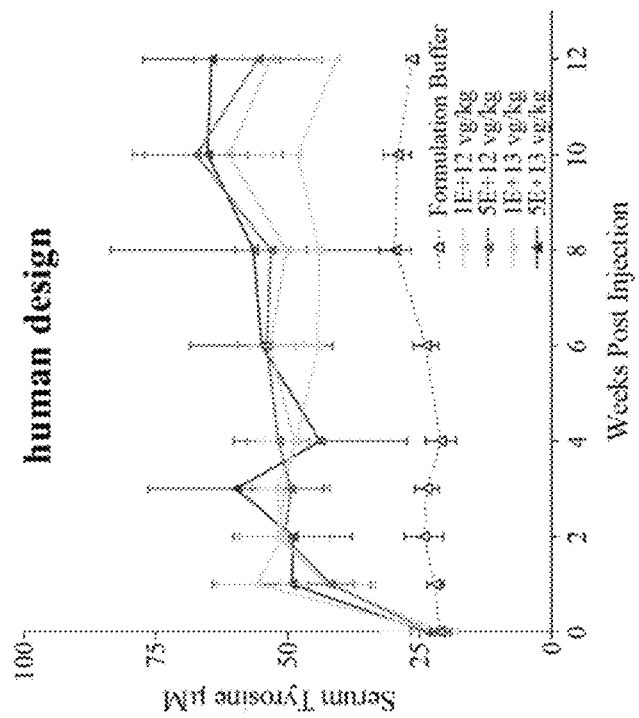
Figure 10C:
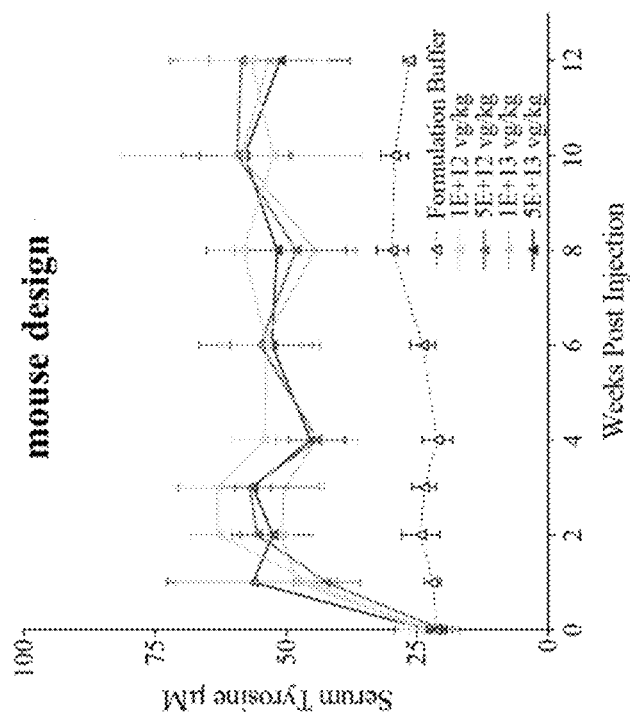
Figures 10E, 10F:
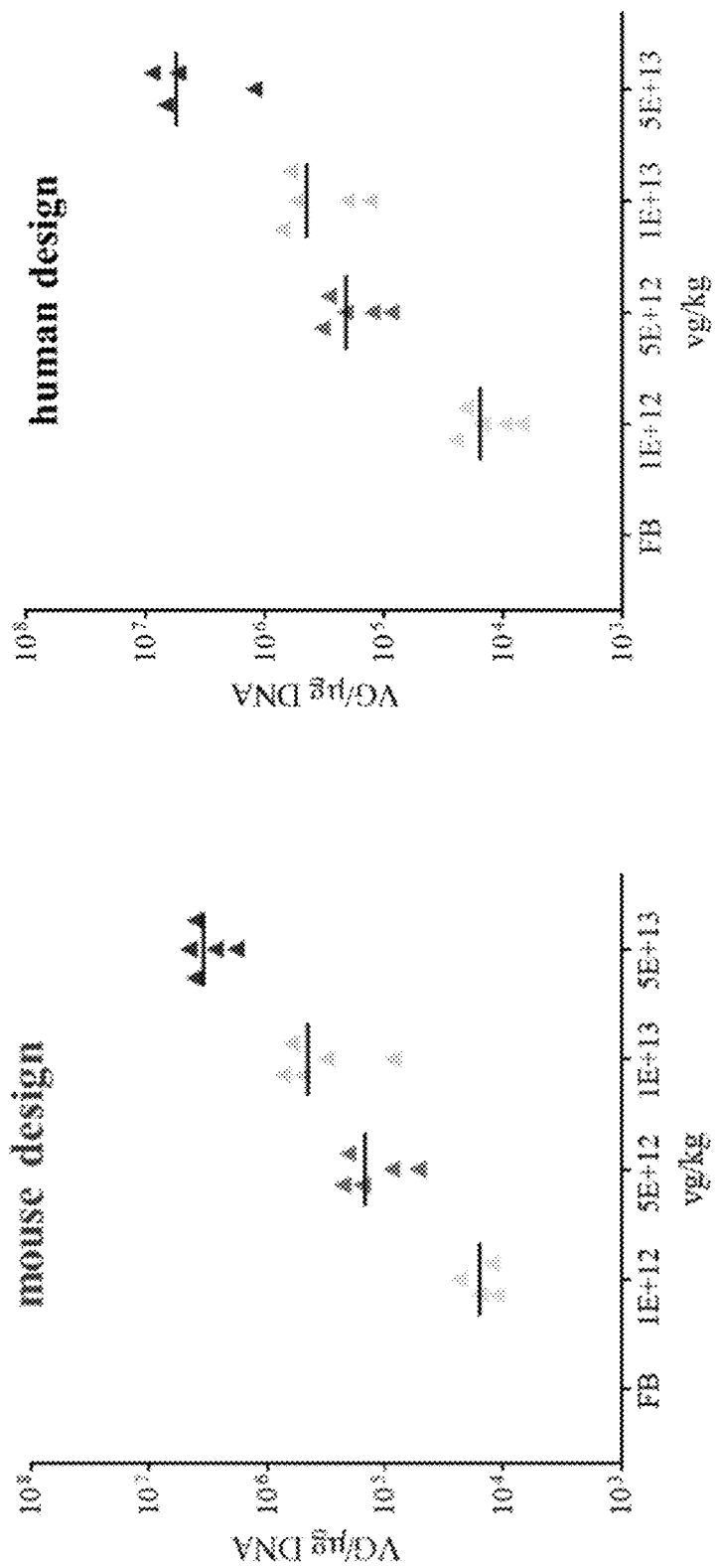
Figure 10I:
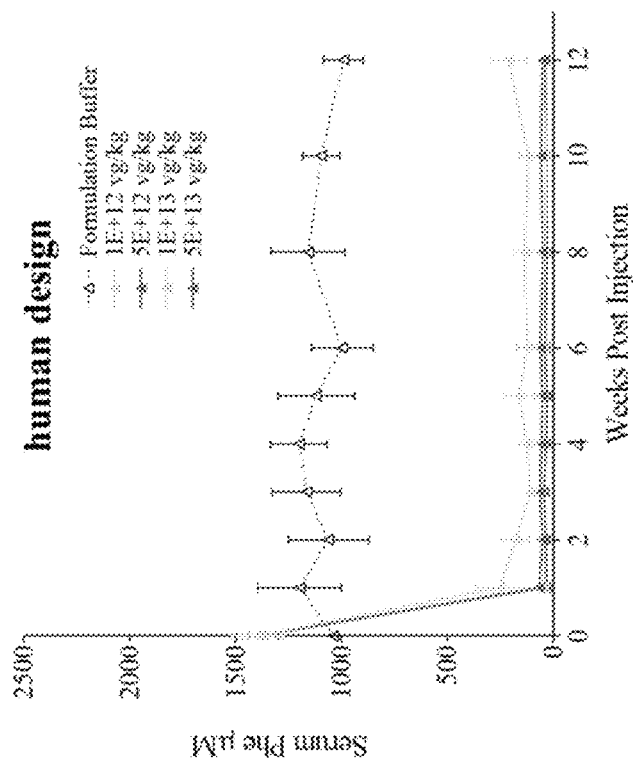

The human design vector comprises human homology arm sequences and would not be expected to integrate into the mouse genome via homologous recombination due to sequence differences, accordingly the human design vector served as an episomal-only control in these experiments. As shown, 4-week-old mice dosed with the human design vector packaged in AAVHSC15 capsid (FIG. 10B) exhibited an improvement in serum Phe reduction, similar to mice administered the mouse design vector (FIG. 10A). A corresponding increase in blood Tyr concentration was also observed in the 4-week-old mice dosed with the human design vector packaged in AAVHSC15 capsid (FIG. 10D) and in the mice dosed with the mouse design vector (FIG. 10C). As shown in FIGS. 10E and 10F, a dose response was observed for vector genome levels detected in the liver of 4-week-old mice dosed with the human design vector (FIG. 10F) or the mouse design vector (FIG. 10E) packaged in AAVHSC15 capsid. A dose response was also observed for mRNA levels detected in the liver of 4-week-old mice dosed with the human design vector (FIG. 10H) or the mouse design vector (FIG. 10G) packaged in AAVHSC15 capsid.

Figure 10J:
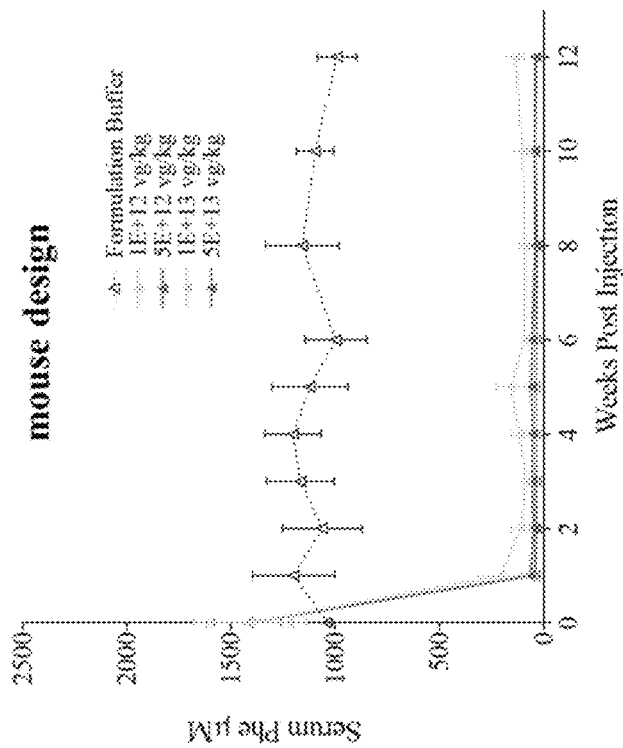
Figure 10L:
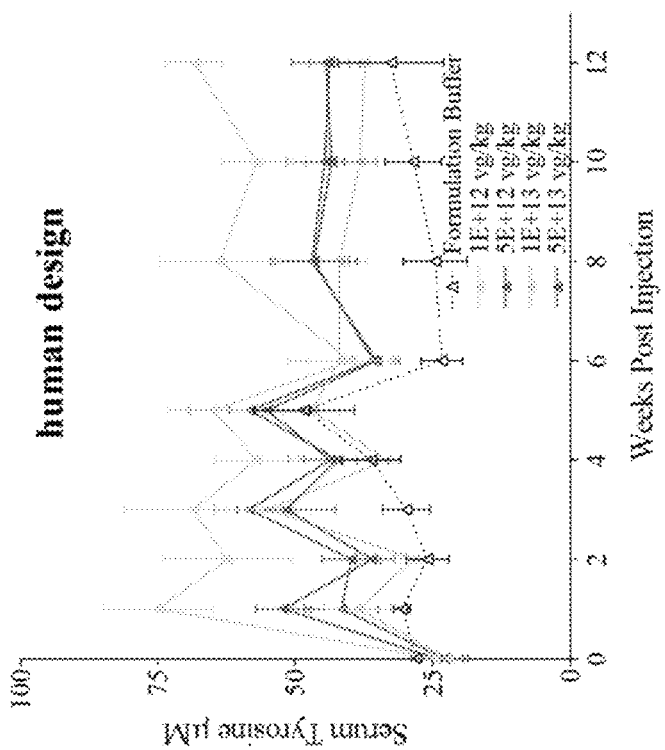
Figure 10K:
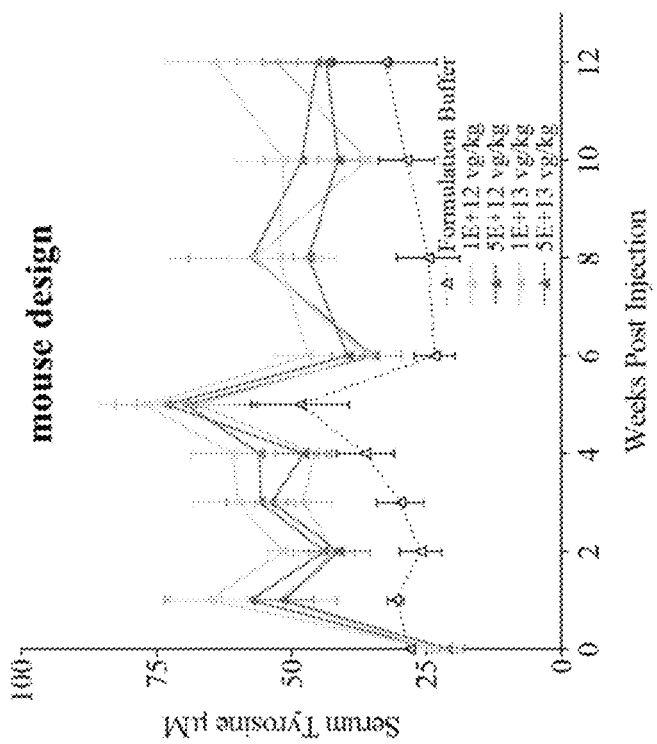
Figure 10N:
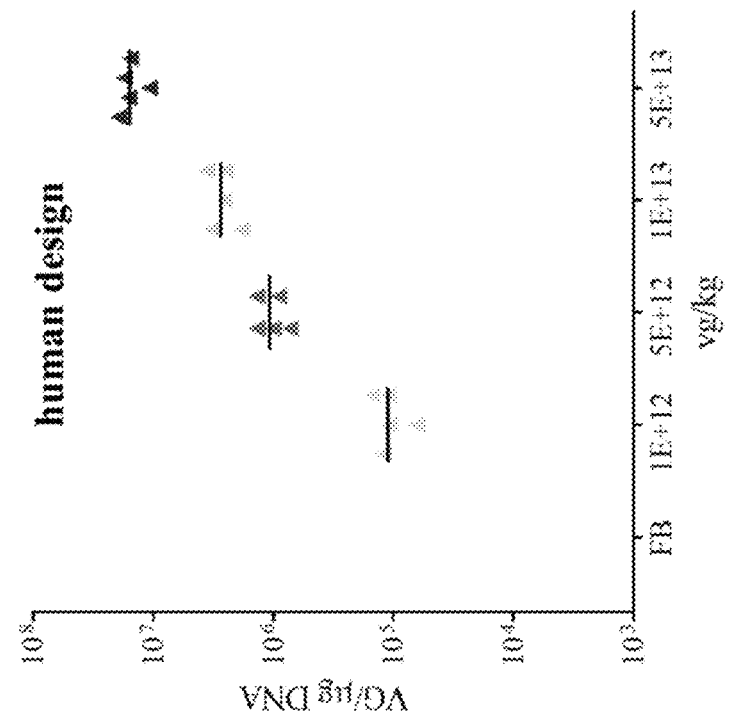
Figure 10M:
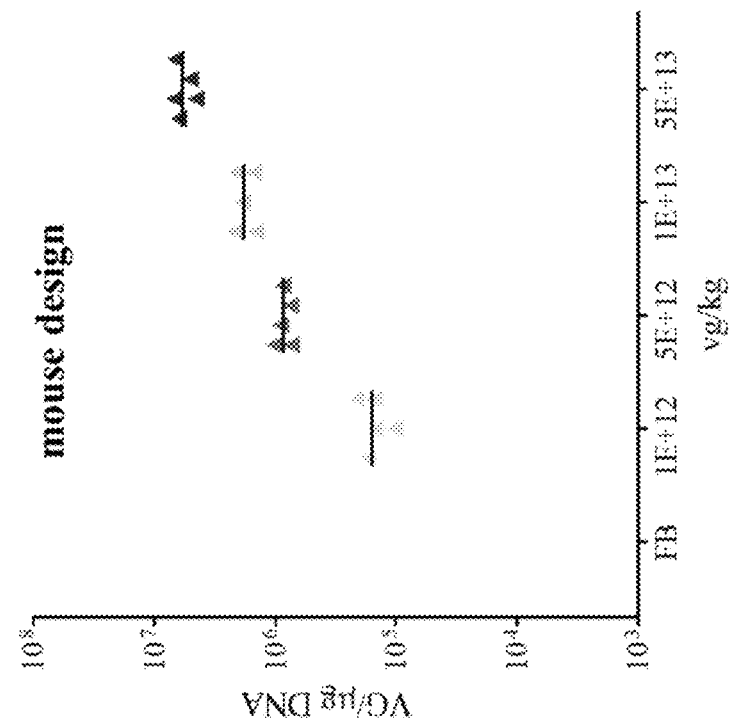

At 10 weeks old, mice dosed with the human design vector packaged in AAVHSC15 capsid (FIG. 10I) were found to have a similar reduction in serum Phe levels, compared to mice dosed with the mouse design vector (FIG. 10H). A corresponding increase in blood Tyr concentration was also observed in the 10-week-old mice dosed with the human design vector packaged in AAVHSC15 capsid (FIG. 10K) and in mice dosed with the mouse design vector (FIG. 10J). As shown in FIGS. 10M and 10N, a dose response was observed for vector genome levels detected in the liver of 10-week-old mice dosed with the human design vector (FIG. 10N) or the mouse design vector (FIG. 10M) packaged in AAVHSC15 capsid. A dose response was also observed for mRNA levels detected in the liver of 10-week-old mice dosed with the human design vector (FIG. 10P) or the mouse design vector (FIG. 10O) packaged in AAVHSC15 capsid.

Example 7: Effect of a Single Dose of Mouse-Specific Vector or Human-Specific Vector To evaluate the effect of the age of PAHenu2 mice on the response to a single dose of the mouse-specific gene transfer/gene editing AAV vector (PAH-006m-LP-1; "mouse design") or the human-specific gene transfer/gene editing AAV vector (hPAH-hl1C-032-LP1-SD3; "human design"), mice at 2-, 4-, and 10-weeks of age were selected. This allowed for a comparison between the effect of pediatric liver growth (2- and 4-week-old mice) and the liver of an adult (10-week-old mice). A single 1E14 vg/kg dose of the mouse design vector packaged in AAVHSC15 or the human design vector packaged in AAVHSC15 was intravenously administered to PAHenu2 mice at 2-, 4-, or 10-weeks of age. A total of four to five male mice in each age group were administered the respective packaged vectors. Formulation buffer was administered as control. As the human design vector does not integrate into the mouse Pah locus, it provides a control to demonstrate the effect of episomal expression on mice of different ages. In this example, after an official titering procedure, the titer of the lot used was accordingly adjusted to 9.07E13 vg/kg for the mouse design and 1.06E14 vg/kg for the human design. The various dosing cohorts studied are set forth in Table 2.

TABLE 2

Dosing Cohorts

| Group | Test Article | Dose Level (vg/kg) | Number of mice dosed/Sex (age at dosing) | Necropsy (weeks post-administration) |
|---|---|---|---|---|
| 1 | Formulation buffer | NA | 5/M (2-weeks) | 43 weeks |
| 2 | Mouse design vector packaged in AAVHSC15 | 1E + 14 (9.07E13) | 5/M (2-weeks) | |
| 3 | | | 4/M (4-weeks) | |
| 4 | | | 4/M (10-weeks) | |
| 5 | | | 4/M (2-weeks) | 2 weeks |
| 6 | | | 4/M (2-weeks) | 4 weeks |
| 7 | | | 4/M (2-weeks) | 8 weeks |
| 8 | Formulation buffer | NA | 4/M (2-weeks) | 42 weeks |
| 9 | Human design vector packaged in AAVHSC15 | 1E + 14 (1.06E14) | 4/M (2-weeks) | |
| 10 | | | 4/M (4-weeks) | |
| 11 | | | 4/M (10-weeks) | |
| 12 | | | 4/M (2-weeks) | 2 weeks |
| 13 | | | 4/M (2-weeks) | 4 weeks |
| 14 | | | 4/M (2-weeks) | 8 weeks |
| 15 | Mouse design vector packaged in AAVHSC15 | | 4/M (4-weeks) | 42 weeks |

As set forth in Table 2, Groups 1-4 were sacrificed 43 weeks post-administration, and Groups 8-11, and 15 were sacrificed 42 weeks post-administration. Serum Phe and Tyr levels were examined over time for Groups 1-4, 8-11, and 15 (FIGS. 11A-11D). FIGS. 11E-11K show the vector genome levels and mRNA levels detected in the livers of mice at the necropsy time points indicated in Table 2. mRNA levels in the livers of Groups 5-7 mice were not measured.

Figure 11B:
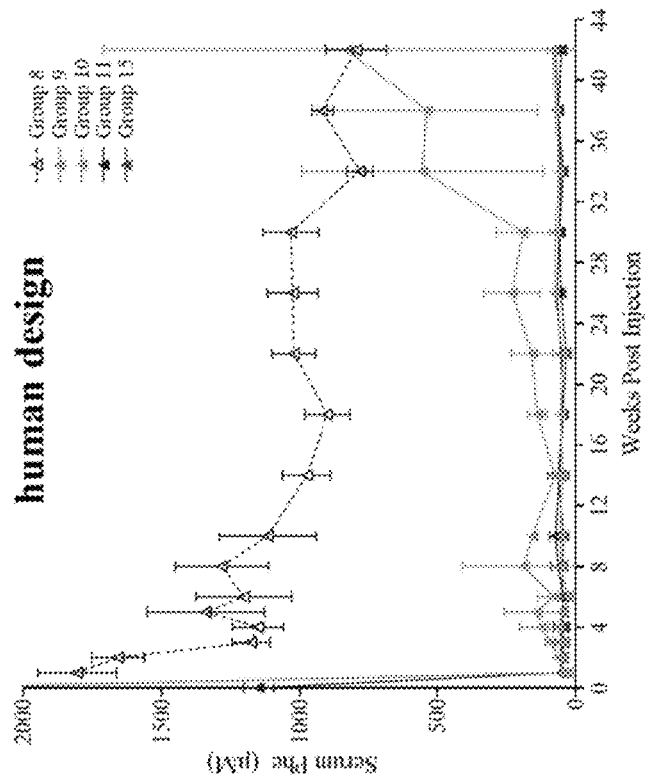
Figure 11A:
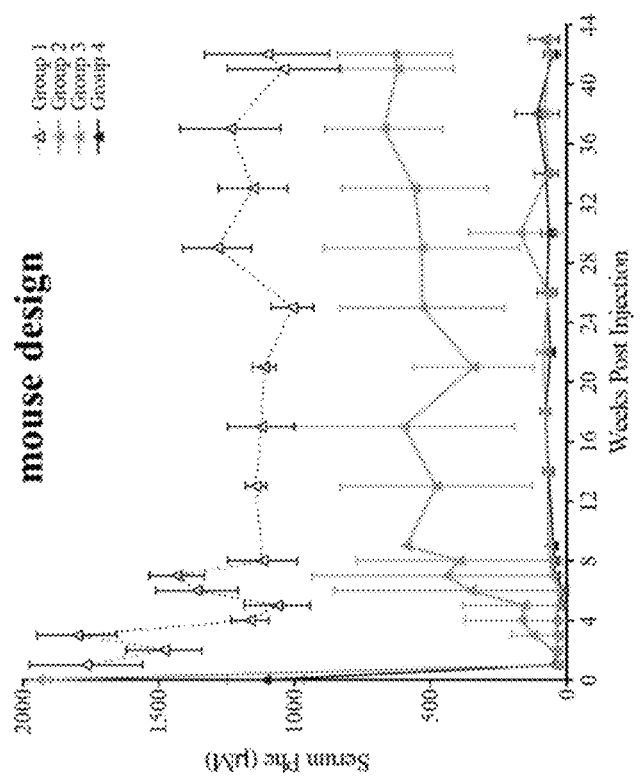

In mice treated with the mouse design vector, serum Phe levels were reduced to normal levels within one week following administration of the vector (FIG. 11A). For the treated 4- and 10-week-old mice (Groups 3 and 4), the reduction in Phe levels was maintained through 43 weeks, demonstrating long term durability of response to treatment. For the 2-week-old mice, the results were variable. A corresponding increase in serum Tyr concentration was observed in the 4- and 10-week-old mice through 43 weeks (FIG. 11C). FIG. 11E shows the vector genome levels detected in the liver of 2-, 4-, and 10-week-old mice treated with the mouse design vector. FIG. 11I shows the mRNA levels detected in the liver of 2-, 4-, and 10-week-old mice treated with the mouse design vector.

In mice treated with the human design vector, serum Phe levels were reduced by the one week time point following administration of the vector (FIG. 11B). For the treated 4- and 10-week-old mice (Groups 10 and 11), the reduction in Phe levels was maintained through 43 weeks, indicating long term durability of response to treatment. In the treated 2-week-old mice (Group 9), Phe levels maintained at clinically relevant levels of ≤360 µM through 30 weeks. A corresponding increase in serum Tyr concentration was observed in Groups 9 (through 30 weeks), 10 (through 42 weeks), and 11 (through 42 weeks) (FIG. 11D). These data indicate that a 1E14 vg/kg dose of the human design vector packaged in AAVHSC15 is sufficient to provide sustained efficacy through the period of liver growth in a juvenile mouse, and that the effect is sustained for at least 30 weeks post-administration. FIG. 11F shows the vector genome levels detected in the liver of 2-, 4-, and 10-week-old mice treated with the human design vector. FIG. 11J shows the mRNA levels detected in the liver of 2-, 4-, and 10-week-old mice treated with the human design vector.

Figure 11K:
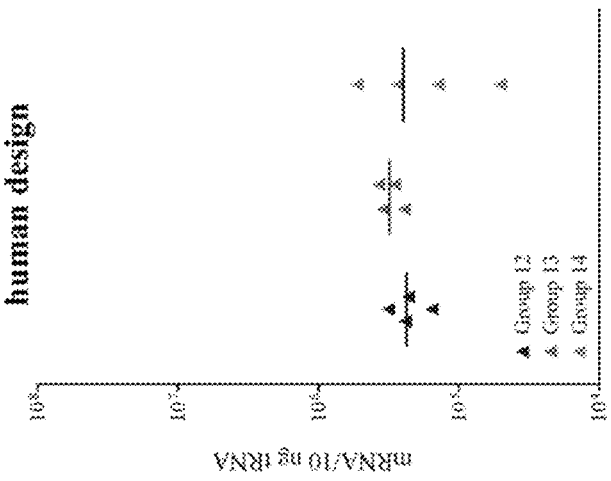

FIGS. 11G and 11H show that in 2-week-old mice treated with the mouse design vector (FIG. 11G; Groups 5-7) and 2-week-old mice treated with the human design vector (FIG. 11H; Groups 12-14), vector genome levels were sustained up to 8 weeks post-administration. FIG. 11K shows that mRNA levels of 2-week-old mice treated with the human design vector were sustained up to 8 weeks post-administration.

Example 8: Kinetics and Durability of Integration in Adult PAH$^{enu2}$ Mice

Figure 12C:
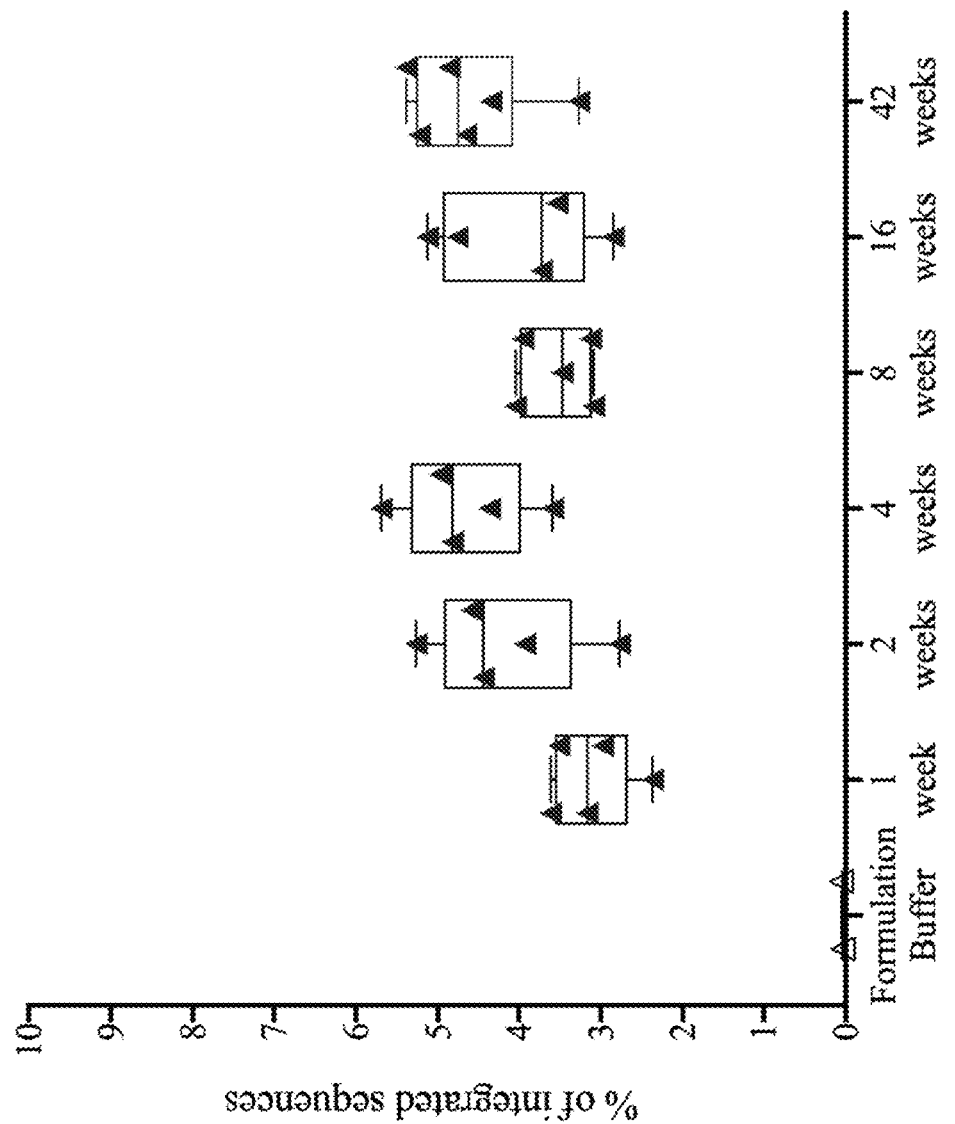

To determine kinetics and durability of vector integration over time, 10-week-old male PAH$^{enu2}$ mice were administered a mouse-specific gene transfer/gene editing AAV vector (PAH-006m-LP-1) packaged in AAVHSC15 capsid at a dose of 1E14 vg/kg. Six cohorts were sacrificed at 1, 2, 4, 8, and 16 weeks post-dosing (five mice per cohort). The kinetics of integration was investigated by monitoring serum Phe levels over time, vector genome levels over time, PAH transgene mRNA expression levels over time, and targeted integration levels overtime, at the various time points. It was found that vector genome levels, PAH transgene mRNA expression levels, and integration frequencies were stable over time (FIGS. 12A-12C).

FIGS. 12A and 12B show a time course of vector genome levels (FIG. 12A) and PAH transgene mRNA expression levels (FIG. 12B) in PAH$^{enu2}$ mice administered PAH-006m-LP-1 packaged in AAVHSC15 capsid at a dose of 1E14 vg/kg. The vector genome and the mRNA levels over time were found to be stable up to 42 weeks. Vector genome levels were measured using quantitative PCR using a coding sequence specific primer and probes relative to input genomic DNA target. Measurement of expression was performed by quantitative RT-PCR using coding sequence specific primers and probes relative to total RNA.

A long-read next generation sequencing (NGS) method was developed to quantitate integrated versus unintegrated alleles. Long-read sequencing was selected due to the length of the homology arms requiring a read through of the integration sequence and into the genomic DNA. The method was able to distinguish between integrated alleles, wild-type alleles, and vector genomes that are present in a given sample. PCR is performed using three primers specific to i) the genomic region; ii) a region specific to the integrated allele; and iii) a region specific to the wild-type allele. The frequency of on-target vector integration was determined by competitively amplifying both wild-type and integrated alleles at the PAH region using DNA derived from the livers of treated animals. The long-read sequencing of the amplified products covered the homology arm, which was identical across genomic, integrated, and vector genome sequences. The adjoining sequences, which were also covered by long-read sequencing, determine whether the source of the read was from wild-type, integrated, or vector genomes. Contiguous sequences that included both the genomic DNA and the silently altered hPAH transgene were tallied as integrated alleles, while sequences that included only the genomic DNA without the silently altered hPAH transgene in the target integration site were tallied as wild-type alleles. Percentage of integrated sequences were calculated as the number of reads mapped to the integrated reference divided by the total number of reads mapped to the integrated reference, reads mapped to the wild-type reference, and reads mapped to vector genome concatemers. FIG. 12C shows a time course of targeted integration frequency in PAH$^{enu2}$ mice administered PAH-006m-LP-1 packaged in AAVHSC15 capsid at a dose of 1E14 vg/kg. On-target integration was detected at one week post-dosing, achieved peak levels by about 2 weeks, and remained consistent through 42 weeks.

Figure 12D:
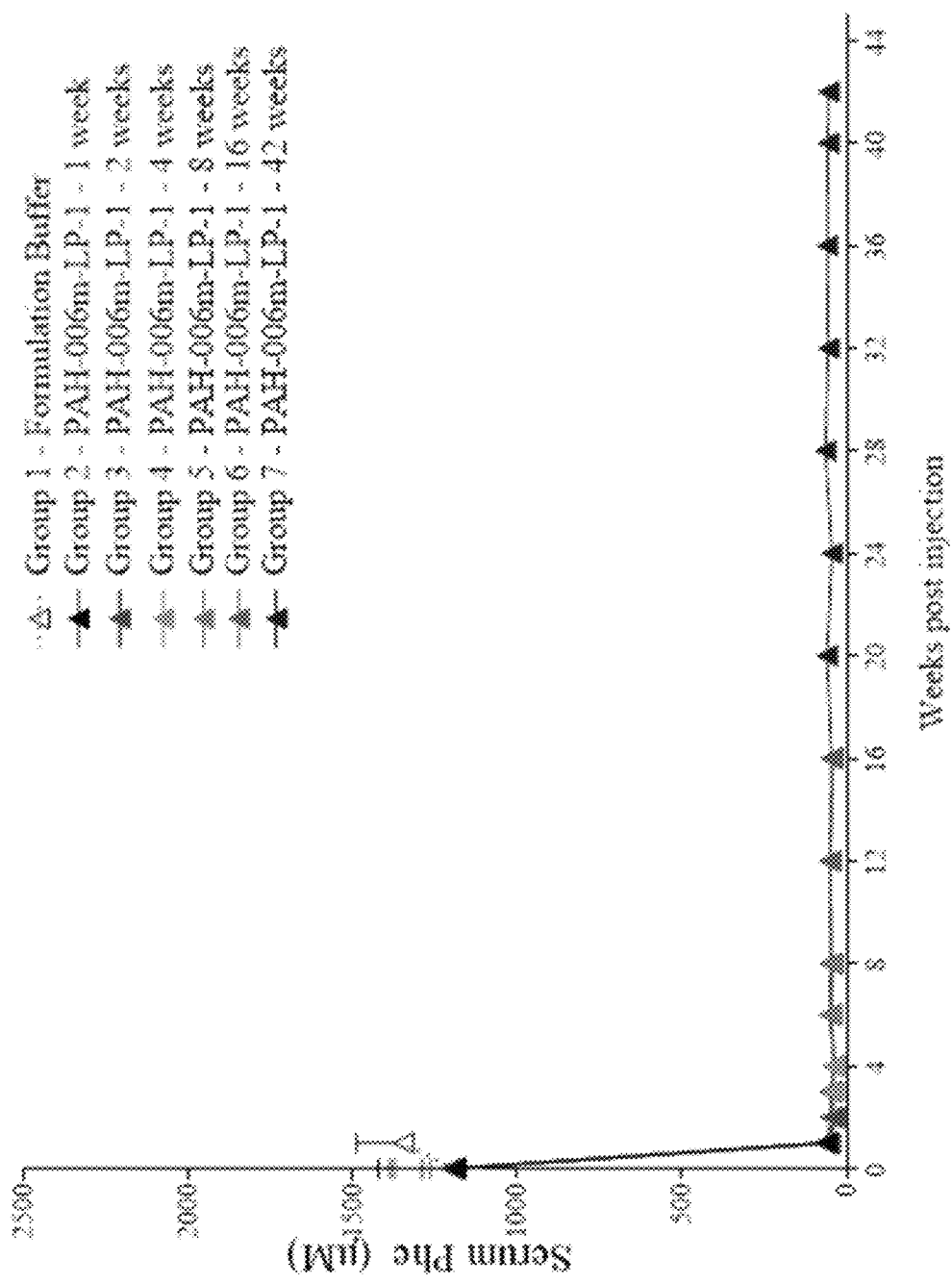
Figure 12E:
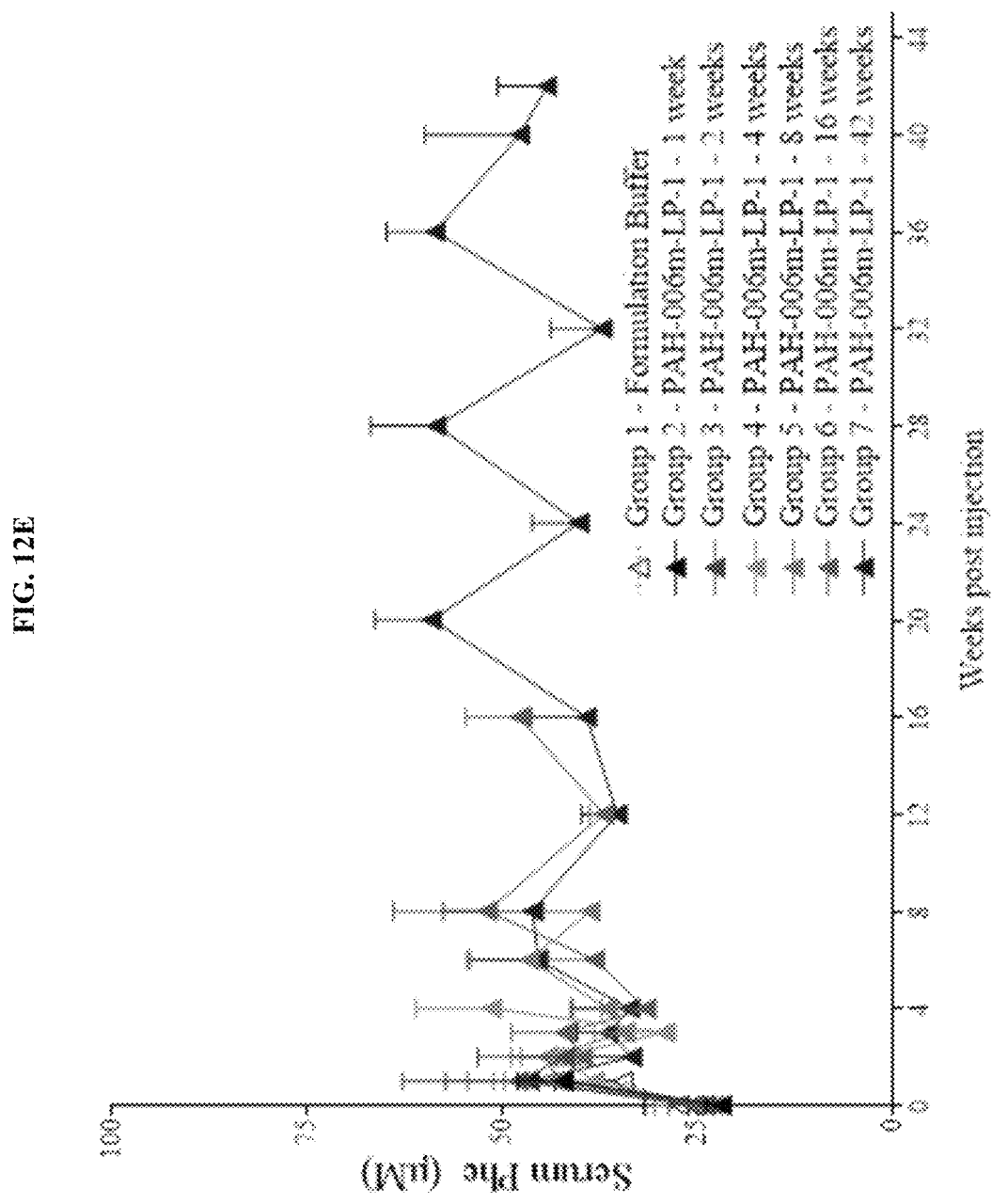

FIGS. 12D and 12E are graphs showing the effect on serum Phe (FIG. 12D) and Tyr (FIG. 12E) in PAH$^{enu2}$ mice administered PAH-006m-LP-1 packaged in AAVHSC15 capsid at a dose of 1E14 vg/kg, up to 42 weeks post-injection.

Example 9: In Vivo Efficacy of hPAH-hI1C-032-LP1-SD3

To determine kinetics and durability of integration of a human specific gene transfer/gene editing vector over time, male humanized liver FRG mice ("HuLiv" mice; see, Example 2) were administered the human-specific gene transfer/gene editing vector, hPAH-hI1C-032-LP1-SD3, packaged in AAVHSC15 capsid, at a dose of 7E13 vg/kg (Groups 1 and 3) or 2E14 vg/kg (Groups 2 and 4), and sacrificed at 4 (Groups 1 and 2) or 12 weeks (Groups 3 and 4) post-dosing (six male mice per cohort). Control FRG mice were administered formulation buffer and sacrificed at 4 (Group 5) or 12 weeks (Group 6) post-administration.

Figure 13B:
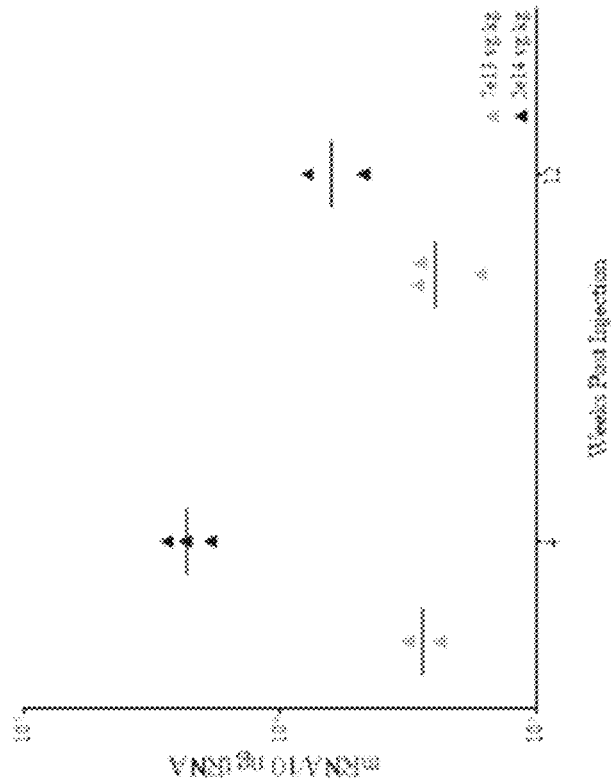
FIGS. 13A and 13B are plots showing the effect of hPAH-hI1C-032-LP1-SD3 packaged in AAVHSC15 on the level of vector genomes detected per ug of genomic DNA, and the level of mRNA expression detected per 10 ng of total RNA in human hepatocytes isolated from HuLiv mice, respectively, at the indicated doses and timepoints.
Figure 13A:
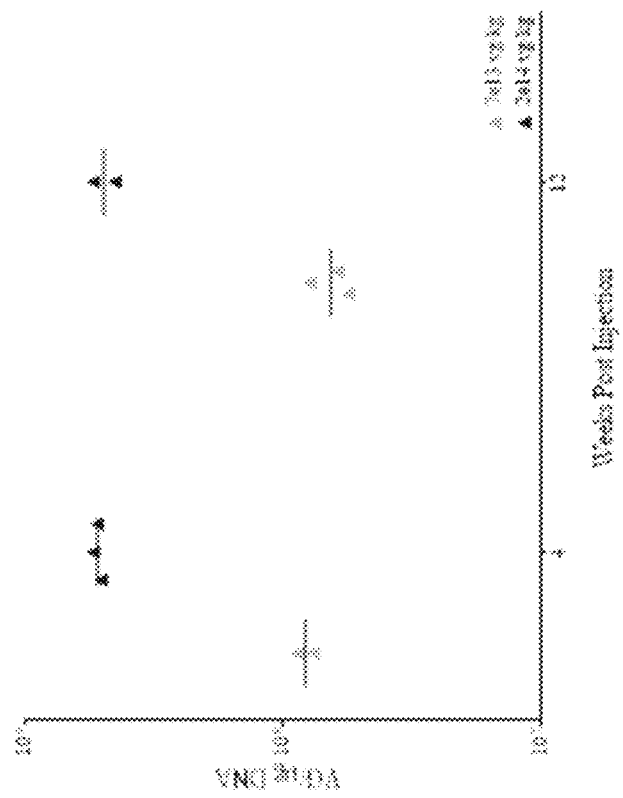
Figure 13C:
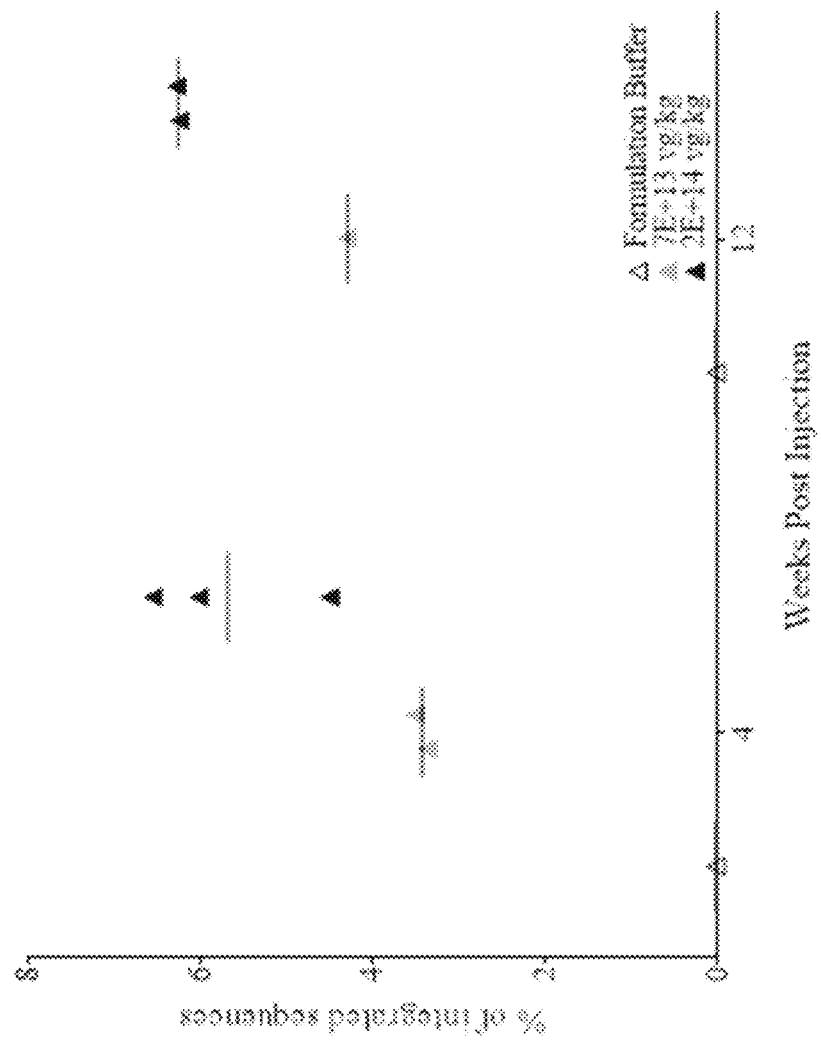
FIG. 13C is a plot showing the frequency of on-target insertion detected in human hepatocytes isolated from HuLiv mice at various time points post-dosing of hPAH-hI1C-032-LP1-SD3 packaged in AAVHSC15, at the indicated doses.
Figure 14A:
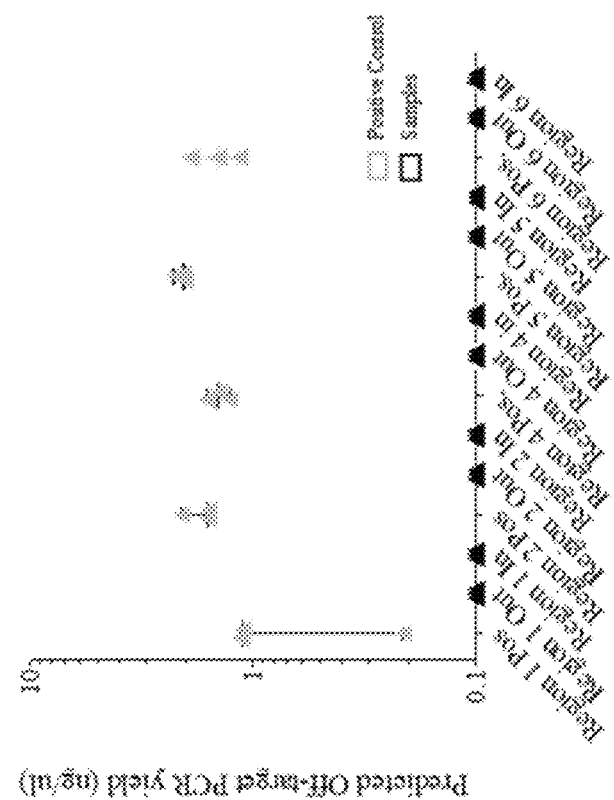
Figure 14B:
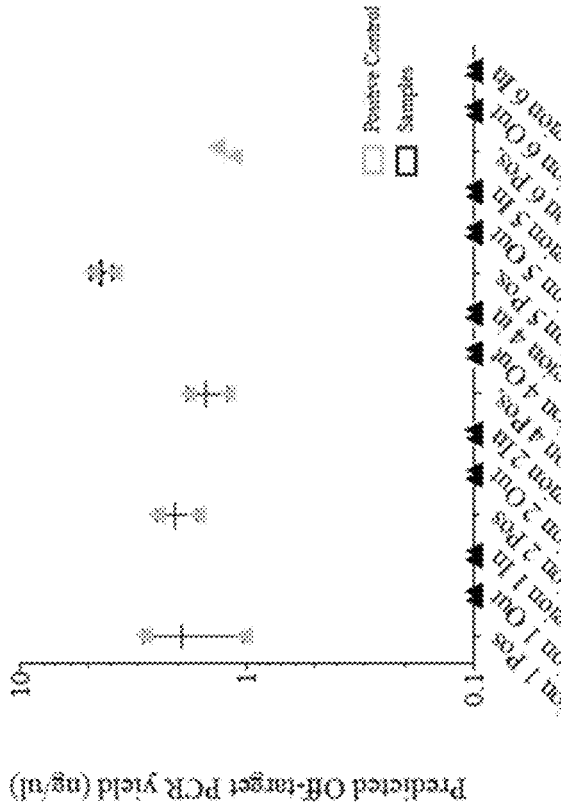

FIGS. 13A and 13B show the vector genome levels and mRNA levels detected in human hepatocytes isolated from HuLiv mice at 4 and 12 weeks after administration of hPAH-hI1C-032-LP1-SD3 packaged in AAVHSC15, at the indicated doses. As shown, the level of vector genomes (FIG. 13A) and mRNA expression (FIG. 13B) in human hepatocytes were found to be dose responsive and stable over time up to 12 weeks. Vector genome levels were measured using quantitative PCR using a coding sequence specific primer and probes relative to input genomic DNA target. Measurement of expression was performed by quantitative RT-PCR using coding sequence specific primers and probes relative to total RNA. FIG. 13C shows the frequency of on-target integration detected in human hepatocytes isolated from HuLiv mice at 4 and 12 weeks after administration of hPAH-hI1C-032-LP1-SD3 packaged in AAVHSC15, at the indicated doses. As shown, the level of on-target integration in human hepatocytes was found to be dose responsive and stable over time up to 12 weeks. Measurement of targeted integration was carried out using the long-read NGS method described in Example 8.

Given that homologous recombination may be driven by short stretches of sequence similarity between the homology arms of the vector and an off-target location in the genome, a PCR-based assay was developed to specifically test for integration into genomic regions that contain sequence similar to the homology arms. The method bioinformatically predicted the most likely regions to undergo off-target homologous recombination in human cells transduced with vector containing homology arms specific to the human PAH locus. These predicted regions were selected based on the highest sequence similarity to the homology arms. A PCR-based method was designed to specifically test transduced samples for any occurrence of off-target integration in the predicted regions. Using this PCR-based method, integration to a level of 1:10000 DNA molecules was able to be detected.

Predicted off-target integration sites were selected based on two criteria: a minimum sequence length of 35 bp; and a minimum sequence identity of 60% relative to the homology arms. Six regions of the genome were identified that met these criteria via bioinformatic alignment against Genome Reference Consortium Human Build 38. PCR primers that allow specific amplification for off-target integration at 5 of these 6 regions were designed. Region 3 was found to be in a highly repetitive region and was dropped from further analysis because specific primers could not be generated. As positive controls ("Pos"), specific control DNAs spiked into genomic DNA, were run for each specific region down to a dilution of 1:10,000, representing 0.010% and the limit of detection of the PCR-based method. For each predicted region, integration-specific primer pairs targeting homologous recombination in either direction (inward ("In") or outward ("Out") from the region of homology) were tested independently to query for off-target integration. Off-target integration was defined as positive if a distinct PCR band of the correct size was identified in a sample.

FIGS. 14A-14D show the results of predicted off-target integration determined by the PCR-based method described above, performed on genomic DNA samples isolated from 10-week-old male humanized liver FRG mice administered the human-specific gene transfer/gene editing vector, hPAH-hI1C-032-LP1-SD3, packaged in AAVHSC15 capsid, at a dose of 7E13 vg/kg (FIGS. 14A and 14C) or 2E14 vg/kg (FIGS. 14B and 14D), and sacrificed at 4 (FIGS. 14A and 14B) or 12 weeks (FIGS. 14C and 14D) post-dosing (six male mice per cohort). As shown, no integration was detected at the predicted off-target integration sites.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

We claim:

1. A recombinant adeno-associated virus (rAAV) comprising: (a) an AAV capsid comprising an AAV capsid protein; and (b) an rAAV genome comprising: (1) an editing element for editing a target locus in a phenylalanine hydroxylase (PAH) gene, comprising a PAH coding sequence operably linked to a transcriptional regulatory element, wherein the PAH coding sequence comprises the nucleotide sequence set forth in SEQ ID NO: 28; (ii) a 5' homology arm nucleotide sequence positioned 5' of the editing element, having homology to a first genomic region 5' to the target locus; and (iii) a 3' homology arm nucleotide sequence positioned 3' of the editing element, having homology to a second genomic region 3' to the target locus.

2. The rAAV of claim 1, wherein the transcriptional regulatory element is capable of mediating transcription in a hepatocyte, a renal cell, a brain cell, a pituitary gland cell, an adrenal gland cell, a pancreatic cell, a urinary bladder cell, a gallbladder cell, a colon cell, a small intestine cell, or a breast cell, optionally wherein:

the transcriptional regulatory element is endogenous to the PAH gene; or the transcriptional regulatory element is exogenous to the PAH gene, optionally wherein:
the transcriptional regulatory element is liver specific, optionally wherein the transcriptional regulatory element comprises one or more elements selected from the group consisting of a human albumin promoter, a human transthyretin (TTR) promoter, a human ApoE/C-I hepatic control region (HCR) 1 or 2, a human ApoH promoter, a human SERPINA1 (hAAT) promoter, and a hepatic specific regulatory module thereof;
the transcriptional regulatory element comprises a nucleotide sequence at least 90% identical to a sequence selected from the group consisting of SEQ ID NO: 25, 26, 27, and 69;
the transcriptional regulatory element comprises a nucleotide sequence at least 90% identical to the nucleotide sequence set forth in SEQ ID NO: 27;
the transcriptional regulatory element comprises the nucleotide sequence set forth in SEQ ID NO: 27; or
the nucleotide sequence of the transcriptional regulatory element consists of the nucleotide sequence set forth in SEQ ID NO: 27.

3. The rAAV of claim 1, wherein the editing element further comprises an intron element positioned 5' to the PAH coding sequence and 3' to the transcriptional regulatory element, optionally wherein the intron element is an exogenous intron element, optionally an SV40 intron element, optionally wherein:
the SV40 intron element comprises a nucleotide sequence at least 90% identical to the nucleotide sequence set forth in SEQ ID NO: 29;
the SV40 intron element comprises the nucleotide sequence set forth in SEQ ID NO: 29; or the nucleotide sequence of the SV40 intron element consists of the nucleotide sequence set forth in SEQ ID NO: 29.

4. The rAAV of claim 1, wherein the editing element further comprises a polyadenylation sequence 3' to the PAH coding sequence, optionally wherein the polyadenylation sequence is an exogenous polyadenylation sequence, optionally an SV40 polyadenylation sequence, optionally wherein
the SV40 polyadenylation sequence comprises a nucleotide sequence at least 90% identical to the nucleotide sequence set forth in SEQ ID NO: 31;
the SV40 polyadenylation sequence comprises the nucleotide sequence set forth in SEQ ID NO: 31; or
the nucleotide sequence of the SV40 polyadenylation sequence consists of the nucleotide sequence set forth in SEQ ID NO: 31.

5. The rAAV of claim 1, wherein:
the nucleotide sequence 5' to the target locus is in an intron of a PAH gene, optionally in intron 1 of a PAH gene; and/or
the nucleotide sequence 3' to the target locus is in an intron of a PAH gene, optionally in intron 1 of a PAH gene.

6. The rAAV of claim 1, wherein the PAH gene is a human PAH gene, optionally wherein the human PAH gene is wild-type or a variant PAH gene.

7. The rAAV of claim 1, wherein the editing element comprises a nucleotide sequence selected from the group consisting of SEQ ID NO: 25, 26, 27, 29, 31, 50, 51, 52, 69, and 70.

8. The rAAV of claim 1, wherein:
the 5' homology arm nucleotide sequence is at least 90% identical to the first genomic region;

the 3' homology arm nucleotide sequence is at least 90% identical to the second genomic region;
the first genomic region is located in a first editing window, and the second genomic region is located in a second editing window, optionally wherein:
the first editing window consists of the region of the human genome corresponding to the nucleotide sequence set forth in SEQ ID NO: 37;
the second editing window consists of the region of the human genome corresponding to the nucleotide sequence set forth in SEQ ID NO: 38;
the first genomic region consists of the region of the human genome corresponding to the nucleotide sequence set forth in SEQ ID NO: 37; and/or
the second genomic region consists of the region of the human genome corresponding to the nucleotide sequence set forth in SEQ ID NO: 38.

9. The rAAV of claim 1, wherein:
each of the 5' and the 3' homology arm nucleotide sequences independently has a length of about 100 to about 2000 nucleotides;
the 5' homology arm comprises a nucleotide sequence that is at least 90% identical to the nucleotide sequence set forth in SEQ ID NO: 23;
the nucleotide sequence of the 5' homology arm consists of the nucleotide sequence set forth in SEQ ID NO: 23;
the 3' homology arm comprises a nucleotide sequence that is at least 90% identical to the nucleotide sequence set forth in SEQ ID NO: 24; and/or
the nucleotide sequence of the 3' homology arm consists of the nucleotide sequence set forth in SEQ ID NO: 24.

10. The rAAV of claim 1, wherein the rAAV genome comprises a nucleotide sequence that is at least 85% identical to the nucleotide sequence set forth in SEQ ID NO: 43.

11. The rAAV of claim 1, wherein the rAAV genome further comprises a 5' inverted terminal repeat (5' ITR) nucleotide sequence 5' of the 5' homology arm nucleotide sequence, and a 3' inverted terminal repeat (3' ITR) nucleotide sequence 3' of the 3' homology arm nucleotide sequence, optionally wherein:
the 5' ITR nucleotide sequence is at least 85% identical to the nucleotide sequence set forth in SEQ ID NO: 14, and/or the 3' ITR nucleotide sequence is at least 85% identical to the nucleotide sequence set forth in SEQ ID NO: 18; and/or
the rAAV genome comprises the nucleotide sequence set forth in SEQ ID NO: 73, 74, 75, or 76.

12. The rAAV of claim 1, wherein the rAAV genome comprises a nucleotide sequence that is at least 85% identical to the nucleotide sequence set forth in SEQ ID NO: 45.

13. The rAAV of claim 1, wherein:
the AAV capsid protein comprises an amino acid sequence that is at least 95% identical to the amino acid sequence of amino acids 203-736 of SEQ ID NO: 1, 2, 3, 4, 5, 6, 7, 8, 9, 10, 11, 12, 13, 15, 16, or 17, optionally wherein:
(i) the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G;

(ii) (a) the amino acid in the capsid protein corresponding to amino acid 626 of SEQ ID NO: 16 is G, and the amino acid in the capsid protein corresponding to amino acid 718 of SEQ ID NO: 16 is G; (b) the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M; (c) the amino acid in the capsid protein corresponding to amino acid 505 of SEQ ID NO: 16 is R, and the amino acid in the capsid protein corresponding to amino acid 687 of SEQ ID NO: 16 is R; (d) the amino acid in the capsid protein corresponding to amino acid 346 of SEQ ID NO: 16 is A, and the amino acid in the capsid protein corresponding to amino acid 505 of SEQ ID NO: 16 is R; or (e) the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C; and/or (iii) the capsid protein comprises the amino acid sequence of amino acids 203-736 of SEQ ID NO: 1, 2, 3, 4, 5, 6, 7, 8, 9, 10, 11, 12, 13, 15, 16, or 17;

the AAV capsid protein comprises an amino acid sequence that is at least 95% identical to the amino acid sequence of amino acids 138-736 of SEQ ID NO: 1, 2, 3, 4, 5, 6, 7, 8, 9, 10, 11, 12, 13, 15, 16, or 17, optionally wherein:

(i) the amino acid in the capsid protein corresponding to amino acid 151 of SEQ ID NO: 16 is R; the amino acid in the capsid protein corresponding to amino acid 160 of SEQ ID NO: 16 is D; the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G;

(ii) (a) the amino acid in the capsid protein corresponding to amino acid 626 of SEQ ID NO: 16 is G, and the amino acid in the capsid protein corresponding to amino acid 718 of SEQ ID NO: 16 is G; (b) the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M; (c) the amino acid in the capsid protein corresponding to amino acid 505 of SEQ ID NO: 16 is R, and the amino acid in the capsid protein corresponding to amino acid 687 of SEQ ID NO: 16 is R; (d) the amino acid in the capsid protein corresponding to amino acid 346 of SEQ ID NO: 16 is A, and the amino acid in the capsid protein corresponding to amino acid 505 of SEQ ID NO: 16 is R; or (e) the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C; and/or (iii) the capsid protein comprises the amino acid sequence of amino acids 138-736 of SEQ ID NO: 1, 2, 3, 4, 5, 6, 7, 9, 10, 11, 12, 13, 15, 16, or 17; and/or the AAV capsid protein comprises an amino acid sequence that is at least 95% identical to the amino acid sequence of amino acids 1-736 of SEQ ID NO: 1, 2, 3, 4, 5, 6, 7, 8, 9, 10, 11, 12, 13, 15, 16, or 17, optionally wherein:

(i) the amino acid in the capsid protein corresponding to amino acid 2 of SEQ ID NO: 16 is T; the amino acid in the capsid protein corresponding to amino acid 65 of SEQ ID NO: 16 is I; the amino acid in the capsid protein corresponding to amino acid 68 of SEQ ID NO: 16 is V; the amino acid in the capsid protein corresponding to amino acid 77 of SEQ ID NO: 16 is R; the amino acid in the capsid protein corresponding to amino acid 119 of SEQ ID NO: 16 is L; the amino acid in the capsid protein corresponding to amino acid 151 of SEQ ID NO: 16 is R; the amino acid in the capsid protein corresponding to amino acid 160 of SEQ ID NO: 16 is D; the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q;

the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G;

(ii) (a) the amino acid in the capsid protein corresponding to amino acid 2 of SEQ ID NO: 16 is T, and the amino acid in the capsid protein corresponding to amino acid 312 of SEQ ID NO: 16 is Q; (b) the amino acid in the capsid protein corresponding to amino acid 65 of SEQ ID NO: 16 is I, and the amino acid in the capsid protein corresponding to amino acid 626 of SEQ ID NO: 16 is Y; (c) the amino acid in the capsid protein corresponding to amino acid 77 of SEQ ID NO: 16 is R, and the amino acid in the capsid protein corresponding to amino acid 690 of SEQ ID NO: 16 is K; (d) the amino acid in the capsid protein corresponding to amino acid 119 of SEQ ID NO: 16 is L, and the amino acid in the capsid protein corresponding to amino acid 468 of SEQ ID NO: 16 is S; (e) the amino acid in the capsid protein corresponding to amino acid 626 of SEQ ID NO: 16 is G, and the amino acid in the capsid protein corresponding to amino acid 718 of SEQ ID NO: 16 is G; (f) the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M; (g) the amino acid in the capsid protein corresponding to amino acid 505 of SEQ ID NO: 16 is R, and the amino acid in the capsid protein corresponding to amino acid 687 of SEQ ID NO: 16 is R; (h) the amino acid in the capsid protein corresponding to amino acid 346 of SEQ ID NO: 16 is A, and the amino acid in the capsid protein corresponding to amino acid 505 of SEQ ID NO: 16 is R; or (i) the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C; and/or (iii) the capsid protein comprises the amino acid sequence of amino acids 1-736 of SEQ ID NO: 1, 2, 3, 4, 5, 6, 7, 8, 9, 10, 11, 12, 13, 15, 16, or 17.

14. A pharmaceutical composition comprising an rAAV of claim 1.

15. The rAAV of claim 1, wherein the editing element comprises a nucleotide sequence that is at least 85% identical to the nucleotide sequence set forth in SEQ ID NO: 52.

16. The rAAV of claim 1, comprising:
(a) an AAV capsid comprising: a capsid protein comprising the amino acid sequence of amino acids 203-736 of SEQ ID NO: 16; a capsid protein comprising the amino acid sequence of amino acids 138-736 of SEQ ID NO: 16; and/or a capsid protein comprising the amino acid sequence of amino acids 1-736 of SEQ ID NO: 16; and
(b) an rAAV genome comprising a nucleotide sequence that is at least 85% identical to the nucleotide sequence set forth in SEQ ID NO: 43.

17. The rAAV of claim 1, comprising:
(a) an AAV capsid comprising: a capsid protein comprising the amino acid sequence of amino acids 203-736 of SEQ ID NO: 16; a capsid protein comprising the amino acid sequence of amino acids 138-736 of SEQ ID NO: 16; and/or a capsid protein comprising the amino acid sequence of amino acids 1-736 of SEQ ID NO: 16; and
(b) an rAAV genome comprising a nucleotide sequence that is at least 85% identical to the nucleotide sequence set forth in SEQ ID NO: 45.

18. A polynucleotide comprising the nucleic acid sequence set forth in SEQ ID NO: 43, 45, 51, or 52.

* * * * *